United States Patent
Mikhno et al.

(10) Patent No.: US 10,304,183 B2
(45) Date of Patent: May 28, 2019

(54) REGULARIZATION OF IMAGES

(71) Applicants: THE TRUSTEES OF COLUMBIA UNIVERSITY IN THE CITY OF NEW YORK, New York, NY (US); The Research Foundation for The State University of New York, Albany, NY (US)

(72) Inventors: Arthur Mikhno, Staten Island, NY (US); Elsa D. Angelini, New York, NY (US); Andrew F. Laine, New York, NY (US); Todd Ogden, Teaneck, NJ (US); Ramin Parsey, Mountain Lakes, NJ (US); Joseph John Mann, Riverdale, NY (US)

(73) Assignees: The Trustees of Columbia University in the City of New York, New York, NY (US); The Research Foundation for the State University of New York, Albany, NY (US)

( * ) Notice: Subject to any disclaimer, the term of this patent is extended or adjusted under 35 U.S.C. 154(b) by 16 days.

(21) Appl. No.: 15/256,435

(22) Filed: Sep. 2, 2016

(65) Prior Publication Data

US 2017/0039706 A1 Feb. 9, 2017

Related U.S. Application Data

(63) Continuation-in-part of application No. PCT/US2015/018817, filed on Mar. 4, 2015.
(Continued)

(51) Int. Cl.
*G06T 11/00* (2006.01)
*A61B 6/00* (2006.01)
(Continued)

(52) U.S. Cl.
CPC ............ *G06T 7/0012* (2013.01); *A61B 6/037* (2013.01); *A61B 6/481* (2013.01); *A61B 6/501* (2013.01);
(Continued)

(58) Field of Classification Search
CPC ... G06T 7/0012; G06T 11/003; G06T 11/006; G06T 15/08; G06T 2207/10104;
(Continued)

(56) References Cited

U.S. PATENT DOCUMENTS 6,546,275 B2 4/2003 Carroll
7,091,489 B2 8/2006 Schlyer et al.
(Continued)

OTHER PUBLICATIONS

Mikhno et al. "Brain tissue selection procedures for image derived input functions derived using independent components analysis." Engineering in Medicine and Biology Society (EMBC), 2012 Annual International Conference of the IEEE. IEEE, 2012.*
(Continued)

*Primary Examiner* — Katrina R Fujita
(74) *Attorney, Agent, or Firm* — Wilmer Cutler Pickering Hale and Dorr LLP

(57) ABSTRACT

The present disclosure is directed to iterative regularized reconstruction methods. In certain embodiments, the methods incorporate locally-weighted total variation denoising to suppress artifacts induced by PSF modeling. In certain embodiments, the methods are useful for suppressing ringing artifacts while contrast recovery is maintained. In certain embodiments, the weighting scheme can be extended to noisy measures introducing a noise-independent weighting scheme. The present disclosure is also directed to a method for quantifying radioligand binding in a subject without collecting arterial blood. In certain embodiments, the methods incorporate using imaging data and electronic health
(Continued)

records to predict one or more anchors, which are used to generate an aterial input function (AIF) for the radioligand.

18 Claims, 99 Drawing Sheets
(46 of 99 Drawing Sheet(s) Filed in Color)

Related U.S. Application Data

(60) Provisional application No. 61/952,739, filed on Mar. 13, 2014, provisional application No. 61/947,739, filed on Mar. 4, 2014.

(51) Int. Cl.
| | | |
|---|---|---|
| *G06T 7/00* | (2017.01) | |
| *A61B 6/03* | (2006.01) | |
| *G06T 15/08* | (2011.01) | |

(52) U.S. Cl.
CPC .......... *A61B 6/5205* (2013.01); *A61B 6/5258* (2013.01); *G06T 11/003* (2013.01); *G06T 11/006* (2013.01); *G06T 15/08* (2013.01); *G06T 2207/10104* (2013.01); *G06T 2207/10108* (2013.01); *G06T 2207/30016* (2013.01); *G06T 2211/424* (2013.01)

(58) Field of Classification Search
CPC . G06T 2207/10108; G06T 2207/30016; G06T 2211/424; A61B 6/037; A61B 6/481; A61B 6/501; A61B 6/5205; A61B 6/5258
See application file for complete search history.

(56) References Cited

U.S. PATENT DOCUMENTS

| | | |
|---|---|---|
| 7,769,217 B2 | 8/2010 | Hamill |
| 8,299,438 B2 | 10/2012 | Fenchel et al. |
| 8,885,906 B2* | 11/2014 | Weitzel ................. G06T 11/008 382/131 |
| 2007/0040123 A1 | 2/2007 | Gagnon et al. |
| 2011/0160543 A1 | 6/2011 | Parsey et al. |
| 2011/0268334 A1* | 11/2011 | Ra ......................... G06T 3/4053 382/131 |
| 2012/0089015 A1 | 4/2012 | Gagnon et al. |
| 2013/0156699 A1* | 6/2013 | Mann ................. A61K 51/0461 424/1.89 |
| 2013/0299708 A1 | 11/2013 | Yamada |
| 2013/0301896 A1* | 11/2013 | Vija ....................... G06T 11/005 382/131 |
| 2014/0328528 A1* | 11/2014 | Ra ......................... G06T 11/005 382/131 |
| 2014/0334702 A1* | 11/2014 | El Fakhri .............. G06T 11/005 382/131 |

OTHER PUBLICATIONS

Green, Geoffrey Clarence. Wavelet-based denoising of cardiac PET data. Carleton University, 2005.*
Keuper et al. "Blind deconvolution with PSF regularization for wide-field microscopy." Biomedical Imaging (ISBI), 2012 9th IEEE International Symposium on. IEEE, 2012.*
Reader et al. "Generalization of the image space reconstruction algorithm." Nuclear Science Symposium and Medical Imaging Conference (NSS/MIC), 2011 IEEE. IEEE, 2011.*
Hahn, A., et al., "Application of image-derived and venous input functions in major depression using [carbonyl-$^{11}$C]WAY-100635," Nucl. Med. Biol., vol. 40, pp. 371-377 (2013).
Alstrup, A. K. O., et al., "Effects of anesthesia and species on the uptake or binding of radioligands in vivo in the Gottingen minipig," Biomed. Res. Int., vol. 2013, Article 808713, pp. 1-9, 10 total pages (2013).
Kriplani, A., et al., "Feasibility studies for extracting an Input Function for Quantitative Positron Emission Tomography using a Wrist Scanner," IEEE 33rd Annual Northeast Bioengineering Conference 2007 (NEBC '07), pp. 51-53 (2007).
Mikhno, A., et al., "Combining brain imaging data with electronic health records to non-invasively quantify [$^{11}$C] DASB binding," 2014 IEEE-EMBS International Conference on Biomedical and Health Informatics (BHI), pp. 732-735 (2014).
Levey, A. S., et al., "A More Accurate Method to Estimate Glomerular Filtration Rate from Serum Creatinine: A New Prediction Equation," Ann. Intern. Med., vol. 130, No. 6, pp. 461-470, (Mar. 16, 1999).
Lopresti, B. J., et al., "Simplified Quantification of Pittsburgh Compound B Amyloid Imaging PET Studies: A Comparative Analysis," J. Nucl. Med., vol. 46, No. 12, pp. 1959-1972 (Dec. 2005).
Parker, B. J. and Feng, D., "Graph-Based Mumford-Shah Segmentation of Dynamic PET With Application to Input Function Estimation," IEEE Transactions on Nuclear Science, vol. 52, No. 1, pp. 79-89 (Feb. 2005).
Kang, E.-H., et al., "Platelet Serotonin Transporter Function and Heart Rate Variability in Patients with Panic Disorder," J. Korean Med. Sci., vol. 25, pp. 613-618 (2010).
Fung, E. K., et al., "A Multimodal Approach to Image-Derived Input Functions for Brain PET," 2009 IEEE Nucl. Sci. Symp. Conf. Rec., M05-154, pp. 2710-2714 (2009).
Kauppila, E., et al., "Influence of Serotonin Transporter Gene Polymorphism (5-HTTLPR Polymorphism) on the Relation Between Brain 5-HT Transporter Binding and Heart Rate Corrected Cardiac Repolarization Interval," PLoS One, vol. 8, Issue, 1, e50303, pp. 1-4 (Jan. 2013).
O'Sullivan, F., et al., "Kinetic Quantitation of Cerebral PET-FDG Studies Without Concurrent Blood Sampling: Statistical Recovery of the Arterial Input Function," IEEE Trans. Med. Imaging, vol. 29, No. 3, pp. 610-624 (Mar. 2010).
Zanderigo, F., et al., "Reference region approaches in PET: a comparative study on multiple radioligands," J. Cereb. Blood Flow Metab., vol. 33, pp. 888- 897 (2013).
Starr, I., et al., "Studies Made by Simulating Systole at Necropsy. IV. On the Relation between Pulse Pressure and Cardiac Stroke Volume, Leading to a clinical method of estimating cardiac output from blood pressure and age," Circulation, vol. 9, pp. 648-663 (May 1954).
International Search Report and Written Opinion for International Patent Application No. PCT/US2015/018817 dated Sep. 17, 2015 (9 pages).
Mourik, J. E. M., et al., "Partial volume corrected image derived input functions for dynamic PET brain studies: Methodology and validation for [$^{11}$C]flumazenil," Neuroimage, vol. 39, pp. 1041-1050 (2008).
Chen, K., et al., "Noninvasive Quantification of the Cerebral Metabolic Rate for Glucose Using Positron Emission Tomography, $^{18}$F-Fluoro-2-Deoxyglucose, the Patlak Method, and an Image Derived Input Function," J. Cereb. Blood Flow Metab., vol. 18, pp. 716-723 (1998).
Chen, K., et al., "Characterization of the image-derived carotid artery input function using independent component analysis for the quantitation of [18F] fluorodeoxyglucose positron emission tomography images," Phys. Med. Biol., vol. 52, pp. 7055-7071 (2007).
Thielemans, K., et al., "STIR: software for tomographic image reconstruction release 2," 2006 IEEE Nucl. Sci. Symp. Conf. Rec., M06-359, pp. 2174-2176 (2006).
Wong, K.-P., et al., "Estimation of input function and kinetic parameters using simulated annealing: application in a flow model," IEEE Transactions on Nuclear Science, vol. 49, No. 3, pp. 707-713 (Jun. 2002).
Stevens, L. A., et al., "Comparison of Drug Dosing Recommendations Based on Measured GFR and Kidney Function Estimating Equations," Am. J. Kidney Dis., vol. 54, No. 1, pp. 33-42 (Jul. 2009).
Kropholler, M. A., et al., "Evaluation of reference tissue models for the analysis of [$^{11}$C](R)-PK11195 studies," J. Cereb. Blood Flow Metab., vol. 26, pp. 1431-1441 (2006).

(56) References Cited

OTHER PUBLICATIONS

Bentourkia, M'hamed, "Kinetic modeling of PET-FDG in the brain without blood sampling," Comput. Med. Imaging Graph., vol. 30, pp. 447-451 (2006).
Mifflin, M. D et al "A new predictive equation for resting energy expenditure in healthy individuals," Am. J. Clin. Nutr., vol. 51, pp. 241-247 (1990).
Gibaldi, M. and Perrier, D., "Pharmacokinetics," Second Edition, Revised and Expanded, Drugs and the Pharmaceutical Sciences, vol. 15, Marcel Dekker, Inc., New York, 1982 (57 pages).
Liptrot, M., et al., "Cluster analysis in kinetic modelling of the brain: a noninvasive alternative to arterial sampling," Neuroimage, vol. 21, pp. 483-493 (2004).
Graham, Michael M., "Physiologic smoothing of blood time-activity curves for PET data analysis," J. Nucl. Med., vol. 38, pp. 1161-1168 (1997).
Naganawa, M., et al., "Extraction of a plasma time-activity curve from dynamic brain PET images based on independent component analysis," IEEE Trans. Biomed. Eng., vol. 52, No. 2, pp. 201-210 (Feb. 2005).
Schain, M., et al., "Arterial input function derived from pairwise correlations between PET-image voxels," J. Cereb. Blood Flow Metab., vol. 33, pp. 1058-1065 (2013).
Mikhno, A., et al., "Locally Weighted Total Variation Denoising for Ringing Artifact Suppression in PET Reconstruction Using PSF Modeling," 2013 IEEE 10$^{th}$ Int. Symp. Biomed. Imaging: From Nano to Macro, San Francisco, CA, USA, 4 pages (Apr. 7-11, 2013).
Zanotti-Fregonara, P., et al., "Image-derived input function for brain PET studies: many challenges and few opportunities," J. Cereb. Blood Flow Metab., vol. 31, pp. 1986-1998 (2011).
Zanotti-Fregonara, P., et al., "Comparison of eight methods for the estimation of the image-derived input function in dynamic [$^{18}$F]-FDG PET human brain studies," J. Cereb. Blood Flow Metab., vol. 29, pp. 1825-1835 (2009).
Zanotti-Fregonara, P., et al., "Comparison of 3 Methods of Automated Internal Carotid Segmentation in Human Brain PET Studies: Application to the Estimation of Arterial Input Function," J. Nucl. Med., vol. 50, pp. 461-467 (2009).
Innis, R. B., et al., "Consensus nomenclature for in vivo imaging of reversibly binding radioligands," J. Cereb. Blood Flow Metab., vol. 27, pp. 1533-1539 (2007).
Mosteller, R. D., "Simplified calculation of body-surface area," N. Engl. J. Med., vol. 317, p. 1098 (Oct. 22, 1987).
Gunn, R. N., et al., "Positron emission tomography compartmental models," J. Cereb. Blood Flow Metab., vol. 21, pp. 635-652 (2001).
Ogden, R. T., et al., "In vivo quantification of serotonin transporters using [$^{11}$C]DASB and positron emission tomography in humans: modeling considerations," J. Cereb. Blood Flow Metab., vol. 27, pp. 205-217 (2007).
Ogden, R. T., et al., "Simultaneous estimation of input functions: an empirical study," J. Cereb. Blood Flow Metab., vol. 30, pp. 816-826 (2010).
Parsey, R. V., et al., "Metabolite Considerations in the In Vivo Quantification of Serotonin Transporters Using $^{11}$C-DASB and PET in Humans," J. Nucl. Med., vol. 47, pp. 1796-1802 (2006).
Parsey, R. V., et al., "Acute occupancy of brain serotonin transporter by sertraline as measured by [$^{11}$C]DASB and positron emission tomography," Biol. Psychiatry, vol. 59, pp. 821-828 (2006).
Nadler, S. B., et al., "Prediction of blood volume in normal human adults," Surgery, vol. 51, No. 2, pp. 224-232 (Feb. 1962).
Kirkpatrick, S., et al., "Optimization by simulated annealing," Science, vol. 220, No. 4598, pp. 671-680 (May 13, 1983).
Ametamey, S. M., et al., "Human PET Studies of Metabotropic Glutamate Receptor Subtype 5 with $^{11}$C-ABP688," J. Nucl. Med., vol. 48, pp. 247-252 (2007).
Slavin, A. J., et al., "The structure of the remnant of HR Del," Mon. Not. R. Astron. Soc., vol. 266, pp. L55-L59 (1994).
Tsuchida, T., et al., "Noninvasive Measurement of Cerebral Metabolic Rate of Glucose Using Standardized Input Function," J. Nucl. Med., vol. 40, pp. 1441-1445 (1999).
Bai and Esser, "The Effect of Edge Artifacts on Quantification of Positron Emission Tomography," 2010 IEEE Nuclear Science Symposium Conference Record, pp. 2263-2266 (2010).
Boksa, "A way forward for research on biomarkers for psychiatric disorders," J. Psychiatry Neurosci., 38(2), pp. 75-77 (2013).
Charnay and Léger, "Brain serotonergic circuitries," Dialogues Clin. Neurosci., 12(4), pp. 471-487 (2010).
Chinn et al., "Accurately Positioning and Incorporating Tissue-Scattered Photons into PET Image Reconstruction," 2006 IEEE Nuclear Science Symposium Conference Record, pp. 1746-1751 (2006).
Choi and Wette, "Maximum Likelihood Estimation of the Parameters of the Gamma Distribution and Their Bias," Technometrics, 11(4), pp. 683-690 (1969).
Defrise et al., "Image Reconstruction Algorithms in PET," Positron Emission Tomography, pp. 63-91 (2005).
Gaitanis et al., "Studying the properties of the updating coefficients in the OSEM algorithm for iterative image reconstruction in PET," Computer Methods and Programs in Biomedicine, 99, pp. 219-229 (2010).
Ginovart et al., "Positron Emission Tomography Quantification of [$^{11}$C]-DASB Binding to the Human Serotonin Transporter: Modeling Strategies," Journal of Cerebral Blood Flow and Metabolism, 21, pp. 1342-1353 (2001).
Ichise et al., "Linearized Reference Tissue Parametric Imaging Methods: Application to [$^{11}$C]DASB Positron Emission Tomography Studies of the Serotonin Transporter in Human Brain," J. Cereb. Blood Flow Metab., 23, pp. 1096-1112 (2003).
Insel, "Disruptive insights in psychiatry: transforming a clinical discipline," J. Clin. Invest., 119(4), pp. 700-705 (2009).
Israel-Jost, "FA-SART: A Frequency-Adaptive Algorithm in Pinhole SPECT Tomography," SIAM Journal on Scientific Computing, 30(2), pp. 819-836 (2008).
Kim et al., "Pet Imaging of Serotonin Transporters with [$^{11}$C]DASB: Test-Retest Reproducibility Using a Multilinear Reference Tissue Parametric Imaging Method," J. Nucl. Med., 47(2), pp. 208-214 (2006).
Kotasidis et al., "Advanced kinetic modelling strategies: towards adoption in clinical PET imaging," Clin. Trans. Imaging, 2, pp. 219-237 (2014).
Merikangas et al., "Lifetime and 12-month Prevalence of Bipolar Spectrum Disorder in the National Comorbidity Survey Replication," Arch. Gen. Psychiatry, 64, pp. 543-552, 1039 (2007).
Mourik et al., "In vivo validation of reconstruction-based resolution recovery for human brain studies," Journal of Cerebral Blood Flow & Metabolism, 30(2), pp. 381-389 (2010).
Orero et al., "Promising results on PSF correction applied in the reconstruction process of a small animal PET image," 2011 IEEE Nuclear Science Symposium Conference Record, pp. 2870-2873 (2011).
Parsey et al., "Higher Serotonin 1A Binding in a Second Major Depression Cohort: Modeling and Reference Region Considerations," Author manuscript, published in final edited form as: Biological Psychiatry, 68(2), pp. 170-178 (2010), 21 pages.
Rapisarda et al., "Evaluation of a New Regularization Prior for 3-D PET Reconstruction Including PSF Modeling," IEEE Transactions on Nuclear Science, 59(1), pp. 88-101 (2012).
Rapisarda et al., "Image-based point spread function implementation in a fully 3D OSEM reconstruction algorithm for PET," Physics in Medicine and Biology, 55, p. 4131-4151 (2010).
Reader and Zaidi, "Advances in PET Image Reconstruction," PET Clin., 2, pp. 173-190 (2007).
Reader et al., "EM Algorithm System Modeling by Image-Space Techniques for PET Reconstruction," IEEE Transactions on Nuclear Science, 50(5), pp. 1392-1397 (2003).
Rodriguez, "Total Variation Regularization Algorithms for Images Corrupted with Different Noise Models: A Review," Journal of Electrical and Computer Engineering, 2013, article ID 217021, 18 pages (2013).

(56) References Cited

OTHER PUBLICATIONS

Rudin et al., "Nonlinear total variation based noise removal algorithms," Physica D, 60, pp. 259-268 (1992).

Schmidt and Turkheimer, "Kinetic modeling in positron emission tomography," The Quarterly Journal of Nuclear Medicine, 46(1), pp. 70-85 (2002).

Shepp and Vardi, "Maximum Likelihood Reconstruction for Emission Tomography," IEEE Transactions on Medical Imaging, MI-1(2), pp. 113-122 (1982).

Singh and Rose, "Biomarkers in psychiatry," Nature, 460, pp. 202-207 (2009).

Snyder et al., "Noise and Edge Artifacts in Maximum-Likelihood Reconstructions for Emission Tomography," IEEE Trans. Med. Imaging, MI-6(3), pp. 228-238 (1987).

Son et al., "Individually Differentiated Serotonergic Raphe Nuclei Measured with Brain PET/MR Imaging" Radiology, 272(2), pp. 541-548 (2014).

Song et al., "Adult Raphe-Specific Deletion of Lmx1b Leads to Central Serotonin Deficiency," PLoS One, 6(1), e15998, pp. 1-9 (2011).

Stute and Comtat, "Practical considerations for image-based PSF and blobs reconstruction in PET," Physics in Medicine & Biology, 58, pp. 3849-3870 (2013).

Sureau et al., "Impact of Image-Space Resolution Modeling for Studies with the High-Resolution Research Tomograph," Journal of Nuclear Medicine, 49(6), pp. 1000-1008 (2008).

Thielemans et al., "Impact of PSF modelling on the convergence rate and edge behavior of EM images in PET," 2010 IEEE Nuclear Science Symposium Conference Record, pp. 3267-3272 (2010).

Tong et al., "Properties and Mitigation of Edge Artifacts in PSF-Based PET Reconstruction," IEEE Transactions on Nuclear Science, 58(5), pp. 2264-2275 (2011).

Watson, "Estimating effective model kernel widths for PSF reconstruction in PET," 2011 IEEE Nuclear Science Symposium Conference Record, pp. 2368-2374 (2011).

Yan, "EM-type Algorithms for Image Reconstruction with Background Emission and Poisson Noise," ISVC 2011 Proceedings of the 7th International Conference on Advances in Visual Computing, Part I, pp. 33-42 (2011).

Mikhno et al., "Locally weighted total variation denoising for PSF modeling artifact suppression in PET reconstruction," 2014 IEEE 11th International Symposium on Biomedical Imaging (ISBI), pp. 971-974 (2014).

Lee et al., "Pragmatic Fully 3D Image Reconstruction for the MiCES Mouse Imaging PET Scanner," Physics in Medicine and Biology, 49, pp. 4563-4578 (2004).

Rahmim et al., "Resolution modeling in PET imaging: Theory, practice, benefits, and pitfalls," Med. Phys., 40(6),15 pages (2013).

\* cited by examiner (a) without noise (b) with Poisson noise (a) without noise (b) with Poisson noise (a) True  (b) MLEM i400  (c) PSF-MLEM i400 (s20)  (d) gPSF-MLEM i400 (s20)

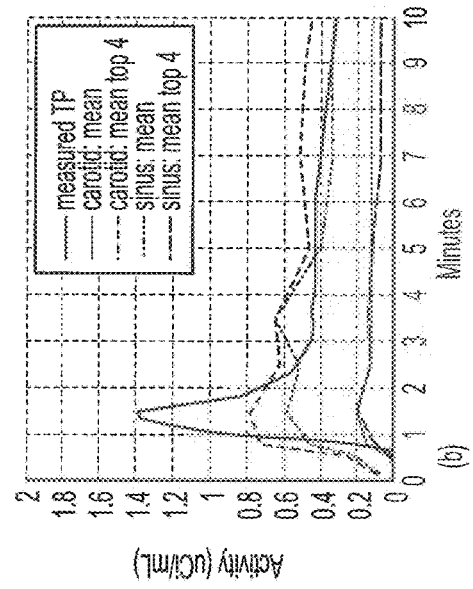
FIG. 42
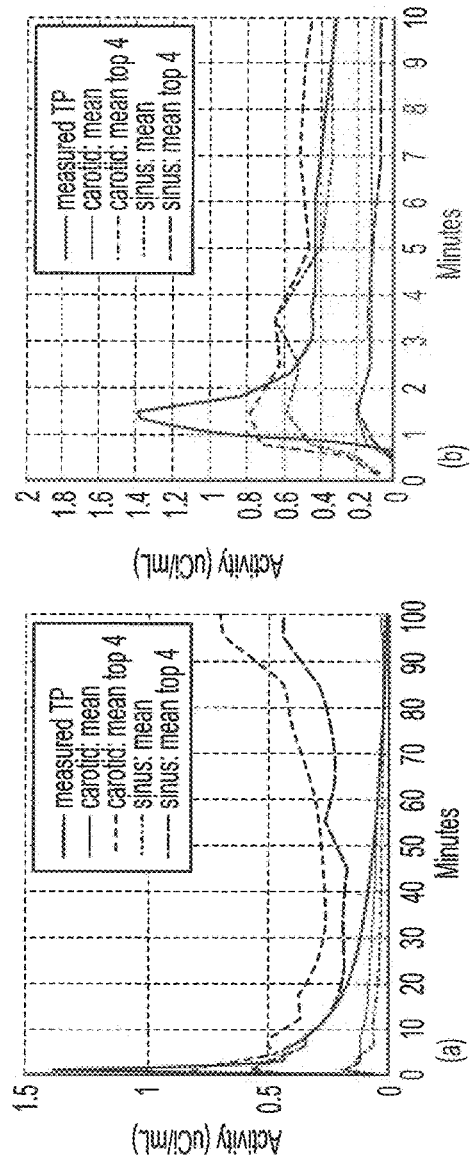
FIG. 41
FIG. 43A
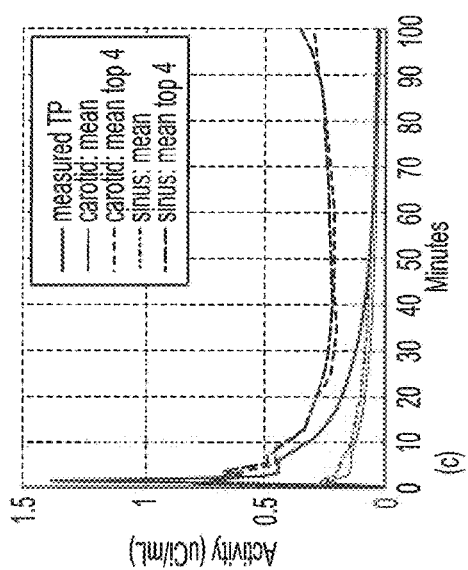
FIG. 43B

FIG. 51
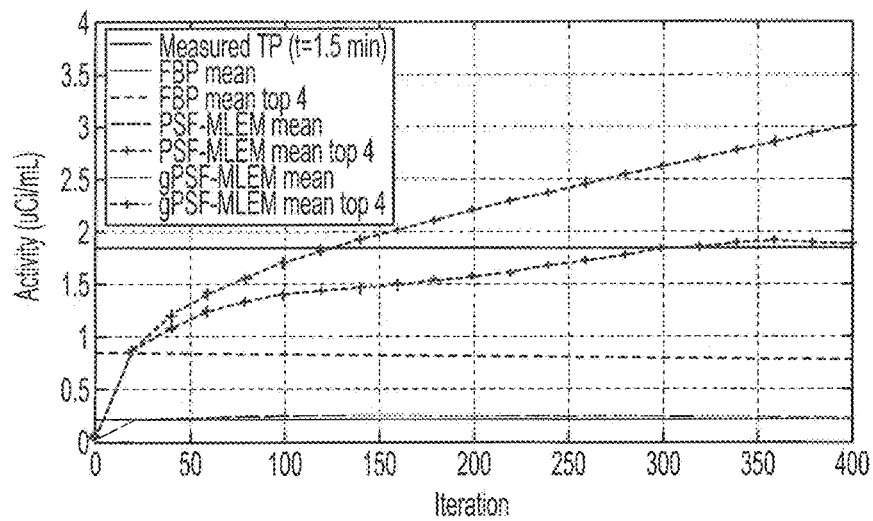
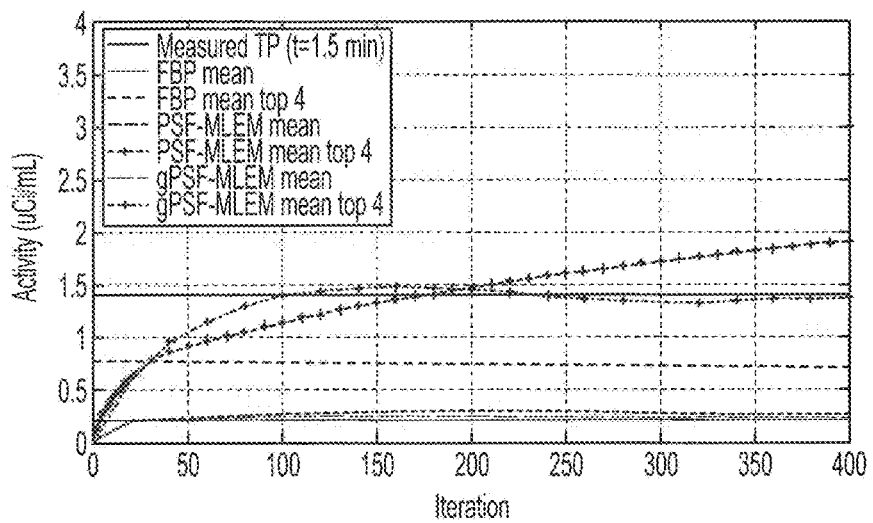
FIG. 52

FIG. 57A
FIG. 57B
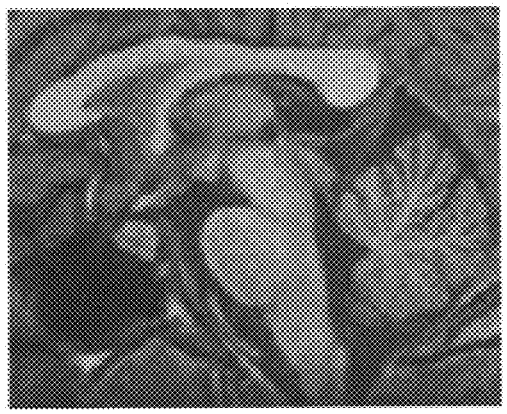
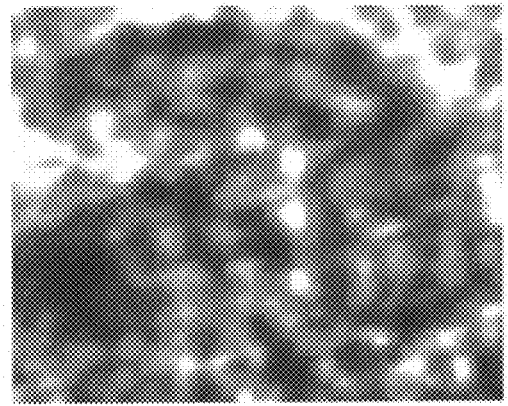
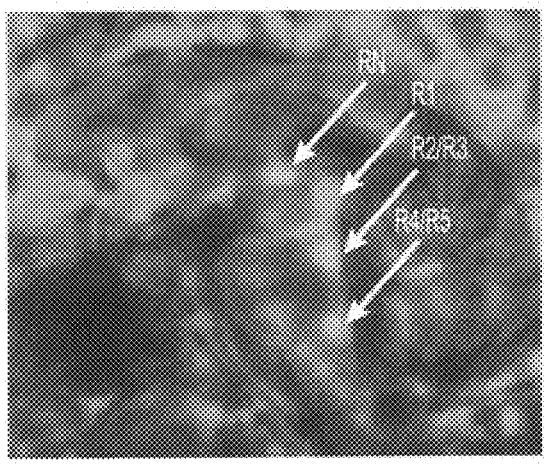
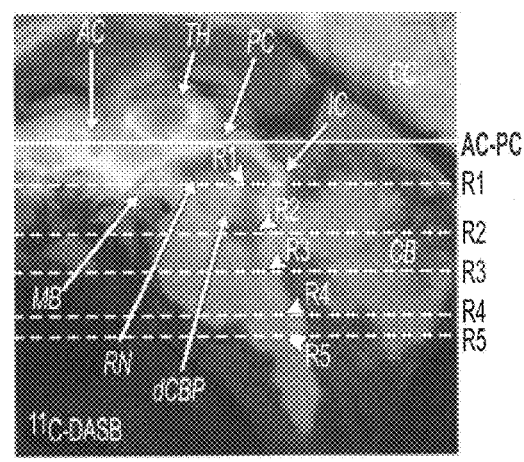
FIG. 58
FIG. 59

- Maximum likelihood expectation maximization (MLEM)

$$\underset{\text{next image estimate}}{\text{}} \underset{\substack{\nearrow \\ \text{iteration}}}{\lambda_b^{k+1}} = \frac{\boxed{\lambda_b^k}}{BP_b 1} BP_b \frac{y_d}{P_d \boxed{\lambda_b^k}} = \boxed{\lambda_b^k} u_b^k \underset{\text{multiplicative update}}{\nwarrow}$$

with labels: current image estimate, measured projection data, voxel, back projector, forward projector

- Projectors that incorporate PSF kernel (PSF-MLEM)

$$P_d(\bullet)_b = \Sigma \, [(\bullet) * PSF]_b \, p_{bd} \qquad BP_b(\bullet)_d = PSF^T * \Sigma \, [(\bullet)]_d \, p_{bd}$$

modified forward projector  modified back projector

FIG. 60

(1) standard TV regularization $\quad \hat{\lambda}^k = \min_\theta \frac{1}{2}\|\lambda^k - \theta\|^2 + \beta|\nabla\theta|$ (2) locally weighted amount of regularization $\quad \tilde{\lambda}_b^k = \lambda_b^k + \boxed{w_b}\Delta\hat{\lambda}_b^k \quad \hat{\tilde{\lambda}}_b^k = \lambda_b^k + (\hat{\lambda}_b^k - \hat{\tilde{\lambda}}_b^k)$ (3) incorporate regularized image in MLEM $\quad \lambda_b^{k+1} = \frac{\tilde{\lambda}_b^k}{BP_b 1} BP_b \frac{y_d}{P_d \tilde{\lambda}_b^k} = \lambda_b^k u_b^k$ (4) repeat over N iterations

FIG. 63

$$C_b = \min_k \left| 1 - \left( w_b^k \right) \right| \leq \epsilon$$

iterations to convergence — $C_b$
multiplicative update — $w_b^k$
convergence threshold — $\epsilon$ $$w_b = 1 - \frac{C_b - \min(c)}{\max(c - \min(c))}$$

voxel weight — $w_b$

FIG. 64

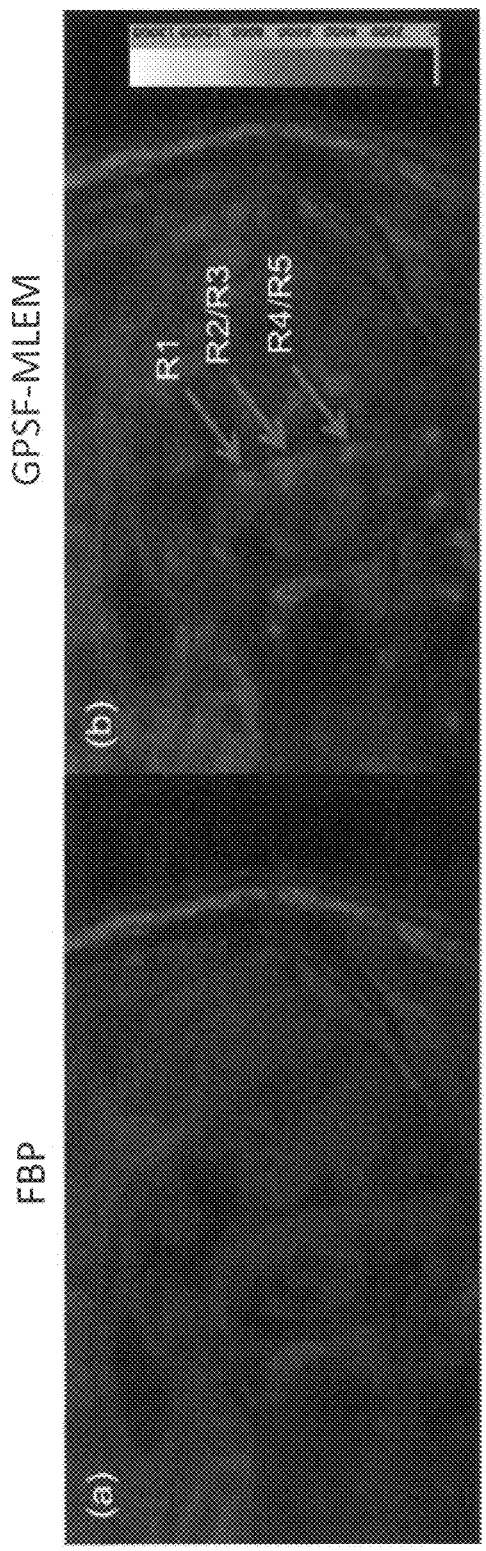
Figs. 87A-B
R1 – dorsal raphe nucleus, R2 = median raphe nucleus, R3 – nucleus raphe magnus, R4 = nucleus obscuris, R5 – nucleus pallidus.

| pAIF40 Top-Model | |
|---|---|
| VARIABLE | FREQUENCY(%) |
| MeanGlu*BrainTACsum | 41.2 |
| Triglycerides*BrainTACsum | 38.2 |
| Dose*RDW | 8.1 |
| Dose*eRMR | 3.7 |
| pAUC Top-Model | |
| VARIABLE | FREQUENCY(%) |
| ColdGlu2*BrainTACsum | 37.5 |
| RDW*BSA | 24.3 |
| RDW*eRMR | 9.6 |
| MeanGlu*BrainTACsum | 6.6 |

Figure 90

| Scan Type | Counts | β | ε |
|---|---|---|---|
| Simulated | ~220 million | 0.001 | $8\times10^{-4}$ |
| ACR Phantom | ~120 million | 0.001 | $9\times10^{-3}$ |
| Clinical | ~10-30 million | 0.0005 | 0.02 |

FIG. 92

| Male (N= 38), Female (N=57) | | | |
|---|---|---|---|
| Variable | Mean (STD) | min | max |
| Age (y) | 38 (12) | 19 | 64 |
| Weight (lb) | 165 (41) | 102 | 279 |
| Height (in) | 66 (3) | 60 | 73 |

FIG. 93

| Variable | Mean (STD) | min | max |
|---|---|---|---|
| pre-scan $\Delta t$ (h) | 2.3 (1.2) | 9 | 0.5 |
| post-scan $\Delta t$ (h) | 4.9 (1.4) | 1.9 | 7.8 |
| BPSysPre (mmHg) | 122 (17) | 90 | 189 |
| BPDiasPre (mmHg) | 75 (9) | 53 | 107 |
| HRpre (beats/min) | 72 (11) | 45 | 100 |
| BPSysPost | 122 (17) | 93 | 178 |
| BPDiasPost | 76 (12) | 54 | 128 |
| HRpost | 73 (12) | 48 | 105 |

FIG. 94

| Initial Predictors (92) | | |
|---|---|---|
| Chemistry (21) | Hematology (14) | LBMI |
| A/G Ratio | WBC | eTBV |
| Albumin | RBC | eTPV |
| Alk Phos | Hemoglobin | eGFR |
| ALT(SGPT) | Hematocrit | $eGFR_{BSA}$ |
| AST(SGOT) | MCV | eGFR5 |
| BUN | MCH | $eGFR5_{BSA}$ |
| Calcium | MCHC | RMR |
| Chloride | RDW | Osm gap |
| Cholesterol | Platelets | rCalcium |
| $CO_2$ | Neut Absolute | Blood viscosity |
| Creatinine | Lymph Absolute | Anion gap |
| Globulin | Mono Absolute | BUN:Crt ratio |
| Glucose | Eosin Absolute | Plas. Osm. |
| LDH | Baso Absolute | |
| Phosphorous | Urinalysis (3) | Vitals (24) |
| Potasium | Specific gravity | Heart Rate |
| Sodium | Urobilinogen | Blood Pressure |
| T. Bilirubin | pH | MAP |
| Total Protein | | PP |
| Triglyceride | Demographics(4) | CO |
| Uric Acid | Weight | x2 (pre, post) |
| | Height | x2 (closest, avg) |
| Thyroid (5) | Age | |
| T3 Uptake | Sex | PET (4) |
| TSH | | Cerebellar ROI |
| Thyroxine Free | Derived (16) | Injected Dose |
| Thyroxine Total | BMI | Injected Mass |
| Triodothyroninine | BSA | Specific Acitivity |
| | | Total Plasma |

FIG. 95

| Screened Predictors (56) | |
|---|---|
| Individual (10) | Dose/var |
| Cerebellar ROI (CER) | BPDias x4 |
| Total Plasma (TotPlas) | MAP x4 |
| Injected Dose (ID) | CO x3 (pre,post,closest) |
| HR x3 (pre,post,avg) | PP x3 |
| Weight | $CO_2$ |
| BSA | |
| eTBV | Interaction (15) |
| eTPV | CER*HR x2 (post,avg) |
| | Height*COpost |
| Dose/var (31) | HRpost*TotPlas |
| Weight | HRpost*Weight |
| Height | Eosin*BPDias x2 (pre,closest) |
| BMI | MAPclosest*CER |
| BSA | pH*InjectedMass |
| LBMI | pH*SpecificActivity |
| eTBV | RDW*SpecificActivity |
| eTPV | SpecificActivity$^2$ |
| eRMR | ThyroxineFree*TotPlas |
| HR x4 (pre,post,closest,avg) | eTPV*PPpost |
| BPSys x4 | Chloride*TotPlas |

FIG. 96

|  | Average $R^2$ |
|---|---|
| Models with Total Plasma variable | |
| CER + HRavg*CER + HRpost*TotPlas | 0.718 |
| CER + HRavg*CER + HRpost*TotPlas + Eosin*BPDiasPre | 0.737 |
| CER + HRavg*CER + HRpost*TotPlas + ID/BSA + ID/eRMR | 0.796 |
| CER + ID/eRMR + ID/HRpre + TotPlas + Eosin*DBPclosest + pH*SpecificActivity | 0.823 |
| | |
| Models without Total Plasma variable | |
| CER + ID/HRpre + Eosin*DBPclosest | 0.703 |
| CER + ID/HRpre + Eosin*DBPclosest + ID/COpost | 0.714 |
| CER + ID/HRpre + Eosin*DBPclosest + ID/Weight + ID/DBPpost | 0.781 |
| CER + ID/HRclosest + Eosin*DBPclosest + ID/eTBV + ID/eRMR + ID/SBPpost | 0.814 |

FIG. 97

| Quantity | Mean (STD) | min | max |
|---|---|---|---|
| Age (years) | 38 (12) | 19 | 64 |
| Weight (lb) | 165 (41) | 102 | 279 |
| Height (in) | 66 (3) | 60 | 73 |
| pre-scan $\Delta t$ (h) | 2.3 (1.2) | 9 | 0.5 |
| post-scan $\Delta t$ (h) | 4.9 (1.4) | 1.9 | 7.8 |
| BPs_pre (mmHg) | 122 (17) | 90 | 189 |
| BPs_post | 122 (17) | 93 | 178 |
| BPd_pre (mmHg) | 75 (9) | 53 | 107 |
| BPd_post | 76 (12) | 54 | 128 |
| HR_pre (beats/min) | 72 (11) | 45 | 100 |
| HR_post | 73 (12) | 48 | 105 |

Heart rate (HR), systolic blood pressure (BPs) and diastolic blood pressure (BPd) were collected pre- and post- PET scan, represented here by the pre-scan and post-scan interval $\Delta t$.

FIG. 98

| Descriptive statistics for demographics and vitals measures | | | |
|---|---|---|---|
| Quantity | Mean (STD) | min | max |
| Age (years) | 38 (12) | 19 | 64 |
| Weight (lb) | 165 (41) | 102 | 279 |
| Height (in) | 66 (3) | 60 | 73 |
| pre-scan $\Delta t$ (h) | 2.3 (1.2) | 9 | 0.5 |
| post-scan $\Delta t$ (h) | 4.9 (1.4) | 1.9 | 7.8 |
| BPs_pre (mmHg) | 122 (17) | 90 | 189 |
| BPs_post | 122 (17) | 93 | 178 |

| Initial Predictors (94) | | | |
|---|---|---|---|
| Chemistry (21) | Thyroid (5) | Urinalysis (3) | Demographics (4) |
| A/G Ratio | T3 Uptake | Specific Grav Urine | Weight |
| Albumin | TSH | Urobilinogen | Height |
| Alk Phos | Thyroxine Free | pH | Age |
| ALT(SGPT) | Thyroxine Total | | Sex |
| AST(SGOT) | Triiodothyronine | Derived (16) | |
| BUN | | BMI | Vitals (24) |
| Calcium | Hematology (14) | BSA | HR |
| Chloride | WBC | LBMI | BPs, BPd |
| Cholesterol | RBC | eTBV | MAP |
| CO2 | Hemoglobin | eTPV | PP |
| Creatinine | Hematocrit | eGFR | eCO |
| Globulin | MCV | eGFRBSA | x2 (pre, post) |
| Glucose | MCH | eGFR5 | x2 (closest, avg) |
| LDH | MCHC | eGFR5BSA | |
| Phosphorus | RDW | eRMR | PET (7) |
| Potassium | Platelets | Osmolarity Gap | CERsum |
| Sodium | Neut Absolute | rCalcium | TPsum |
| T. Bilirubin | Lymph Absolute | Blood viscosity | ID |
| Total Protein | Mono Absolute | Anion gap | eID50, λcal |
| Triglyceride | Eosin Absolute | BUN:Crt ratio | Injected Mass |
| Uric Acid | Baso Absolute | Plasma osmolarity | Specific Activity |

Data include the following measures: 21 blood chemistry, 5 thyroid panel, 14 hematology, 3 urinalysis, 4 demographic, 24 vitals, and 7 PET measures. An additional 16 derived variables (e.g. BMI, eTBV) were calculated from a combination of blood chemistry, hematology and demographic variables.

FIG. 100

| AIF50 Screened Predictors (56) | | | AUC Screened Predictors (52) | | |
|---|---|---|---|---|---|
| Individual | ID/var | | Individual | ID/var | Interaction |
| CERsum | MAP x4 | | CERsum | eGFR5BSA | eTBV*Potassium |
| TPsum | eCO x3 | | TPsum | eRMR | eRMR*Potassium |
| ID | PP x3 | | ID | osmGAP | eRMR*TotalProtein |
| eTBV | CO2 | | eID50 | rCalcium | eGFR5BSA*PP_post |
| eTPV | | | eTBV | BloodViscosity | Height*Urobilinogen |
| BSA | Interaction | | eTPV | PlasmaOsmolality | Height*Globulin |
| Weight | CERsum*MAP_closest | | BSA | HR x3 (post, closest, avg) | Height*TotalProtein |
| HR x3 (pre,post,avg) | CERsum*HR (post,avg) | | eRMR | MAP_avg | Weight*PP_post |
| | TPsum*Chloride | | Weight | | LBMI*TotalProtein |
| ID/var | TPsum*ThyroxineFree | | Height | Interaction | BSA*PP_post |
| Weight | HR_post*TPsum | | | CERsum*eID50 | BPd_pre*EosinAbsolute |
| Height | HR_post*Weight | | | CERsum*Acal | BPd_post*EosinAbsolute |
| BMI | BPd_pre*Eosin | | ID/var | CERsum*eCOpost | |
| BSA | BPd_closest*Eosin | | Weight | TPsum*HR (pre, avg, closest) | |
| LBMI | eTPV*PP_post | | Height | TPsum*ThyroxineFree | |
| eTBV | Height*eCO_post | | BMI | TPsum*osmGAP | |
| eTPV | pH*InjectedMass | | BSA | TPsum*PlasmaOsmolality | |
| HR x4 (pre,post,closest,avg) | pH*SpecificActivity | | LBMI | TPsum*Sodium | |
| BPs x4 | RDW*SpecificActivity | | eTBV | eTPV*PP_post | |
| BPd x4 | SpecificActivity^2 | | eTPV | eTBV*PPpost | |
| | | | eGFRBSA | | |

Predictors listed underneath ID/var are normalized ID values, while * is an interaction between two predictor (multiplication of values).

FIG. 101

| pAIF50.top9model | | pAUC.top9model | |
|---|---|---|---|
| Variable | Frequency.(%) | Variable | Frequency.(%) |
| CERsum | 34.7 | TPsum | 26.8 |
| TPsum | 22.9 | CERsum | 24.7 |
| HR_post*TPsum | 13.9 | BSA*PP_post | 18.4 |
| BPd_pre*Eosin | 13.7 | eGFR5BSA*PP_post | 17.9 |
| HR_avg*CERsum | 12.9 | eTBV*Potassium | 14.5 |
| ID/HR_pre | 4.2 | eID50 | 12.6 |
| BPd_closest*Eosin | 3.4 | CERsum*eID50 | 12.4 |
| TPsum*Chloride | 2.4 | eRMR*Potassium | 5.8 |
| ID/HR_closest | 1.6 | Height | 2.1 |
| Weight*HR_post | 1.3 | LBMI*TotalProtein | 2.1 |
| ID/eRMR | 1.1 | TPsum*PlasmaOsmolality | 1.6 |
| HR_post*CERsum | 0.8 | TPsum*HR_avg | 1.3 |
| ID/HR_avg | 0.5 | TPsum*Sodium | 1.3 |
| ID/BPd_post | 0.3 | Height*Urobilinogen | 1.3 |
| ID/HR_post | 0.3 | TPsum*osmGAP | 1.3 |

FIG. 102

REGULARIZATION OF IMAGES

This application is a continuation-in-part of International Application No. PCT/US2015/018817 filed Mar. 4, 2015, which claims the benefit of and priority to U.S. provisional patent application Ser. No. 61/947,739, filed Mar. 4, 2014, and U.S. provisional patent application Ser. No. 61/952,739, filed Mar. 13, 2014, the disclosures of which are hereby incorporated by reference in their entireties for all purposes.

This invention was made with government support under grant MH095338 awarded by the National Institutes of Health. The Government has certain rights in this invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All publications, patent applications, patents, and other references mentioned herein are incorporated by reference in their entirety. The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference. In the case of inconsistencies, the present disclosure will prevail.

BACKGROUND

Quantification of nuclear imaging and tomographic brain images acquired with the use of injected contrast agents, or tracers, require measurement of tracer blood concentration over the course of the scan. The blood concentration curve is used to account for metabolism, clearance and availability of the tracer to diffuse in the brain. Typically sampling is done via an arterial catheter, a procedure which is costly, risky to patients, time consuming, requires specialist, as well as expensive and error prone blood chemistry analysis. While some techniques exist that reduce number of required blood samples from 20 down to 1-3 for some tracers. The requirement of blood sampling limits clinical utility of many research tracers—it is not feasible to conduct tracer blood analysis in a clinic. Also, many research centers cannot conduct fully quantitative studies using many of the available tracers due to the added expense of blood sampling and analysis. There is a need for methods that are totally non-invasive (i.e. zero blood samples). This invention addresses this need. Iterative reconstruction with point spread function (PSF) modeling improves contrast recovery in positron emission tomography (PET) images, but also introduces ringing artifacts and over enhancement that is contrast and object size dependent. There is a need for mitigating these artifacts. The methods described herein address this need.

SUMMARY OF THE INVENTION

Quantification of nuclear imaging and tomographic brain images acquired with the use of injected contrast agents, or tracers, require measurement of tracer blood concentration over the course of the scan. In certain aspects, the invention relates to methods that are totally non-invasive (i.e. zero blood samples) imaging.

In certain aspects, the invention relates to iterative regularized reconstruction methods that incorporate locally-weighted total variation denoising designed to suppress artifacts induced by PSF modeling. The reconstruction methods described herein can be evaluated on a simulated cylindrical phantom. As described herein, the methods of the present disclosure are useful for suppressing ringing artifacts while contrast recovery is maintained. In certain embodiments, the weighting scheme can be extended to noisy measures introducing a noise-independent weighting scheme.

In certain aspects, the invention relates to a computer implemented method for reconstructing positron emission tomography (PET) image data, the method comprising: (a) administering a radioligand to a subject, (b) generating a PET scan acquisition comprising a plurality voxels counts corresponding to an anatomical structure of the subject, wherein the PET scan acquisition comprises: (i) a transmission sinogram comprising a plurality voxels counts corresponding to the anatomical structure of the subject; (ii) an emission sinogram comprising detected coincidence events emitted from the anatomical structure of the subject; and (iii) a normalization scan; (c) calculating a weight for each voxel of the PET scan acquisition using iterative maximum likelihood expectation maximization (MLEM) reconstruction to generate a 3D weight map, and (d) performing TV-gPSF-MLEM on the 3D weight map to generate a reconstructed image. In certain embodiments, the weight for each voxel is determined based on the point-wise convergence rate. In certain embodiments, the weight for each voxel is calculated at 3×3×3 window of each voxel. In certain embodiments, MLEM reconstruction is performed until convergence. In certain embodiments, MLEM reconstruction is performed for at least 200 iterations. In certain embodiments, TV-gPSF-MLEM is performed until convergence. In certain embodiments, TV-gPSF-MLEM is performed for at least 500 iterations. In certain embodiments, the PET scan acquisition comprises list mode data. In certain embodiments, the PET scan acquisition comprises randoms data. In certain embodiments, the PET scan acquisition comprises an attenuation map. In certain embodiments, the transmission sinogram is an attenuation coefficient map. In certain embodiments, the radioligand is a [11C]-WAY radioligand.

In certain aspects, the invention relates to a computer implemented method quantifying radioligand binding in a subject without collecting arterial blood from the subject, the method comprising: (a) administering a radioligand to the subject; (b) performing a PET scan of an anatomic structure of the subject; and (c) generating a predicted single time-point anchor for the subject. In certain embodiments, the radioligand is a [11C]-DASB radioligand. In certain embodiments, the predicted single time-point anchor is generated from PET data for the subject and a health record of the patient. In certain embodiments, the health record comprises demographic information for the subject. In certain embodiments, the health record comprises blood workup information for the subject. In certain embodiments, the health record comprises urinalysis information for the subject. In certain embodiments, the health record comprises heart rate and blood pressure information collected before and after the administering of step (a). In certain embodiments, the PET data comprises injected dose, injected mass, tracer specific activity, and the metabolite-corrected arterial input function information for the subject. In certain embodiments, the PET data comprises gray matter cerebellar activity information for the subject.

In certain embodiments, the anatomical structure is a brain structure. In certain embodiments, the subject is a human. In certain embodiments, the radioligand is selected from the group consisting of [11C]-DTBZ, 11CFE-CIT, [18F]-dopa, [11C]-dopa, [11C]PIB, [18F]-CFT, [11C]-RTI- 32, [18F]-FP-CIT, [11C]-methylphenidate, [123I]-β-CIT, [123I]-FP-CIT, [123I]-altropane, [99mTc]-TRODAT-1, [11C]-dihydrotetrabenazine, [99mTc]-MHMPAO, [99mTc]-ethylcystein dimer, [99mTc]-DTPA, [99mTc]-gluceheptonate, [99mTc]-sestamibi, [99mTc]-tetrofosmin, [99mTc]-labelled sulphur colloid, H215O, [18F]-fluorodeoxyglucose, [13N]-ammonium, [15O]-butanol, 113Xe, 15O2, [11C]-CFT, [123I]-IPT, [11C]-SCH23390, [11C]-raclopride, [11C]-FLB456, [11C]-methylspiperone, [18F]-spiperone, [18F]-fluroethylspiperone, [76Br]-bromospiperone, [123I]-eppidepride, [123I]-iodobenzamide, [11C]-BATA, [18F]-2-fluorothoxydazoxan, [11C]-methyltryptophan, [11C]-MDL100907, [18F]-altanserin, [18F]-serpeptone, [11C]-MP4A, [11C]-physostigmine, [18F]-fluoroethozybenzoessamicol, [11C]-vesamicol, [123I]-benzovesamicol, [11C]-tropanylbenylate, [11C]-NMPB, [18F]-FP-TZTP, [123I]-QNB, [11C]-MPA, [11C]-A-85380, [18F]-A-85380, [123I]-A-85380, [11C]-dothiepin, [11C]-carfentenil, [18F]-cyclofoxy, [11C]-diprenorphine, [11C]-flumazenil, [11C]-RO15-4513, [11C]-PK11195, [18F]-PK11195, [123I]-PK11195, [18F]-SPARQ, [11C]-GR205171, [11C]-SCH 442416, [11C]-CNS 5161, [18F]-FDDNP, [11C]-SB13, [123I]-IMPY, and [11C]-carfentenil.

BRIEF DESCRIPTION OF THE FIGURES

The patent or application file contains at least one drawing executed in color. Copies of this patent or patent application publication with color drawing(s) will be provided by the United States Patent and Trademark Office upon request and payment of the necessary fee.

FIGS. 41, 42, 43A-43B show the signal calculated from on the FBP reconstructed images for subject 1 (FIGS. 41-42) and subject 2 (FIGS. 43A-B). Carotid signal was calculated as the average within the entire ROI (thin solid line) and the average of 4 highest voxels within the ROI (short dashed line). Sagittal sinus signal was calculated as the average within the entire ROI (dot-dash line) and the average of 4 highest voxels within the ROI (long dashed line). The reference total plasma (TP) curve. Signal from blood vessels from FBP images underestimates the peak of the TP curve.

FIG. 51-52 shows recovery of TP from the signal within carotid arteries. Results are shown for average within ROI, average of the top 4 values within the ROI, for FBP (thin solid line; short dashed line), PSF-MLEM (long dashed line; upper dashed line with crosshair), and gPSF-MLEM (thin dashed line; lower dashed line with crosshair). The measured peak TP values are displayed for reference (thick solid line).

FIGS. 57A, 57B, 58, and 59 show PET/MR fusion images of raphe nuclei in the midline brainstem obtained with reconstruction using gPSF-MLEM on a single 5 minute PET frame acquired 10-15 minutes post radioligand injection. A representative midline sagittal section of the brainstem regions are shown on (FIG. 57A) 3T MRI anatomic image, (FIG. 57B) PET image reconstructed with 400 iterations of gPSF-MLEM, (FIG. 58) PET/MR fusion image. For reference results from a previous study with [11C]-DASB high resolution HRRT PET and 7T MRI are shown with corresponding labels [88]. Image a was used for section localization. The reference MR image (FIG. 59) indicates the anatomic locations of several landmark structures; these anatomic locations corroborate the locations of molecular activities in the corresponding PET/MR fusion images shown in FIGS. 58 and 59. The solid white line is AC-PC. AC=anterior commissure, CB=cerebellum, CC=cerebral cortex, dCBP=decussation of the superior cerebellar peduncle, IC=inferior colliculus, MB=mammillary body, PC=posterior commissure, R2=raphe nucleus 2, R3=raphe nucleus 3, R4=raphe nucleus 4, RN=red nucleus, TH=thalamus.

FIG. 60 shows the MLEM and PSF-MLEM algorithm.

FIG. 63 shows the insertion of locally-weighted total variation within the PSF-MLEM algorithm.

FIG. 64 shows the use of the MLEM convergence rate to create a weight for each voxel.

FIGS. 87A-87B show reconstructed images of a short 5-minute PET acquisition with FBP reconstruction (FIG. 87A) and gPSF-MLEM reconstruction (FIG. 87B).

FIG. 90 shows the medical health record best combination of variables most frequently selected to predict the area under the curve (AUC) and 40-minute plasma value (AIF40) for FDG. "MeanGlu" refers to the mean of two or more cold blood glucose measurements. "BrainTACsum" refers to the sum of a portion of the whole brain time activity curve. "Dose" refers to the PET Injected Dose. "RDW" refers to the red cell distribution width. "eRMR" refers to the estimated resting metabolic rate. "ColdGlu2" refers to the second measurement of the cold blood glucose. "BSA" refers to body surface area.

FIG. 92 shows settings for experimental setups.

FIG. 93 shows descriptive statistics for the subjects.

FIG. 94 shows summary statistics for vitals.

FIG. 95 shows that the combination of EHR, PET, demographics, vitals and derived variables amounted to 92 initial predictors.

FIG. 96 shows predictors used for model development.

FIG. 97 shows top models in terms of average $R^2$ with and without total plasma.

FIG. 98 shows descriptive statistics for demographics and vital measures.

FIG. 99A shows one-tissue compartmental (1TC) model of radioligand transfer from plasma into the target and reference tissues. $C_p$ is the concentration of radioligand in the arterial plasma, $K_1$ is the rate constant for transfer from the arterial plasma to the tissue, where free (F), non-specific (NS) and specific (S) binding are aggregated in the same compartment, $k_2$ is the transfer rate constant from the tissue back to the plasma, and $K_1^{ref}$ and $k_2^{ref}$ are rate constants for a reference tissue that is devoid of specific binding. FIG. 99B shows descriptive statistics for demographics and vital measures.

FIG. 100 shows initial set of 94 variables considered as potential predictors.

FIG. 101 shows predictors for AIF50 and AUC variables. A total of respectively 56 and 52 variables met the inclusion criteria outlined in the text for AIF50 and AUC. Highlighted variables appeared to be important for both AIF50 and AUC.

FIG. 102 shows frequency of predictor variable appearance in the bootstrapped models selected by the top-model prediction approach. Predictors with the 15 highest frequencies are shown for the pAIF50 predictive model and for the pAUC predictive model.

DETAILED DESCRIPTION

Figure 1:
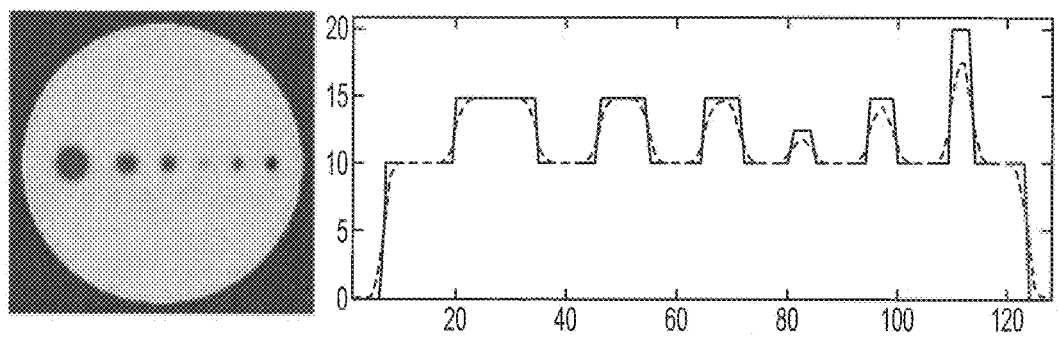
FIG. 1 shows cylindrical phantom blurred with a 4.5 mm FWHM Gaussian kernel (left) and horizontal profile of pixel intensities through the midline (right) on: the actual phantom (dashed line) and the ideal phantom (solid line), shown for reference.

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

In certain aspects, the methods and compositions described herein relate to a non-invasive method for estimating the tracer blood concentration without blood samples. In certain embodiments, tracer blood concentration can be inferred directly imaging and electronic record data.

In certain aspects, the invention relates to a model and schema for predicting individual tracer metabolic and clearance rates as well as other pharmacokinetic parameters, and combine these predictions with an optimization framework that "deconvolves" the dynamic (time-series) brain imaging data. In certain aspects, the methods described herein relate to the finding the imaging signal contains some information about time series shape profile of the tracer blood curve. In certain embodiments, electronic health records data can be used to constrain (or scale) the curve.

Many PET tracers cannot be used clinically because quantification of acquired images requires blood sampling. For example, existing technologies estimate tracer blood concentration curves using PET imaging data and one (1) blood sample. A limitation of these technologies is a hard constraint of the need for at least blood sample. In certain aspects, the methods described herein remove the need for all blood sampling. In certain aspects, predictions for the blood sample and curve shape parameters are added, as well as added constrains within the SIME algorithm.

Certain existing technologies estimate tracer blood concentration curves using PET imaging data and some information about the patient (weight, height, gender, etc.). However, this is done for a tracer that does not metabolize (e.g. FDG). This means the imaging signal in the blood regions in the image is already highly correlated to the tracer blood concentrations. Also, basic patient characteristics (e.g. height, weight) are used to predict the curve shape directly. In certain aspects, the methods described herein do not "predict" the curve shape, and instead predict pharmacokinetic parameters (e.g. AUC, clearance, peak concentration) using electronic health records (100+ variables). In certain aspects, the methods described herein utilize these predictions as constraints in an optimization framework that uses imaging data to estimate tracer blood concentration curve shape.

In certain aspects, the methods described herein can be performed without obtaining a blood sample from a patient. In certain aspects, the methods can be used to individualized prediction and can used in connection with complex tracers that metabolize, have complex body diffusion patterns, and do not have reference regions. In some embodiments, such tracers cannot be quantified by any other means.

In certain aspects, the methods described herein can be used in connection with PET (positron emission tomography), MRI (magnetic resonance imaging), SPECT (single-photon emission computed tomography), CT (computed tomography). In certain aspects, the methods described herein can be used in connection with any imaging technique where the concentration of the tracer agent in the blood is needed.

In certain aspects, the methods described herein can be used as a software package or online platform to research centers. In certain aspects, the methods described herein can be integrated in, or improve clinical scanners. In certain aspects, the methods and composition described herein can be paired with other devices such as the Wrist PET scanner. In certain aspects, the methods and composition described herein can be paired with other devices, which currently cannot measure tracers that are highly metabolized.

In certain aspects, the imaging methods described herein can be used to image a brain. In certain aspects, the imaging methods described herein can be used on any organ, including, but not limited to the prostate. In certain aspects, the methods described herein can be used to image, or quantify tumors or expression from tumors.

In certain aspects, described herein are iterative regularized reconstruction methods that incorporate locally-weighted total variation denoising designed to suppress artifacts induced by PSF modeling. The reconstruction methods described herein can be evaluated on a simulated cylindrical phantom. As described herein, the methods of the present disclosure are useful for suppressing ringing artifacts while contrast recovery is maintained. In certain embodiments, the weighting scheme can be extended to noisy measures introducing a noise-independent weighting scheme.

As described herein, including the Point Spread Function (PSF) in reconstructions can improve resolution but leads to contrast dependent ringing and over-enhancement artifacts. Previous attempts to mitigate these artifacts include the method of Rapisarda. Rapisarda uses a variational prior with local weights based on an energy function calculated at 3×3×3 window of each pixel. At each pixel a decision is made as to what weight is used based on the value of the energy function. In effect the decision is, if there is more potential artifact apply a higher weight, where there is less potential artifact apply a smaller weight. The Rapisarda method removes noise and ringing artifact but also suppresses the intensity in small structures. In contrast, the methods described herein do not use a single binary decision. Instead the local weights are learned from the data by conducting a first-pass iterative reconstruction without PSF. Weights are calculated based on analysis of the evolution of each pixel over many iterations. Faster evolution tends to be related to one type of artifact while slower evolution to another type of artifact. By adjusting the weights according to the "convergence rate" different artifacts can be mitigated at different levels. The biggest advantage lies in performance in very small structures (at or below the resolution limit). Thus, the methods described herein provide a method for mitigating artifacts, denoise and provide better recovery of intensity in small regions. This is particularly relevant for small tumors or small brain structures. In PET, small brain structures could also be Amyloid plaques as detected by PET.

In certain embodiments, the methods described herein can be extended to real phantom and clinical data acquired on scanner. In certain embodiments, the methods described herein can be used for enhancement of structures smaller than the advertised resolution of PET scanner.

In certain embodiments, the methods described herein can be used to improve the inherently low-resolution of PET technology. In certain embodiments, localizing and quantification of objects at or below the resolution of the PET scanner could improve tumor detection, brain imaging diagnosis and treatment monitoring (especially with Alzheimer's disease and atrophy), small nuclei and ganglion structures in the brain, as well as other diseases and conditions. In particular embodiments, the methods described herein can be used to provide tumor detection with PET, quantification of amyloid plaques as detected with PET tracers, and quantification of PET signal from small brain structures.

As used herein, the term "brain image data" refers to a representation of brain structure or activity. Examples include, but are not limited to, brain scanning technologies such as MRI, and PET scanning, and other available methods of measuring and recording brain structure or activity.

As used herein a "neurological disorder" is a disorder comprising neurological and/or psychiatric features. Examples include diseases that affect the brain or the mind, including, but not limited to Alzheimer's disease, Parkinson's disease, Mild Cognitive Impairment, depression, pain, psychosis, epilepsy, dementia, migraine, schizophrenia and other psychotic disorders, bipolar disorder, mood disorders such as major or clinical depression, anxiety disorders such as generalized anxiety disorder, somatoform disorders (Briquet's disorder), factitious disorders such as Munchausen syndrome, dissociative disorders such as dissociative identity disorder, sexual disorders such as dyspareunia and gender identity disorder, eating disorders such as anorexia nervosa, sleep disorders such as insomnia and narcolepsy, impulse control disorders such as kleptomania, adjustment disorders, personality disorders such as narcissistic personality disorder, tardive dyskinesia, tourettes, autism, and others, and those described in: Adams & Victor's Principles Of Neurology by Maurice Victor, Allan H. Ropper, Raymond D. Adams.

In one aspect the determination of critical brain areas and the determination of the determining whether a subject has, or at risk of having a neurological disorder can involve the collection of MRI and PET images from one or more subjects from two groups of subjects (e.g. a group comprising individuals having a neurological disorder and a reference group comprising individuals not having a neurological disorder).

In one aspect the determination of critical brain areas and the determination of the determining whether a subject has, or at risk of having a brain tumor can involve the collection of MRI and PET images from one or more subjects from two groups of subjects (e.g. a group comprising individuals having a brain tumor and a reference group comprising individuals not having a brain tumor).

In one embodiment, the PET scan can be performed using a radioligand. In another embodiment, the PET signal can be from a specific radioligand such as one that binds to molecules found in altered amounts in Alzheimer's Disease. In another embodiment, the PET signal can be from a specific radioligand useful for measuring brain blood flow or metabolism. In one embodiment, a radioligand suitable for use in connection with the methods described herein can be [carbonyl-11C]WAY-100,635. As described herein, the radioligand [carbonyl-C-11]-WAY-100,635 is also referred to as "[11C]-WAY". As described herein, the radioligand [18F]-fluorodeoxyglucose is also referred to as "[18F]-FDG". In another embodiment, the radioligand can be [O-methyl-11C]WAY-100,635. In still a further embodiment, the radioligand is selected from the group consisting of [11C]-DTBZ, [11C]-FE-CIT, [18F]-dopa, [11C]-dopa, [11C]-PIB, [18F]-CFT, [11C]-RTI-32, [18F]-FP-CIT, [11C]-methylphenidate, [123I]-β-CIT, [123I]-FP-CIT, [123I]-altropane, [99mTc]-TRODAT-1, [11C]-dihydrotetrabenazine, [99mTc]-MHMPAO, [99mTc]-ethylcysteine dimer, [99mTc]-DTPA, [99mTc]-glucoheptonate, [99mTc]-sestamibi, [99mTc]-tetrofosmin, [99mTc]-labelled sulphur colloid, H215O, [18F]-fluorodeoxyglucose, [13N]-ammonium, [15O]-butanol, 113Xe, 15O2, [11C]-CFT, [123I]-IPT, [11C]-SCH23390, [11C]-raclopride, [11C]-FLB456, [11C]-methylspiperone, [18F]-spiperone, [18F]-fluroethylspiperone, [76Br]-bromospiperone, [123I]-eppidepride, [123I]-iodobenzamide, [11C]-BATA, [18F]-2-fluorothoxydazoxan, [11C]-methyltryptophan, [11C]-DASB, [11C]-MDL100907, [18F]-altanserin, [18F]-serpeptone, [11C]-MP4A, [11C]-physostigmine, [18F]-fluoroethozybenzoessamicol, [11C]-vesamicol, [123I]-benzovesamicol, [11C]-tropanylbenylate, [11C]-NMPB, [18F]-FP-TZTP, [123I]-QNB, [11C]-MPA, [11C]-A-85380, [18F]-A-85380, [123I]-A-85380, [11C]-dothiepin, [11C]-carfentenil, [18F]-cyclofoxy, [11C]-diprenorphine, [11C]-flumazenil, [11C]-RO15-4513, [11C]-PK11195, [18F]-PK11195, [123I]-PK11195, [18F]-SPARQ, [11C]-GR205171, [11C]-SCH 442416, [11C]-CNS 5161, [18F]-FDDNP, [11C]-SB13, [123I]-IMPY, and [11C]-carfentenil.

In certain aspects, the methods described herein relate to generating and determining brain image data. A variety of brain scanning/imaging technologies are currently available, widely in use and adaptable to the present invention. These include magnetic resonance imaging (MRI), functional magnetic resonance imaging (fMRI), Positron Emission Tomography (PET) scanning/imaging, electroencephalograph (EEG) imaging, magnetoencephalography (MEG) imaging, and Computerized Axial Tomography (CAT) scanning/imaging. Further details on the general topic of imaging can be found in the literature, e.g., in Beaumont and Graham (1983) Introduction to Neuropsychology. New York: The Guilford Press; Changeux (1985) Neuronal Man: The Biology of Mind New York: Oxford University Press; Malcom (1994) Mind Fields: Reflections on the Science of Mind and Brain. Grand Rapids, Mich.: Baker Books; Lister and Weingartner (1991) Perspectives on Cognitive Neuroscience. New York: Oxford University Press; Mattson and Simon (1996) The Pioneers of NMR and Magnetic Resonance in Medicine. Dean Books Company; Lars-Goran and Markowitsch (1999) Cognitive Neuroscience of Memory. Seattle: Hogrefe & Huber; Norman (1981) Perspectives on Cognitive Science. New Jersey: Ablex Publishing Corporation; Rapp (2001) The Handbook of Cognitive Neuropsychology. Ann Arbor, Mich.: Psychology Press; Purves et al. (2001) Neuroscience, Second Edition Sinauer Associates, Inc. Sunderland, Mass.; and, The Molecular Imaging and Contrast Agent Database (published on line, current through the present date: http://www.ncbi.nlm.nih.gov/books/bookres-.fcgi/micad/home.html).

For example, Magnetic Resonance Imaging (MRI) uses magnetic fields and radio waves to produce dimensional images of brain structures. In MRI, a large magnet creates a magnetic field around the head of the patient, through which radio waves are sent. The magnetic field to aligns the nuclear magnetization of hydrogen atoms in water in the body. Radio frequency fields are used to systematically alter the alignment of this magnetization, causing the hydrogen nuclei to produce a rotating magnetic field detectable by the scanner. In one embodiment, differences in image data can be determined, by normalization on a standard brain atlas. Brain atlases suitable for use with the methods described herein include, but are not limited to the Talairach brain atlas and the Montreal Neurological Institute (MNI) brain atlas.

Positron Emission Tomography (PET) can measure a variety of physical parameters, including, but not limited to, absolute blood flow, glucose metabolism, and the level of a particular molecule in the brain. PET scans can also be used to distinguish patients based on diagnosis, assign risk or adverse events (e.g. suicide), or to predict treatment response.

The methods described herein an also be used to generate image data from other anatomic structures including other organs, tissues or body structures. Exemplary body structures that can be imaged according to the methods described herein include but are not limited to diaphragm, chest wall, rib cage, rib, spine, sternum or pelvis breast, head/neck, chest, abdomen, extremities (e.g. arms, legs, hands and feet). Exemplary organs that can be imaged according to the methods described herein include but are not limited to organs such as stomach, lymph nodes, heart, lung, liver, and prostate.

The methods described herein can be used to generate image data from a human. The methods described herein can also be used to generate image data from a non-human animal, including, but not limited to dog, cat, pig, sheep, mouse, rat, horse, human, chimpanzee, and orangutan, fish etc.

PET Reconstruction (PSF-MLEM)

PET iterative reconstruction and resolution modeling include maximum likelihood expectation maximization (MLEM) and projectors that incorporate PSF kernel (PSF-MLEM). PSF-MLEM provides improvement in resolution but multiple artifacts can be introduced by PSF modeling in the MLEM reconstruction. These artifacts include poorly recovered levels of activity, edge artifacts at borders of large regions, and over-enhancement of small structures.

Total-Variation (TV)-PSF-MLEM (TV-PSF-MLEM)

Described herein is the incorporation of a total-variation (TV) regularization process in the PSF-MLEM reconstruction. The TV is spatially weighted. The local weights are learned from the data by conducting a first-pass iterative reconstruction without PSF. Weights are calculated based on analysis of the evolution of each pixel over many iterations. Faster evolution tends to be related to one type of artifact while slower evolution to another type of artifact. By adjusting the weights according to the "convergence rate" different artifacts can be mitigated at different levels. The TV regularization is inserted within the PSF-MLEM algorithm (TV-PSF-MLEM). The regularization must vary with the local geometry and contrast. Geometry and contrast are inferred with the MLEM convergence rate. The MLEM convergence rate is used to create a weight for each voxel. For noisy data, the average weight inside a 3×3×3 neighborhood around voxel b is computed. In some embodiments, the average weight inside a spatial neighborhood includes one or more voxels around voxel b, for example the voxels within a 3×3×3 window around voxel b. The size of the spatial neighborhood can be based on a variety of factors, including but not limited to, the size of the imaging data, the resolution of the imaging data, and the area of interest within the image.

Gradual PSF (gPSF-MLEM)

To mitigate 'hot-spot' artifacts a modification of the method was devised, based on empirical intuition. Instead of using the same FWHM PSF at each iteration, the FWHM is evolved. At the start there is a large FWHM, this is gradually decreased at each iteration until it reaches a target true value in the final iteration. The stopping criteria is pre-defined.

TV-gPSF-MLEM

The locally weighted total variation denoising approach TV-PSF-MLEM and the gPSF-MLEM approach can be combined into a single algorithm, TV-gPSF-MLEM.

In some embodiments, iterative reconstruction in TV-PSF-MLEM, gPSF-MLEM and TV-gPSF-MLEM can be implemented with MLEM, ordered subsets expectation maximization (OSEM) or maximum a posteriori (MAP) iterative reconstruction methods.

Computer Systems

PET imagers can be connected via a network to a network server (e.g., personal computer, minicomputer, mainframe computer, etc.). Image data can be transferred to the server via the network, or, alternatively, data can be stored on a storage medium by the imaging device and physically transferred to the server, where the data can be read from the storage medium. The server can be connected to one or more workstations (e.g., personal computers, minicomputer workstations, mainframe terminals, etc.) for processing the image data in accordance with the methods described herein. The transfer and processing of the image data can be completely or partially automated depending upon the practicalities of a particular implementation.

One of skill in the art will understand that the methods described herein can be practiced with various types of computer system configurations, including hand-held devices, multiprocessor systems, microprocessor-based or programmable consumer electronics, network PCs, minicomputers, mainframe computers, and the like. The invention can also be practiced in distributed computing environments where tasks are performed by remote processing devices that are linked through a communications network.

In addition, the present invention is not described with reference to any particular programming language. It will be appreciated that a variety of programming languages may be used to implement the teachings of the invention as described herein The following examples illustrate the present disclosure, and are set forth to aid in the understanding of the present disclosure, and should not be construed to limit in any way the scope of the present disclosure as defined in the claims which follow thereafter.

EXAMPLES

Example 1: Locally Weighted Total Variation Denoising for Ringing Artifact Suppression in PET Reconstruction Using PSF Modeling Existing and commonly used iterative reconstruction techniques in positron emission tomography (PET) provide a flexible framework for modeling the physics and the scanner geometry, yielding greater image contrast, visual quality and noise robustness than analytical reconstruction methods.

Modeling and accounting for the physics of the emissions (e.g. positron range) and the detection processes (e.g. crystal scattering or depth of interaction) is possible by measuring and incorporating the detector point spread function (PSF) into the reconstruction process. Such approach has been shown to improve spatial resolution and image contrast (Sureau et al, 2008). Unfortunately, this approach also introduces significant edge artifacts such as over enhancement and Gibbs type of ringing that are both contrast and size dependent (leading to up to 70% overshoot in a cylinder phantom) (Bai and Esser, 2010; Thielmans et al., 2010). Mitigation of these artifacts is crucial to ensure image quantification accuracy, especially since reconstruction with PSF modeling is now implemented and widely used in clinical PET/CT systems.

Some work has been done to characterize and compensate for PSF modeling artifacts. Bai et al. showed that the overshoot depends on region sizes and contrast ratios (Bai and Esser, 2010). Snyder et al. observed that the overshoot might be explained by the mismatch between the true and measured PSF (Snyder et al., 1987). Tong et al. reported that ringing frequency and amplitude are related to objects' sizes (Tong et al, 2011). A number of different mitigation strategies have been discussed, such as under sampling the PSF and post-filtering the reconstructed images (Tong et al, 2011). While these approaches reduce artifacts, they also blur the PET images and undermine the benefits of PSF modeling (Snyder et al., 1987). Rapisarda et al. incorporated a new regularization prior into the reconstruction process that locally modifies the image estimate at each iteration in an attempt to locally control edge enhancement (Rapisarda et al., 2012). This method is promising but currently requires optimizing two parameters and while artifacts are suppressed there is loss of contrast recovery.

Total variation (TV) denoising methods have been adapted for Bayesian iterative reconstruction algorithms suitable for use with PET, showing effective suppression of noise and reconstruction of homogenous regions with sharp edges (Yan, 2011). Previous works assumed a uniform distribution of noise and therefore applied TV globally, which is not suitable for localized PSF modeling artifacts. Described herein is a new locally-weighted TV strategy, where denoising weights are derived empirically from the data and are incorporated directly into the iterative reconstruction process. The reconstruction method described herein is also evaluated on a simulated cylindrical phantom image to assess contrast and resolution recovery.

PET Iterative Image Reconstruction: MLEM Algorithm

The estimate of the PET images is computed using the maximum likelihood expectation maximization (MLEM) algorithm (Tong et al., 2011), or ordered subsets expectation maximization (OSEM), an accelerated variation of MLEM that groups projection data into subsets. Following the notation from Rapisarda et al, 2012, the MLEM iterative update equation is given as follows:

$$\lambda_b^{k+1} = \frac{\lambda_b^k}{BP_b 1} BP_b \frac{\gamma_b}{P_d \lambda_{b'}^k} = \lambda_b^k u_b^k \quad (1)$$

where $\lambda_b^k$ represents the counts in a voxel b within the image λ at iteration k, $\gamma_d$ is the measured projection recorded as number of counts along the line of response (LOR) d, and 1 is a unit matrix of the same size as $\gamma_d$. The forward $P_d(\bullet)_b = \Sigma[(\bullet)]_b p_{bd}$ and backward $BP_b(\bullet)_d = \Sigma[(\bullet)]_d p_{bd}$ projectors contain a weight matrix $p_{bd}$ that links the voxel b and LOR d. The term $BP_b 1$ is called the geometric sensitivity, and can be pre-computed prior to reconstruction. Projection terms applied at iteration k can be combined into a multiplicative updating term $u_b^k$.

PSF Modeling

Following the methodology introduced by Rapisadra et al., incorporating the PSF model into (1) is achieved by modifying the projectors as follows:

$$P_d(\bullet)_b = \Sigma[(\bullet)*PSF]_b p_{bd} \quad (2)$$

$$BP_b(\bullet)_d = PSF^T * \Sigma[(\bullet)]_d p_{bd} \quad (3)$$

where PSF represents the PSF kernel and * is a discretized convolution operator as defined in Appendix of Rapisarda et al, 2012. For a symmetric kernel, $PSF=PST^T$ MLEM reconstruction that utilizes Eq. (2)-(3) will be here referred to as PSF-MLEM.

Reconstruction Software and Simulated Data

Reconstructions were performed using the STIR open source C++ software (v2.2) (Thielemans et al, 2012). The modified projectors in Eq. (2) and (3) were written in C++ within STIR. A 200 mm diameter cylindrical phantom object was simulated, with a background intensity equal to 10, three hot spots of diameter 25 mm, 16 mm, 12 mm with a 1.5:1 contrast ratio (CR), and three 8 mm diameter hot spots with CR of 1.25:1, 1.5:1 and 2:1, respectively. The phantom was blurred with a symmetrical 4.5 mm FWHM Gaussian kernel (Mourik et al., 2009) to simulate the resolution loss due to physics inherent in the ECAT HR+ scanner (Siemens/CTI). FIG. 1 illustrates the phantom image with resolution and contrast loss due to blurring.

Total Variation Denoising

Following the notations above within Example 1, at each iteration of Eq. (1) the total variation problem amounts to finding an estimate image $\hat{\lambda}^k$ that satisfies the following optimization problem:

$$\hat{\lambda}^k = \min \frac{1}{2}\|\lambda^k - \hat{\lambda}^k\|^2 + \beta|\nabla\hat{\lambda}^k| \quad (4)$$

where |•| and ||•|| are the $L_1$ and $L_2$ norms, respectively and β is the regularization weight. TV optimization was performed using the toolbox (Yan, 2011) implemented in Matlab (Tremoulheac, Benjamin (2012). Split Bregman method for Total Variation Denoising (www.mathworks.com/matlabcentral/fileexchange/36278), MATLAB Central File Exchange)

Locally-Weighted Total Variation Denoising

Figure 2:
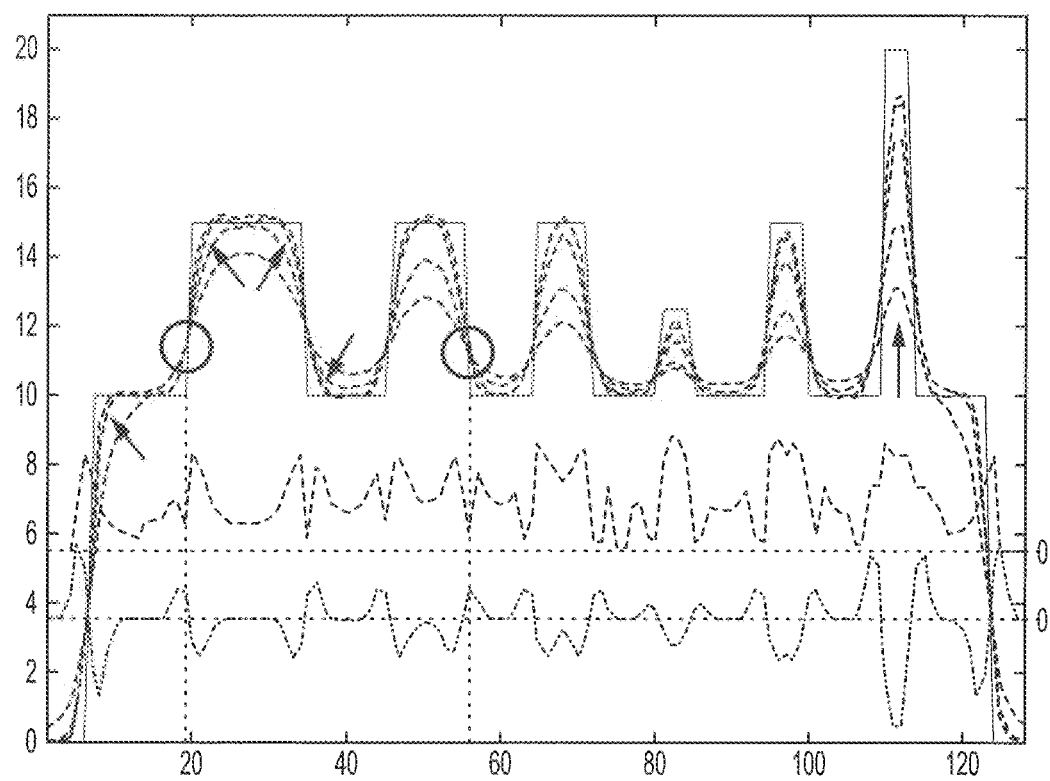
FIG. 2 shows Illustration of how $\lambda^k$ evolves and its relation with the image structure. Ideal phantom's horizontal midline profile (solid line). Reconstructed (MLEM) profiles over several iterations of Eq. 1 (dashed lines, upper half of paned). Number of iterations to convergence (dashed line, bottom half of panel). Second derivative of the blurred phantom's profile (dotted line). Arrows show the dominant direction of evolution of reconstructed profiles over the iterations. Circles highlight the localization of the inflection points of the reconstructed profiles, which take a relatively small number of iterations to converge.

The classical framework given by Eq. (4) minimizes TV over the whole image, while PSF modeling introduces local artifacts. As such, the TV filtered estimate $\hat{\lambda}^k$ was locally integrated into $\lambda_b^k$, reexpressing $\hat{\lambda}^k$ as:

$$\hat{\lambda}_b^k = \lambda_b^k + (\hat{\lambda}_b^k - \lambda_b^k) = \lambda_b^k + \Delta\hat{\lambda}_b^k \quad (5)$$

where, $\Delta\hat{\lambda}_b^k = \hat{\lambda}_b^k - \lambda_b^k$, represents the net change in each voxel b in the on the image estimation after TV denoising. Since TV filtering is only needed at specific voxel locations, TV enforcement is locally constrained by introducing a local weight on each TV filtered voxel, defining $$\dot{\lambda}_b^k = \lambda_b^k + w_b \Delta\hat{\lambda}_b^k \quad (6)$$

where $\dot{\lambda}_b^k$ is the locally weighted TV estimate and $w_b$ is a spatially-varying weight imposed on the net change of each voxel. Note that if $w_b=1$ then $\dot{\lambda}_b = \hat{\lambda}_b$, corresponding to the classical solution to Eq. (4). The PSF-MLEM with TV denoising (TV-PSF-MLEM) algorithm is thus given as follows:

For iteration 1 to N:
Step 1: obtain $\lambda_b^{k+1}$ from $\lambda_b^k$ using Eq. (1)
Step 2: apply Eq. (4) on $\lambda_b^{k+1}$ to obtain $\hat{\lambda}_b^{k+1}$
Step 3: apply Eq. (6) on $\hat{\lambda}_b^{k+1}$ to obtain $\dot{\lambda}_b^{k+1}$
Step 4: repeat from Step 1 using $\lambda_b^k = \dot{\lambda}_b^{k+1}$ Definition of the TV-Denoising Spatial Weights There was a need to design a local weighting scheme such that flat homogenous regions and edges were preserved from the original MLEM estimation, while edge ringing was reduced with TV filtering. Instead of filtering the current estimate relying on its edge maps, a novel approach was chosen to determine if the information learned on the evolution of $\lambda^k$ over the iterations of the MLEM reconstruction could be exploited. FIG. 2 shows, on the phantom's horizontal midline profile, the evolution of $\lambda^k$ over several MLEM iterations (toward convergence), as well as the number of iterations required for each voxel along the profile to converge and the second spatial derivative of the MLEM profile at convergence.

Weighting strategy was based on a few observations: (a) each cylinder's edges have inflection points (defined as zero-crossing of the second spatial derivative) that spatially converge very quickly, (b) the interiors of flat regions converge quickly, while edge refinement continues for a long time (as the peak expands while the support shrinks); (c) the convergence rate for the 8 mm cylinders is contrast dependent, and faster for the cylinder with CR 1.25:1 versus 1.5:1, and (d) while the rate of convergence globally mimics the second derivative of the reconstructed profile, there are many local differences. As such, unique information can be contained in the evolution of the MLEM reconstructions that cannot be derived directly from the structure of the reconstructed image.

Figure 3:
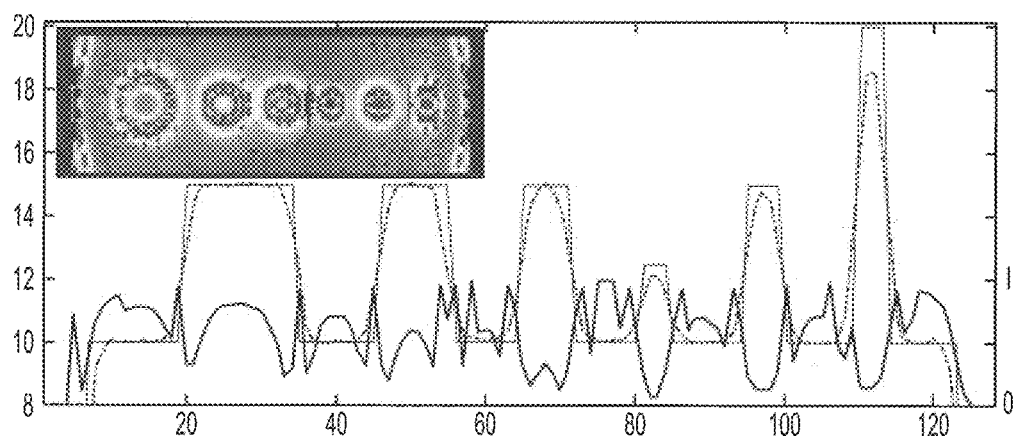
FIG. 3 shows horizontal profiles through the horizontal midline of ideal phantom (thin solid line), MLEM reconstruction at convergence (dashed line) and spatial TV weight $w_b$ (thick solid line), from the spatial weight map (top left). Left and right axes are for the profiles and $w_b$, respectfully.

Based on these observations, a new spatial weight $w_b$ was designed as follows:

$$c_b = \min_k \text{abs}(1 - u_b^k) \leq 1e^{-4} \qquad (7)$$

$$w_b = 1 - \frac{c_b - \min(c_b)}{\max(c_b - \min(c_b))}$$

where $c_b$ is defined as the earliest MLEM iteration k in which voxel b converges (in practice when $u_b^k \simeq 1$), and $w_b$ is derived by normalizing $c_b$ such that $0 \leq w_b \leq 1$. FIG. 3 illustrates the obtained spatial TV-weights $w_b$.

Evaluation Setup on Synthetic Phantom Data

To test whether this spatially weighted TV denoising approach improved image quality, TV-PSF-MLEM was run empirically setting β=0.02. Over several experiments with β={0.005, 0.01, 0.02, 0.04} it was found that β=0.02 yielded optimal ringing suppression without degrading image quality. For the MLEM reconstruction, initialization was with $\lambda^0=1$. The other reconstructions were initialized with the MLEM estimate.

Contrast recovery was quantitatively evaluated using the recovery coefficient (RC) measure, defined as:

$$RC = \sum_{b \in \Omega_{ROI}} \lambda_b^{recon} / \sum_{b \in \Omega_{ROI}} \lambda_b^{true} \qquad (9)$$

where the $\Omega_{ROI}$ is the region of interest (e.g. inside a cylinder), $\lambda^{recon}$ is the reconstruction being evaluated and $\lambda^{true}$ is the original non-blurred (ideal) phantom. RC measures can be above or below one and RC=1 for a perfect reconstruction.

Figure 4:
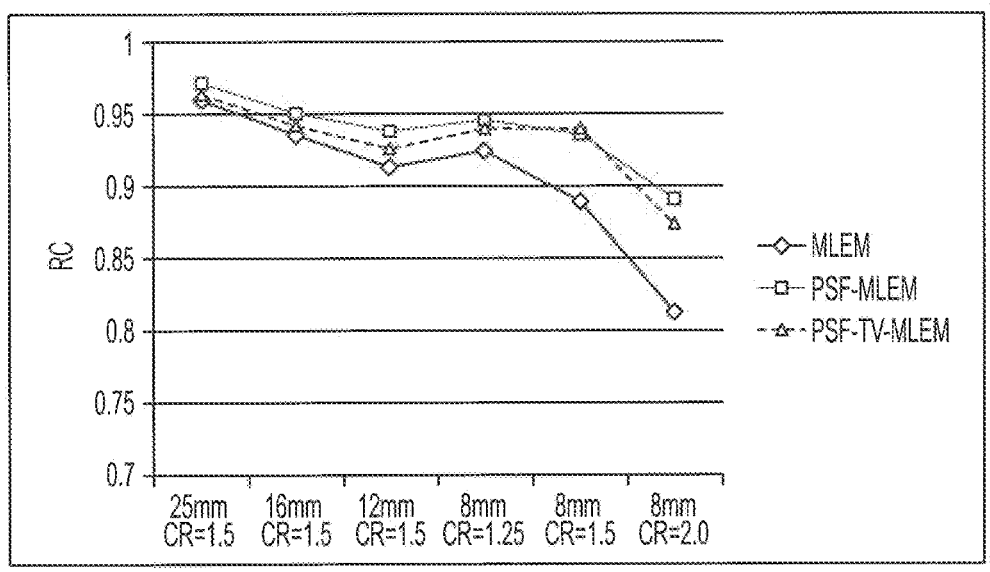
FIG. 4 shows recovery coefficient (RC) measures for different size cylinders and contrast ratios (CR) of different reconstruction routines. The x-axis reports cylinder diameter (mm) and contrast ratio (CR) relative to the background.

The synthetic cylindrical phantom was reconstructed (200 iterations) with the three different algorithms (MLEM, PSF-MLEM and TV-PSF-MLEM) and the RC values were measured inside each six cylinders. TV-PSF-MLEM yielded better RC measures than MLEM, and only slightly lower than PSF-MLEM, in all cylinders (FIG. 4).

Evaluation of Ringing Artifacts at Edges

Figure 5:
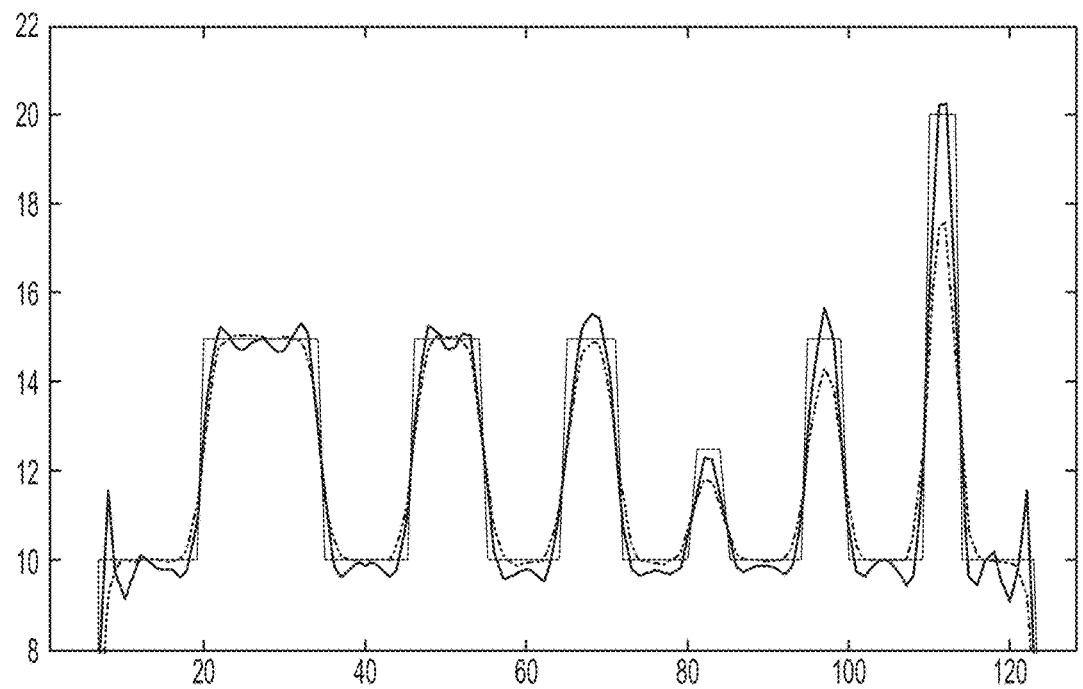
FIG. 5 shows horizontal midline profile through the ideal (thin solid line), MLEM (dashed line) and PSF-MLEM (thick solid line) reconstructions.

To evaluate ringing artifacts, the resulting images were visually compared. For the PSF-MLEM reconstruction, results, illustrated in FIG. 5, show that MLEM had no ringing artifact, PSF-MLEM generates ringing in the background and at edges of the 25 mm and 16 mm cylinders, as well as over enhancement of the 12 mm cylinder. For the 8 mm cylinders there were contrast-dependent over- and under-enhancement.

Figure 6:
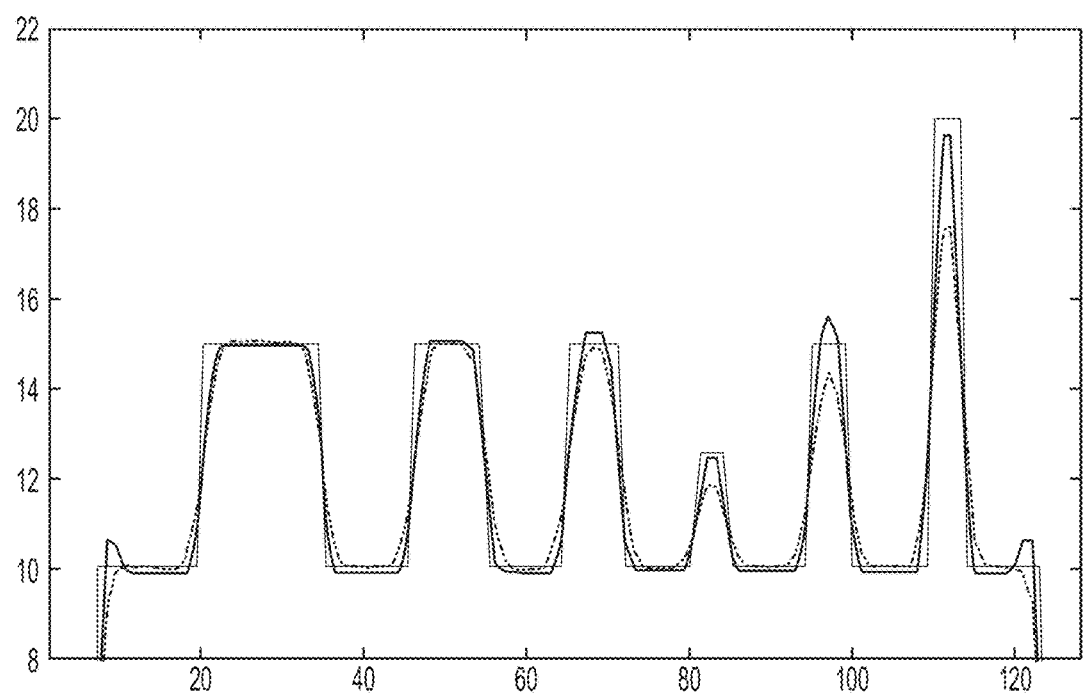
FIG. 6 shows horizontal midline profile through the ideal (thin solid line), MLEM (dashed line) and TV-PSF-MLEM (thick solid line) with β=0.02 reconstructions.
Figure 7:
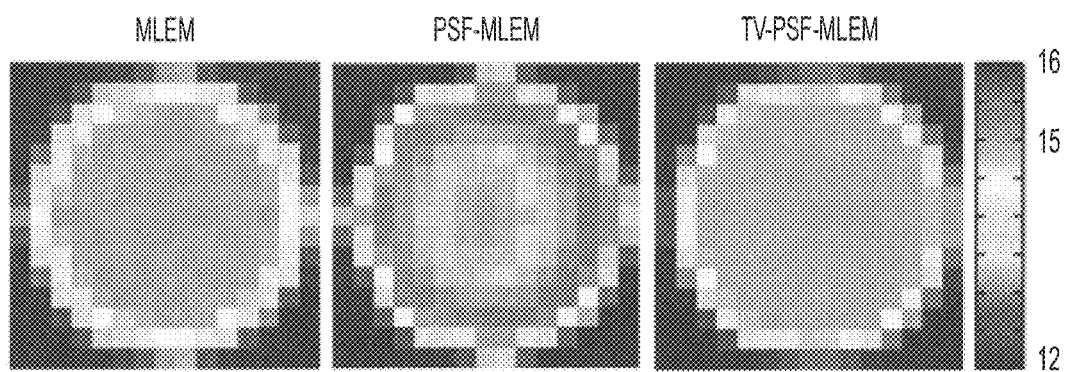
FIG. 7 shows images of the 25 mm cylinder with three reconstructions (MLEM, PSF-MLEM, TV-PSF-MLEM). TV-PSF-MLEM removes PSF related ringing artifacts and restores homogeneity and contrast level that is similar to the true phantom.

For the TV-PSF-MLEM reconstruction, results, illustrated in FIG. 6, show that ringing artifacts were suppressed on all cylinders edges. The contrast in the 25 mm and 16 mm cylinders was very well recovered, and over-estimation of the 12 mm cylinder intensity was reduced, compared to PSF-MLEM reconstruction (cf. FIG. 5). The contrast in the 8 mm cylinders was similar for TV-PSF-MLEM and PSF-MLEM reconstructions, demonstrating that locally-weighted TV denoising can suppress ringing within large structures while maintaining the contrast in small regions. In addition to removing ringing artifacts, TV also enforces homogeneity in large regions. This effect is illustrated in FIG. 7 in the 25 mm cylinder, where MLEM yielded a noisy image, PSF-MLEM induced heterogeneity and ringing at the edge, while TV-PSF-MLEM prevented the ringing and enforced homogeneity inside the cylinder.

Conclusions

TV denoising was introduced in the PSF-MLEM iterative reconstruction method for PET images. This method was evaluated on a synthetic phantom image with multiple cylinders varying in size and contrast. Results showed that TV-PSF-MLEM maintains the good contrast recovery properties of PSF-MLEM while reducing ringing artifacts at edges.

These results can also be applied on more complex synthetic phantoms. The proposed reconstruction method needs can also be employed in objects with greater variations in size and contrast and including negative contrast (i.e. cold spots). Robustness with respect to the presence of Poisson noise in the sinogram can also be evaluated. Regarding the methodology itself, the influence of the TV parameter β needs can be evaluated. Stopping criterions of the reconstruction process can be derived and optimized separately for each of the reconstruction approaches, instead of using the same fixed number of iterations. In certain embodiments, the reconstruction method can also be employed in connection with a physical phantom.

Example 2: Locally Weighted Total Variation Denoising for PSF Modeling Artifact Suppression in Pet Reconstruction Incorporating the point spread function (PSF) into the iterative MLEM reconstruction of PET images introduces contrast and size dependent ringing and over enhancement artifacts. As described herein, TV-PSF-MLEM can be used to suppress these artifacts based on the introduction of a locally-weighted total variation regularization within the MLEM reconstruction algorithm. On non-noisy PET measures, the TV spatial weights can be computed based on the point-wise convergence rate of a preliminary MLEM reconstruction, for each voxel. The TV-PSF-MLEM weighting scheme can be extended to noisy measures introducing a noise-independent weighting scheme. As described herein, the performance of TV-PSF-MLEM weighting scheme having a noise-independent weighting scheme can be compared to a state of the art PET denoising method. Results on numerical phantoms show that the TV-PSF-MLEM method offers substantial advantages in the recovery of small cylinders and gains in contrast recovery of larger cylinders.

Iterative reconstruction techniques, such as the maximum likelihood expectation maximization (MLEM), and ordered subsets expectation maxization (OSEM), provide a flexible framework in positron emission tomography (PET) imaging for modeling the physics and the scanner geometry, yielding greater image contrast, visual quality and noise robustness than analytical reconstruction methods. Incorporating the point spread function (PSF) of the scanner into the iterative MLEM reconstruction process (called PSF-MLEM) improves spatial resolution but introduces significant contrast and size dependent over-enhancement and ringing artifacts (Bai and Esser, 2011; Thielemans, et al., 2010). The over-enhancement artifacts can be explained by the mismatch between the true and the measured PSF, while the ringing artifacts are related to object sizes (Tong et al., 2011). Most approaches previously proposed to compensate ringing artifacts tend to blur the PET data which undermine the benefits of including the PSF in the reconstruction (Tong et al., 2011).

A promising approach was recently proposed by Rapisarda et al. for artifact suppression by incorporating a new regularization prior into the reconstruction process that locally modifies the image estimate at each iteration in an attempt to locally control edge enhancement (Rapisarda et al, 2012). This method provides excellent ringing suppression in the image, especially for large structures, but also tends to suppress the benefits of PSF modeling in smaller objects.

As described herein, TV-PSF-MLEM can be used to suppress PSF-MLEM artifacts based on a locally weighted total variation regularization applied at each iteration (Mikhno et al., 2013). Amplitude of the weights specifies the amount of TV regularization at each voxel. These local weights can be precalculated based on the convergence rate of MLEM at each voxel because the convergence rate is directly related to the object size and contrast and that artifact magnitudes are directly proportional to this convergence rate. Noiseless simulations show that TV-PSF-MLEM suppress ringing artifact while providing edge and contrast recovery, beyond that of standard MLEM, especially in small cylinders. In this example, the TV-PSF-MLEM formalism is extended to simulations corrupted with Poisson noise. A new weighting scheme is introduced robust to noise and results are presented, comparing to the Rapisarda method that is also based on a regularization prior.

Iterative Image Reconstruction: MLEM Algorithm

The estimate of the PET image is computed using the MLEM algorithm [Shepp and Vardi, 1982], or OSEM algorithm [M. Hudson, R. S. Larkin, Accelerated image reconstruction using ordered subsets of projection data, IEEE Trans. Med. Imag. (13) (1994) 601-609], and following the notation from Rapisarda et al., 2012, leads to the following iterative update equation:

$$\lambda_b^{k+1} = \frac{\lambda_b^k}{BP_b 1} BP_b \frac{y_b}{P_d \lambda_{b'}^k} = \lambda_b^k u_b^k \qquad (1)$$

where $\lambda_b^k$ represents the intensity of the voxel b within the image $\lambda$ at iteration k, $y_d$ is the sinogram measure, equal to the number of counts along the line of response (LOR) d, and 1 is a unit matrix of the same size as $y_d$. Following the methodology introduced in Rapisarda et al., 2012, incorporating the PSF model into Eq. (1) is achieved by modifying the projector P and backprojector BP as follows:

$$P_d(\bullet)_b = \Sigma((\bullet)*PSF)_b \rho_{bd}$$

$$BP_b(\bullet)_d = PSF^T * \Sigma[(\bullet)]_d \rho_{bd} \qquad (2)$$

where PSF represents the PSF kernel and * is a discretized convolution operator as defined in Appendix of Thielemans et al., 2012. For a symmetric kernel, PSF=$PSF^T$. Hereafter PSF-MLEM shall refer to the situation when PSF is a non-zero matrix, and MLEM when PSF=1.

Simulation Framework: Software and Phantom

Figure 8:
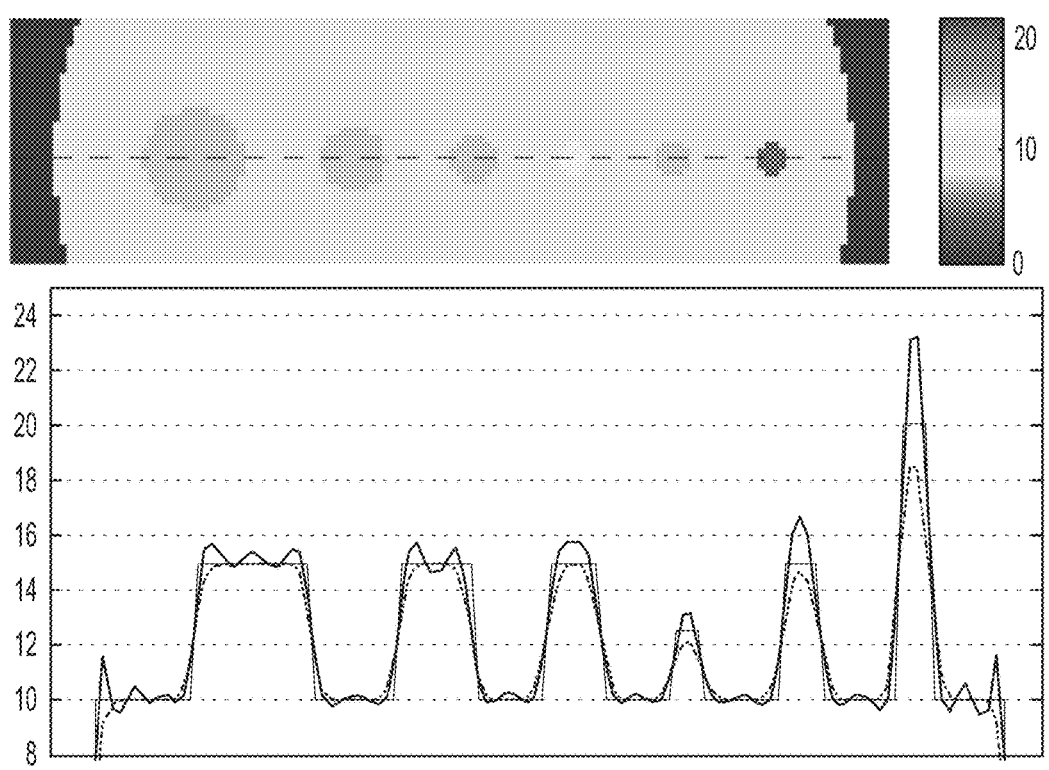
FIG. 8 shows (top) Middle portion of the simulated cylindrical phantom object with inset cylinders of various diameters. (bottom) Center profiles (along the dashed line above) of reconstructions with MLEM (dashed line), PSF-MLEM (thick solid line), and ideal phantom (thin solid line).

Methodological developments were performed using simulated sinograms. PET image reconstructions were performed using the STIR open source C++ software (v2.2) (Thielemans et al., 2012). The modified projectors in Eq. (2) were implemented in C++ within the STIR source code. A 200 mm diameter cylindrical phantom object was simulated, with a background intensity equal to 10, three hot spots of diameter 25 mm, 16 mm, 12 mm with a 1.5:1 contrast ratio (CR), and three 8 mm diameter hot spots with CR of 1.25:1, 1.5:1 and 2:1, respectively. The phantom was blurred with a symmetrical 4.5 mm FWHM Gaussian kernel (Mikhno et al., 2013) to simulate the resolution loss inherent to the ECAT HR+ scanner (Siemens/CTI). FIG. 8 illustrates the phantom image with resolution and contrast loss due to blurring, as well as the ringing and over-enhancement artifacts of PSF-MLEM. Poisson noise was added to the sinogram measures $y_d$ with a scale factor scale as follows:

$y_d$=scale×Poisson($y_d$÷scale)

TV Regularization Prior (Rapisarda Method)

A Bayesian formulation of the iterative reconstruction algorithm can be used, leading to a maximum a posteriori (MAP) estimate that includes an a priori probability term. Rapisarda proposed the following iterative MAP estimate (Rapisarda et al., 2012):

$$\lambda_b^{k+1} = \frac{\lambda_b^k}{BP_b[1 - \alpha D_b \lambda_b^k]} BP_b \frac{y_d}{P_d \lambda_{b'}^k} \qquad (3)$$

where $\alpha$ weights the contribution of the value $D_b$ at pixel b of a regularization prior D defined as:

$$D[\lambda] = \nabla \cdot \left( \phi'(|\nabla \lambda|) \frac{\nabla \lambda}{|\nabla \lambda|} \right) \qquad (4)$$

The term $\phi'(x)$ is called the variational prior and is based on a modification of the generalized p-Gaussian kernel:

$$\phi'(x) = \begin{cases} x^{(p-1)} & x < \delta \\ 1 - \frac{d(d+\delta)}{d+x} & x \geq \delta \end{cases} \qquad (5)$$

where d=$(1-\delta^{p-1})$, with $\delta$ being a gradient threshold.

TV-PSF-MLEM: Algorithm

As described herein, TV-PSF-MLEM is a locally-weighted total variation regularization scheme for PSF-MLEM reconstruction. Its components briefly herein. Using previous notations, at each iteration of Eq. (1) the total variation problem amounts to finding an estimate image $\hat{\lambda}^k$ that satisfies:

$$\hat{\lambda}^k = \min_{\Theta} \frac{1}{2} \|\lambda^k - \Theta\|^2 + \beta |\nabla \Theta| \qquad (6)$$

where $|\bullet|$ and $\|\bullet\|$ are the $l_1$ and $l_2$ norms, respectively and $\beta$ is a positive scalar regularization weight. The classical framework given by Eq. (6) minimizes TV over the whole image. Instead, local weights $w_b$ were introduced for each individual pixels b as follows:

$\dot{\lambda}_b^k$ is defined the locally weighted TV estimate:

$$\dot{\lambda}_b^k = \lambda_b^k + w_b \Delta \hat{\lambda}_b^k \qquad (7)$$

where $w_b$ is a spatially-varying weight imposed on the net change of each voxel and $\Delta \hat{\lambda}_b^k$, is defined as:

$$\hat{\lambda}_b^k = \lambda_b^k + (\hat{\lambda}_b^k - \lambda_b^k) = \lambda_b^k + \Delta \hat{\lambda}_b^k \qquad (8)$$

Note that if $w_b$=1 then $\dot{\lambda}_b = \hat{\lambda}_b$, corresponding to the classical solution to Eq. (6).

The convergence rate, derived from the value of $u_b$ in Eq. (1), is used for the definition of the spatial weights $w_b$, as detailed in Mikhno et al., 2013, using the following values:

$$c_b = \min_k |1 - u_b^k| \leq \epsilon \qquad (9)$$

Figure 9:
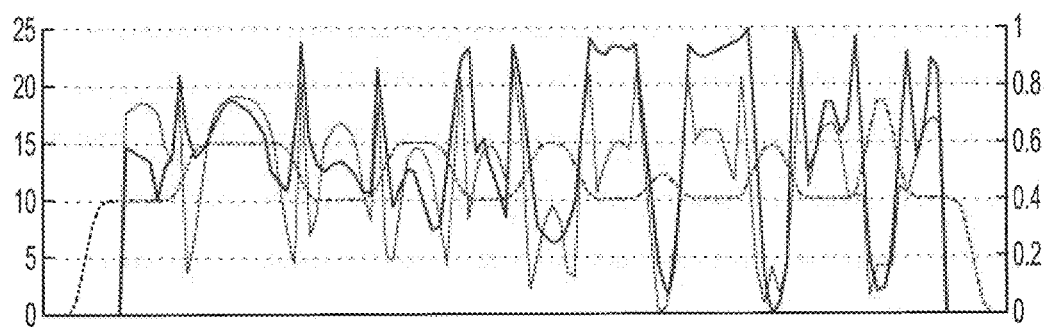
FIG. 9 shows local TV weights calculated using Eq. (9) of Example 2 with noiseless data (thin solid line) and using Eq. (10) of Example 2 with noisy data (thick solid line). The profile of the MLEM reconstruction (dashed line) is shown as a reference. Left and right y-axes correspond to MLEM and weights, respectively.

-continued $$w_b = 1 - \frac{c_b - \min(c_b)}{\max(c_b - \min(c_b))}$$

where $c_b$ is defined as the earliest MLEM iteration k at which voxel b converges (in practice when $u_b^k \approx 1$), $w_b$ is derived by normalizing $c_b$ such that $0 \le w_b \le 1$, and $\epsilon$ is a convergence threshold ($\epsilon = 1 \times 10^{-4}$ in Mikhno et al., 2013). FIG. 9 illustrates the spatial TV-weights $w_b$ obtained with this approach for nonnoisy and noisy measures. PSF-MLEM with TV denoising method (TV-PSF-MLEM) is summarized in Algorithm 1.

Algorithm 1 TV-PSF-MLEM algorithm
Data: $\lambda_0$, k=0, i=1, Result: $\lambda_b^N$, Initialize: $\lambda_b^0 = \lambda_0$
while k≤N do
  $\lambda_b^{k+1} \leftarrow \lambda_b^k$ from Eq. (1)
  $\hat{\lambda}_b^{k+1} \leftarrow \lambda_b^{k+1}$ from Eq. (6)
  $\tilde{\lambda}_b^{k+1} \leftarrow \hat{\lambda}_b^{k+1}$ from Eq. (7)
  $\lambda_b^{k+1} b \leftarrow \tilde{\lambda}_b^{k+1}$, k←k+1

TV-PSF-MLEM: TV Spatial Weights for Noisy Data

Figure 10A:
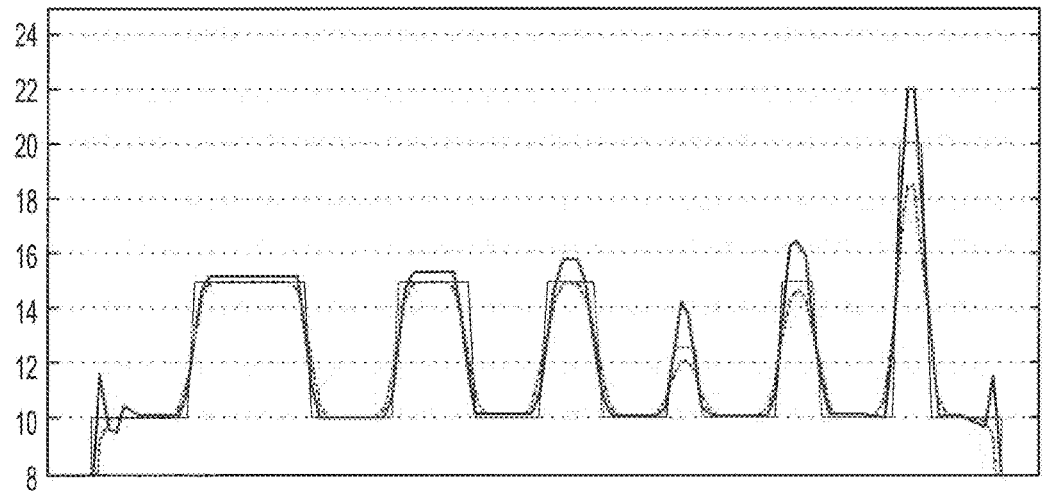
FIGS. 10A-10B show TV-PSF-MLEM reconstruction with oracle weights for simulated phantom with (a) and without (b) added Poisson noise to the sinogram. Horizontal profile lines through the center of the image are shown for ideal phantom (thin solid line), 200 iterations of MLEM using Eq. (1) (dashed line), and 500 iterations of TV-PSF-MLEM with oracle weights (thick solid line) initialized with 200 iterations of MLEM.
Figure 10B:
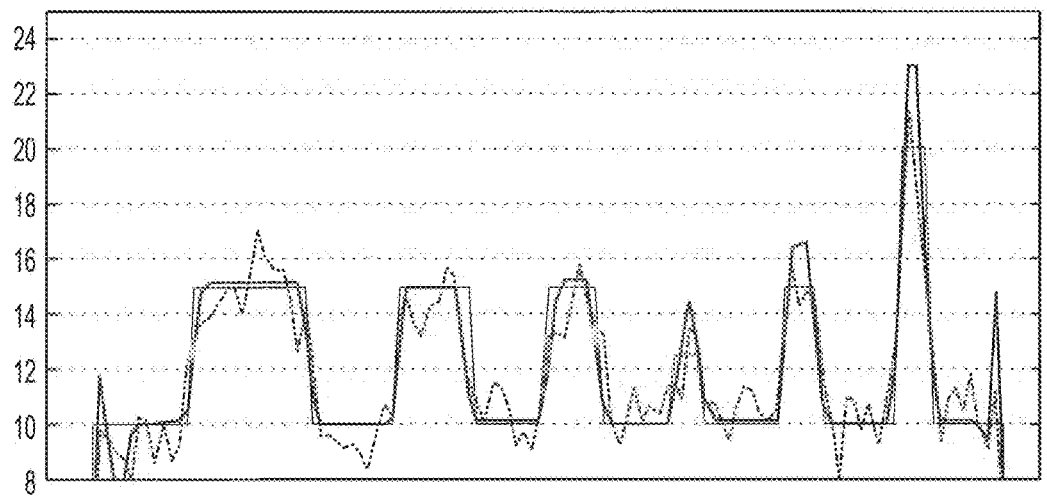

From Eq. (9) it can be seen that weights depend on the convergence rate of individual voxels b and will therefore be highly affected by the presence of noise. To adapt the approach to noisy data, the oracle approach was studied where ideal weights (derived from the noiseless case) were applied to TV-PSF-MLEM reconstruction of the noisy sinograms, corrupted with Poisson noise. Results, illustrated in FIG. 10, show that reconstructions after 500 iterations were similar with and without noise, with good suppression of noise and ringing artifact, but with some over enhancement of the 8 mm cylinders in both cases. To approximate these oracle weights using the iterative MLEM reconstructions from the noisy data, a local spatial aggregation of the convergence rates estimates $u_b^k$ from Eq. (1) was used, using the average kernel of size n×n with n=3, along with a modified value for $\epsilon$: $\epsilon = 5 \times 10^{-4}$. Results illustrated in FIG. 9, show that such approach leads to a profile of the local weights that mimics well the general shape of the oracle weights although local differences in magnitude exist. Thus, the calculation of the parameter $c_b$ used in Eq. (9), on noisy data becomes:

$$\hat{u}_b^k = \Sigma_{b \in N_b} u_b^k \quad (10)$$

where $N_b$ is the 3×3 neighborhood around voxel b, $\hat{u}_b^k$ replaces $u_b^k$ in Eq. (9) for noisy data.

Experimental Setup Using Synthetic Phantom Data

Performance of MLEM, PSF-MLEM, TV-PSF-MLEM, and the Rapisarda method was quantitatively assessed using the recovery coefficient, Eq. (11). For TV-PSF-MLEM the regularization weight β=0.02 was used as in Mikhno et al., 2013, and for the Rapisarda method parameters were set as recommended by in Rapisarda et al, 2012: p=1.33, δ=0.3, and α=0.002. In an attempt to suppress over-enhancement in the 8 mm cylinders, as observed in FIG. 10, a minimum cutoff value for the $w_b$ values was set (stemming from the observation that $w_b$ in those cylinders were lower than anywhere else in the image). By increasing $w_b$ values more TV regularization is enforced to prevent overshooting. Experiments were run until convergence, corresponding to: 200 iterations for MLEM and 500 iterations for TV-PSF-MLEM and Rapisarda.

$$RC = \Sigma_{b \in \Omega_{ROI}} \lambda_b^{recon} / \Sigma_{b \in \Omega_{ROI}} \lambda_b^{true} \quad (11)$$

Evaluation of Artifact Suppression

Figure 11:
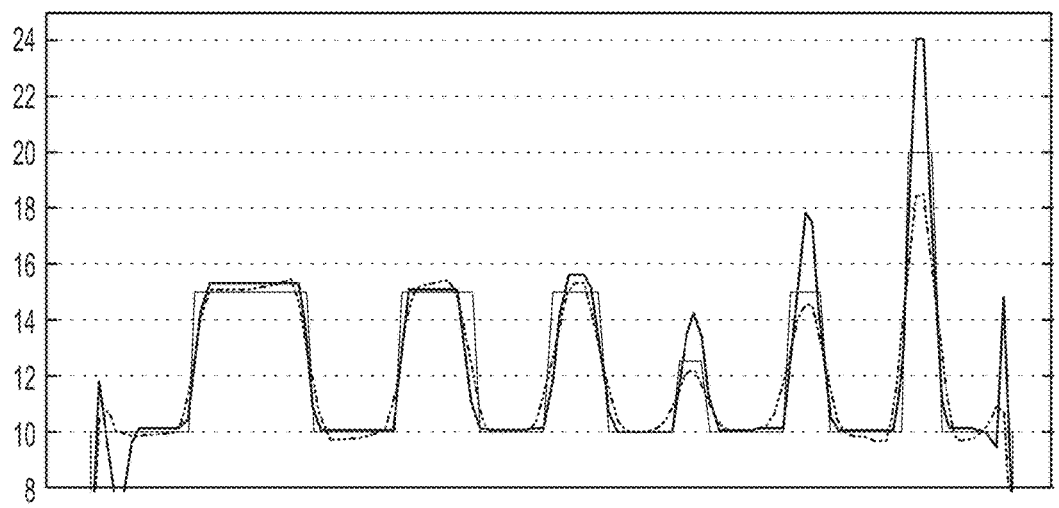
FIG. 11 shows reconstruction results on simulated phantom with Poisson noise. Center profile is shown for: (thin solid line) ideal phantom, (dashed line) 500 iterations of Rapisarda using Eq. (3), and (thick solid line) 500 iterations of TV-PSF-MLEM with average weights calculated using Eq. (10). Reconstructions were initialized with 200 MLEM iterations.
Figure 12:
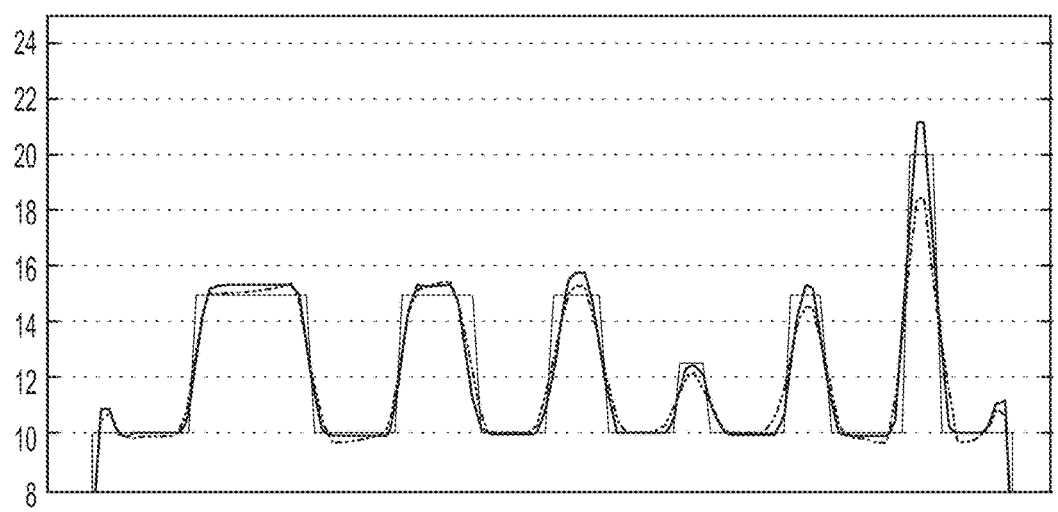
FIG. 12 shows Reconstruction results on simulated phantom with Poisson noise and $w_b$, cutoff value. Center profile is shown for: (thin solid line) ideal phantom, (dashed line) 500 iterations of Rapisarda Eq. (3) from Example 2, and (thick solid line) 500 iterations of TV-PSF-MLEM with average weights, Eq. (10) from Example 2, and $w_b$ cutoff=0.2. Reconstructions were initialized with 200 MLEM iterations.

Visually TV-PSF-MLEM and Rapisarda reconstructions provide very comparable results in large cylinders (≥12 mm), as seen in FIG. 11. In smaller cylinders, the Rapisarda method underestimates while the TV-PSF-MLEM overestimates the activity. TV-PSF-MLEM appears more homogenous in the background and in larger cylinders. At the outer edges of the phantoms artifacts in the TV-PSF-MLEM reconstruction are due to the non regularization with local weights $w_b$ there. The overshoot in small cylinders and background edges is largely remedied by applying a simple cutoff, FIG. 12.

Figure 13:
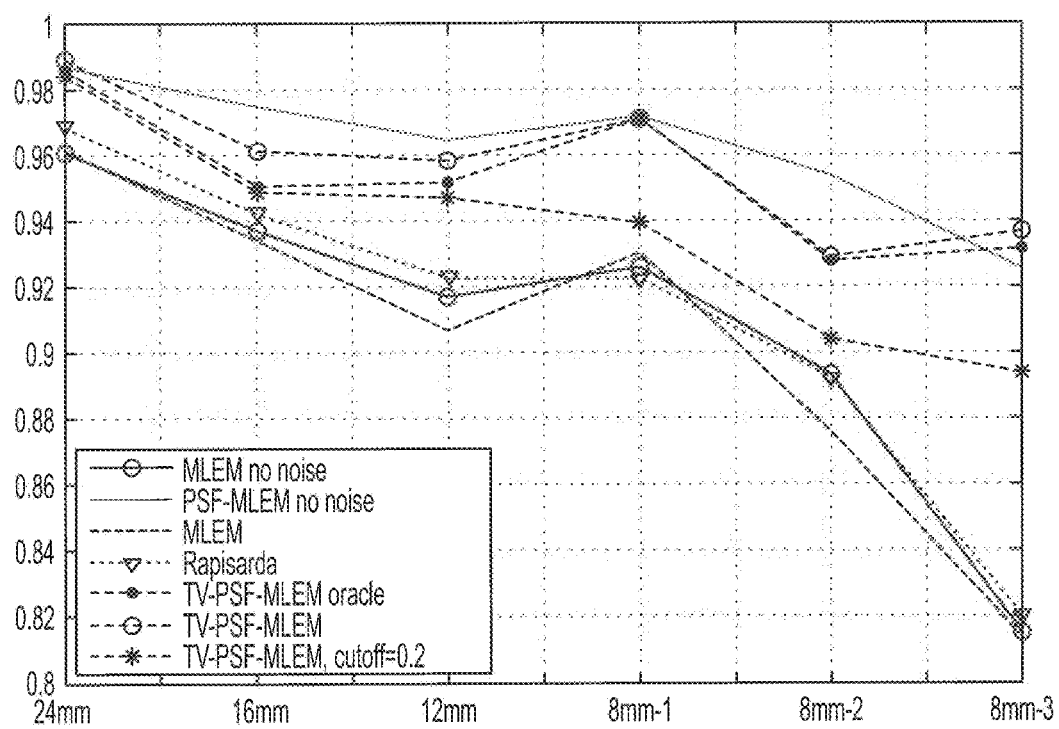
FIG. 13 shows recovery coefficients (RC) of cylinders (x-axis) with different reconstruction methods on noisy (dashed lines) and non-noisy (solid lines) data. MLEM and PSF-MLEM are shown on non-noisy data as references for the expected worst and best RC value.

The performance characteristic of the two methods is better understood in terms of RC values, reported in FIG. 13 for the different cylinders. The Rapisarda method yields RCs for all cylinders that closely track the noiseless MLEM estimate, with slightly higher RCs for cylinder diameters≥12 mm, and outperforming standard MLEM on noisy data. Hence this method provides excellent noise suppression but greatly limits the contrast enhancement gained from PSF modeling as it does not recover contrast loss due to blurring effects. In contrast, TV-PSF-MLEM (with or without cutoff on the $w_b$) yields higher RC values for all cylinders. For the 24 mm and 8 mm-1 cylinders, the recovery level on noisy data approaches the recovery level of PSF-MLEM (without noise). When a cutoff value is applied on the wb, all RC values are higher than with the Rapisarda method, especially in the highest contrast 8 mm cylinder.

Two ML iterative PET reconstruction algorithms that both exploit local regularization of the image data were compared: the TV-PSF-MLEM method described herein and the Rapisarda method described in Rapisarda et al., 2012. The simulation results described herein demonstrate that in the presence of noise, the V-PSF-MLEM method described herein is robust and provides advantages in terms of visual quality and contrast recovery, especially in small structures. The V-PSF-MLEM method described herein can also be employed with varying levels of noise, higher contrast ratios, real phantom objects and clinical data.

Example 3: Reconstruction Based Resolution Recovery

A fundamental limitation of PET technology is the image resolution of 8-12 mm, which varies based on scanner and application. In molecular imaging every millimeter matters. Improving the resolution by a single millimeter could open the door to a wide range of applications. More reliable detection of small tumors could translate into earlier diagnosis and better prognosis. The need for quantifying of signal from internal carotid arteries in the brain, that are on the order of 6-8 mm in diameter, has been discussed. Reliable quantitation of carotid signal could facilitate estimation of the arterial input function and lead to less invasive PET quantification. Another application of interest is the quantification of signal from raphe nucleus in the brain, whose five nuclei are spherical structures that are roughly 5-6 mm in diameter. The raphe is a major site of serotonin receptors and regulator of serotonin utilization through the brain. Only a few voxels from this region are visible on a typical PET scan. Better localization and quantification of this region could greatly improve understanding of neurological disorders that are related to the serotonergic system. The resolution of PET images is dependent on many physical factors (e.g. attenuation, scatter, non-collinearity, etc.), noise, and reconstruction framework. Specifically, attainable resolution with analytical methods such as FBP are limited due to overwhelming noise present in the emission data. The MLEM approach, based on modeling the emission data as a Poisson process, improves resolution recovery but also amplifies noise and therefore requires regularization which further degrades resolution. Previous works have shown that incorporating the PSF model into MLEM reconstruction improves resolution and reduces noise. However, PSF modeling also introduces ringing and over-enhancement artifact, as well as low-frequency noise into the image, which again prevents full realization in resolution improvement. The last five years has seen a growing body of research around mitigating PSF modeling artifacts, as the topic is gaining traction due to the possibility of increasing the fundamental resolution limit of PET for all scanners. Unfortunately, the solutions proposed thus far reduce PSF artifact at the cost of smoothing the image and thereby depreciating the theoretical benefits of PSF modeling. The existing methods, including the current state-of-the-art, and their limitations are discussed herein. Disclosed herein is a strategy based on total variation denoising and revised PSF model. The performance of these approaches are compared to the state-of-the-art technique.

Background

Smaller PSF

One approach is to use a reconstruction filter that underestimates the true PSF. This approach, originally referred as the resolution kernel method [58], was framed as a reconstruction algorithm that estimated a desired blurred version of the object, and not the object itself, thus utilizing underestimated resolution widths. The approach is very effective at suppressing edge artifacts [66]. Watson [67] suggested allowing a degree of underestimation of the PSF. The thought was that direct use of measured PSF values within reconstruction actually overestimated the PSF because reconstructions include additional "numerical" mechanisms of blurring, primarily due to image discretization and the projection operations. Watson proposed a first order approximation to estimate the "numerical" blur and subsequently the amount by which modeled PSF had to be underestimated with respect to the measured PSF. Nonetheless, this cannot entirely explain the observed edge artifacts, because in a number of works the "true" PSF actually had the exact same structure as the model [68].

Image Filtering

Snyder proposed to estimate a blurred version of the true object, which does not contain the high frequencies unavailable in the data [58]. This is achieved by using a resolution kernel to modify the PSF kernel used in reconstruction, or equivalently through under-modeling PSF in reconstruction. Similar methods are also suggested in [56]. However, these mitigation methods potentially lead to resolution degradation, thus reducing the benefits of PSF modeling.

Frequency Modulation

Performing object-specific modulation transfer analysis, Tong et al. [66] attempted to determine the amplified frequency band in the Fourier domain corresponding to ringing artifacts at the edges, which were shown to be stable for phantoms of different sizes and contrast levels. A band suppression filter was designed to attenuate frequencies thought to be related the edge artifacts. This technique achieved enhanced resolution performance relative to a simple low-pass filter. Still, images appeared smoothed, with less overall sharpness.

Regularization Prior

The most promising approach thus far was proposed by Rapisarda et al. [69] which is based on a Bayesian formulation of the iterative reconstruction algorithm. The maximum a posteriori (MAP) estimate is used instead of MLEM. This includes an a priori probability term that is based on a local image gradient. Rapisarda proposed the following iterative MAP estimate:

$$\lambda_b^{k+1} = \frac{\lambda_b^k}{BP_b[1-\alpha D_b \lambda_b^k]} BP_b \frac{y_d}{P_d \lambda_{b'}^k} \qquad (5.1)$$

where $\alpha>0$ weights the contribution of the value $D_b$ at pixel b of a regularization prior:

$$D[\lambda] = \nabla \cdot \left( \phi'(|\nabla \lambda|) \frac{\nabla \lambda}{|\nabla \lambda|} \right) \qquad (5.2)$$

The term $\varphi'(x)$ is called the variational prior and is based on a modification of the generalized p-Gaussian:

$$\phi'(x) = \begin{cases} x^{(p-1)} & x < \delta \\ 1 - \frac{d(d+\delta)}{d+x} & x \geq \delta \end{cases} \qquad (5.3)$$

where $d=(1-\delta^{P-1})$ with d being a gradient threshold. The gradient at each voxel location of the image estimate is used to locally switch between two denoising behaviors. If the local gradient is greater than the specified threshold $\delta$ a modified prior that better preserves edges (i.e. less smoothing), otherwise the generalized p-Gaussian prior is used whose smoothing effect is stronger than a Gaussian TV prior.

Limitations

While prior approaches tend to reduce ringing artifact, this comes at an expenses of image resolution, and a reduction in theoretically attainable resolution gains from resolution modeling. Furthermore, none of the existing methods have studied over-enhancement artifact and hot-spot artifact, and therefore quantitative performance for small structures cannot be inferred from these studies. An important use of resolution modeling is to enable detection and quantification from structures that previously was not possible with standard MLEM. It is toward this goal that PSF artifact was studied and compensation methods were developed with specific focus on quantification accuracy.

Described herein is three new resolution recovery and PSF artifact suppression approaches. The first is a locally weighted denoising strategy with edge preservation. The second is, for the first time, the use of a variable PSF model to reduce hot-spot artifacts. Finally, an integrated method that unifies these two approaches. After introducing the methodology and preliminary analyses with simulated data, extensive evaluation with real data acquired of an ACR phantom is detailed in order to understand performance characteristics. The application of this approach to clinical data is described in Example 4.

Locally Weighted Total Variation Denoising

A new locally weighted regularization method designed specifically for PSF artifact suppression, where local weights are empirically derived from the image and incorporated directly into the iterative reconstruction process is described. By 'learning' regularization weights from properties of the data related PSF artifact formation, over-enhancement and ringing artifacts are effectively compensated and prevented as they are formed during the iterative reconstruction process.

PSF-MLEM (Assuming Pre-Corrected Data)

The maximum likelihood estimate of the PET images is typically computed using the maximum likelihood expectation maximization (MLEM) algorithm [50], where the iterative update equation is $$\lambda_b^{k+1} = \frac{\lambda_b^k}{BP_b 1} BP_b \frac{y}{P_d \lambda_{b'}^k} = \lambda_b^k u_b^k \quad (5.4)$$

$$P_d(\bullet)_b = \Sigma[(\bullet)]_b p_{bd} \quad (5.5a)$$

$$BP_b(\bullet)_d = \Sigma[(\bullet)]_d p_{bd} \quad (5.5b)$$

Figure 14:
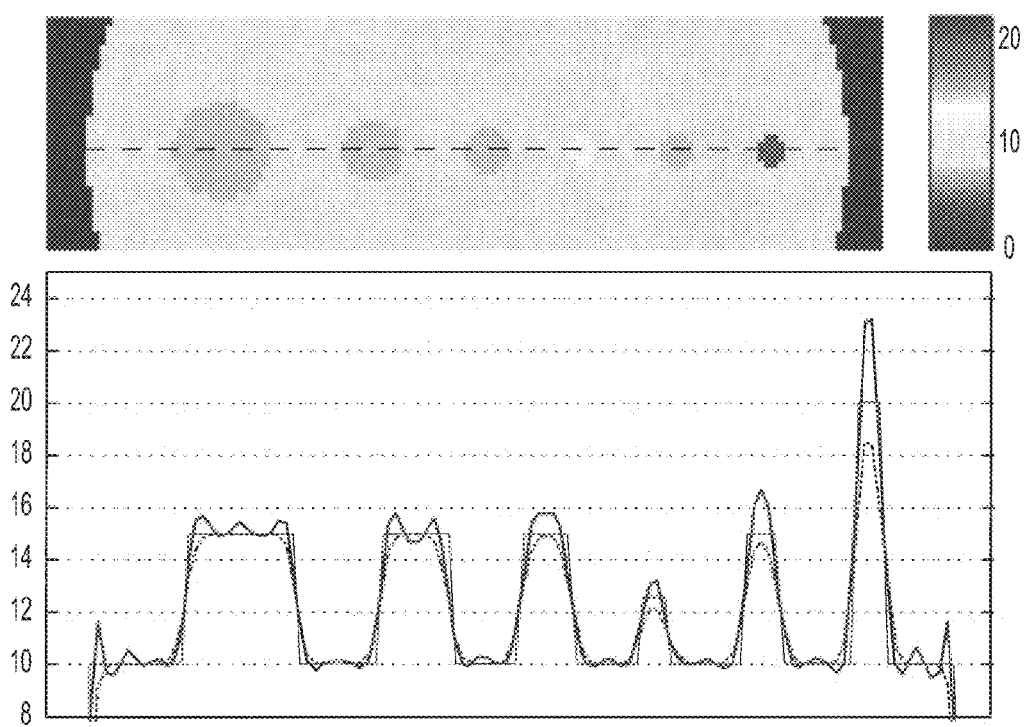
FIG. 14 shows simulated cylinder reconstructed with MLEM (dashed line) and PSF-MLEM. In small 8 mm cylinders MLEM underestimates the activity. PSF-MLEM yields better recovery in 8 mm cylinders but results in contrast and size dependent over-estimation and ringing artifacts.

$_b$ $\lambda_b^k$ represents the counts in a voxel b within the image $\lambda$ at iteration k, $y_d$ is the measured projection recorded as number of counts along the line of response (LOR) d, and 1 is a unit matrix of the same size as $y_d$. The forward projector of (5.5a) and backward projector of (5.5b) projectors contain a weight matrix $p_{bd}$ that links the voxel b and LOR d. The term $BP_b 1$ is called the geometric sensitivity, and can be pre-computed prior to reconstruction. Projection terms applied at iteration k can be combined into a multiplicative updating term $u_b^k$. Following [69], incorporating the PSF model into Eq. (5.4a) is achieved by modifying the projectors as follows:

$$P_d(\bullet)_b = \Sigma[(\bullet)*PSF]_b p_{bd} \quad (5.6a)$$

$$BP_b(\bullet)_d = PSF^T*\Sigma[(\bullet)]_d p_{bd} \quad (5.6b)$$

where PSF represents the PSF kernel and * is a discretized convolution operator as defined in the Appendix of [69]. For a symmetric kernel, PSF=PSF$^T$ MLEM reconstruction that utilizes (5.6a) and (5.6b) will be here referred to as PSF-MLEM. The problem of PSF artifacts can be seen more clearly in FIG. 14, where MLEM and PSF-MLEM were used to reconstruct a simulated cylindrical phantom that consisted of 24 mm, 16 mm, 12 mm, and three 8 mm cylinders with different contrast ratios (CR). Good recovery is seen with MLEM for the larger 12-24 mm cylinders while contrast-dependent underestimation is visible for 8 mm cylinders. PSF-MLEM enables recovery of activity but introduces object size dependent ringing artifacts and overcompensates the intensities in 8 mm cylinders.

TV-PSF-MLEM

Following the notations above, at each iteration of (5.4) the total variation problem amounts to finding an estimate image $\lambda^{\wedge k}$ that satisfies the following optimization problem:

$$\hat{\lambda}^k = \min \frac{1}{2}\|\lambda^k - \hat{\lambda}^k\|^2 + \beta |\nabla \hat{\lambda}^k| \quad (5.7)$$

where |•| and ||•|| are the $L_1$ and $L_2$ norms, respectively and $\beta$ is a regularization weight. TV optimization will be implemented in Matlab. The classical framework given by (5.7) minimizes TV over the whole image whereas PSF modeling introduces very localized artifacts. Therefore, it is proposed to locally integrate the TV filtered estimate $\hat{\lambda}_b^k$ into $\lambda_b^k$, re-expressing $\hat{\lambda}_b^k$ as:

$$\hat{\lambda}_b^k = \lambda_b^k + (\hat{\lambda}_b^k - \lambda_b^k) = \lambda_b^k + \Delta\hat{\lambda}_b^k \quad (5.8)$$

where, represents the net change in each voxel b on the image estimation after TV regularization. Since TV filtering is only needed at specific voxel locations it is proposed to locally constrain TV enforcement by introducing a local weight on each TV filtered voxel, defining:

$$\hat{\lambda}_b^k = \lambda_b^k + w_b \Delta\hat{\lambda}_b^k \quad (5.9)$$

where $\lambda_b^k$ is the locally weighted TV estimated and $\omega_b$ is a spatially-varying weight imposed on the net change of each voxel. Note that if $\omega_b=1$ then $\hat{\lambda}_b = \hat{\lambda}_b$ corresponding to the classical solution to (5.7). The approach is summarized in Algorithm 5.1).

---

Algorithm 5.1 TV-PSF-MLEM algorithm
Data: N,$\lambda_o$,l,k = 0, Result: $\lambda_b^N$, Initialize: $\lambda_b^0$

---

MLEM step:

--- while k ≤ l do
$\lambda_b^{k+1} \leftarrow \lambda_b^k$ from (5.41), k ← k + 1
TV-PSF-MLEM step:

--- while (l + n) ≥ k > l do
$\lambda_b^{k+1} \leftarrow \lambda_b^k$ from (5.4, 5.6a, 5.6b)
$\hat{\lambda}_b^{k+1} \leftarrow \lambda_b^{k+1}$ from (5.8)
$\hat{\lambda}_b^{k+1} \leftarrow \hat{\lambda}_b^{k+1}$ from (5.9)
$\lambda_b^{k+1} \leftarrow \hat{\lambda}_b^{k+1}$, k ← k + 1

---

Learning Local Weights from Data.

Figure 15:
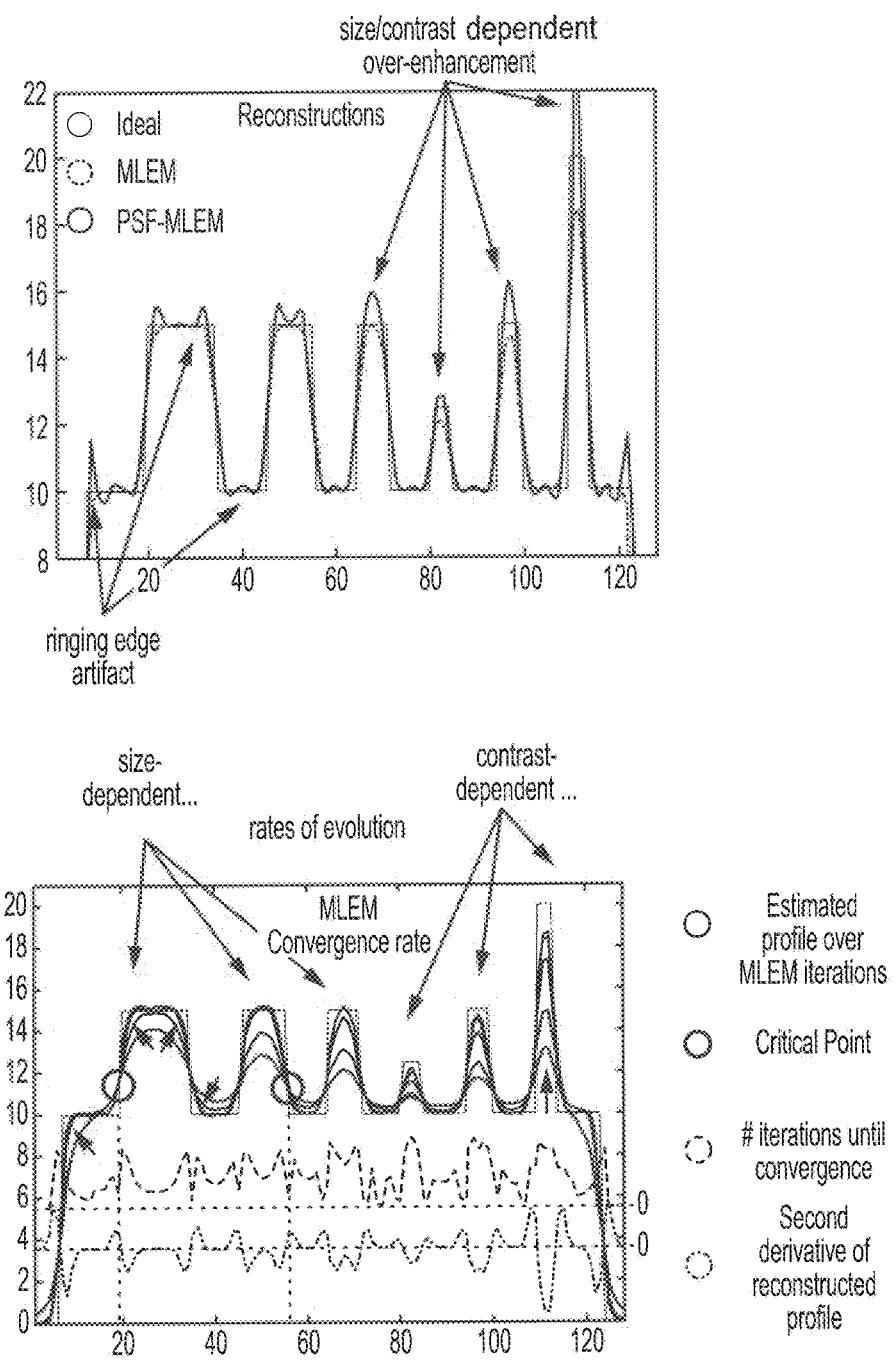
FIG. 15 shows and illustration of how $\lambda^k$ evolves and its relation with the image structure. Horizontal midline profile of ideal phantom (thin solid line). Reconstructed (MLEM) profiles over several iterations of (5.4) (thick solid lines). Number of iterations to convergence (dashed line). Second derivative of the blurred phantom's profile (dotted line). Arrows show the dominant direction of evolution of reconstructed profiles over the iterations. Circles highlight the localization of the inflection points of the reconstructed profiles, which take a relatively small number of iterations to converge.

A local weighting scheme needed to be designed such that flat homogenous regions and edges were preserved from the original MLEM estimation, while edge ringing was reduced with TV filtering. Instead of filtering the current estimate relying on its edge maps, a novel approach was chosen, to see if it was possible to exploit the information learned on the evolution of $C_P^{PK}$ (t|$\theta^{PK}$) over the iterations of the MLEM reconstruction. FIG. 15 shows, on the phantom's horizontal midline profile, the evolution of $\theta^{PK}$ over several MLEM iterations (toward convergence), as well as the number of iterations required for each voxel along the profile to converge and the second spatial derivative of the MLEM profile at convergence.

The weighting strategy was based on a few observations: (a) each cylinder's edges have inflection points (defined as zero-crossing of the second spatial derivative) that spatially converge very quickly, (b) the interiors of flat regions converge quickly, while edge refinement continues for a long time (as the peak expands while the support shrinks); (c) the convergence rate for the 8 mm cylinders is contrast dependent, and faster for the cylinder with CR 1.25:1 versus 1.5:1, and (d) while the rate of convergence globally mimics the second derivative of the reconstructed profile, there are many local differences. This indicates that there can be unique information contained in the evolution of the MLEM reconstructions that cannot be derived directly from the structure of the reconstructed image.

Figure 16:
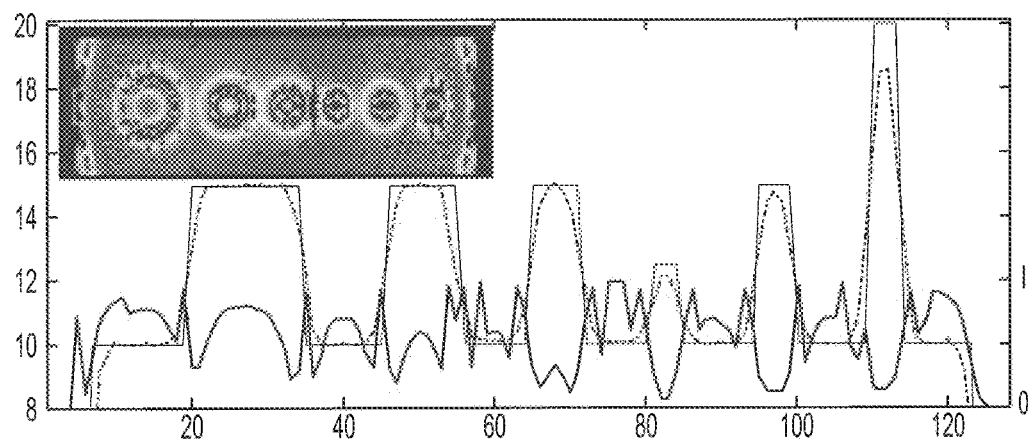
FIG. 16 shows horizontal profiles through the horizontal midline of ideal phantom (thin solid line), MLEM reconstruction at convergence (dashed line) and spatial TV weight $w_b$ (thick solid line), from the spatial weight map (top left). Left and right axes are for the profiles and $w_b$, respectfully.

It was proposed to use the convergence rate, derived from the value of $u_b$ from (5.4), for the definition of the spatial weights $w_b$, as detailed in [70, 71], using the following values:

$$c_b = \min_k |1 - u_b^k| \leq \varepsilon \quad (5.10)$$

$$w_b = 1 - \frac{c_b - \min(c)}{\max(c - \min(c))} \quad (5.11)$$

where $c_b$ is defined as the earliest MLEM iteration k at which voxel b converges (in practice when $u_b \sim 1$), $w_b$ is derived by normalizing $c_b$ such that $0 \leq w_b \leq 1$, and c is a convergence threshold (empirically determined to be $\varepsilon=1\times10^{-3}$). FIG. 16 shows the weights calculated from MLEM of a noiseless phantom.

Figure 17A:
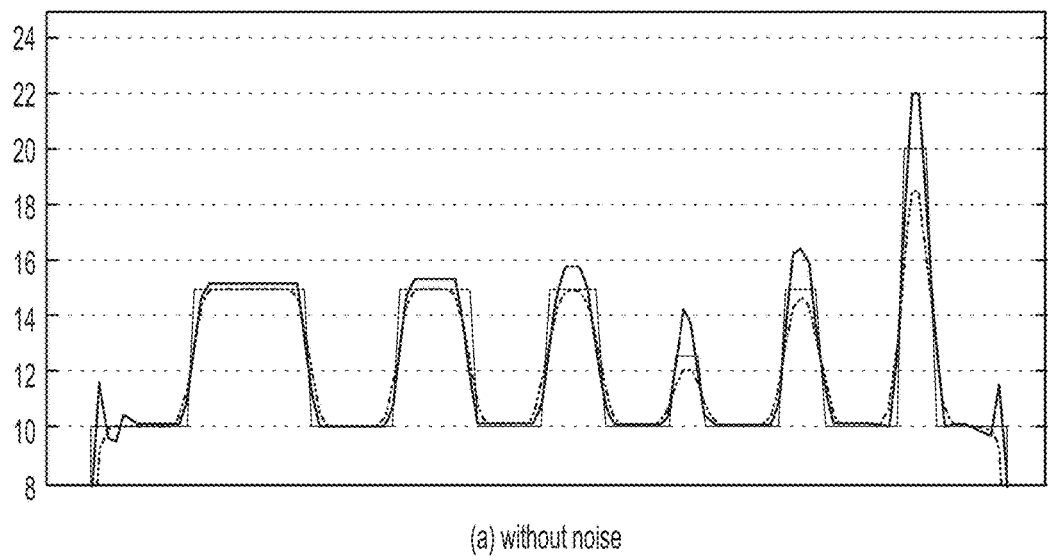
FIGS. 17A-17B show TV-PSF-MLEM reconstruction with oracle weights for simulated phantom without (a) and with (b) added Poisson noise to the sinogram. (thin solid line) Horizontal profile lines through the center of the image are shown for ideal phantom, (dashed line) 200 iterations of MLEM using (5.4), and (thick solid line) 500 iterations of TV-PSF-MLEM with oracle weights initialized with 200 iterations of MLEM of the oracle weights although local differences in magnitude exist.
Figure 17B:
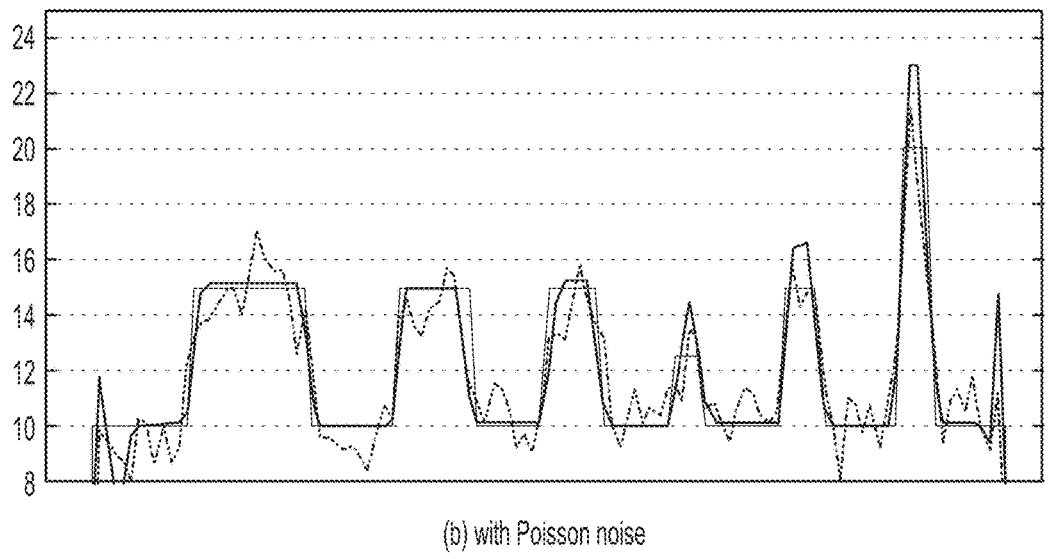

From (5.11) it can be seen that weights depend on the convergence rate of individual voxels b and will therefore be highly affected by the presence of noise. To adapt the approach to noisy data, the oracle approach was first studied where ideal weights (derived from the noiseless case) were applied to TV-PSF-MLEM reconstruction of the noisy sinograms, corrupted with Poisson noise. Results, illustrated in FIGS. 17a-b, show that reconstructions after N=500 iterations were similar with and without noise, with good suppression of noise and ringing artifact, but with some over enhancement of the 8 mm cylinders in both cases. To approximate these oracle weights using the iterative MLEM reconstructions from the noisy data, it was proposed to use a local spatial aggregation of the convergence rates estimates $u_b^k$ from (5.1), using the average kernel of size n×n within n=3, along with a modified value for ε: ε=5×10$^{-4}$.

Thus, the calculation of the parameter $c_b$ of (5.11), on noisy data becomes:

$$u_b^k = \sum_{b \in N_b} u_b^k \tag{5.12}$$

where $N_b$ is the 3×3 neighborhood around voxel b, and replaces $u_b^k$ in Eq. (4.47) for noisy data.

Figure 18:
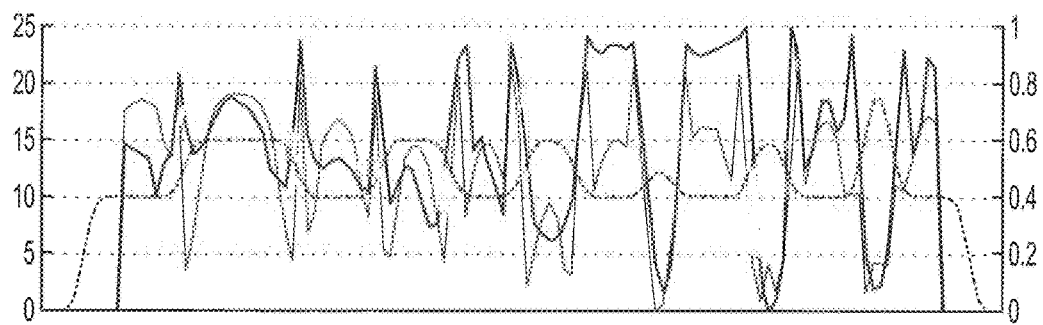
FIG. 18 shows local TV weights calculated using (5.11) with noiseless data (thin solid line) and using (5.12) with noisy data (thick solid line). The profile of the noiseless MLEM reconstruction (dashed line) is shown as a reference. Left and right y-axes correspond to MLEM pixel intensities and weights $w_b$, respectively. The general shape of the noisy weights mimics that of the noiseless weights.

FIG. 18 illustrates the spatial TV-weights $w_b$ obtained with this approach for noiseless and noisy measures.

gPSF-MLEM Algorithm

As described above the introduction of the PSF model in the MLEM iterative reconstruction introduces ringing and over-enhancement artifacts.

Figure 19:
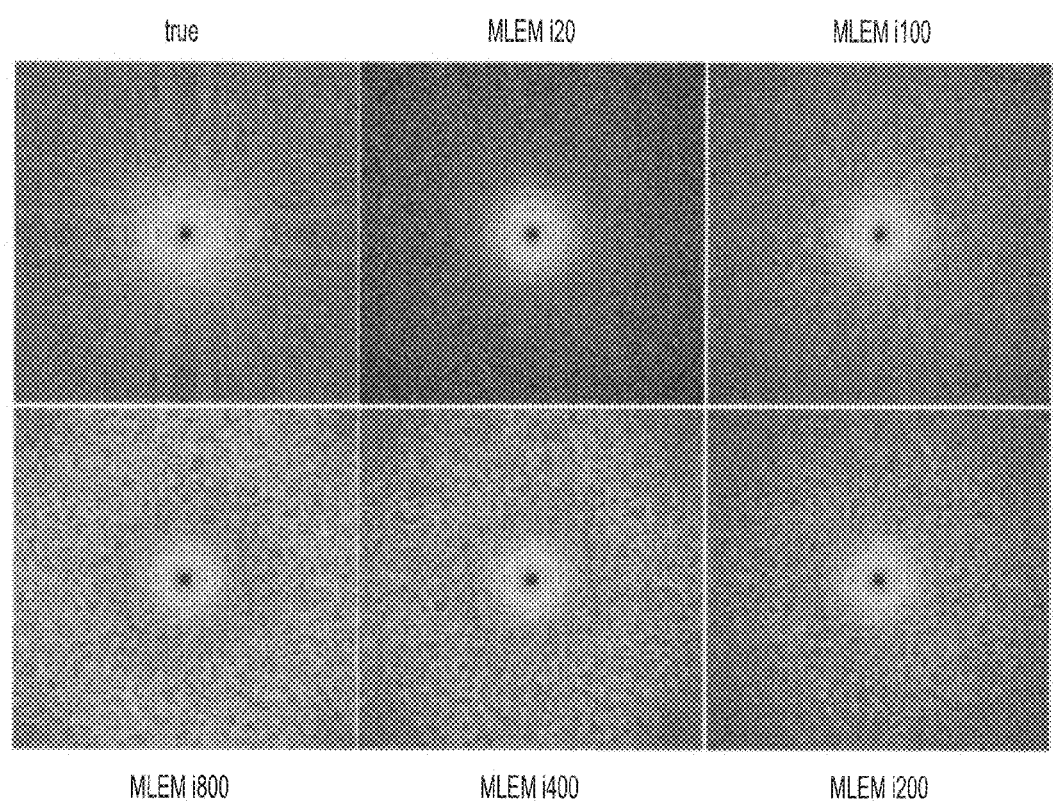
FIG. 19 shows 2D Fourier spectrum images for several iterations (i) of MLEM.

To mitigate these effects a TV regularization scheme has been introduced which controls well these two artifacts. However, TV-PSF-MLEM remains sensitive to the choice of the number of iterations at which to stop the reconstruction. It is well known that standard MLEM and PSF-MLEM does not converge in the presence of noise without regularization, as it progressively amplifies noise with increasing iterations [45]. This can be seen by comparing the 2D Fourier spectra of the true (simulated) and progressive iterations of MLEM estimates (FIG. 19). MLEM first recovers low-frequency components, and then progressively recovers higher frequencies, but at the cost of reconstructing noise. When reconstructing noisy sinograms, MLEM and PSF-MLEM has to therefore be stopped rather early, sacrificing good contrast recovery capabilities.

By observing the 2D Fourier spectrum for PSF-MLEM significant attenuation of high frequencies and enhancement of low frequency coefficients with increasing iterations can be seen. The reason for these effects can be seen from the reformulated PSF-MLEM equations of (5.4) incorporating projectors from (5.6a) and (5.6b):

$$\lambda_b^{k+1} = \underbrace{\frac{\lambda_b^k}{PSF^T * \sum_d 1_d p_{bd}}}_{\text{Part C}} PSF^T * \underbrace{\sum_d \left( \frac{y}{\sum [\lambda^k * PSF]_{b'} p_{b'd}} \right)_d p_{bd}}_{\text{Part B}} \tag{5.13}$$

Figure 20:
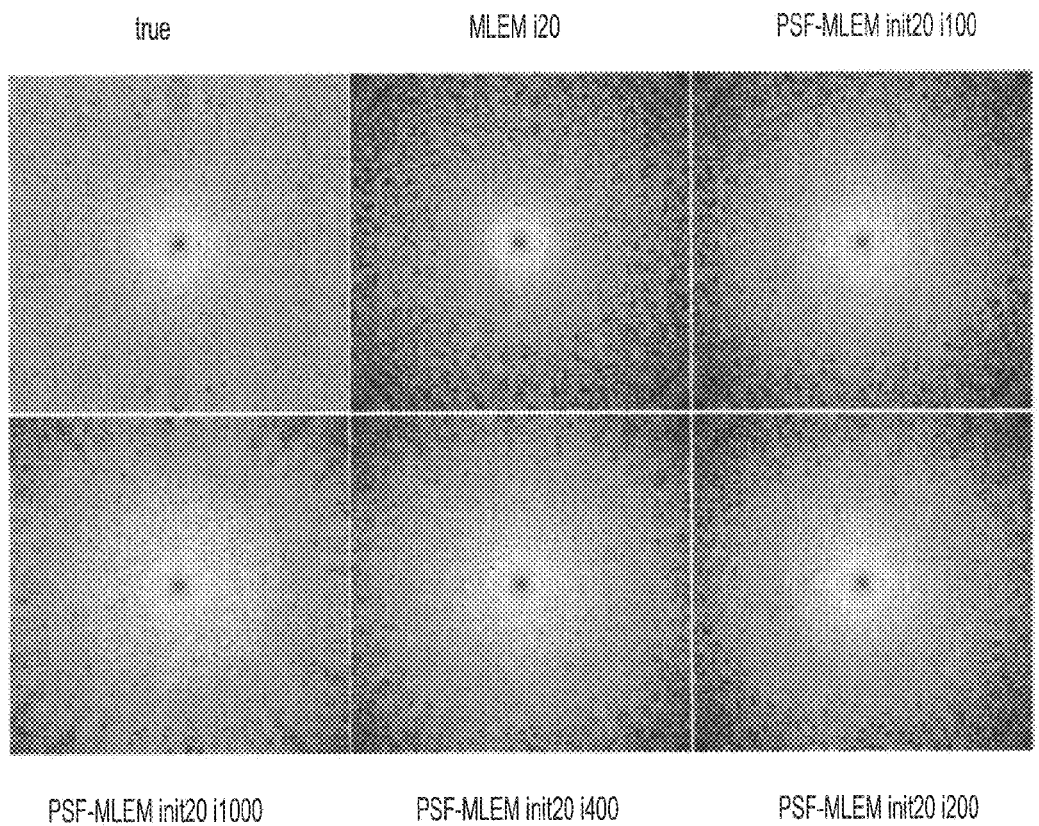
FIG. 20 shows 2D Fourier spectrum images for several iterations (i) of PSF-MLEM.

In Part A, it can be seen that the current image estimate $\lambda^k$ is convolved with the PSF. This effectively low pass filters the frequencies of the estimate image determined by the FWHM of the PSF kernel. The projection estimate sinogram is compared directly with the measured sinogram data $y_d$. As iterations progress the high frequency noise present in $y_d$ is transferred into low-frequencies of the band-limited estimate. In fact, increasing low frequency noise can be seen in 2D Fourier spectrums of the PSF-MLEM reconstruction (FIG. 20).

Figure 21:
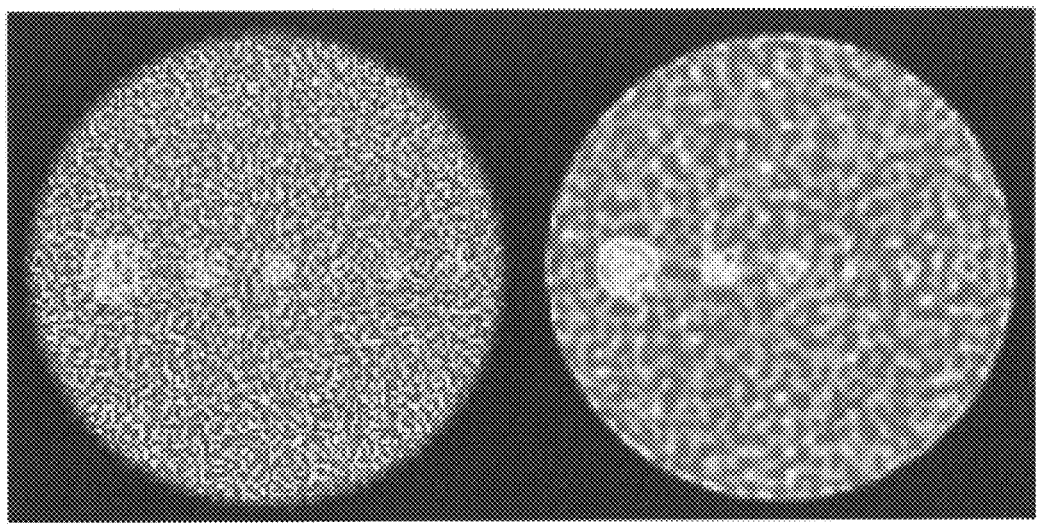
FIG. 21 shows an illustration of MLEM and PSF-MLEM after 800 iterations. PSF-MLEM was initialized after 20 iterations of MLEM (init20). Over-enhancement, hot-spot artifacts, and the cluttered background noise pattern are clearly visible on the PSF-MLEM image.
Figure 22A:
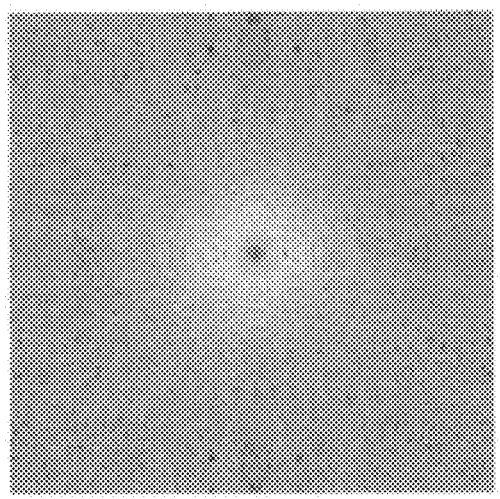
FIGS. 22A-22D show 2D Fourier spectrums from (a) noiseless simulated phantom and after 400 iterations of (b) MLEM, (c) PSF-MLEM, (d) gPSF-MLEM. Both PSF-MLEM and gPSF-MLEM were initialized with 20 iterations of MLEM.
Figure 22B:
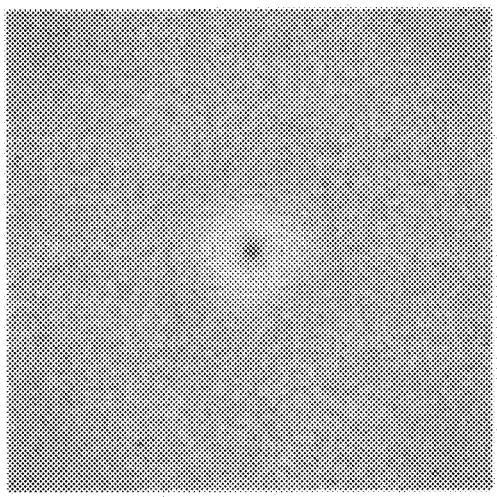
Figure 22C:
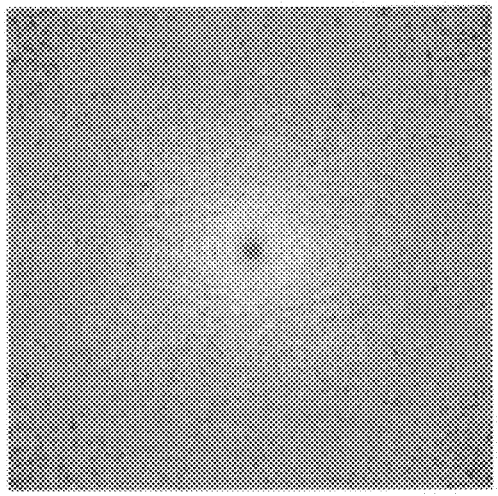
Figure 22D:
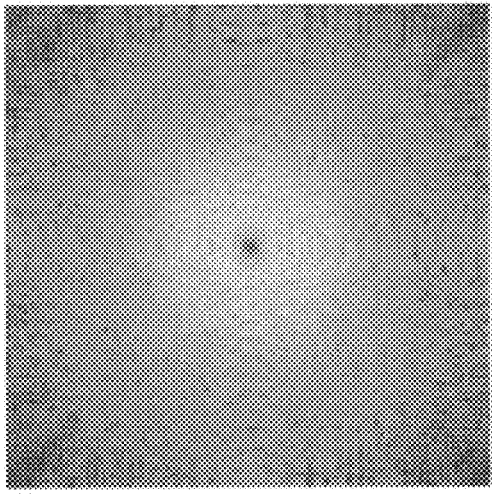
Figures 23A, 23B, 23C, 23D:
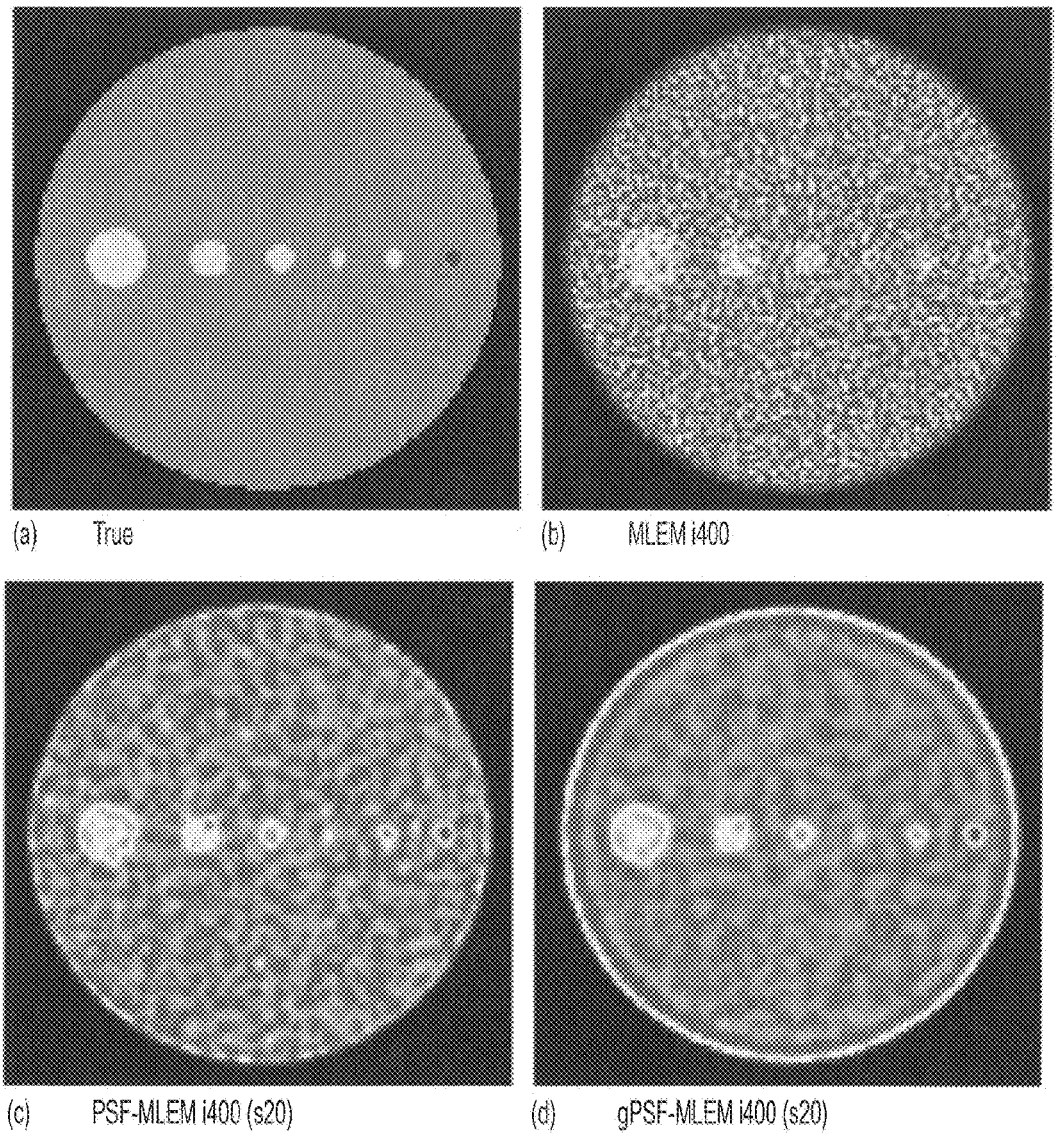
FIGS. 23A-23D show Results from 400 iterations of MLEM, PSF-MLEM and gPSF-MLEM. PSF-MLEM and gPSF-MLEM were initialized with 20 iterations of MLEM.

Such high-to-low frequency noise transfer induces coupling of noisy voxels with neighboring voxels, leading to formation of unnatural, isolated and clustered, hot-spot artifacts. Such artifacts can easily be seen even in simulated data with a small amount of Poisson noise added to the sinogram, as shown in FIG. 21. It can be seen that the clustered noise pattern in the PSF-MLEM reconstructed image is not present with MLEM. Moreover, there does not appear to be a one-to-one relationship between the PSF-MLEM 'hot spots' and background noises pattern and the speckled noise structure of the MLEM estimate. In data acquired from a real scanner these artifacts could only increase due to added noise contributions from randoms, scatter, and attenuation effects.

In order to help reduce the formation of 'hot spot' artifacts a novel approach to control the spread of noise across the frequency spectrum was developed. Instead of using a fixed PSF kernel, a much larger FWHM PSF is started with and gradually evolved, by decreasing, the FWHM at each iteration of the PSF-MLEM reconstruction procedure. Since the high-frequency noise component will be mostly removed by convolution of the image estimate with a large FWHM Gaussian function, the image estimate is able to take form gradually without the undue of effects of noise in early iterations. As iterations progress, and FWHM of the PSF decreases, the object will be gradually enhanced as higher spatial frequencies are introduces into the image estimate. This gradual PSF-MLEM (or gPSF-MLEM) approach is terminated when the desired FWHM is reached. The desired value is the measured FWHM of the system.

PSF-MLEM also introduces some specific artifacts, looking like correlated noise cluttered patterns in space and cluttered low-frequency coefficients in Fourier. To prevent such noise reconstruction, it was proposed to use gradual PSF introduction, but from large to small kernel size, rather than the inverse. Using a large kernel first enables to update the non-noisy pre-approximation provided by the MLEM with a low-passed update map. The PSF kernel size support is then iteratively reduced to the size of the true PSF kernel as provided by the scanner manufacturer. This iterative reduction enables to use more detailed update maps with more spatial details at later iterations when the data and the reconstructed sinograms are in better agreements, despite the noise. The ability of the proposed gradual PSF (denoted gPSF) scheme in limiting noise reconstruction is clearly illustrated where a FT spectrum is seen very well constrained in the high frequencies.

To formalize the approach the PSF kernel is first parameterized according to the FWHM as follows:

$$PSF(x, y, z) = \frac{1}{\sigma^3 (2\pi)^{3/2}} \exp\left(-\frac{x^2 + y^2 + z^2}{2\sigma^2}\right) \tag{5.13}$$

$$\sigma = \frac{FWHM}{2\sqrt{2\ln 2}}$$

Next, a functional form for the FWHM is created such that it varies with iterations, and incorporate this function directly into the symmetric 3D Gaussian PSF model:

$$PSF^k(x, y, z) = \frac{(2\sqrt{2\ln 2})^3}{f(k)^3 (2\pi)^{3/2}} \exp\left(-\frac{4\ln 2}{f(k)^2}[x^2 + y^2 + z^2]\right) \tag{5.14}$$

-continued $$f(k) = \begin{cases} S & k < L \\ S - \dfrac{(k-1)(S-R)}{n} & k \leq L+N \end{cases}$$

where, $f(k)$ is the FWHM at iteration k, l is the number of iterations of standard MLEM, n is the number iterations it takes to linearly decrease the FWHM from the starting value S to the final value R in mm. Finally, the gradual PSF (gPSF) procedure is expressed as follows:

$$\lambda_b^{k+1} = \frac{\lambda_b^k}{\sum 1_d p_{bd}} \sum \left( \frac{y_d}{\sum [\lambda^k]_{b'} p_{b'd}} \right) p_{bd} \qquad (5.15)$$

$$\lambda_b^{k+1} = \frac{\lambda_b^k}{(PSF^k)^T * \sum 1_d p_{bd}} (PSF^k)^T * \begin{cases} k < N \\ (L+N) \geq k \geq L \end{cases}$$

$$\sum \left( \frac{y_d}{\sum [\lambda^k * PSF^k]_{b'} p_{b'd}} \right)_d p_{bd}$$

The choice of L (number of MLEM iterations) and N (number of steps) are to be empirically determined on an application specific basis.

Applying the gPSF-MLEM approach to the simulated phantom, using S=10 mm, R=4.5 mm (the true system FWHM), a 2D Fourier spectrum is seen that is quite different from both MLEM and PSF-MLEM (FIGS. 22a-d). The low- and high-frequency speckled pattern in the Fourier spectrum is no longer present. In fact, the low frequency region better resembles the true spectrum.

FIGS. 23a-d show that MLEM reconstruction is quite noisy. PSF-MLEM introduces low-frequency noise pattern and produces a hot-spot artifact in the second largest cylinder. These artifacts are markedly reduced with gPSF-MLEM while the contrast of the hot cylinders are maintained. The cylinders are more rounded and the low-contrast 8 mm cylinder stands out more against the background. The drawback of gPSF-MLEM is a visible increase in ringing artifact.

TV-gPSF-MLEM

Two strategies have been outlined to mitigate PSF artifacts. TV-PSF-MLEM, locally weighted total variation denoising approach designed to reduce ringing and over-enhancement, and gPSF-MLEM to help reduce 'hot-spot' artifacts and background noise. The approaches have been unified into a single algorithm (Algorithm 4.2). Several variables must be pre-specified: L (number of MLEM iterations), S (starting FWHM of the PSF), R (terminal FWHM of the PSF), N (number of gPSF steps), as well as the initial estimate $\lambda_b^0$. Typically $\lambda_b^0$ is simply uniform image of ones. The total number of iterations of the algorithm is calculated as L+N. With both approaches, one must also chose c (convergence threshold), and β (TV regularization parameter).

Algorithm 4.2 TV-gPSF-MLEM algorithm
Data: N,$\lambda_o$,S,R,L,β,k = 0, Result: $\lambda_b^N$, Initialize: $\lambda_b^0$ MLEM step:

while k ≤ L do
$\lambda_b^{k+1} \leftarrow \lambda_b^k$ from (5.4), k ← k + 1
TV-gPSF-MLEM step:

while (L + N) ≥ k > L do
$\boldsymbol{\lambda}_b^{k+1} \leftarrow \lambda_b^k$ from (5.15)
$\hat{\lambda}_b^{k+1} \leftarrow \boldsymbol{\lambda}_b^{k+1}$ from (5.8)

Algorithm 4.2 TV-gPSF-MLEM algorithm
Data: N,$\lambda_o$,S,R,L,β,k = 0, Result: $\lambda_b^N$, Initialize: $\lambda_b^0$ $\lambda_b^{k+1} \leftarrow \hat{\lambda}_b^{k+1}$ from (5.9)
$\lambda_b^{k+1} \leftarrow \lambda_b^{k+1}$, k ← k + 1

Experiments and Performance with Simulated Data

In this section sensible parameter configurations are investigated using a simulated cylindrical phantom on real data from an ACR phantom. To get a sense of performance improvement with this approach results to a state-of-the-art approach Rapisarda method were also compared.

Simulation Setup and Performance Metrics

Figure 24:
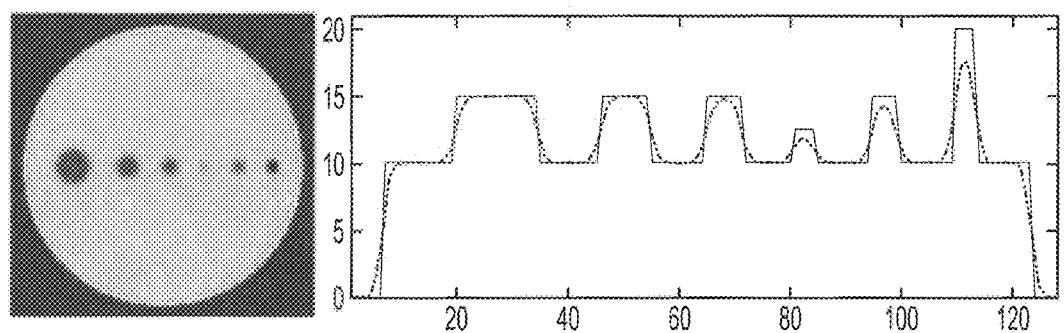
FIG. 24 shows cylindrical phantom blurred with a 4.5 mm full width half maximum (FWHM) Gaussian kernel (left) and horizontal profile of pixel intensities through the midline (right) on: the actual phantom (dashed line) and the ideal phantom (thin solid line), shown for reference.

All numerical simulations was generated using the Software for Tomographic Image Reconstruction (STIR) open source C++ software (v2.2) [72]. The modified projectors of (5.6a) and (5.6b) were incorporated with C++ routines within STIR. A 200 mm diameter cylindrical phantom object was simulated, with a background intensity equal to 10, three hot spots of diameter 25 mm, 16 mm, 12 mm with a 1.5:1 CR, and three 8 mm diameter hot spots with CR of 1.25:1, 1.5:1 and 2:1, respectively. The phantom was blurred with a symmetrical 4.5 mm FWHM Gaussian kernel to simulate the resolution loss due to physics inherent in the ECAT HR+ scanner (Siemens/CTI). FIG. 24 shows the proposed simulated and blurred phantom images as specified above.

The following measures were used to assess performance:

Visual inspection to compare contrast, signs of visible artifact, and recovery of small structures.

Quantitatively evaluate contrast recovery using the recovery coefficient (RC) measure, defined as $$RC = \sum_{b \in \Omega_{ROI}} \lambda_b^{recon} \Big/ \sum_{b \in \Omega_{ROI}} \lambda_b^{true} \qquad (5.16)$$

where the $\Omega_{ROI}$ is the region of interest (e.g. inside a cylinder), $\lambda^{recon}$ is the reconstruction being evaluated and $\lambda^{true}$ is the original non-blurred (ideal) phantom. RC measures can be above or below one and RC=1 for a perfect reconstruction.

Noiseless Simulations

Figure 25:
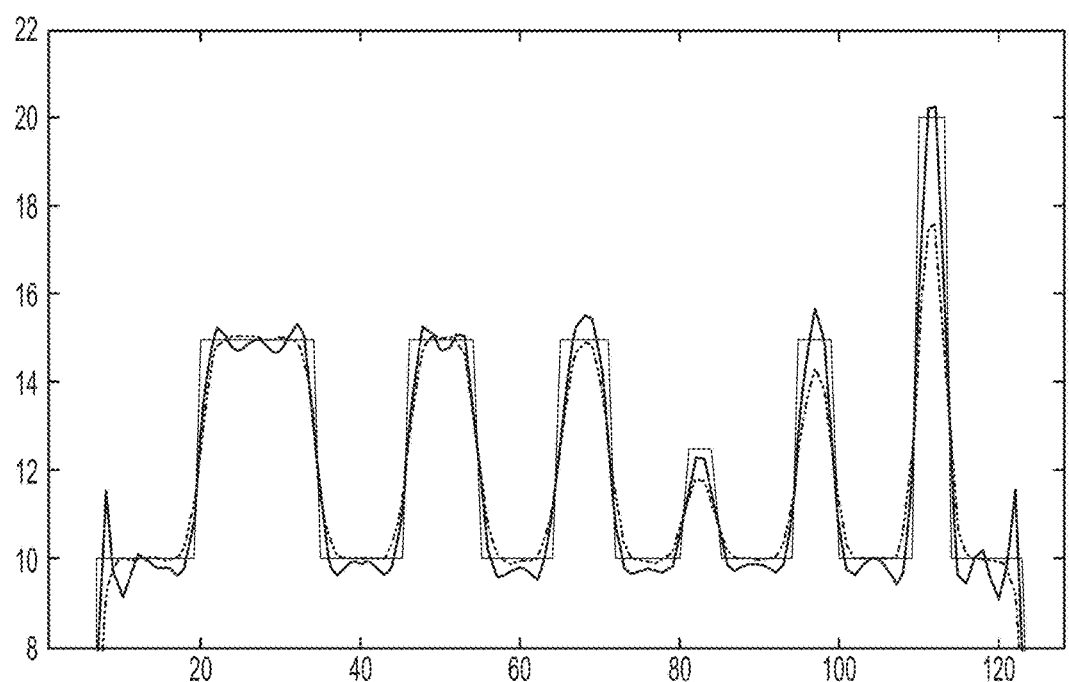
FIG. 25 shows horizontal midline profile through the ideal (thin solid line), MLEM (dashed line) and PSF-MLEM (thick solid line) reconstructions.

To evaluate ringing artifacts, the resulting images were visually compared. For the PSF-MLEM reconstruction, results, illustrated in FIG. 25, show that MLEM had no ringing artifact (as expected), PSF-MLEM generates ringing in the background and at edges of the 25 mm and 16 mm cylinders, as well as over enhancement of the 12 mm cylinder. For the 8 mm cylinders there were contrast-dependent over- and under-enhancement.

Figure 26:
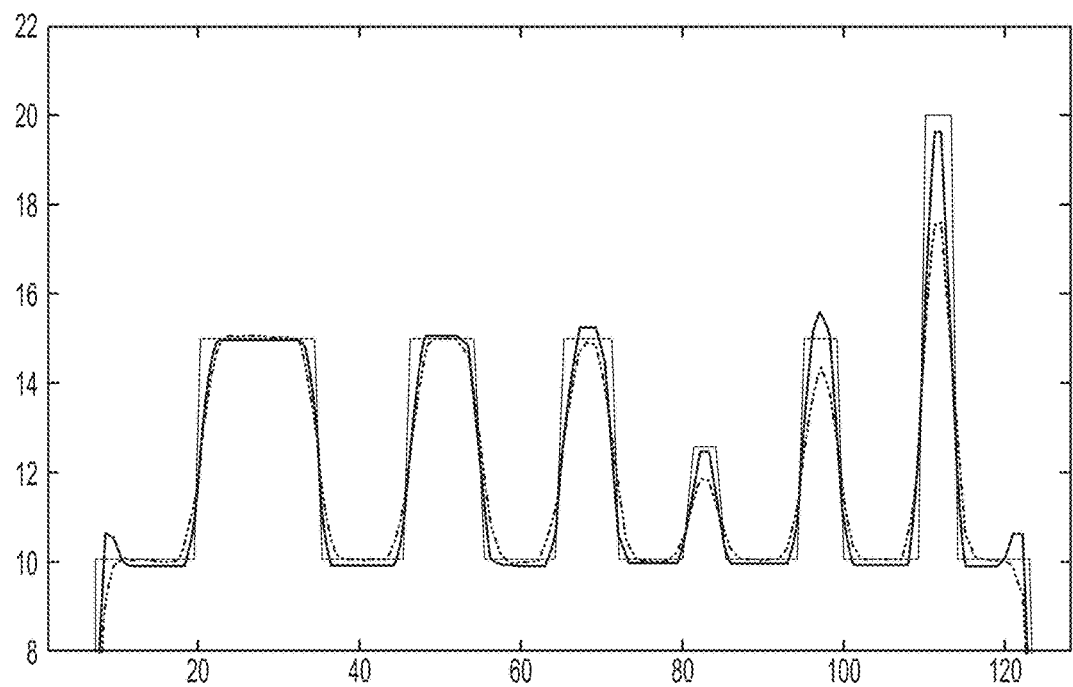
FIG. 26 shows horizontal midline profile through the ideal (thin solid line), MLEM (dashed line) and TV-PSF-MLEM (thick solid line) with $\beta=0.02$ reconstructions.

To test whether the spatially weighted TV denoising approach improved image quality, TV-PSF-MLEM was run empirically setting β=0.02. Over several experiments with β={0.005, 0.01, 0.02, 0.04} it was found that β=0.02 yielded optimal ringing suppression without degrading image quality. For the MLEM reconstruction, it was initialized with $\lambda_o$=1. The other reconstructions were initialized with the MLEM estimate. The synthetic cylindrical phantom was reconstructed (200 iterations) with the three different algorithms (MLEM, PSF-MLEM and TV-PSF-MLEM) and the RC values were measured inside each six cylinders. TV- PSF-MLEM yielded better RC measures than MLEM, and only slightly lower than PSF-MLEM, in all cylinders (FIG. 26).

Figure 27:
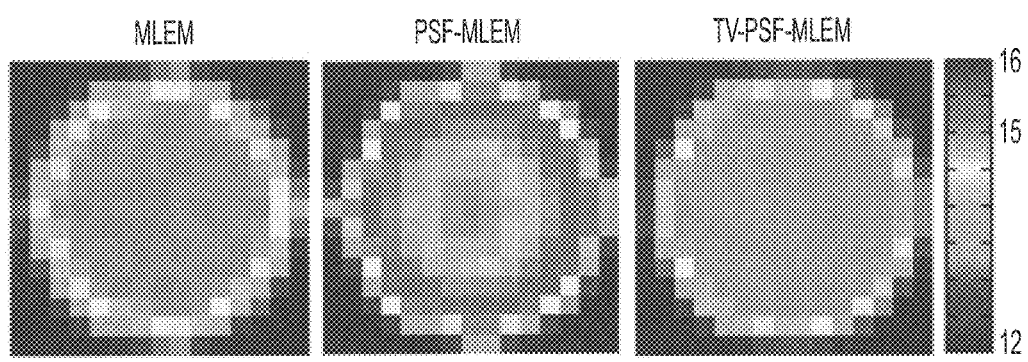
FIG. 27 shows images of the 25 mm cylinder with three reconstructions (MLEM, PSF-MLEM, TV-PSF-MLEM. TV-PSF-MLEM removes PSF-related ringing artifacts and restores homogeneity and contrast level that is similar to true phantom.

For the TV-PSF-MLEM reconstruction, ringing artifacts were suppressed on all cylinders edges. The contrast in the 25 mm and 16 mm cylinders was very well recovered, and over-estimation of the 12 mm cylinder intensity was reduced, compared to PSF-MLEM reconstruction. The contrast in the 8 mm cylinders was similar for TV-PSF-MLEM and PSF-MLEM reconstructions, demonstrating that locally-weighted TV denoising can suppress ringing within large structures while maintaining the contrast in small regions. In addition to removing ringing artifacts, TV also enforces homogeneity in large regions. This effect is illustrated in FIG. 27 in the 25 mm cylinder, where MLEM yielded a noisy image, PSF-MLEM induced heterogeneity and ringing at the edge, while TV-PSF-MLEM prevented the ringing and enforced homogeneity inside the cylinder.

The evaluation of the TV-PSF-MLEM approach on synthetic noiseless phantom shows that it maintains the good contrast recovery properties of PSF-MLEM while reducing ringing artifacts at edges.

Simulations with Added Poisson Noise

The simulations were repeated with added noise. Poisson noise was added to the measures $y_d$ using with scale factor=1 as follows:

$$y_d = \text{Poisson}(S_d \times \text{scale})/\text{scale}$$

where Poisson operator implies a random drawing from a Poisson distribution with mean Sd*scale, S is the true noiseless sinogram, $S_d$ is the value of the sinogram at bin d, and scale is the scaling factor that sets the amount of Poisson noise added.

Performance of MLEM, PSF-MLEM, TV-PSF-MLEM, and the Rapisarda method was quantitatively assessed using the recovery coefficient defined in (5.16). Experiments were with N=200 for MLEM and N=500 for TV-PSF-MLEM and Rapisarda. For TV-PSF-MLEM the regularization weight $\beta$=0.02 was used as in [71], and for the Rapisarda method parameters were set as recommended by the authors in [69]: p=1.33, $\delta$=0.3, and $\alpha$=0.002.

Figure 28:
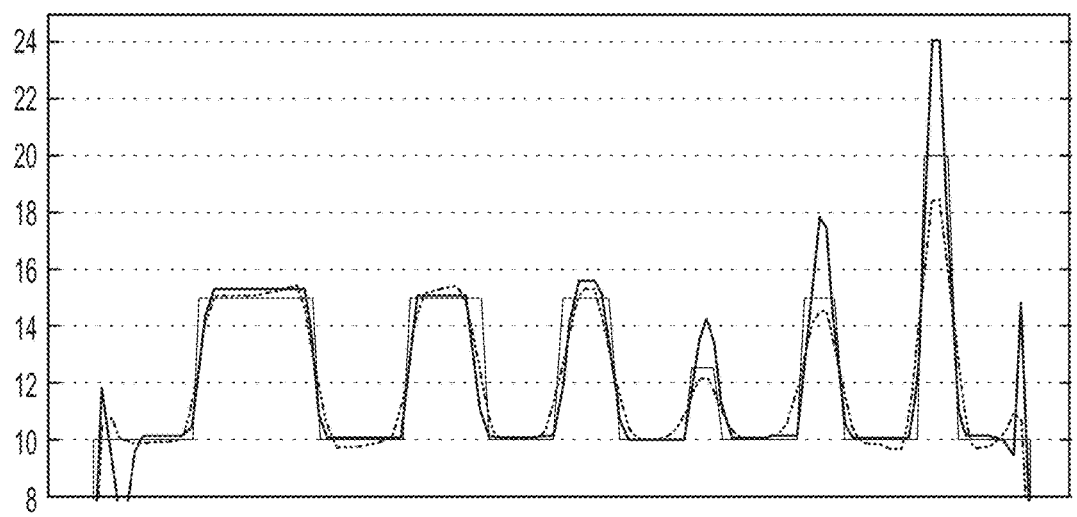
FIG. 28 shows reconstruction results on simulated phantom with Poisson noise. Center profile is shown for: (thin solid line) ideal phantom, (dashed line) 500 iterations of Rapisarda using Eq. (3) from Example 2 and (thick solid line) 500 iterations of TV-PSF-MLEM with average weights calculated using Eq. (10) from Example 2. Reconstructions were initialized with 200 MLEM iterations.

Visually TV-PSF-MLEM and Rapisarda reconstructions provide very comparable results in large cylinders ($\geq$12 mm), as seen in FIG. 28. In smaller cylinders, the Rapisarda method underestimates while the TV-PSF-MLEM overestimates the activity. TV-PSF-MLEM appears more homogenous in the background and in larger cylinders. At the outer edges of the phantoms artifacts in the TV-PSF-MLEM reconstruction are due to the non regularization with local weights $w_b$ there.

Figure 29:
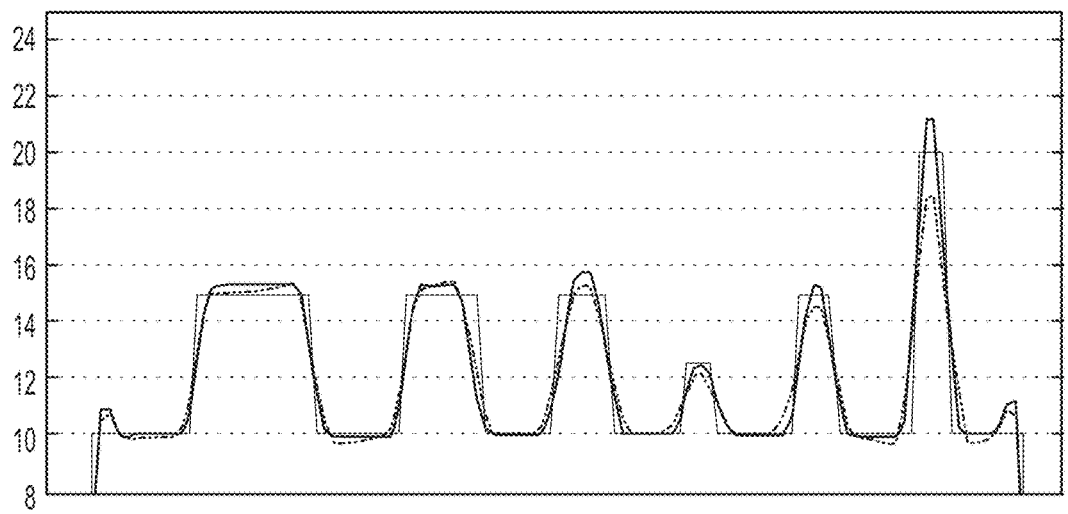
FIG. 29 shows reconstruction results on simulated phantom with Poisson noise and $w_b$ cutoff value. Center profile is shown for: (thin solid line) ideal phantom, (dashed line) 500 iterations of Rapisarda, and (thick solid line) 500 iterations of TV-PSF-MLEM with average weights, and wt cutoff=0.2. Reconstructions were initialized with 200 MLEM iterations.

In an attempt to suppress over-enhancement in the 8 mm cylinders, as observed in FIG. 28, a minimum cutoff value was set for the $w_b$ values (stemming from the observation that $w_b$ in those cylinders were lower than anywhere else in the image). By increasing $w_b$ values more TV regularization was enforced to prevent overshooting. The overshoot in small cylinders and background edges is largely remedied by applying a simple cutoff, as shown in FIG. 29.

Performance of TV-PSF-MLEM on Simulated Data

Figure 30:
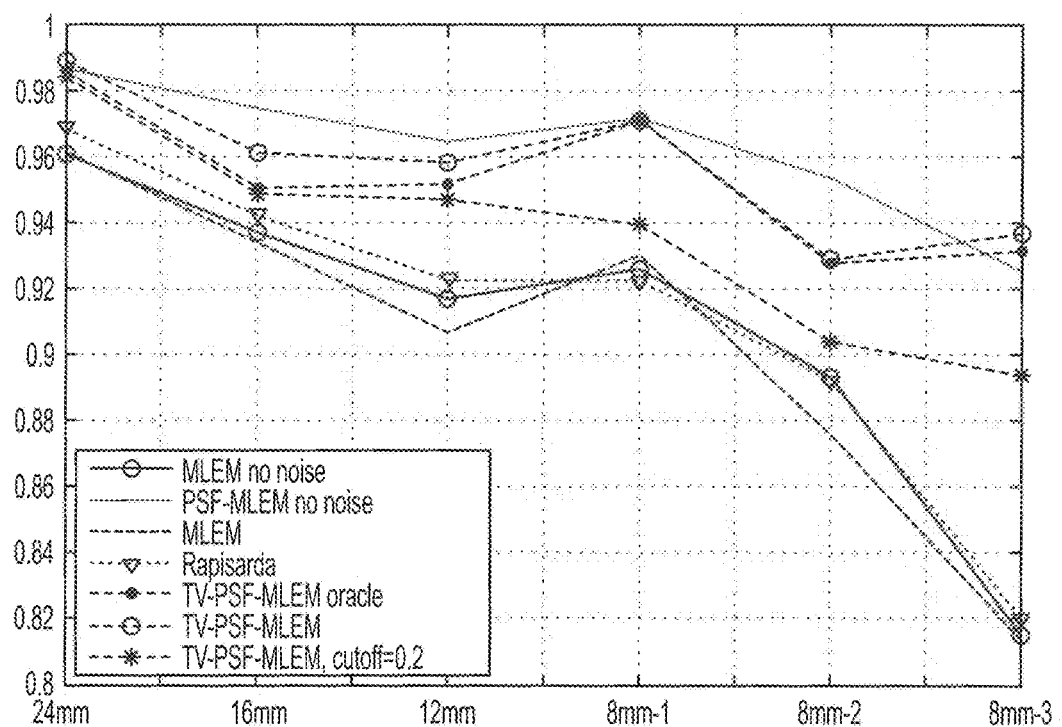
FIG. 30 shows recovery coefficients (RC) of cylinders (x-axis) with different reconstruction methods on noisy (dashed lines) and non-noisy (solid lines) data. MLEM and PSF-MLEM are shown on non-noisy data as references for the expected worst and best RC value.

The performance characteristic of the two methods is better understood in terms of RC values, reported in FIG. 30 for the different cylinders. The Rapisarda method yields RCs for all cylinders that closely track the noiseless MLEM estimate, with slightly higher RCs for cylinder diameters$\geq$12 mm, and outperforming standard MLEM on noisy data. Hence this method provides excellent noise suppression but greatly limits the contrast enhancement gained from PSF modeling as it does not recover contrast loss due to blurring effects. In contrast, TV-PSF-MLEM (with or without cutoff on the $w_b$) yields higher RC values for all cylinders. For the 24 mm and 8 mm cylinders the recovery level on noisy data approaches the recovery level of PSF-MLEM without noise. When a cutoff value is applied on the $w_b$, all RC values are higher than with the Rapisarda method, especially in the highest contrast 8 mm cylinder.

Two ML iterative PET reconstruction algorithms that both exploit local regularization of the image data were compared: the proposed TV-PSF-MLEM method and the Rapisarda method. The simulation results demonstrate that in the presence of noise, the proposed method is robust and provides advantages in terms of visual quality and contrast recovery, especially in small structures.

Experiments and Performance with Acquired Data

Experimental Setup and Data Acquisition

Figure 31:
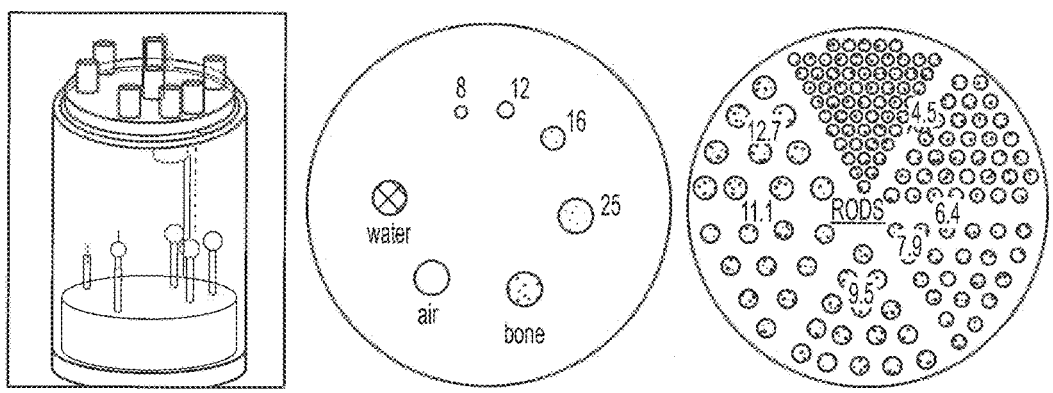
FIG. 31 shows ACR cylindrical phantom with 4 thin-walled hot cylinders (8 mm, 12 mm, 16 mm and 25 mm), and three cold 25 mm cylinders that mimic attenuation of "bone", "air" and "water". The bottom of the phantom contains cold 8.8 cm tall rods of different diameters (12.7 mm, 11.1 mm, 9.5 mm, 7.9 mm, 6.4 mm and 4.8 mm) spaced by a triangular grid pattern.

To investigate the effect of edge artifacts on the quantification of PET images, a PET phantom developed for brain and cardiac imaging applications was scanned (P. D. Esser, Ph.D., constructed by Data Spectrum, Hillsborough, N.C.). This phantom is a cylinder with 15.3 cm outer diameter (OD) and 14.1 cm inner diameter. There are eight cylindrical inserts. The three cold inserts (16 mm inner diameter each) were filled with air, water and bone equivalent epoxy. The other five inserts are 1.5 inches tall and have inner diameter of 4, 6, 8, 12 and 16 mm respectively and were filled with high concentrations of FDG. The axial length of all cylindrical inserts was 25.4 mm with a wall thickness of 1 mm. In addition, the phantom has 6 solid spheres with diameters between 3.2 mm and 19.1 mm and 6 sections of cold rods with diameters ranging from 3.2 mm to 11.1 mm. The background was activated with FDG. The phantom is shown in FIG. 31.

The phantom was scanned on a ECAT HR+ scanner (Siemens Molecular Imaging, Knoxville, Tenn.). The total activity in the background was about 1 mCi. The concentration ratio between hot cylindrical inserts and background was roughly 4:1. After a 10 minute transmission scan, emission data was acquired for 45 minutes. This yielded 140 million prompts, 10 million delayed and 130 million net true events.

Noise Model

As discussed above, the TV regularization is based on the Gaussian noise model was used to develop the TV-PSF-MLEM approach. Although Gaussian noise is common assumption for many fields of imaging, tomographic imaging and in particular PET has been associated Poisson noise. This is an important distinction, as it has been shown proper selection of a TV regularization approach, tailored for specific noise cases, is important for good noise recovery. Here the noise properties of the acquired ACR phantom data were studied for several noise distributions, namely: Gaussian/Normal, Poisson, and Gamma. The fits were qualitatively evaluated using Q-Q plots and overlays of estimated PDFs on histograms. Since the interest is in iterative reconstruction it is important to understand the noise structure over iterations. As seen, early iterations of MLEM are relatively smooth, consist of low-frequencies, and little noise. At latest iterations the noise overwhelms the data. Thus it is not clear if the TV regularization approach needs to be dynamically adapted to the changing image structure over iterations.

Figure 32:
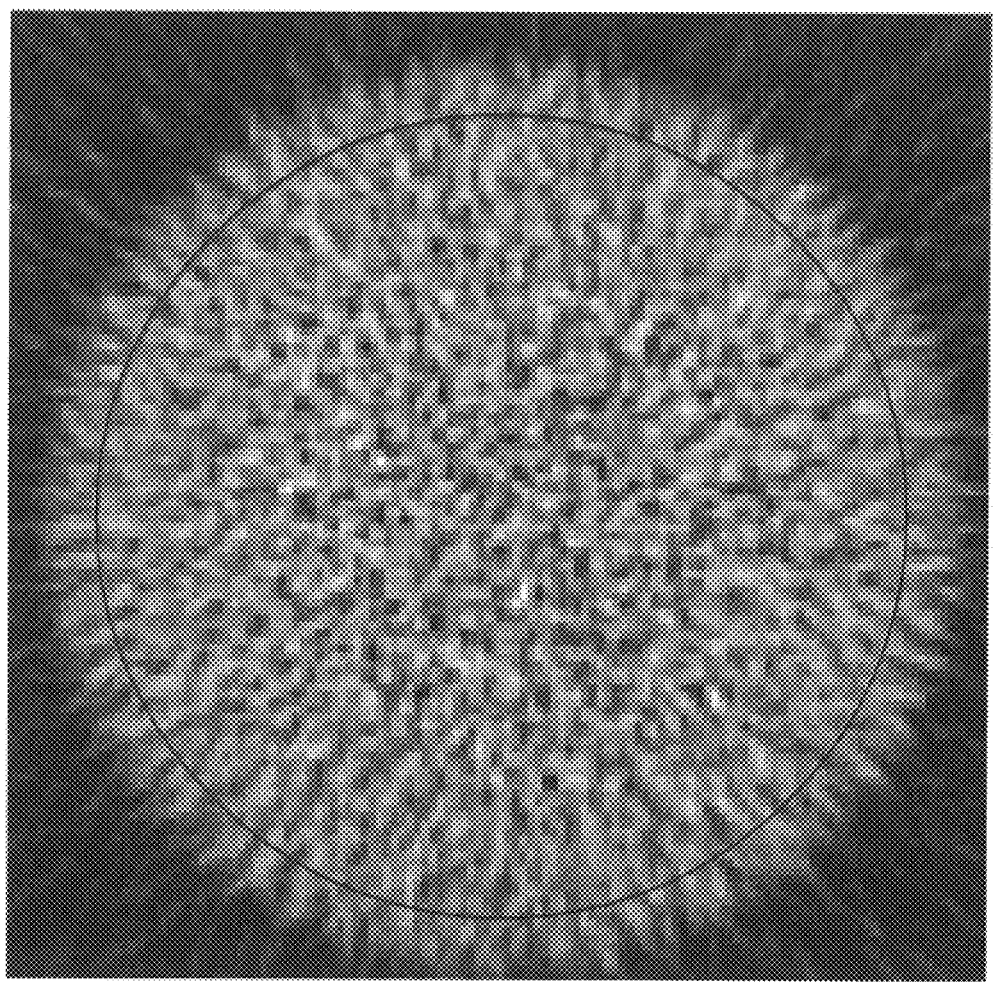
FIG. 32 shows uniform slice of the ACR phantom and the circular ROI (thin solid line) used for noise modeling.

In addition to quantitative performance assessment the underlying noise distribution was estimated in order to determine the most appropriate noise model for TV denoising. The proposed TV approach is based on the assumption of a Gaussian noise model. However, it is widely assumed that PET data is Poisson. Others have derived the TV formulation for Poisson distributed data, and it has been shown to yield better results when the TV noise model is Poisson [73]. It is important to know whether the assumption of a Gaussian noise in the PET image is reasonable and appropriate, and to infer the impact of the noise model on performance. Therefore the noise model was estimated using the ACR phantom. The phantom was reconstructed separately with FBP and several iterations of MLEM. A large cylindrical ROI was drawn on a section of the phantom that had a uniform background, as depicted in FIG. 32.

The voxel values with this background ROI were used to estimate parameters of the Normal, Poisson, Gamma distribution. The equations and relevant parameters for these distribution is provided:

Normal Density and ML Parameter Estimators:

$$f(x, \mu, \sigma) = \frac{1}{\sigma\sqrt{2\pi}} e^{-\frac{(x-\mu)^2}{2\sigma^2}}, \hat{\mu} = \frac{1}{n}\sum_{i=1}^{n} x_i, \quad (5.17)$$

$$\sigma = \frac{1}{n-1}\sum_{i=1}^{n}(x_i - \hat{\mu})^2$$

Poisson Density and ML Parameter Estimators:

$$f(k; \lambda) = \frac{\lambda^k e^{-\lambda}}{k!}, \hat{\lambda} = \frac{1}{n}\sum_{i=1}^{n} x_i \quad (5.18)$$

Gamma Density and ML Parameter Estimators:

$$f(x, k, \theta) = \frac{x^{k-1} e^{-\frac{x}{\theta}}}{\theta^k (k-1)!}, k = \frac{3 - s + \sqrt{(s-3)^2 + 24s}}{12s}, \quad (5.19)$$

$$\hat{\theta} = \frac{1}{kN}\sum_{i=1}^{n} x_i,$$

where k is within 1.5% of being the correct value, s is as estimated as:

$$s = \ln\left(\frac{1}{N}\sum_{i=1}^{N} x_i\right) - \frac{1}{N}\sum_{i=1}^{N} \ln(x_i)$$

and the explicit value for k can calculated using the Newton-Raphson method [74].

The quality of the fit is inspected with Q-Q plots and overlay of the estimated distribution on the histogram generated from the voxel values. Overlays of the fitted distributions shown in FIG. 33. The Poisson distribution only captures the middle 50% of the data and thus provides a poor fit to the data. Interestingly, the fit appears worse with increasing iterations. The Gaussian distribution fits the data relatively well at every iteration with the exception that it appears slightly off center and does not entirely capture the skewness of the histogram. Surprisingly, the Gamma distribution appears to provide the best fit. It captures both the mean, amplitude and skewness of the underlying histogram at every iteration.

Figure 34:
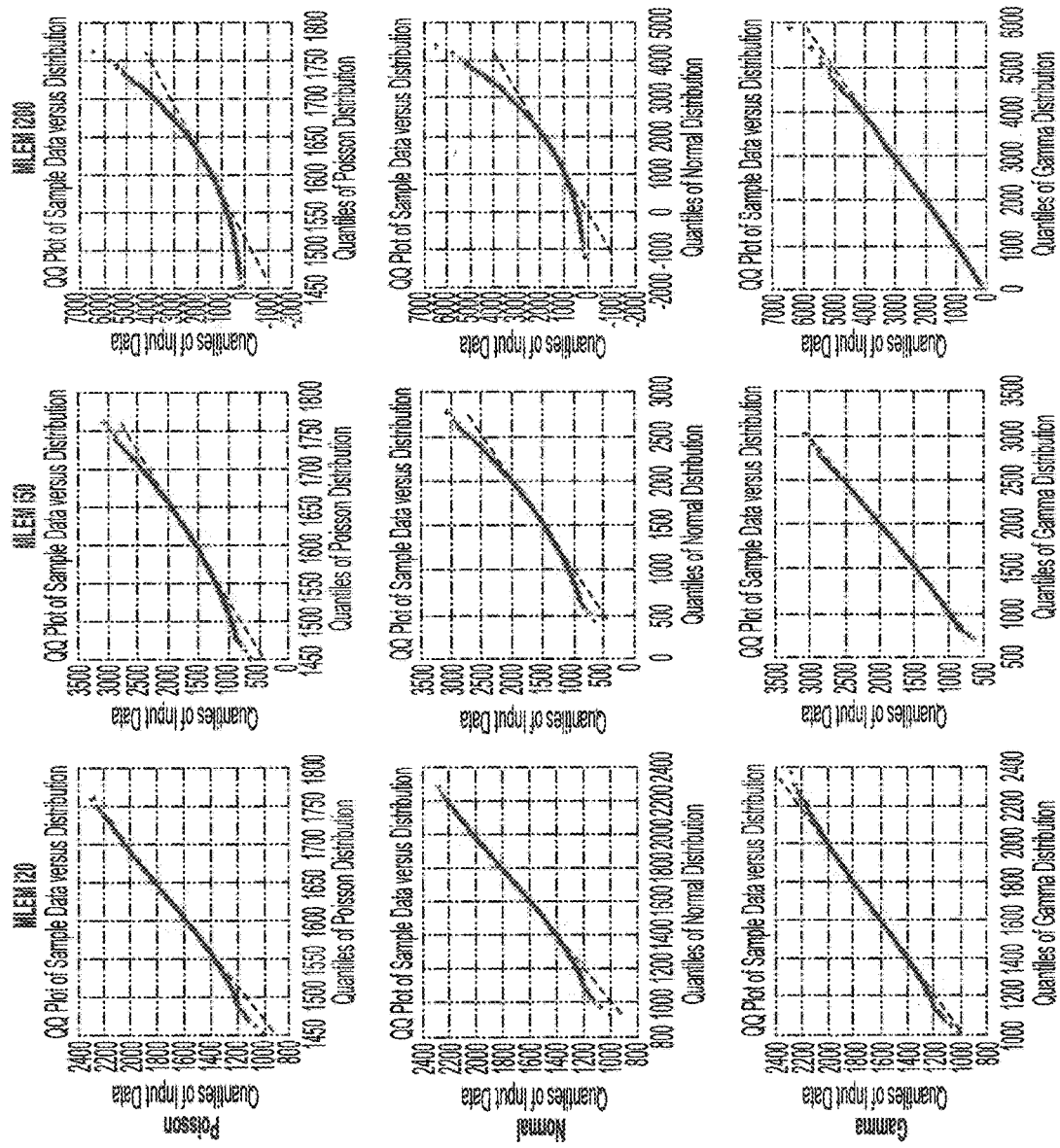
FIG. 34 shows Q-Q plots for different noise models and several iterations of MLEM.

The Q-Q plots confirms and clarifies the visual observations, shown in FIG. 34. For the Gaussian distribution the Q-Q plot is fairly linear in the early iteration (i20) but then becomes bowl shaped at later iterations. This strong non-linear pattern indicates that this distribution fits the central quantiles but does not capture skewness well. In contrast, the Q-Q plots for the Gamma distribution are fairly linear in all quantiles and at all MLEM iterations.

It appears that the Gamma distribution provides the best fit to the data. This is somewhat unexpected because Gamma is the distribution of choice for modeling Speckle noise, which is typically associated with Ultrasound imaging and not with PET. One possible explanation for this finding is that Speckle noise is an artifact of the MLEM reconstruction procedure, having to do with the repeated multiplication of attenuation and normalization on the estimate, and divisions between the measured data and this estimate. In fact, the Gaussian distribution provides the best fit to pre-corrected data reconstructed with FBP. Another possibility is that the open source reconstruction framework being used introduces this noise component through its implementation of Ray Tracing in the forward and backward projector, which has been known to introduce artifacts (verbal communication). Changing the number of rays used may mitigate some noise effects.

It has been confirmed that in fact the reconstructed data is not Poisson distributed and therefore the TV denoising approach derived from with the Poisson noise model need not be considered. The Gaussian distribution provides a reasonable fit to the data, although it does not capture skewness as well as the Gamma distribution. While TV denoising under Gamma noise has been previously developed [73], in this case using this approach would likely be of minimal impact. Additional experiments are necessarily to study the underlying effects of attenuation, normalization, scatter model, acquisition parameters, count rate, and reconstruction implementation to choose Gamma over Gaussian.

A Gaussian TV denoising approach was used for all subsequent experiments.

Performance Metrics

The results were assessed with the 'hot contrast recovery' and 'background variance' measures as defined below.

$$\text{Hot Contrast Recovery: } CR_{hot} = 100 \frac{\mu_S/\mu_B - 1}{R - 1}$$

where $CR_{hot}$ is the 'hot contrast recovery', $\mu_S$ is the average activity in the hot region, $\mu_B$ is the average activity in the background region, and R is the true hot:background signal ratio.

$$\text{Background Variance: } STD = \sqrt{\frac{1}{N-1}\sum_{b \in ROI}(\lambda_b - \mu_B)^2}$$

where STD is the 'background variance', $\lambda_b$ is the activity in voxel b of a given region of interest, $\mu_B$ is the average activity in the background region.

Qualitative Evaluation

Figure 35:
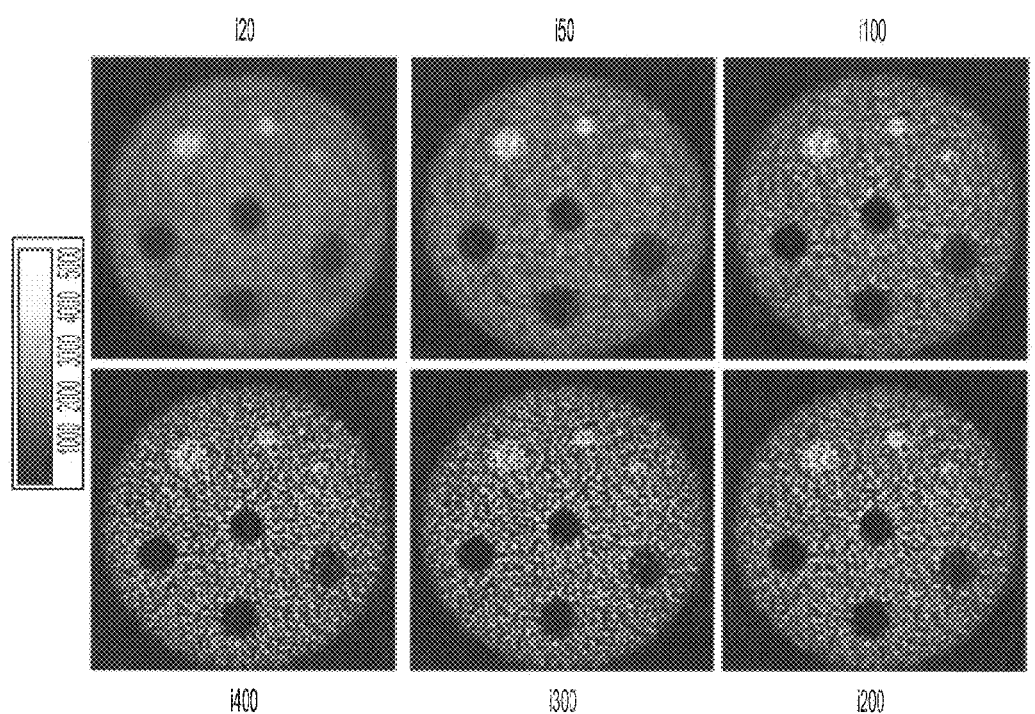
FIG. 35 shows ACR phantom reconstructed with MLEM, shown for several iterations.

The MLEM reconstruction over several iterations is shown in FIG. 35. In early iterations (e.g. i20, i50) the basic structure of the object is present but there is poor recovery of the 8 mm cylinder, that is difficult to make out visually. There is also visible activity in the large 24 mm cold cylinders, indicating a spillover of activity from the background. At later iterations (i.e. i100-i400), increasing noise inherent with the MLEM approach overwhelms the structural integrity of the image.

Figure 36:
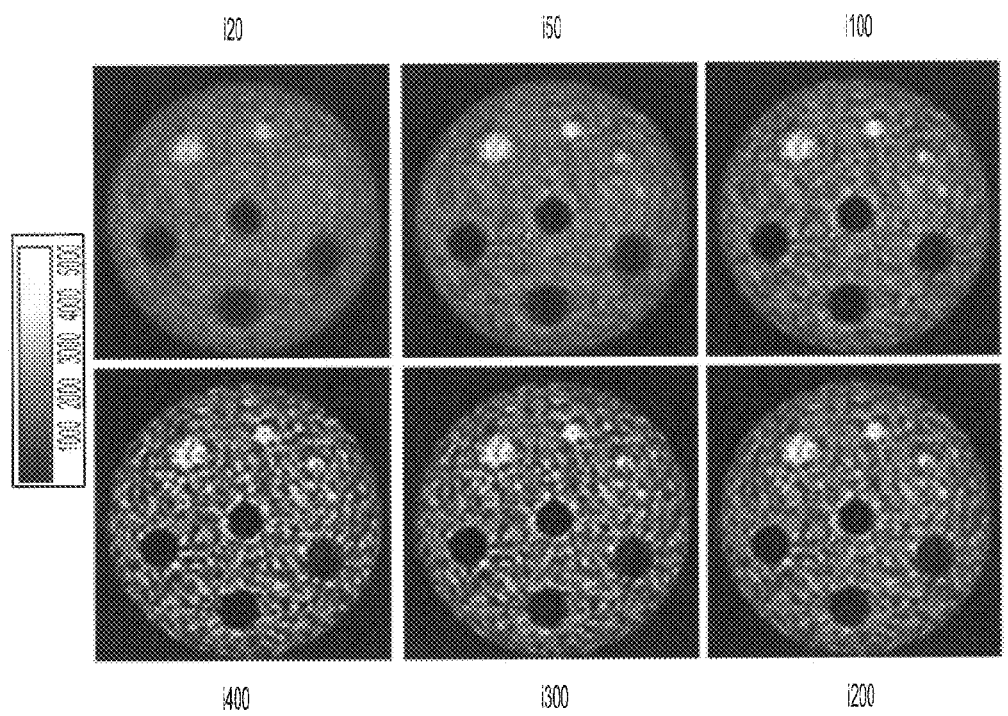
FIG. 36 shows ACR phantom reconstructed with PSF-MLEM, shown for several iterations.

PSF-MLEM reconstructions over several iterations are shown in FIG. 36. In early iterations (i.e. i20, i50) the image looks smooth with little background noise. In later iterations (i.e. i100-i400) there is improved contrast of all cylinders over any iteration of MLEM. The 8 mm cylinder is now clearly visible. However, by iteration 200 many hot-spots appear in the background that should not be there. By iteration 400 most of the volume is corrupted by hot-spot artifact. In addition, the break in continuity in the middle of the 24 mm and 16 mm cylinder indicates a possible ringing artifact.

Figure 37:
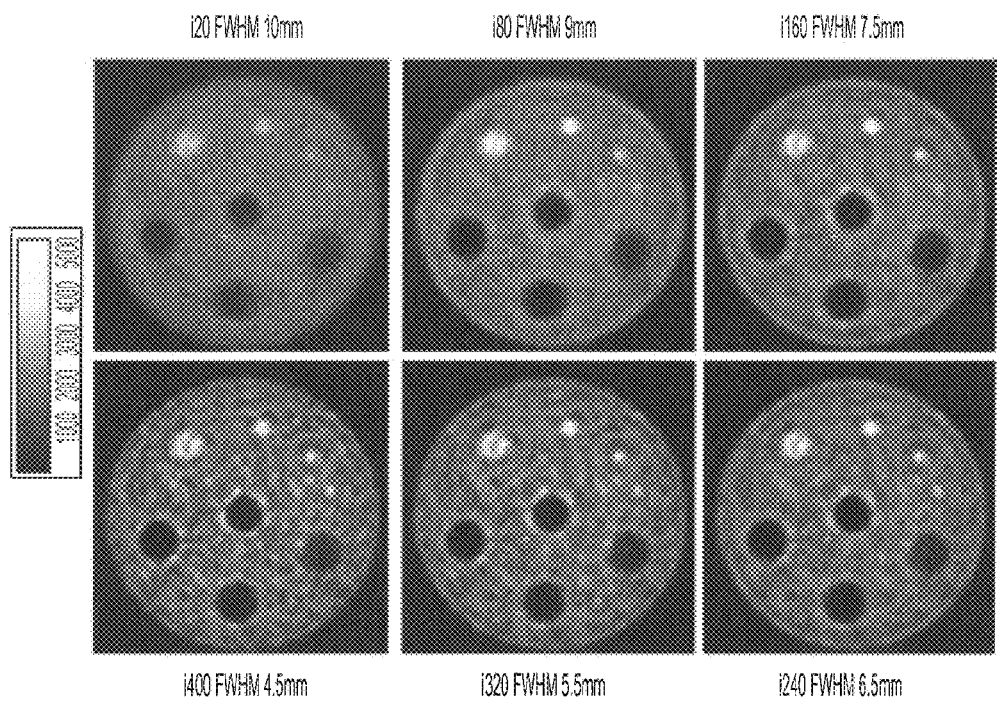
FIG. 37 shows ACR phantom reconstructed with gPSF-MLEM, shown for several iterations.

Results with gPSF-MLEM are shown in FIG. 37. There appears to be a further reduction of background noise, visually increased contrast of hot cylinders, an improvement over both MLEM and PSF-MLEM. In particular, the 8 mm and 16 mm cylinders have higher contrast and are more distinct from the background when compared to PSF-MLEM. There are also many fewer hot-spots than with PSF-MLEM. Interestingly, the gap in the middle of the 12 mm cylinder of the PSF-MLEM reconstruction is not present with gPSF-MLEM.

Next, the ACR phantom data was reconstructed with MLEM, PSF-MLEM, gPSF-MLEM, TV-PSF-MLEM, TV-gPSF-MLEM, and the competing Rapisarda method for comparison. For visual clarify MLEM results are shown at iteration 100. All other methods were initiated with 20 iterations of MLEM and then run for an additional 380 iterations, for a total of 400 iterations. Results are shown for hot cylinders (FIG. 38) and the small cold rod section (FIG. 39).

For the hot cylinders, Rapisarda and PSF-MLEM yield seemingly identical results, with many hot-spot artifacts, low-frequency noise, and what appears to be ringing artifact (hole in the middle) in the 24 mm and 16 mm cylinder. TV-PSF-MLEM appears substantially reduces the background noise, removes many hot-spot artifacts, and improves the visual contrast of the hot cylinders. A few hot-spot artifacts are still present. The ringing artifact in the 24 mm and 16 mm cylinder is also visible. TV-gPSF-MLEM provides a further improvement in visual quality. Most notably, spot artifacts are no longer visible, the hot cylinders have better visual fidelity and are more circular, and also appear more homogenous. In particular, the 16 mm cylinder does not show visible ringing artifact and the 12 mm appears more circular with sharp borders.

For the cold rods, with MLEM it is difficult to make out the 12.9 mm, 11.1 mm and partial outline of the 9.5 mm rods are visible. PSF-MLEM and Rapisarda again appear very similar. The 12.9, 11.1m, and 9.5 mm rods are much clearer than MLEM, although they are not circular in appearance and contain substantial noise in the interior. It is difficult to discern the 7.9 mm and smaller rods and many hot-spot artifacts are present. TV-PSF-MLEM improves roundness and contrast of the 12.9 mm, 11.1 mm and 9.5 mm rods. The 7.9 mm and 6.4 mm rods now clearly visible. Many hot-spot artifacts are still evident. With gPSF-MLEM, all rods grids except the smallest 4.8 mm rods discernible. Although, some rods within the visible grids are not circular and contain elements of noise. Hot-spot artifacts are substantially reduced over PSF-MLEM. Combining gPSF-MLEM with TV denoising, TV-gPSF-MLEM yields the optimal visual quality image. Most hot-spot artifacts have been removed, all rod grids except the smallest 4.9 mm rods are clearly visible, most of individual rods are circular in appearance.

In conclusion, both gPSF-MLEM, TV-PSF-MLEM and especially TV-gPSF-MLEM yield substantial improvements in overall visual quality, visual contrast of hot and cold cylinders, and the cold rods. An added benefit the gPSF is a notable reduction of hot-spot artifacts.

Quantitative Evaluation

The recovered average intensity within the 25 mm, 16 mm, 12 mm and 8 mm cylinders, and the measured value, is shown for all reconstructions. MLEM underestimates the measured value for all cylinders in all iterations. The average intensity plateaus within 50-100 iterations for the 24 mm, 16 mm and 8 mm cylinders, while for the 12 mm cylinder average intensity peaks at iteration ~60 and then gradually decreases. This is likely due to noise buildup inherent in the MLEM approach. Rapisarda and PSF-MLEM yield nearly identical profiles. PSF-MLEM overestimates activity within all except the 12 mm cylinder, and does not appear to converge after 400 iterations. For the 12 mm cylinder, PSF-MLEM appears to converge at around iteration ~200. Interestingly, gPSF-MLEM results in an oscillatory profile, yet the recovered value after 400 iterations is closer to the measured values than any other approach. TV-gPSF-MLEM shows a highly divergent recovery pattern, large over-estimation after 400 iterations, for all but the 8 mm cylinder where it underestimates.

Conclusions

Three novel techniques for PET reconstruction have been introduced: TV-PSF-MLEM, which uses a locally weighted total variation denoising model; gPSF-MLEM which gradual deduces the FWHM of the PSF; and TV-gPSF-MLEM combines gPSF-MLEM with TV denoising. These approaches were evaluated both qualitatively and quantitatively, and compared against MLEM and PSF-MLEM, two techniques that are commonly implemented in most clinical and research PET cameras.

All the approaches reduce background noise reduce hot-spot artifact over PSF-MLEM. TV-MLEM-PSF shows good CR (a few percent less than PSF-MLEM) with the least background variance of any method. For contrast recovery, gPSF-MLEM achieves higher CR than TV-PSF-MLEM and has the best compromise between maximum CR and variance. For recovering activity concentration, gPSF-MLEM outperforms all other methods, recovering activity in all hot-cylinders that is closest to the measured value.

The Rapisarda method was also evaluated and showed nearly identical qualitative and quantitative results to PSF-MLEM. One possible reason for this paradoxical result is that the tuning parameters used (as recommended by the authors) were based on experiments with scans containing 50 million counts. The ACR phantom scan has ~120 million counts. Parameter values may be sensitive to the count rate. For this reason Rapisarda method was excluded from subsequent analyses.

Overall, TV-gPSF-MLEM yields the best visual quality while gPSF-MLEM is most accurate quantitatively.

Example 4: Application to Clinical Data

Described herein are results of applying the reconstruction techniques described above on clinical PET brain image data. Specifically, two distinct applications are highlighted. The first application is the recovery of radioactivity concentration from internal carotid arteries in the brain, which can be used as a scaling factor for the IDIF approach. A second application is the localization of the raphe nuclei in the PET image. While there are five nuclei, only one or two are large enough to be visible on a typical PET image. Improving localization and enabling quantification from additional nuclei would facilitate development of a biomarker for predicting major depressive disorder.

Description of clinical PET data

Data collection is described in [75], briefly PET images were acquired on an ECAT EXACT HR+ scanner (Siemens/CTI) at the Columbia University PET center. After a 10-minute transmission scan, the [11C]-WAY radioligand was injected and emission data were collected in 3D mode for 110 min as 20 frames of increasing duration (3×20 s, 3×1 min, 3×2 min, 2×5 min, 9×10 min). Reconstruction was performed using filtered back-projection with attenuation correction using the transmission data, scatter correction was performed using a model-based approach. The reconstruction and estimated image filters were Shepp 0.5 (2.5 mm FWHM), the Z filter was all-pass 0.4 (2.0 FWHM) and the zoom factor was 3.0. Images were reconstructed to a 128×128×63 matrix. Following radiotracer injection, 30 arterial samples were collected, 24 samples automatically every 5 seconds for the first 2 min, and 6 samples manually thereafter at longer intervals. Following centrifugation, plasma was collected in 200 mL aliquots and radioactivity was counted in a gamma counter (Wallac 1480 Wizard 3M Automatic Gamma Counter). TP was measured from each blood sample using a well counter after centrifugation.

Recovery of Blood Radioactivity Concentration from Brain Imaging of Blood Vessels It was discovered that total radioactivity concentration in the total plasma (TP) is correlated with the metabolite corrected arterial input function (AIF). For this reason TP can be used as predictor for the constraints in the proposed nSIME approach. Currently, measurement of TP requires blood sampling. It may be possible to estimate TP from blood vessel measures in the brain PET. A promising ICA approach can be used for estimating TP from [18F]-FDG and [11C]-WAY radioligands. This technique requires a single blood sample taken during the peak blood radioligand concentration. Since the peak time is not known a priori, it is impractical to obtain the peak blood sample during the scan. However, the peak time can be inferred a posteriori from the PET imaging data. A natural approach would be to replace the blood sample with the measurement of the peak signal from the carotid arteries or the sagittal sinus, both large blood vessels in the brain. Unfortunately, direct quantification of signal from blood vessels is currently not possible due their small size (6-8 mm in diameter), which is at or below the resolution of most PET systems. In addition, vessels are difficult to localize and their signal is heavily corrupted by partial volume effect.

The anatomy of major arterial blood supply to the brain is described at www.mayfieldclinic.com/PE-IntracranialStenosis.htm#.VEp7dr7OhvY and www.grhealth.org/spine/spine-glossary/spine-glossary-basilar-artery. Blood is carried to the brain by two paired arteries, the internal carotid arteries and the vertebral arteries. The internal carotid arteries supply the front areas and the vertebral arteries supply the back areas of the brain. After passing through the skull, the right and left vertebral arteries join together to form a single basilar artery. The basilar artery and the internal carotid arteries communicate with each other in a ring at the base of the brain called the Circle of Willis. The anatomy of major veins is described at www.lookfordiagnosis.com/mesh_info.php?term=transverse+sinuses&lang=1.

Several reconstruction approaches designed to improve the visual quality and resolution of PET data are described herein. Here the performance of these techniques for improving the quantitative recovery of the carotid artery signal was assessed. Localization is assessed with an overlay on an MRI acquired with a sequence that enhances carotid artery contrast. Quantitative performance is assessed by comparing recovered signal to arterial blood sampling data. The general behavior of the proposed reconstruction approaches on these clinical scans is also described.

PET Image Pre-Processing

PET data was obtained of 110 minute [11C]-WAY scans for two subjects. This data included; emission sinograms, transmission sinograms, normalization scan, and the accompanying measured AIF from blood sampling. The internal carotid artery and sagittal sinus were manually labeled on a mean PET image consisting of the average activity of the first 2 minutes of acquisition after radioligand injection. Time-activity curves were extracted from the carotid and sagittal sinus ROIs. The time of the peak activity in the blood was determined from the AIF peak. The closest PET frame to this peak time was used for subsequent analysis. For both subjects this turned out to be a one minute frame. The emission data for this frame contained 13 million counts acquired between 1 and 2 minutes post injection. The one-minute frame was reconstructed using STIR with FBP, MLEM, PSF-MLEM, TV-PSF-MLEM, gPSF-MLEM, TV-gPSF-MLEM.

Quantitative Results and Limitations of FBP

Before applying the MLEM approaches, the performance of FBP at recovering signal from blood vessels was evaluated. FBP is the most routine and simplest reconstruction approach. The average signal in the entire region and the average signal of the highest four voxels (top 4) from the carotid and sagittal sinus ROIs was calculated. FIGS. 41, 42, and 43A-B show the measured TP and time activity curves from the blood vessels for two subjects. The FBP values greatly underestimates TP in the peak region (42, 43B), while the mean in the entire region matches well to the tail portion (41, 43A). The mean of the top 4 voxels recovers the peak better but greatly overestimates the tail of the TP curve. The underestimation of the peak is a result of spill out of activity from the vessels that occurs because when signal in blood vessels is much higher than surrounding tissue in the early part of the scan. Overestimation of the tail occurs calculated from the top 4 voxels is likely a result of increasing noise because activity in the blood is very close to zero toward to end of the scan. Spill-in from regions with high activity into blood vessels may be also contributing.

Qualitative Results

Figure 44:
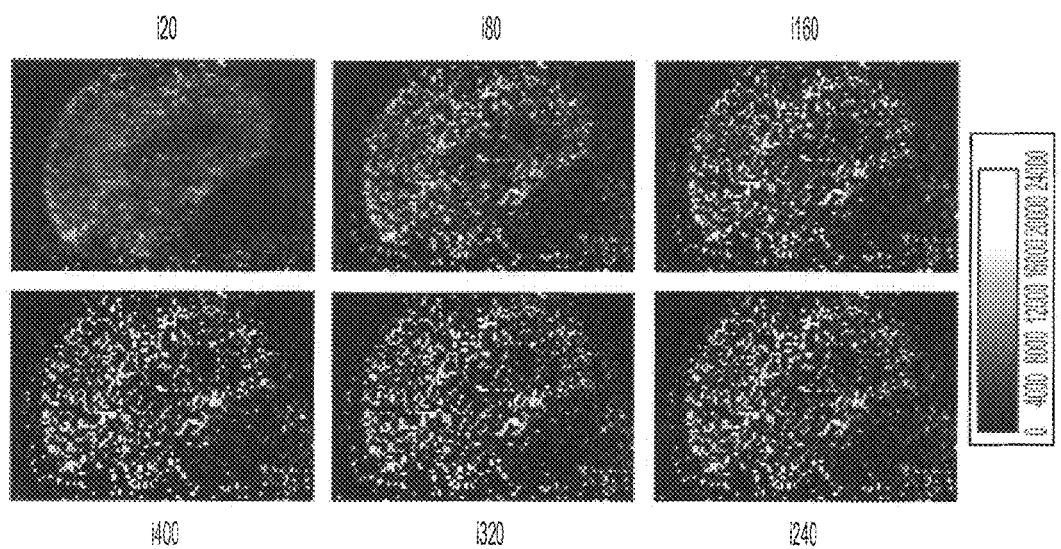
FIG. 44 shows the results for MLEM over 400 iterations. There is little contrast of vasculature in all iterations and noise quickly overwhelms the image structure.

The MLEM reconstructions over several iterations are shown in FIG. 44. Blood vessels are visible in early iterations but with increasing iterations noise dominates the image and much of the image structure are lost. By iteration 400 the blood vessels in the image are hardly discernible.

Figure 45:
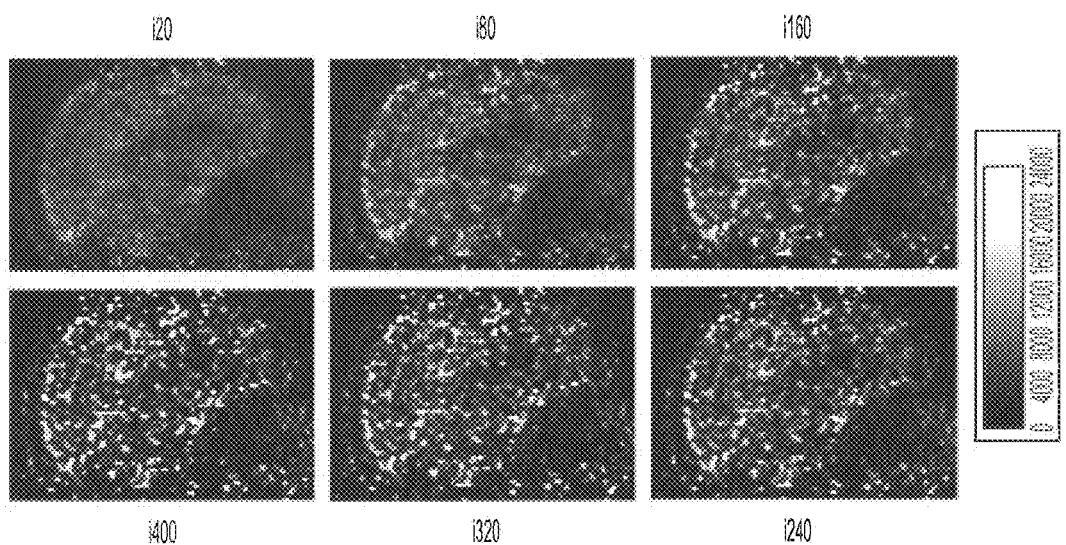
FIG. 45 shows results for PSF-MLEM over 400 iterations. Vasculature is more visible than with MLEM, but it is unclear where to stop iterations. By iteration 400 the image is corrupted by hot-spot artifacts and noise patterns.

PSF-MLEM reconstructions over several iterations are shown in FIG. 45. Blood vessels are identifiable in early iterations, but in later iterations the image, similarly to MLEM, the image is dominated by noise. By iterations 240 many hot spots appear in the background. By iteration 400 most much of the volume contains hot-spot artifacts making it difficult to differentiate blood vessels from background.

Figure 46:
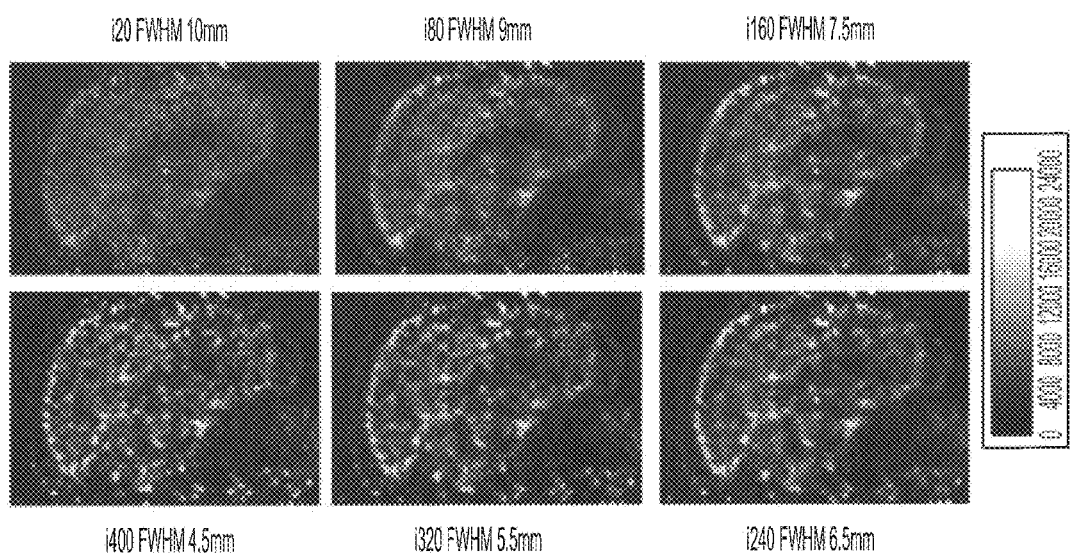
FIG. 46 shows results for gPSF-MLEM over 400 iterations. Visible enhancement of sagittal and straight sinuses is clear. Blood vessels have good contrast, even in early iterations. By iteration 400 the vessels are clearly distinguishable from background. Noise and hot-spot artifacts are reduced over PSF-MLEM.

Reconstructions gPSF-MLEM over several iterations are shown in FIG. 46. Early iterations show a remarkable enhancement of the sagittal sinus around between iterations 160-320. This effect is not present in with the PSF-MLEM reconstruction.

Figure 47:
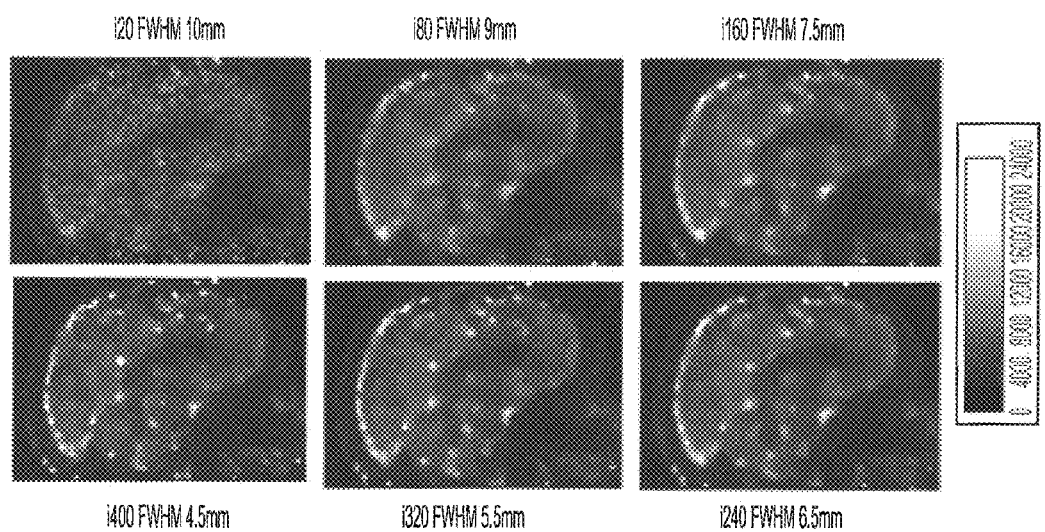
FIG. 47 shows results for TV-gPSF-MLEM over iterations 400 iterations. The sagittal sinus has remarkable contrast, even in early iterations. It can be seen that early iterations appear smoother, with gradually increasing sharpness as iterations progress. By iteration 400 the vessels are well defined with very little background noise present.

Reconstructions with TV-gPSF-MLEM over several iterations are shown in FIG. 47. As with gPSF-MLEM, early iterations show exceptional enhancement of the sagittal sinus. As iterations increase, the image is gradually sharpened, and the width of the sagittal sinus becomes smaller. By iteration 400 the, the sagittal sinus appears sharp and has high contrast relative to the background. The straight sinus is also visible but does not appear contiguous. This is likely because the vessel is not entirely in-plane.

Figure 48:
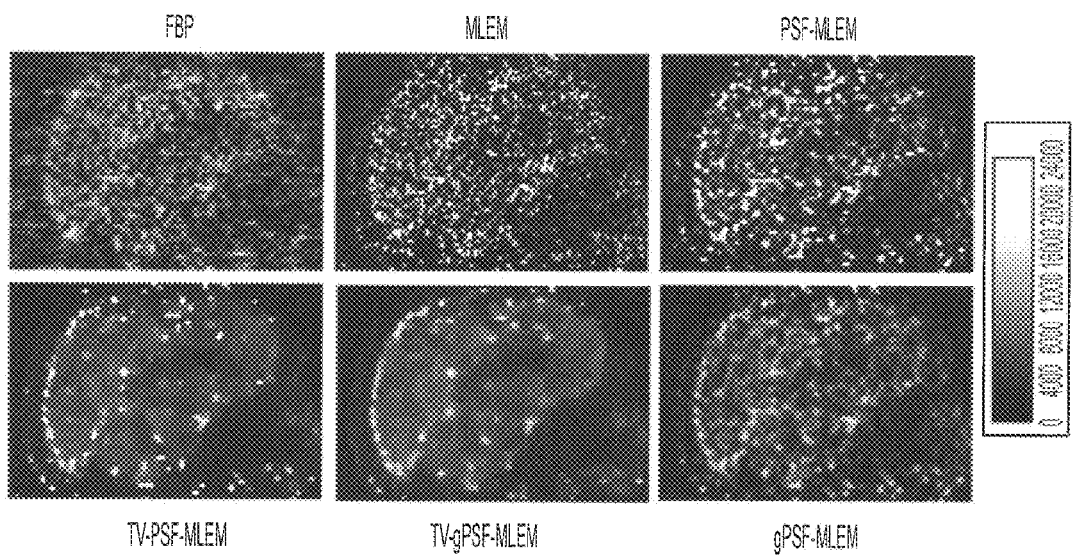
FIG. 48 shows results with FBP and after 400 iterations of all other methods. (first row) Traditional approaches (FBP, MLEM and PSF-MLEM) are heavily corrupted by noise making it difficult to make out blood vessels. PSF-MLEM shows the best contrast but contains substantial artifact. (bottom row) Approaches described herein (TV-PSF-MLEM, gPSF-MLEM and TV-gPSF-MLEM) all show improved vascular contrast and reduction of background noise. As with the ACR phantom experiments, TV-gPSF-MLEM shows a reduction in hot-spot artifacts and more homogenous signal in the vasculature. Edges corresponding to the cortex of the brain are very well defined with the TV approaches.

FIG. 48 shows the FBP reconstruction and all iterative reconstructions after 400 iterations for the sagittal slice that contains the sagittal and straight sinuses. The FBP image is very noisy and the vessels are barely visible, MLEM contains mostly noise and PSF-MLEM is contaminated with by hot-spot artifacts which confound the visibility of the vessels. In contrast, gPSF-MLEM has reduced noise and clearly distinguishable blood vessels. The vessels are also visible with TV-PSF-MLEM, although hot-spot artifacts are present. TV-gPSF-MLEM shows the best contrast with visibly reduced background noise and hot-spot artifacts.

Figure 49:
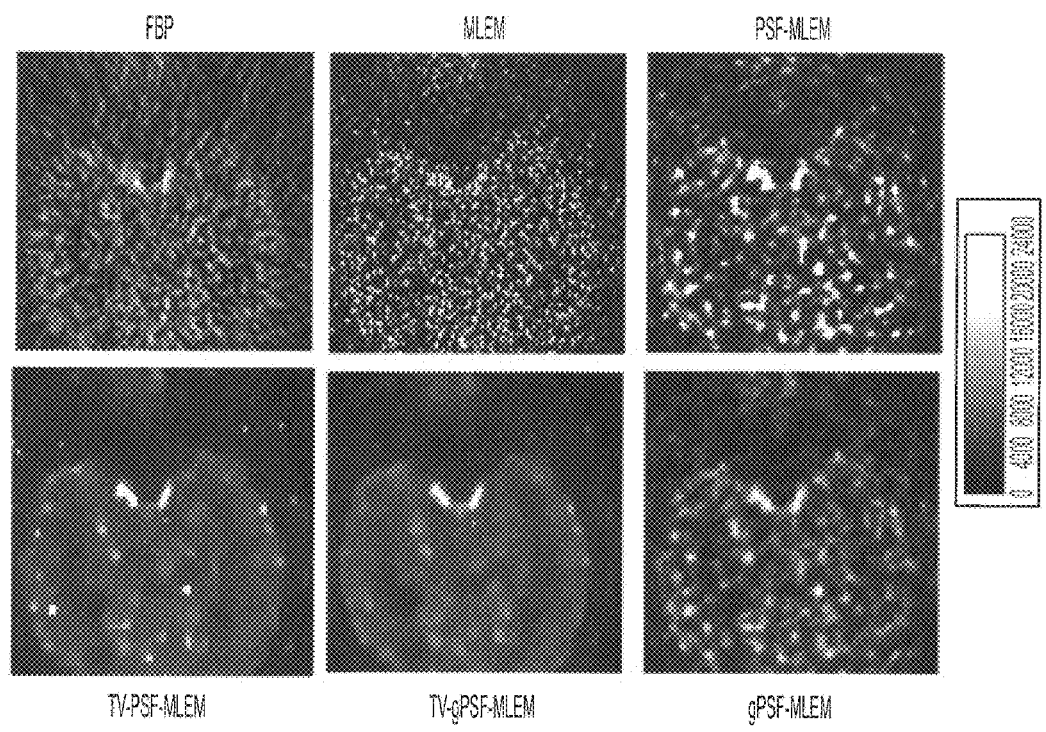
FIG. 49 shows results with FBP and after 400 iterations of all other methods. (first row) Traditional approaches (FBP, MLEM and PSF-MLEM) are heavily corrupted by noise. The carotid arteries are poorly visible with FBP, not distinguishable from the background with MLEM, and appear similar to background hot-spots in PSF-MLEM. (bottom row) Approaches described herein (TV-PSF-MLEM, gPSF-MLEM and TV-gPSF-MLEM) all show improved carotid contrast relative to background, along with reduction of the background noise. TV-gPSF-MLEM demonstrated a marked reduction in hot-spot artifacts, with virtually no remaining artifacts. Edges corresponding to the cortex of the brain are very well defined with the TV approaches.

FIG. 49 shows the FBP reconstruction and all iterative reconstructions after 400 iterations for the axial slice that contains the internal carotid arteries. The internal carotid arteries are visible on the FBP image but the contrast is not great. MLEM again appears as mostly noise. PSF-MLEM improves results, carotid arteries are visible but the image contains multiple hot-spot artifacts that make localization difficult. In contrast, gPSF-MLEM shows reduced noise, better delineation of the cortical edges, and a high contrast of the arteries against the background. With TV-PSF-MLEM, carotids have great contrast and cortical edges are clear, but some hot-spot artifacts are present. TV-gPSF-MLEM shows enhancement of carotids without any hot-spot artifacts, the cortical edges are sharper than with TV-PSF-MLEM.

Figure 50:
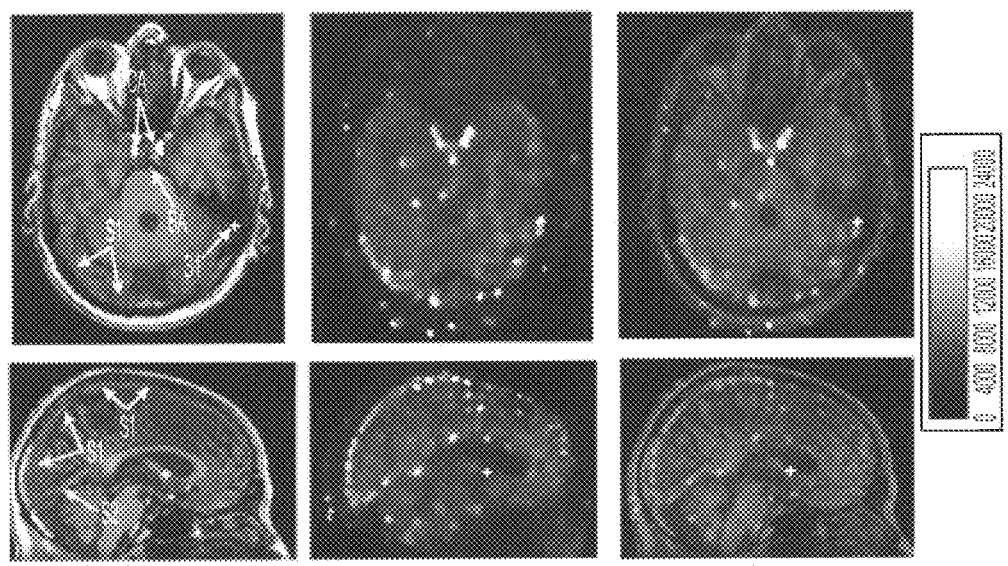
FIG. 50 shows TV-gPSF-MLEM results with supporting arterial contrast MRI. Transaxial slice highlighting several visible arteries and veins on the MRI (top-left). These structures appear as hot-spots on the PET image (top-middle) as seen on PET/MRI overlay (top-left). Sagittal slice of the MRI (bottom-left) highlighting the sagittal (S1) and straight (S2) sinuses. These vessels appear as hot-spots on the PET image (bottom-middle) as seen on the PET/MRI overlay (bottom-right). CA—carotid artery, BA—basilar artery, S1—sagittal sinus, S2—straight sinus.

To confirm that the enhancement of arteries and veins, the structures were identified on the subject's corresponding MRI acquired with an arterial blood enhancement sequence, and evaluated their correspondence to the high contrast areas of the TV-gPSF-MLEM images. FIG. 50 shows the MRI with marked vessel locations, the TV-gPSF-MLEM images, and a 50% opacity overlay of the PET on the MRI. In the axial view (top row), the carotid (CA) and basilar (BA) arteries are clearly visible on the MRI. The high contrast regions in the anterior portion of the PET directly matches the location of CA and BA. Note that the mean diameter for the basilar artery is ~3.2 mm, remarkably signal from this structure is clearly detectable on the TV-gPSF-MLEM reconstructed PET image. The transverse sinus (S1) also shows PET signal but this signal less homogenous than within the carotids. One important area of the sinuses is the confluens sinuum, which is the focal drainage point that collects blood from the entire brain, where straight and sagittal sinuses meet, before routing blood to the left and right transverse sinus. A very intense signal can be seen originating from this area in the axial slice. On the sagittal slice the sagittal and straight sinuses are easily identifiably on MRI. Clear signal from these area is visible on the TV-gPSF-MLEM reconstructed PET image. Again, the signal is not homogenous within these vessels. One possible explanation for this is that the [11C]-WAY radioligand binds specifically in some regions, thus drainage from brain regions into veins occurs unevenly.

Quantitative Results

It was seen that signal within the arteries extracted from the FBP images does not provide good recovery of the TP curve. Mourik et al. [76] suggested that the peak blood signal may be recovered by taking the average within the top 4 voxels of the carotid ROI from PSF-MLEM reconstructed images. Here, this approach was applied to FBP, PSF-MLEM and gPSF-MLEM images. FIGS. 51 and 52 show the average signal within the entire ROI, and the average signal within the top 4 voxels over 400 iterations, except for FBP the same value is shown for all iterations since the algorithm is not iterative. The measured peak TP value, for this subject at 1.5 minutes, is shown for reference (red line). The mean value within the entire ROI is relatively similar among the approaches, but this value greatly overestimates the true activity in the blood. For both subjects, the PSF-MLEM mean top 4 values does not converge over 400 iterations, and in fact appears to be progressively increase. The value may stabilize with additional iterations but looks to be on an increasing trend. By iteration 400 PSF-MLEM overestimates TP by ~60% one subject (top) and ~40% for the other subject (bottom). In contrast, the gPSF-MLEM top 4 values appears to converge nearly exactly to the measured TP value.

Conclusions

Described herein are three new reconstruction approaches (TV-PSF-MLEM, gPSF-MLEM, and TV-gPSF-MLEM) and their evaluation with ACR phantom data with large counts (~120 million). Here these approaches were applied to real clinical scans from two subjects that contain much less counts (~10 million). The primary objective was to determine whether these approaches can help recover contrast of brain vasculature, and also improve quantification of signal form the carotid arteries. It was found that the contrast of the carotid arteries and sagittal sinus are greatly improved with all of the approaches when compared to standard techniques (FBP, MLEM and PSF-MLEM). The signal within the blood vessels corresponds well anatomically to the location of the vessels on the Mill. Remarkably signal form the basilar artery, a ~3.8 mm diameter vessel, is clearly visible on the TV-gPSF-MLEM reconstructed PET image.

A particularly surprising finding was that the images in middle iterations for gPSF-MLEM and TV-gPSF-MLEM have remarkable contrast of the vascular. That is, before all 400 iterations are complete. This type of enhancement can be useful for developing future segmentation strategies.

In terms of quantification of signal from the carotid artery, it was found that quantifying signal from PSF-MLEM reconstructed images does provide good recovery after 400 iterations. This is may be because PSF-MLEM reconstruction does not converge and thus a stopping criteria needs to be identified. Mourik empirically determined the number of iterations that yields the best results in terms of AUC recovery of the AIF. For the subjects, a stopping criteria of 150 iterations would indeed provide a reasonable estimate for the TP value, although with slight over- and underestimation. However, such an approach is unlikely to scale well to large studies, where patient scans will have very different count statistics due to differences in correction factors (i.e. attenuation due to brain size), vessel size and injected dose. Indeed, gPSF-MLEM stabilizes closer to the true TP value and has an implicit stopping criteria built in. It has even been see that after the top 4 value plateaus, it continues to be stable with increasing iterations. In fact, the final gPSF-MLEM top 4 values is closer to the true TP value than any arbitrary stopping criteria would yield with PSF-MLEM.

Imaging of the Raphe Nucleus

Serotonin participates in many diverse functions in the central nervous system and acts as a global homeostatic regulator of emotion, mood, appetite, and sleep, as well as a regulator of motor activity [77]. There are five serotonergic raphe nuclei, with each nucleus having a distinct function. The raphe nuclei are a diverse collection of neurons distributed along the midline of the brainstem and the primary source of serotonergic projections to the forebrain, brainstem, and spinal cord [78]. Previously, these brainstem nuclei were identified in humans only in postmortem brain specimens by using histologic methods [79]. Researchers in several neuroimaging studies have visualized the human raphe nuclei in vivo by using magnetic resonance (MR) imaging [80] and positron emission tomography (PET) [81, 82]. However, the locations and activity of the individual raphe nuclei could not be determined with certainty because of the limited tissue contrast of MR imaging for the raphe nucleus and the limited spatial resolution of PET. Although PET imaging is the only method currently available for visualizing the molecular signatures of the raphe nuclei, its resolution is insufficient for visualizing the raphe nuclei individually.

Major depressive disorder (MDD) is associated with a high degree of morbidity and mortality [83], and is predicted to be the leading cause of disease burden by the year 2030 (World Health Organization, 2004). In order to effectively treat this prevalent disorder, a deeper understanding of its pathophysiology is required [84]. Identification of an MDD biomarker (a characteristic that can be objectively measured and used as an indicator of either normal or pathogenic processes [85, 86]) could provide this enhanced understanding, and improve both diagnosis and treatment options.

The region exhibiting the greatest difference between MDD subjects and controls was the raphe. Furthermore, using a diagnostic threshold, male controls can be distinguished from depressed males with high sensitivity and specificity (both >80%). In females, the separation between diagnostic groups yields much lower sensitivity and specificity. This indicates that there may be a specific biosignature for MDD in males. Identification of such a biosignature could provide a deeper understanding of depression pathology, improve diagnosis and aid in the development of new therapies.

The five nuclei of the raphe are smaller than the resolution of most PET scanners, making this region very difficult to identify on a typical individual PET scan. When they are visible, sometimes only one nucleus is seen, the nuclei may appear as one contiguous structure, or one cannot differentiate neighboring 'hot-spots' from the nuclei due to excessive noise. The raphe is also not visible on MRI. As a result, researchers typically place a very large ROI that that encompasses many nuclei to account for the uncertainty of localization.

The [11C]-WAY radioligand binds the 5-HT1A receptor that binds the endogenous neurotransmitter serotonin. This receptor is the most widespread of all 5-HT receptors and it exists in particularly high densities within the raphe nuclei. Thus [11C]-WAY should in theory provide good contrast of the raphe, but thus far it has not been possible to accurately identify the raphe nuclei summed frames individual scans. The problem becomes more difficult with single frames. Here the new reconstruction approaches were applied to a clinical [11C]-WAY PET scan.

Study Protocol

A 110 minute [11C]-WAY scan was obtained, along with emission, transmission, normalization data. 2 cm$^3$ ellipsoid was manually placed on the raphe nuclei using the mean of all PET frames, completely encompassing the high binding region of the posterior midbrain. The TAC from this ROI was used to select the frame with the highest raphe signal. This turned out be a 5 minute frame containing emission data acquired from 10 to 15 minutes after radioligand injection. The emission data contained 36 million counts.

Qualitative Results

Figure 53:
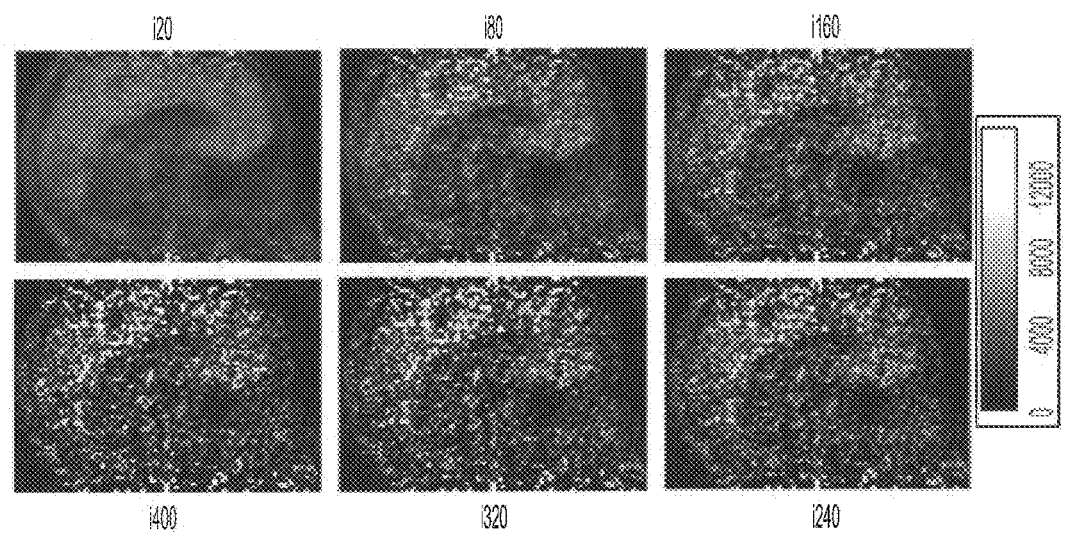
FIG. 53 shows results for MLEM over 400 iterations. It is difficult to identify the location of the raphe, although some faint hot spots are visible in early iterations. Noise quickly overwhelms the image structure.

The MLEM reconstructions over several iterations are shown in FIG. 53. Although the outline of the brainstem is visible, the raphe nuclei are not visible in any of the iterations. By iteration 400 the brain stem in the image is hardly discernible.

Figure 54:
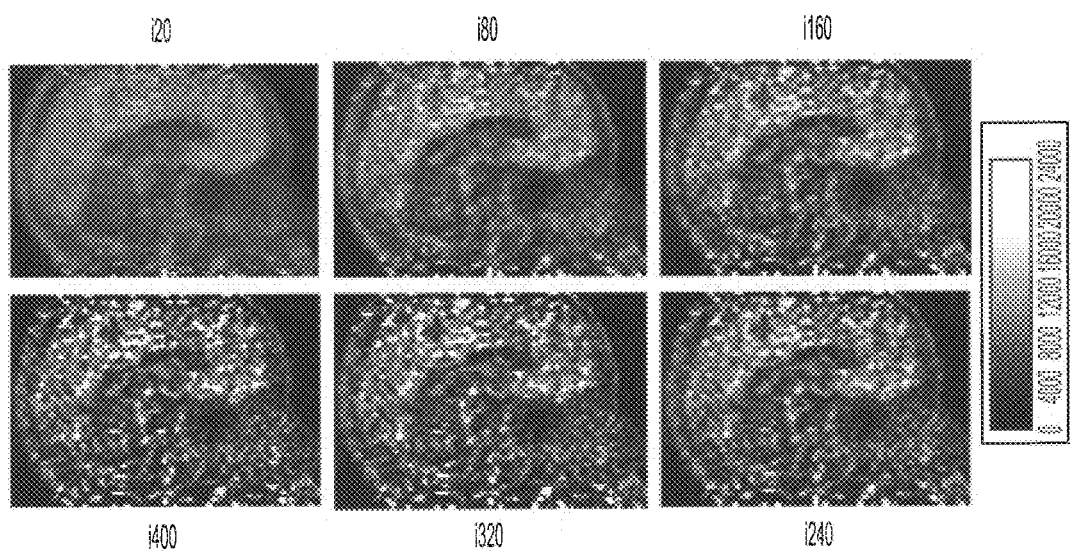
FIG. 54 shows Results for PSF-MLEM over 400 iterations. Raphe is more visible than with MLEM, but it is unclear where to stop iterations. By iteration 400 the image is corrupted by hot-spot artifacts and noise patterns. The raphe nuclei are still visible but difficult to discern against the background hot-spots.

PSF-MLEM reconstructions over several iterations are shown in FIG. 54. By iteration 160, four raphe nuclei are identifiable, although the inferior most nucleus is barely visible. In later iterations the background region around the brainstem becomes increasingly more corrupted by noise, which makes it more difficult to identify each nuclei.

Figure 55:
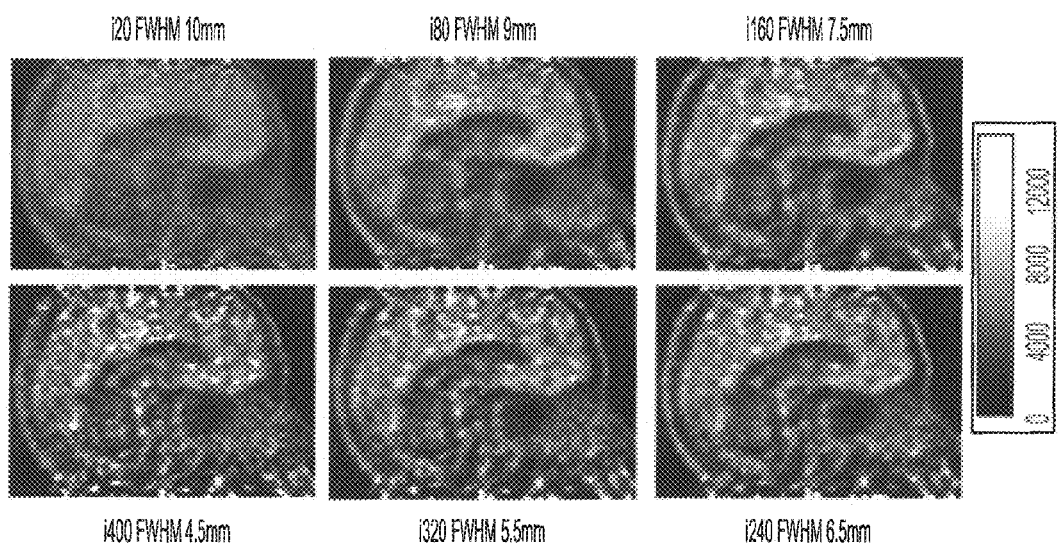
FIG. 55 shows results for gPSF-MLEM over 400 iterations. By iteration 240 all four nuclei are visible, their contrast against the background increases with increasing iterations. By iteration 400 the nuclei are clearly distinguishable from background. Noise and hot-spot artifacts are reduced over PSF-MLEM.

The gPSF-MLEM reconstructions over several iterations are shown in FIG. 55. Four raphe nuclei are poorly identifiable in early iterations, but in later iterations the contrast of each nucleus improves substantially. By iteration 400 the raphe nuclei clearly stand out against the background. There is also reduced hot-spot artifact and reduced noise compared to PSF-MLEM.

Figure 56:
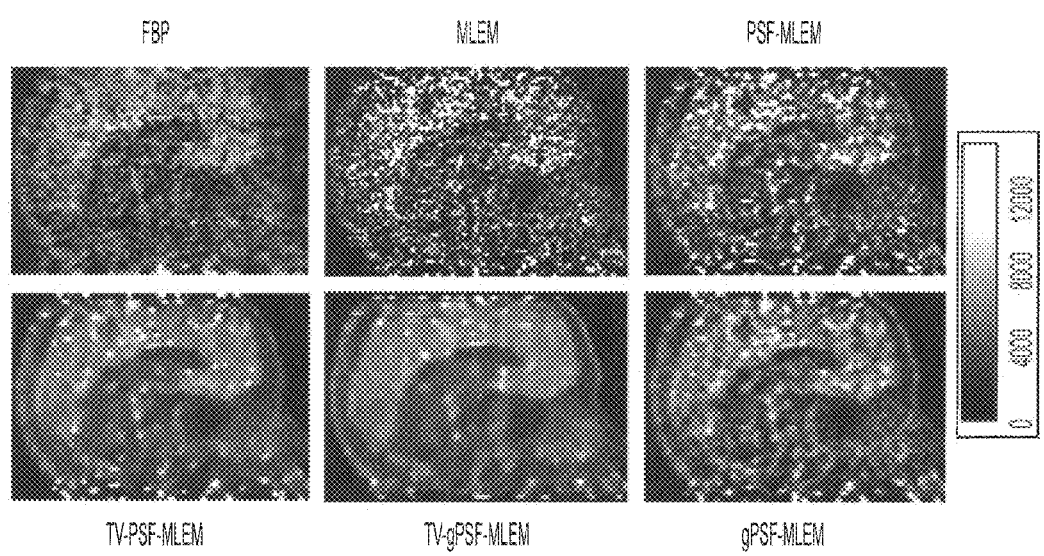
FIG. 56 shows results with FBP and after 400 iterations of all other methods. (first row) Traditional approaches (FBP, MLEM and PSF-MLEM) are heavily corrupted by noise making it difficult to make out the raphe nuclei against background. PSF-MLEM shows the best contrast but contains substantial artifact. (bottom row) Approaches described herein (TV-PSF-MLEM, gPSF-MLEM and TV-gPSF-MLEM) all show improved raphe contrast and reduction of background noise. Edges corresponding to the cortex of the brain are very well defined with the TV approaches.

FIG. 56 shows the FBP reconstruction and all iterative reconstructions after 400 iterations for the sagittal slice that contains the raphe nuclei. The nuclei are not visible on FBP or MLEM images. PSF-MLEM improves results, the nuclei are visible but the image contains multiple hot-spot artifacts in the area of the brainstem that make localization difficult. In contrast, gPSF-MLEM shows reduced noise, better delineation of the cortical edges, and a high contrast of the nuclei against the background. With TV-PSF-MLEM, the cortical edges are even more defined and the nuclei are the only structure with contrast in the brain stem area. Paradoxically, TV-gPSF-MLEM shows reduced contrast of the nuclei, and the most superior nucleus is no longer visible. In addition, there appears to be superior-to-inferior striations in the image. The activity in the cortex appears smeared. Although, cortical edges appear more prominent and well delineated then with any other approach.

To confirm the enhancement of raphe nuclei, the gPSF-MLEM reconstructed image was overlaid on an MRI on which the brainstem is visible. Although the nuclei cannot be distinguished with MRI, their relative location in the brainstem could be assessed. In addition, the PET image of a previously published study was compared with a high resolution PET (HRRT) scan and a 7T MRI. FIGS. 57A-B, 58, and 59 show these images. The brainstem is clearly visible on the MRI (a) and four raphe nuclei are visible on the gPSF-MLEM image. On the overlay image (c) it can be seen that the nuclei located in the posterior brainstem. This corresponds well to the high resolution PET/MRI fusion findings (d). Comparing the overlay in (c) to the high resolution results in (d), which nuclei are actually visible on the [11C]-WAY scan can be approximated. It can be concluded that the three remaining hot-spots are, from superior to inferior: (1) R1; (2) the fused R2/R3; and (3) the fused R4/R5 nuclei.

Conclusion

It was found that the contrast of the raphe nuclei is substantially improved with the gPSF-MLEM and TV-PSF-MLEM approach. PSF-MLEM provides the best contrast of all the common techniques implemented in clinical systems (e.g. FBP, MLEM). However, it also induces noise in the background that make it more difficult to distinguish nuclei from hot-spot artifacts. TV-gPSF-MLEM actually reduced the contrast of the nuclei. This could be due to the interplay between TV and the large FWHM in early iterations. The large FWHM induces smoothing, which could be being enhanced by TV thereby leading to resolution loss in the final result. This may be remedied by changing parameter settings, by reducing the TV weight, or by introducing TV at later iterations. Overall, gPSF-MLEM and TV-PSF-MLEM show remarkable enhancement of the raphe.

Conclusions from Clinical Studies

The performance of TV-PSF-MLEM, gPSF-MLEM and TV-gPSF-MLEM was demonstrated on real clinical data for visualizing and quantifying carotid artery signal, and visualizing the raphe nucleus in the brain. It was found that all the approaches produce images with improved contrast, reduced background noise, and reduced hot-spot artifacts. Overall, the performance of all approaches was better than existing techniques that are currently implemented on clinical PET scanners (i.e. FBP, MLEM and PSF-MLEM).

TV-PSF-MLEM and TV-gPSF-MLEM are sensitive to counts in the image, additional tuning may be required for blood vessel imaging HO million counts) and raphe imaging (~30 million counts). A parameterization scheme can be devised that accounts for different behavior of the gPSF algorithms with respect to differences in count levels in the PET images. The interplay between TV and gPSF can be investigated because as seen TV-gPSF-MLEM may reduce contrast in some situations. The following parameters were manually tuned for the simulated, ACR phantom, and clinical scans: β (TV tuning parameter) of (5.10)) and ε (convergence threshold) of (5.10). The settings for all experimental setups are shown in FIG. 92.

The parameter c appears to be dependent on number of counts in the image, while β may also need to be adjusted but is less sensitive to number of counts. In general, the more counts in the PET images the faster the MLEM reconstruction converges because of better agreement between the reconstruction and the acquired sinogram. Tuning of the TV parameter may not be related to counts in the image, but rather be an application-specific problem. Simulated and ACR phantoms are both cylindrical and symmetrical in shape. On the other hand, the clinical brain scans are not uniform, not truly symmetrical, and contain an inhomogeneous distribution of the radioligand. Therefore, it is plausible that TV parameterization need to be based on expected spatial distribution of the radioligand within the object of interest.

Example 5: PET Resolution Recovery by Embedding a Locally-Weighted Denoising in the MLEM Reconstruction Clinical Relevance of PET Quantification PET quantification is generally described in Kotasidis, F. A. et al. "Advanced kinetic modeling strategies: towards adoption in clinical PET imaging". Clin. Trans. Imaging, 2014. Considerably more information can be extracted from dynamic PET image acquisition protocols, followed by application of appropriate image reconstruction and tracer kinetic modeling techniques. PET kinetic modeling has mainly been restricted to drug development and clinical research applications due to their complexity. To make PET dynamic imaging more feasible and valuable in routine clinical imaging research outcomes are needed in noninvasive input function extraction.

Positron Emission Tomography (PET)

Measures used in PET include radioactivity level, spatial distribution and dynamic (time varying). Analysis of PET includes uptake, kinetics and binding potentials. Usage of PET includes drug occupancy, blood flow, receptor binding, blood volume, and treatment response.

Described herein are new MLEM reconstruction refinements for improved PET image resolution recovery. Performance evaluation on PET clinical scans is described included visualization and quantification of brain blood vessels and visualization of the raphe nuclei.

PET Iterative Reconstruction and Resolution Modeling

PET iterative reconstruction and resolution modeling include maximum likelihood expectation maximization (MLEM) (Shepp, L. A. et al., Maximum likelihood reconstruction for emission tomography. (1982)) and projectors that incorporate PSF kernel (PSF-MLEM) as shown in FIG. 60. PSF-MLEM provides improvement in resolution (Lee, K. et al. Pragmatic fully 3D image reconstruction for the MiCES mouse imaging PET scanner (2004)).

PSF-MLEM Artifacts

Multiple artifacts can be introduced by PSF modeling in the MLEM reconstruction (Bai and Esser, Nuclear Science Symposium Conference Record (NSS/MIC), pp. 2263-2266, 2010; Stute, S. et al. Practical considerations for image-based PSF and blobs reconstruction in PET. (2013). These artifacts include poorly recovered levels of activity, edge artifacts at borders of large regions, and over-enhancement of small structures (A. Rahmin et al., "Resolution modeling in PET imaging: Theory, practice, benefits and pitfalls", Med Physics 2013).

PSF Artifact Mitigation Strategies

PSF artifact mitigation strategies include "resolution-modeling" approaches. "Resolution-modeling" approaches include using smaller FWHM PSF (S. Tong, et al., "Properties and mitigation of edge artifacts in PSF based PET reconstruction", IEEE TNS 2011), post-filter the reconstructed images (Stute & Comtat, "Practical considerations for image-based PSF and blobs reconstruction in PET", PMB 2013), and incorporation of a regularization prior in the reconstruction process (Rapisarda, et al., "Evaluation of a new regularization prior for 3-D PET reconstruction Including PSF modeling," IEEE TNS 2012). However, all of these approaches lead to loss of contrast. Described herein is the incorporation of a total-variation (TV) regularization process in the PSF-MLEM reconstruction. The TV must be spatially weighted.

Figure 61:
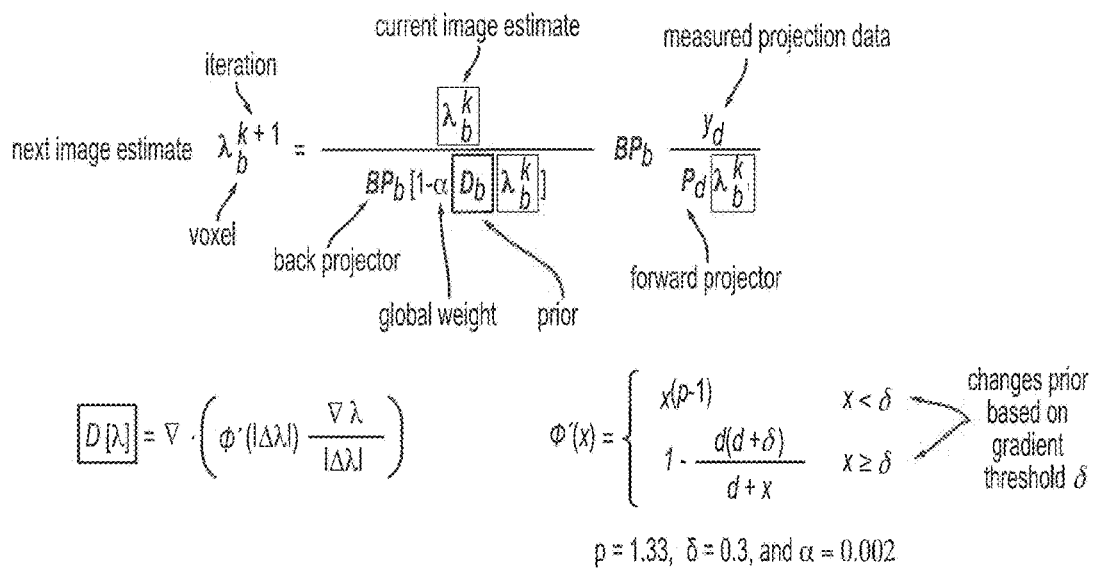
FIG. 61 shows the algorithm for the Rapisarda approach.
Figure 62:
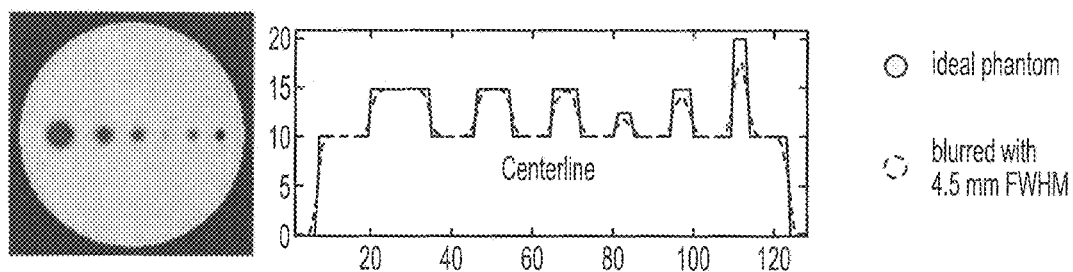
FIG. 62 shows the phantom and cross-section.

The current state of the art approach is the Rapisarda approach (FIG. 61) (Rapisarda, et al., "Evaluation of a new regularization prior for 3-D PET reconstruction Including PSF modeling," IEEE TNS 2012).

Simulated data was generated with the Software for Tomographic Image Reconstruction (STIR). Geometric objects were used with a background (200 mm diameter cylindrical phantom) plus cylindrical objects (25 mm, 16 mm and 8 mm diameter hot spots with different object/background contrast ratios). The PSF was symmetric 4.5 mm FWHM Gaussian kernel to simulate (mimics PSF of Siemens ECAT HR+ scanner). Poisson noise was added on sinogram measures (scaling factor=1). The simulated data was used to study the formation of artifacts and develop the method described herein.

Characteristics of the PSF-MLEM Artifacts

Characteristics of the PSF-MLEM artifacts are shown in FIG. 15. The convergence rate is object size and contrast dependent. Convergence rate varies with object diameter. For large cylinders edge convergence is much slower. There is little variation in convergence when contrast changes. The convergence rate of individual voxels can be used to prevent PSF artifacts from forming.

Locally-Weighted Total Variation

Figure 65:
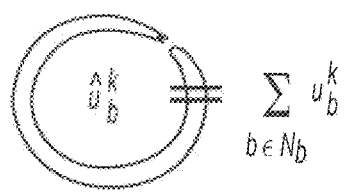
FIG. 65 shows the algorithm to compute the average weight inside a 3×3×3 neighborhood around voxel b for noisy data.

The total variation (TV) regularization is inserted within the PSF-MLEM algorithm (TV-PSF-MLEM) (FIG. 63). The regularization must vary with the local geometry and contrast. Geometry and contrast are inferred with the MLEM convergence rate. The MLEM convergence rate is used to create a weight for each voxel (FIG. 64). For noisy data, the average weight inside a 3×3×3 neighborhood around voxel b is computed (FIG. 65).

Performance on Simulations

The results of TV-PSF-MLEM on simulated data before TV-PSF-MLEM (FIG. 14) and after TV-PSF-MLEM, with and without noise are shown in FIGS. 17a-b. Comparison against the state-of-the-art method from Rapisarda et al. (2012) which uses gradient-based weights and a TV like prior is shown in FIG. 28. TV-PSF-MLEM has similar performance to Rapisarda in large cylinders and has increased sharpness (reduce support) similar to Rapisarda. TV-PSF-MLEM over-estimated the activity in small cylinders. This overestimation can be prevented by applying a minimal cutoff value to the weights (FIG. 29). This allows improved recovery of small cylinders via global thresholding of the weights.

The Recovery Coefficient (RC) quality metric was used to analyze performance on simulations (FIG. 30).

$$RC = \sum_{b \in \Omega_{ROI}} \lambda_b^{recon} / \sum_{b \in \Omega_{ROI}} \lambda_b^{true}$$

Rapisarda had an RC close to MLEM on no-noise data. Rapisarda had robustness to noise, prevention of edge artifacts but poor contrast recovery in 8 mm cylinders. TV-PSF-MLEM had an RC higher than Rapisarda and MLEM (FIG. 30).

Performance on the ACR Phantom

The performance of TV-PSF-MLEM was tested on the ACR Phantom (FIG. 31). The American College of Radiology (ACR) Phantom is a Flangeless Esser PET Phantom™. The inside diameter is 20.4 cm, the inside height is 18.6 cm and the wall thickness is 6.4 cm. The rod diameters are 4.8, 6.4, 7.9, 9.5, 11.1 and 12.7 mm. The thin-walled cylinders are 8, 12, 16, 25 (×3) mm. The solid cylinder (Teflon) is 25 mm. The ECAT HR+ PET scanner was used in 3D mode (septa retracted). Emission sinogram, Transmission sinogram, Normalization file, Scatter model file were used. There were approximately 120 million counts and a 2:1 contrast radio hot/background.

The original TV regularization approach targets image denoising under Gaussian noise (L. I. Rudin, S. Osher, and E. Fatemi, "Nonlinear total variation based noise removal algorithms," Physica D, vol. 60, no. 1-4, pp. 259-268, 1992). There are TV numerical algorithms for different noise models (Rodriguez, P. Total variation regularization algorithms for images corrupted with different noise models: a review. (2013)). The most appropriate noise model for MLEM PET scanner images was determined.

Figure 33:
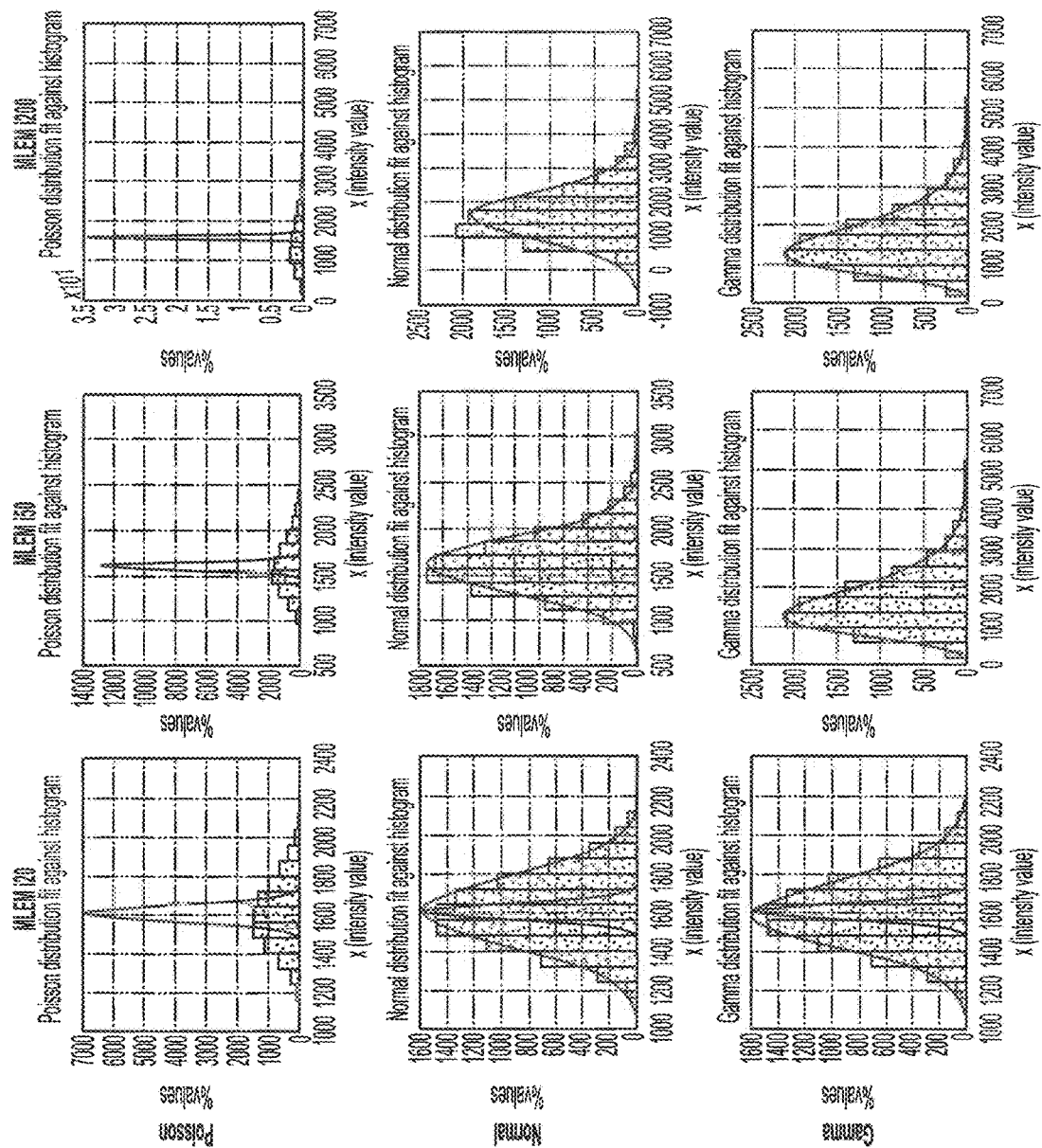
FIG. 33 shows estimated PDFs for different noise models are overlaid over the histogram of the values within the ROI in the uniform of the ACR phantom. Shown for several iterations.

Parameters for Normal, Poisson, and Gamma distributions were estimated (FIG. 32). The fit was evaluated with Q-Q plots (FIG. 34) and the fitted distribution was overlaid over histogram (FIG. 33). This was repeated for different iterations of MLEM.

It was determined that Poisson distribution is not appropriate. In early iterations Normal and Gamma distributions fitted the data well. Gamma distribution was slightly better than Normal in later iterations. Gamma distribution had no explicit expressions for the ML parameters and Newton-Raphson estimation is computationally intensive. The normal distribution fits are very close to Gamma, therefore, TV for Gaussian noise was used.

Figure 66:
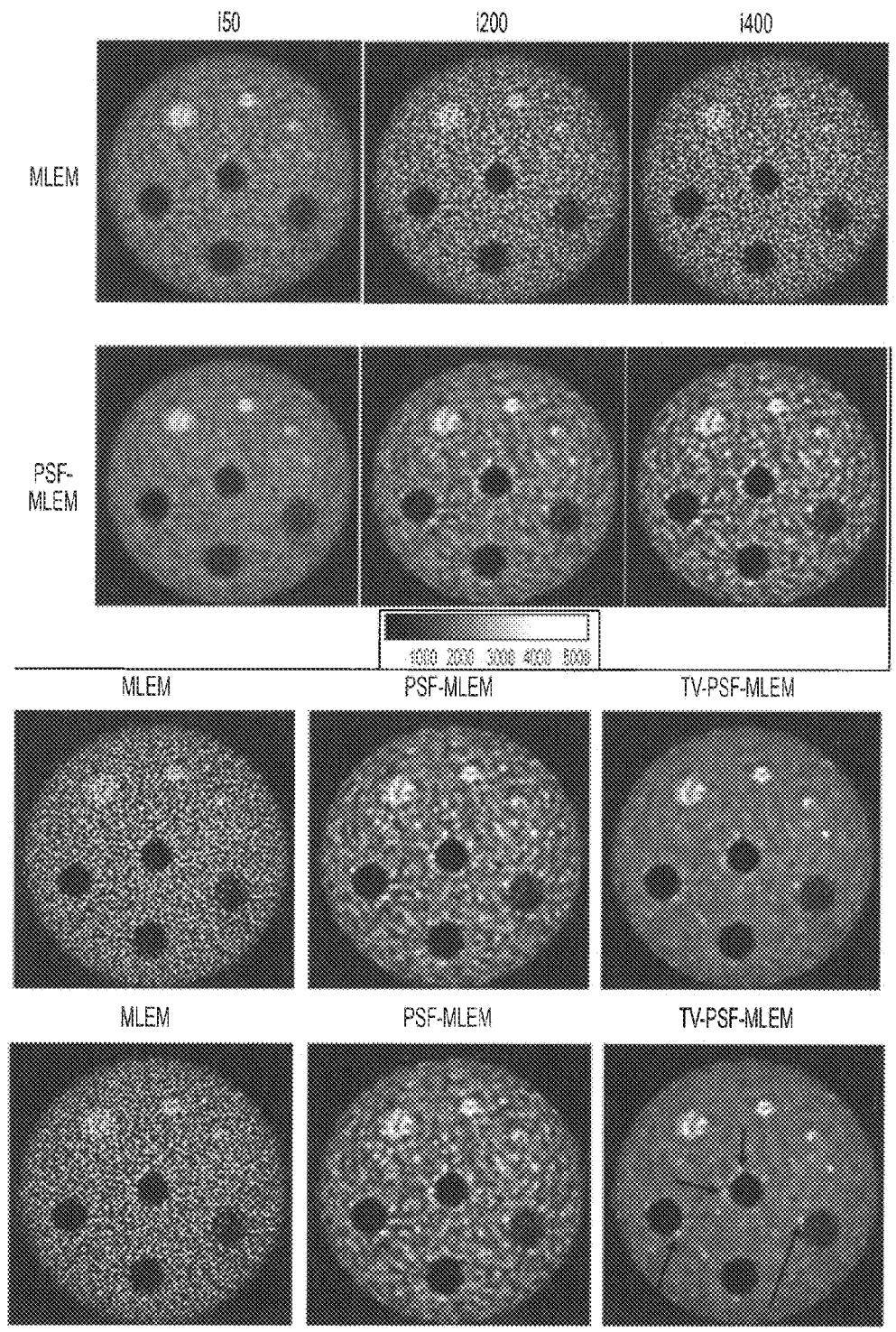
FIG. 66 shows performance of TV-PSF-MLEM on the ACR Phantom. Hot spots are indicated in the bottom panel with arrows.

The performance of TV-PSF-MLEM is shown in FIG. 66. TV-PSF-MLEM had improved hot cylinder contrast and reduced background noise. TV-PSF-MLEM contained 'hot spot' artifacts.

Gradual PSF

To mitigate 'hot-spot' artifacts a modification of the method was devised, based on empirical intuition. Instead of using the same FWHM PSF at each iteration the FWHM is evolved. At the start there is a large FWHM, this is gradually decreased at each iteration until it reaches a target true value in the final iteration. The stopping criteria is pre-defined. On the ACR phantom, start with a 10 mm FWHM and end with a 4.5 mm FWHM over N iterations.

Performance on the ACR Phantom

Figure 38:
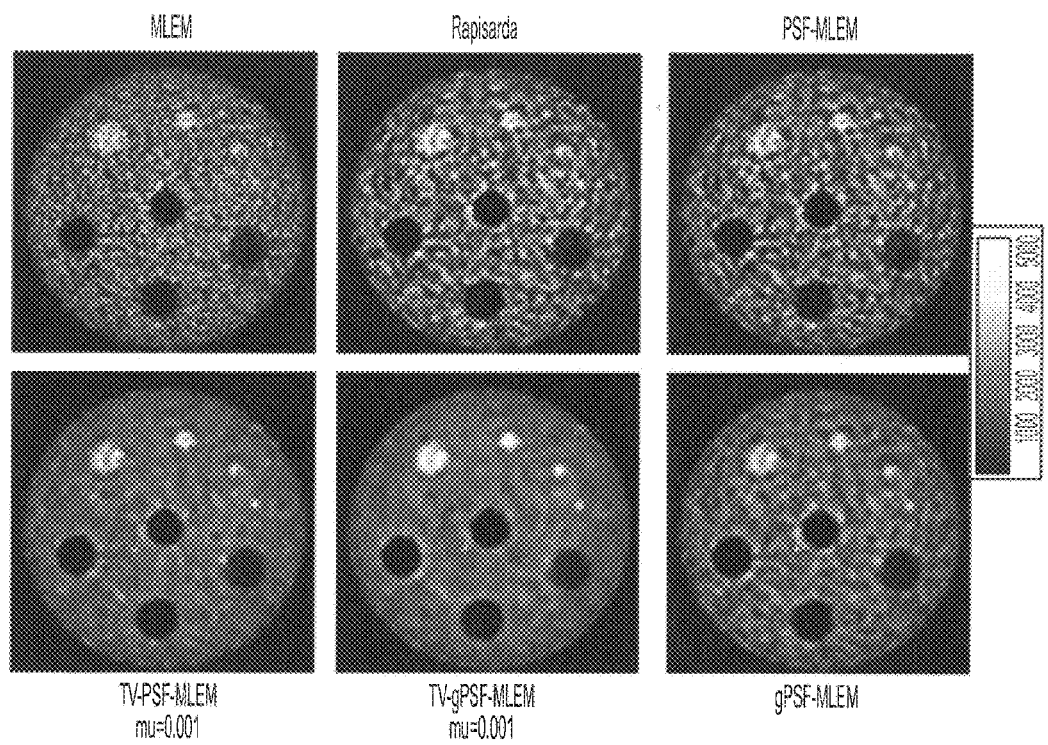
FIG. 38 shows ACR phantom reconstructed with (top-row) MLEM, Rapisarda and PSF-MLEM and the novel approaches described herein (bottom row) TV-PSF-MLEM, gPSF-MLEM and TV-gPSF-MLEM.
Figure 39:
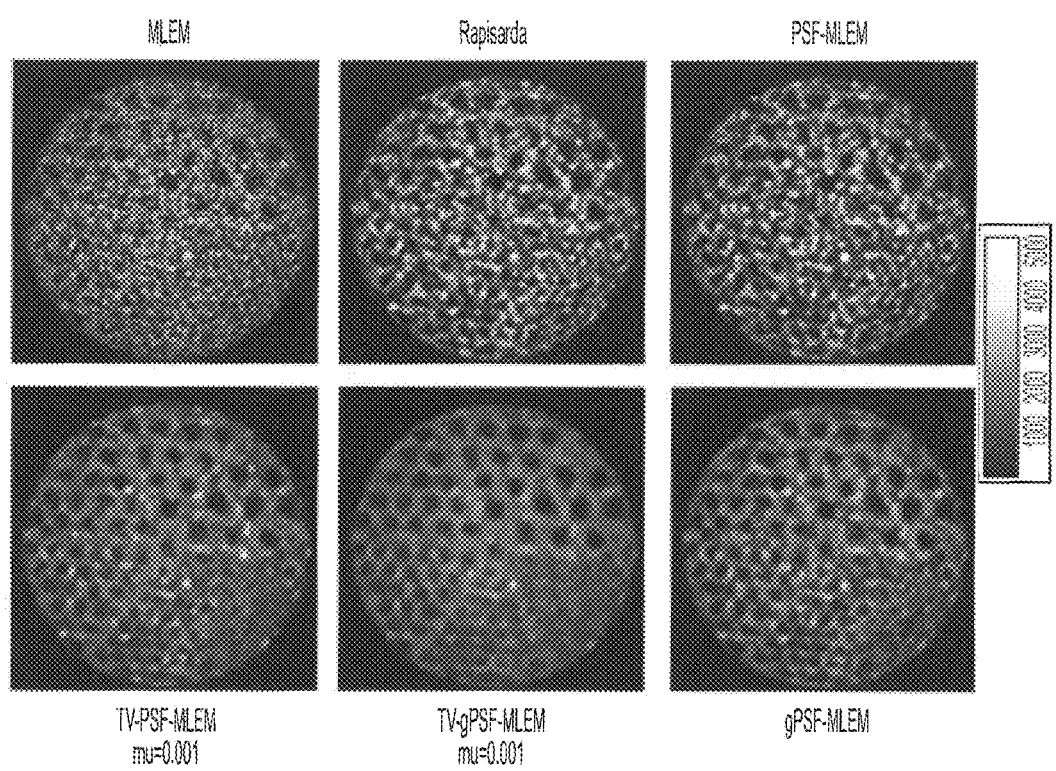
FIG. 39 shows ACR phantom, bottom section of cold rods, reconstructed with (top-row) MLEM, Rapisarda and PSF-MLEM and the novel approaches described herein (bottom row) TV-PSF-MLEM, gPSF-MLEM and TV-gPSF-MLEM.
Figure 40:
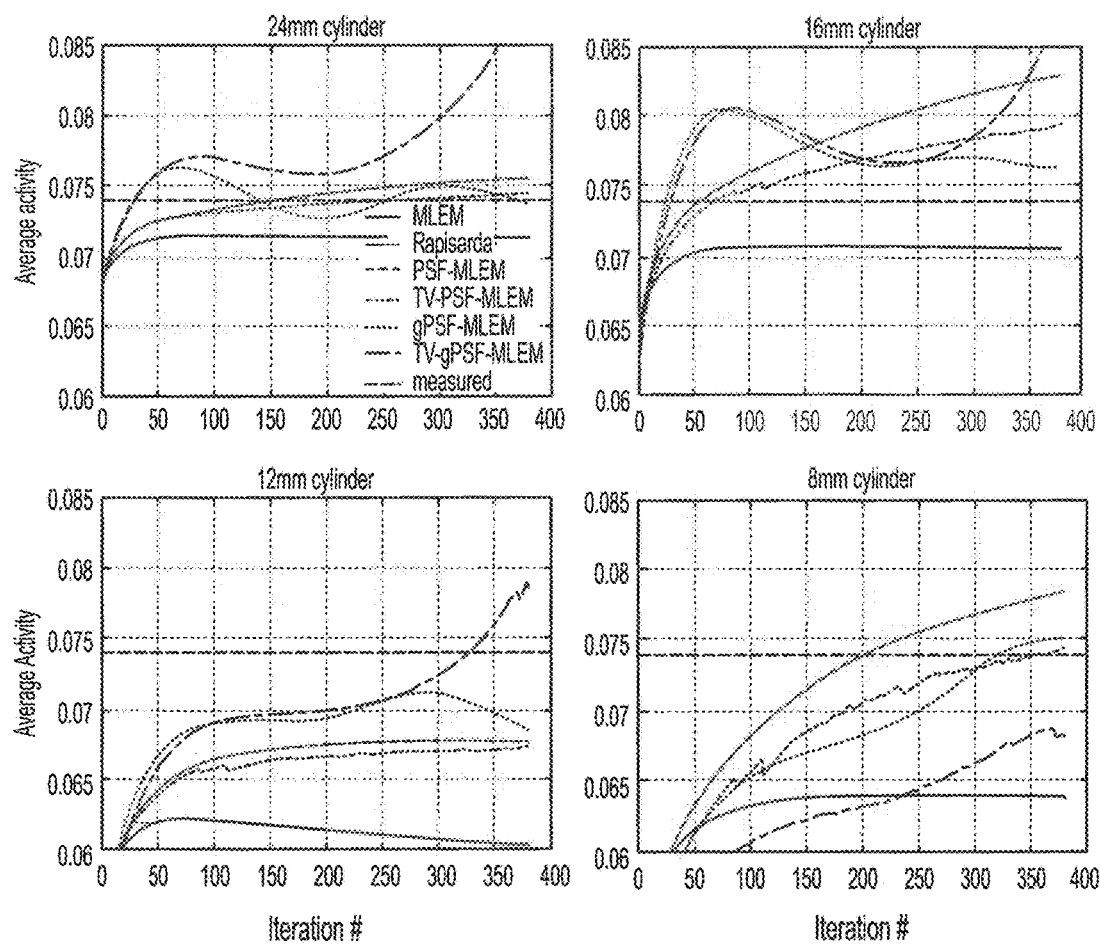
FIG. 40 shows average activity within 24 mm, 16 mm, 12 mm and 8 mm hot cylinders. Measured activity levels are shown for reference (dashed black line). Results for different reconstructions are shown over 400 iterations: MLEM (thick solid line), PSF-MLEM (dashed line), Rapisarda (thin solid line), TV-PSF-MLEM (short dash-dot line), gPSF-MLEM (dotted line), and TV-gPSF-MLEM (long dash-dot line). Of all approaches, gPSF-MLEM provides recovery of activity that is closest to the measured value in all cylinders except the 8 mm, where TV-PSF-MLEM and gPSF-MLEM are both very close.
Figure 67:
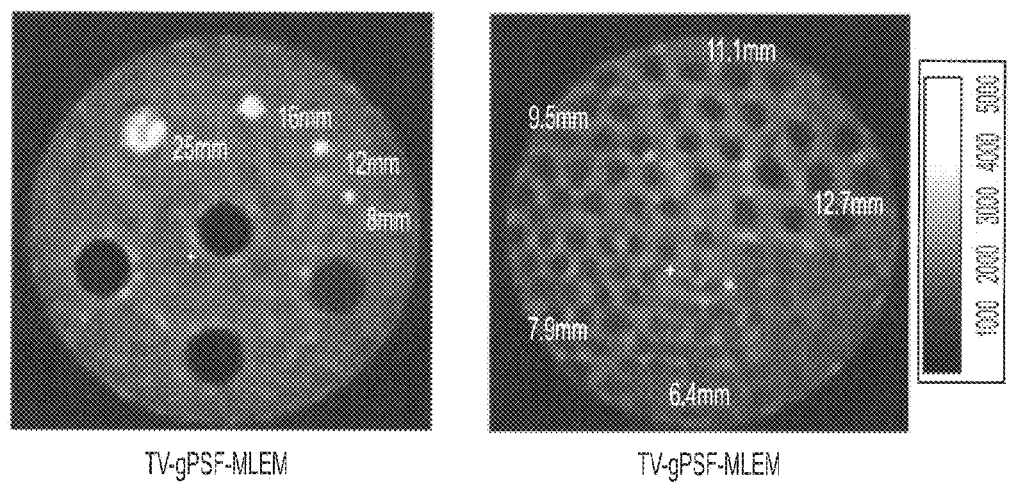
FIG. 67 shows performance of TV-gPSF-MLEM on the ACR Phantom.

Performance of TV-gPSF-MLEM on hot cylinders is shown in FIG. 38. Performance of TV-gPSF-MLEM on cold rods is shown in FIG. 39. The performance of TV-gPSF-MLEM on the ACR Phantom is summarized in FIG. 67.

In summary, TV-PSF-MLEM had background noise suppression and good hot-contrast but many unmitigated 'hot-spot' artifacts. gPSF-MLEM had suppression of 'hot-spot' artifacts and good hot-contrast. TV-gPSF-MLEM had good suppression of PSF artifacts, clearly visible small cylinders (8 mm and 12 mm), natural shapes and sharp edges.

Reconstruction of Clinical Data: Blood Vessels

Signal from blood vessels contains the 'whole blood' tracer activity in the blood. A whole blood measure is needed for vascular correction to further improve kinetic modeling. A whole blood measure can also be used a predictor with the nSIME approach.

Figures 68A, 68B, 68C, 68D, 68E, 68F:
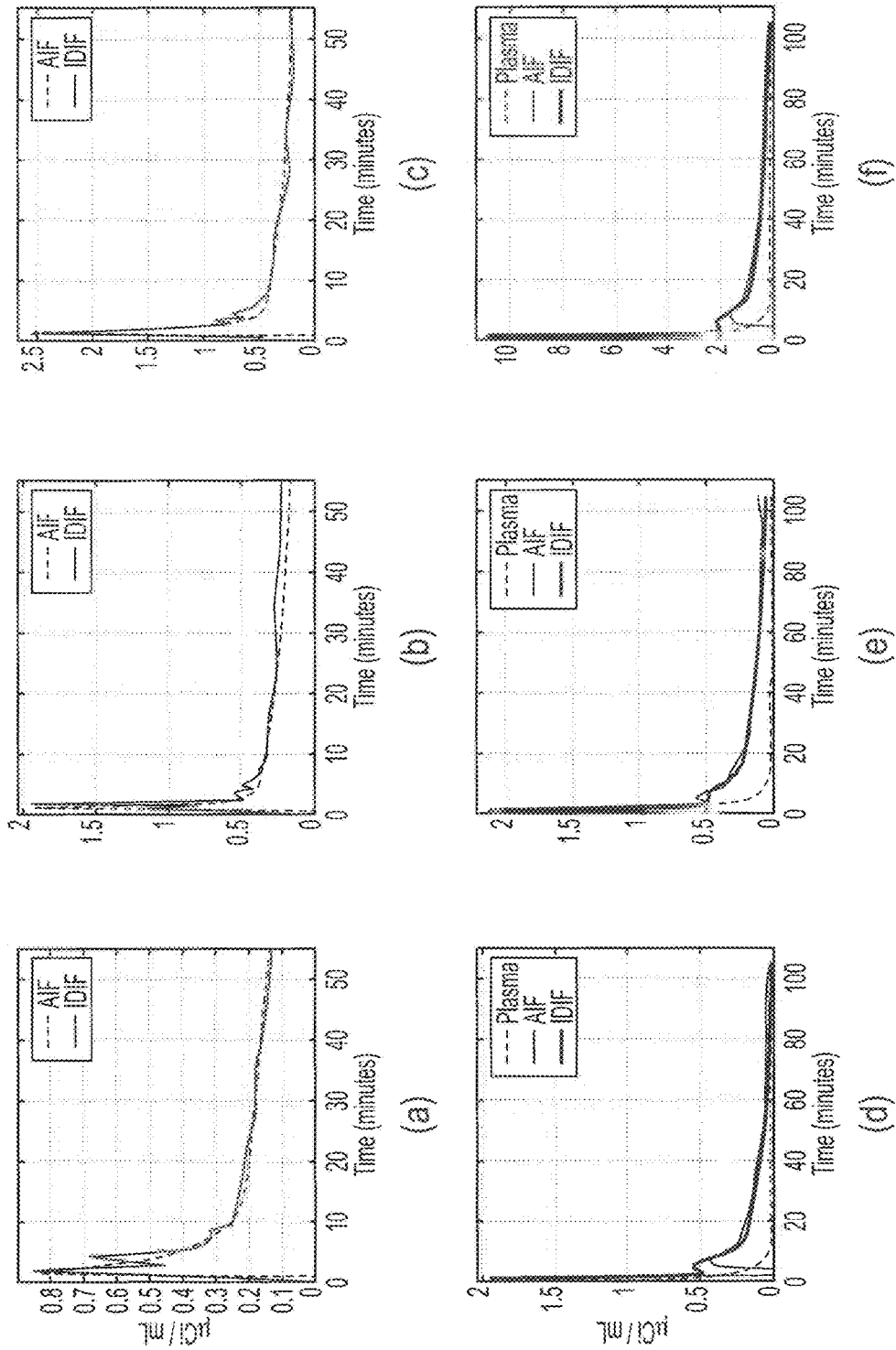
FIGS. 68A-68F shows the arterial input function (AIF), image derived input function (IDIF) for [18F]-FDG (top row) and [11C]-WAY (bottom row). For [11C]-WAY the plasma radioactivity (Plasma) is also shown.

The feasibility of extracting the whole blood (WB) curve using a spatially constrained ICA approach has previously been demonstrated (FIG. 68) (Mikhno A, et al., Brain tissue selection procedures for image derived input functions derived using independent components analysis. Engineering in Medicine and Biology Society (EMBC), 2012 Annual International Conference of the IEEE, pp. 5987-5990). This method still requires blood sample taken during the peak of the WB curve which is not feasible since the peak time is not known a priori.

Figure 69:
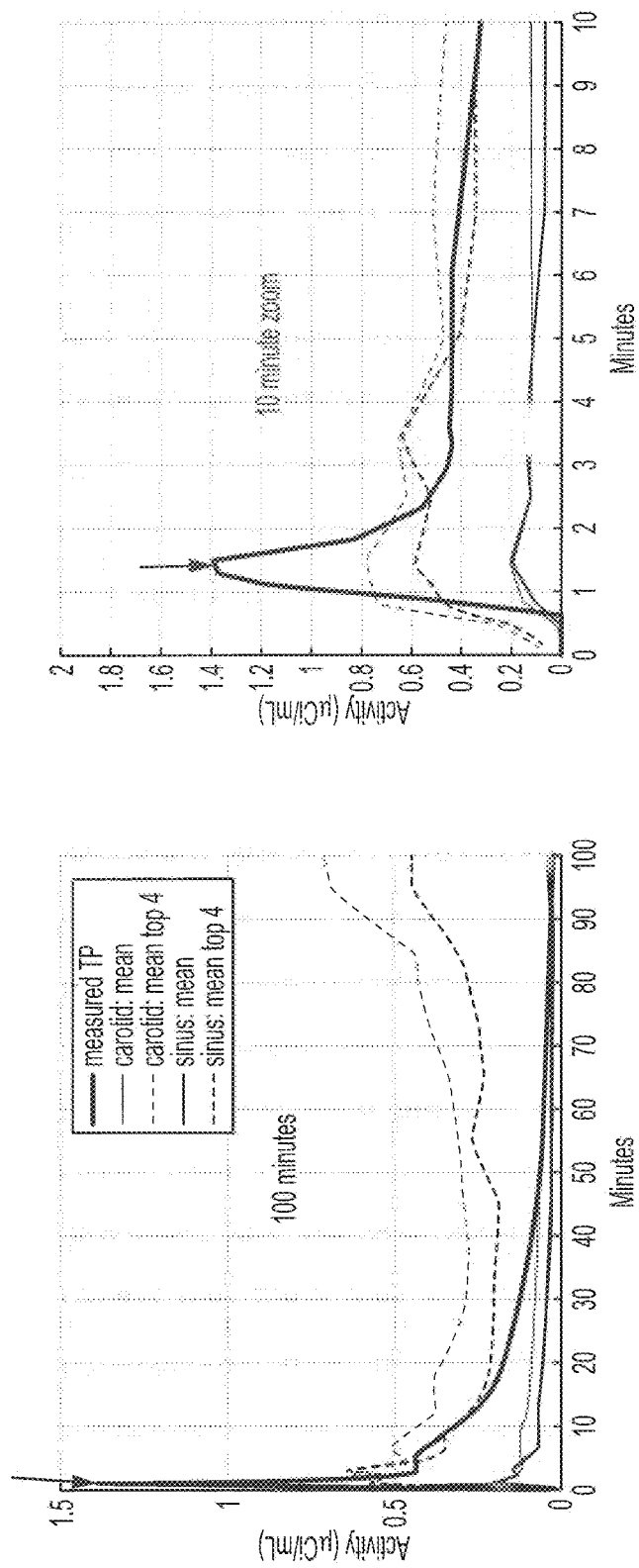
FIG. 69 shows the measured total plasma (TP) and PET FBP signal calculated from blood vessels.

The peak time can be assessed a posteriori from imaging data. The signal is corrupted by partial volume effect, vessels are small (4-6 mm diameter) relative to image resolution. Mourik proposed measuring from top 4 voxels from PSF-MLEM images (FIG. 69) (Mourik, J. E. et al. Partial volume corrected image derived input functions for dynamic PET brain studies: methodology and validation for [11C]-flumazenil. (2008)).

Figure 70:
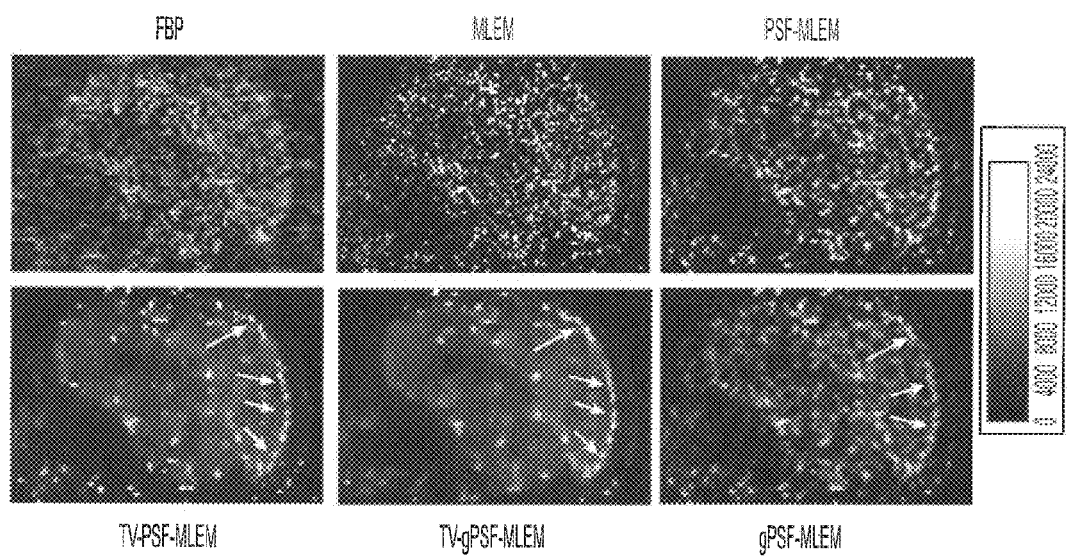
FIG. 70 shows reconstructed PET clinical data of blood vessels.
Figure 71:
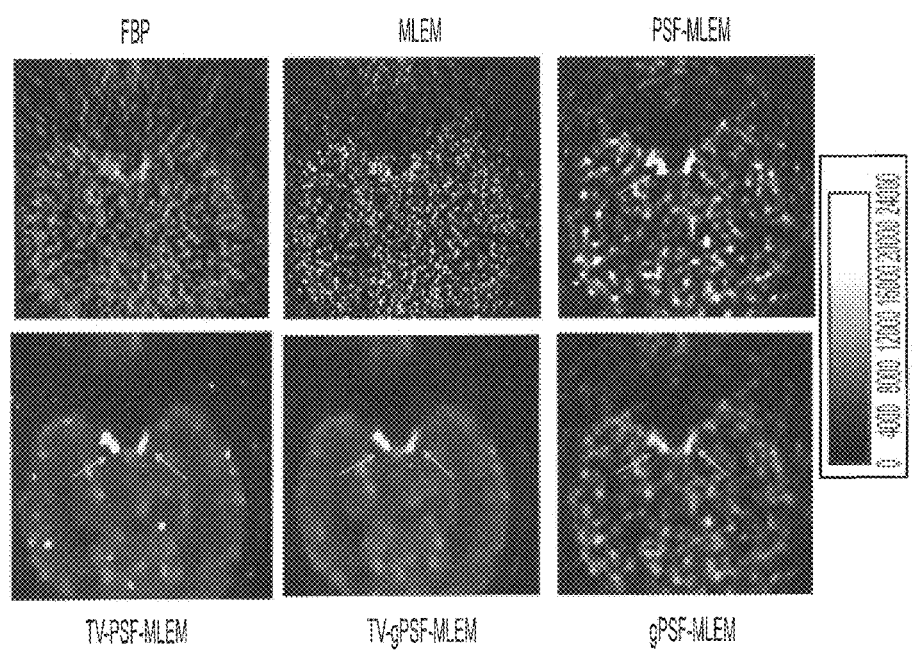
FIG. 71 shows reconstructed PET clinical data of blood vessels.

One minute acquisitions with approximately 10 million counts were performed and reconstructed (FIGS. 70 & 71). Reconstructed PET clinical data of blood vessels shows excellent recovery (FIGS. 51 & 52). The PSF-MLEM top 4 signal does not converge in 400 iterations and overestimates the peak blood value. gPSF-MLEM top 4 value converges and remains stable in later iterations. Sampling from carotids on gPSF-MLEM images may serve as a replacement scaling factor for the ICA IDIF approach.

Reconstruction of Clinical Data: Raphe Nuclei

Serotonin is a global homeostatic regulator of emotion, mood, appetite, sleep, and motor activity. The raphe nuclei release serotonin to the rest of the brain. They are a therapeutic target and diagnostic marker. PET resolution is insufficient for visualization of the raphe nuclei individually. Visualization would require using non-clinical 7T MRI and HRRT PET (Son, Y. D. et al. "Individually differentiated serotonergic raphe nuclei measured with brain PET/MR imaging" (2014)).

Figure 72:
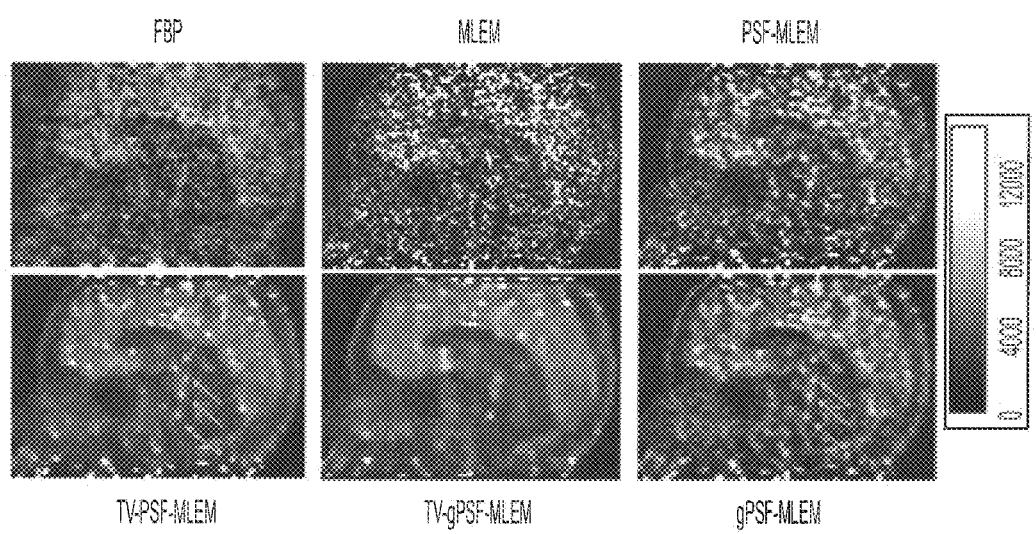
FIG. 72 shows reconstructed PET clinical data of Raphe nuclei.

Five minute acquisitions with approximately 30 million counts were performed and reconstructed (FIG. 72). Reconstructed PET clinical data showed four visible nuclei (FIGS. 57A-B, 58 & 59).

Conclusions

All proposed MLEM refinements improved contrast and reduced background noise. Both gPSF-MLEM and TV-gPSF-MLEM also reduce hot-spot artifacts. Contrast reduction with TV-gPSF-MLEM on the raphe scan could be an image artifact causing a numerical instability. TV parameters are sensitive to counts in the image, the parameters made to be manually tuned (FIG. 92), a parameterization scheme can be defined.

REFERENCES

Sureau et al., "Impact of Image-Space Resolution Modeling for Studies with the High-Resolution Research Tomograph," Journal of Nuclear Medicine, vol. 49, no. 6, pp. 1000-1008, May 2008.

Bai and Esser, "The effect of edge artifacts on quantification of Positron Emission Tomography," in Nuclear Science Symposium Conference Record (NSS/MIC), 2010 IEEE, 2010, pp. 2263-2266.

Thielemans et al., "Impact of PSF modelling on the convergence rate and edge behavior of EM images in PET," in Nuclear Science Symposium Conference Record (NSS/MIC), 2010 IEEE, 2010, pp. 3267-3272.

Snyder et al., "Noise and edge artifacts in maximum-likelihood reconstructions for emission tomography," IEEE Trans Med Imaging, vol. 6, no. 3, pp. 228-238, 1987.

Tong et al., "Properties and Mitigation of Edge Artifacts in PSF-Based PET Reconstruction," IEEE Transactions on Nuclear Science, vol. 58, no. 5, pp. 2264-2275, October 2011.

Rapisarda et al., "Evaluation of a New Regularization Prior for 3-D PET Reconstruction Including PSF Modeling," IEEE Transactions on Nuclear Science, vol. 59, no. 1, pp. 88-101, February 2012.

Yan, "EM-type algorithms for image reconstruction with background emission and Poisson noise," Advances in Visual Computing, pp. 33-42, 2011.

Shepp and Vardi, "Maximum likelihood reconstruction for emission tomography," Medical Imaging, IEEE Transactions on, vol. 1, no. 2, pp. 113-122, 1982.

Thielemans, et al., "STIR: software for tomographic image reconstruction release 2," Physics in Medicine and Biology, vol. 57, no. 4, pp. 867-883, February 2012.

Mourik, et al., Journal of Cerebral Blood Flow & Metabolism, vol. 30, no. 2, pp. 381-389, October 2009.

Mikhno, Angelini, Bai, and Laine, "Locally weighted total variation denoising for ringing artifact suppression in pet reconstruction using PSF modeling," in Biomedical Imaging (ISBI), 2013 IEEE 10th International Symposium on. IEEE, 2013, pp. 1252-1255.

45. M. Defrise, P. E. Kinahan, and C. J. Michel, "Image reconstruction algorithms in PET," Positron Emission Tomography, pp. 63-91, 2005 2005.

50. E. Rapisarda, V. Bettinardi, K. Thielemans, and M. Gilardi, "Image-based point spread function implementation in a fully 3D OSEM reconstruction algorithm for PET," Physics in medicine and biology, vol. 55, p. 4131, 2010.

56. S. Stute and C. Comtat, "Practical considerations for image-based PSF and blobs reconstruction in PET," Phys Med Biol, vol. 58, pp. 3849-70, Jun. 7, 2013.

58. D. L. Snyder, M. I. Miller, L. J. Thomas, and D. G. Politte, "Noise and edge artifacts in maximum-likelihood reconstructions for emission tomography," Medical Imaging, IEEE Transactions on, vol. 6, pp. 228-238, 1987.

66. S. Tong, A. M. Alessio, K. Thielemans, C. Stearns, S. Ross, and P. E. Kinahan, "Properties and mitigation of edge artifacts in PSF-based PET reconstruction," Nuclear Science, IEEE Transactions on, vol. 58, pp. 2264-2275, 2011.

67. C. C. Watson, "Estimating effective model kernel widths for PSF reconstruction in PET," in Nuclear Science Symposium and Medical Imaging Conference (NSS/MIC), 2011 IEEE, 2011, pp. 2368-2374.

68. A. J. Reader, P. J. Julyan, H. Williams, D. L. Hastings, and J. Zweit, "EM algorithm system modeling by image-space techniques for PET reconstruction," Nuclear Science, IEEE Transactions on, vol. 50, pp. 1392-1397, 2003.

69. E. Rapisarda, V. Bettinardi, K. Thielemans, and M. C. Gilardi, "Evaluation of a new regularization prior for 3-D PET reconstruction including PSF modeling," Nuclear Science, IEEE Transactions on, vol. 59, pp. 88-101, 2012.

70. A. Mikhno, E. D. Angelini, and A. F. Laine, "Locally weighted total variation denoising for PSF modeling artifact suppression in PET reconstruction," in Biomedical Imaging (ISBI), 2014 IEEE 11th International Symposium on, 2014, pp. 971-974.

71. A. Mikhno, E. D. Angelini, B. Bai, and A. F. Laine, "Locally weighted total variation denoising for ringing artifact suppression in pet reconstruction using PSF modeling," in Biomedical Imaging (ISBI), 2013 IEEE 10th International Symposium on, 2013, pp. 1252-1255.

72. K. Thielemans, S. Mustafovic, and C. Tsoumpas, "STIR: software for tomographic image reconstruction release 2," in IEEE Nucl Sci Symp Conf Rec, 2006, pp. 2174-2176.

73. P. Rodriguez, "Total variation regularization algorithms for images corrupted with different noise models: a review," Journal of Electrical and Computer Engineering, vol. 2013, p. 10, 2013.

74. S. Choi and R. Wette, "Maximum likelihood estimation of the parameters of the gamma distribution and their bias," Technometrics, vol. 11, pp. 683-690, 1969.

75. R. V. Parsey, R. T. Ogden, J. M. Miller, A. Tin, N. Hesselgrave, E. Goldstein, et al., "Higher serotonin 1A binding in a second major depression cohort: modeling and reference region considerations," Biological psychiatry, vol. 68, pp. 170-8, Jul. 15, 2010.

76. J. E. Mourik, M. Lubberink, U. M. Klumpers, E. F. Comans, A. A. Lammertsma, and R. Boellaard, "Partial volume corrected image derived input functions for dynamic PET brain studies: methodology and validation for [11C]flumazenil," Neuroimage, vol. 39, pp. 1041-50, Feb. 1, 2008.

77. Y. Charnay and L. Leger, "Brain serotonergic circuitries," Dialogues Clin Neurosci, vol. 12, pp. 471-87, 2010.

78. A. Dahlstrom and K. Fuxe, "Localization T. P. Naidich, "Duvernoy's Atlas of the Human Brain Stem and Cerebellum," ed: Am Soc Neuroradiology, 2009.

80. N. N. Song, J. B. Xiu, Y. Huang, J. Y. Chen, L. Zhang, L. Gutknecht, et al., "Adult raphespecific deletion of Lmxlb leads to central serotonin deficiency," PLoS One, vol. 6, p. e15998, 2011.
81. M. Ichise, J. S. Liow, J. Q. Lu, A. Takano, K. Model, H. Toyama, et al., "Linearized reference tissue parametric imaging methods: application to [11C]DASB positron emission tomography studies of the serotonin transporter in human brain," J Cereb Blood Flow Metab, vol. 23, pp. 1096-112, September 2003.
82. J. S. Kim, M. Ichise, J. Sangare, and R. B. Innis, "PET imaging of serotonin transporters with [11C]DASB: test-retest reproducibility using a multilinear reference tissue parametric imaging method," J Nucl Med, vol. 47, pp. 208-14, February 2006.
83. K. R. Merikangas, H. S. Akiskal, J. Angst, P. E. Greenberg, R. M. Hirschfeld, M. Petukhova, et al., "Lifetime and 12-month prevalence of bipolar spectrum disorder in the National Comorbidity Survey replication," Arch Gen Psychiatry, vol. 64, pp. 543-52, May 2007.
84. T. R. Insel, "Disruptive insights in psychiatry: transforming a clinical discipline," J Clin Invest, vol. 119, pp. 700-5, April 2009.
85. P. Boksa, "A way forward for research on biomarkers for psychiatric disorders," J Psychiatry Neurosci, vol. 38, pp. 75-7, March 2013.
86. I. Singh and N. Rose, "Biomarkers in psychiatry," Nature, vol. 460, pp. 202-7, Jul. 9, 2009.
87. E. R. Kandel, J. H. Schwartz, and T. M. Jessell, Principles of neural science vol. 4: McGraw-Hill New York, 2000.
88. Y. D. Son, Z. H. Cho, E. J. Choi, J. H. Kim, H. K. Kim, S. Y. Lee, et al., "Individually differentiated serotonergic raphe nuclei measured with brain PET/MR imaging," Radiology, vol. 272, pp. 541-8, August 2014.

Example 6: Combining Brain Imaging Data with Electronic Health Records to Non-Invasively Quantify [11C]-DASB Binding Quantitative analysis of PET data requires a metabolite corrected arterial input function (AIF) for estimation of distribution volume and related outcome measures. Collecting arterial blood samples adds risk, cost, and patient discomfort to PET studies. Minimally invasive AIF estimation is possible with simultaneous estimation (SIME), but one arterial blood sample is necessary to be used as an anchor value to ensure identifiability of each individual's AIF.

For [11C]-DASB, a widely used serotonin transporter PET tracer, this blood sample is optimally taken 50 minutes after injection. Presented herein is an approach for replacing such a single time-point anchor with a predicted value using brain imaging and electronic health record (EHR) data. Average bootstrap $R^2 > 0.8$ in training data indicates that up to 80% of the variance in [11C]-DASB SIME anchor may be explained by a model including heart rate, blood pressure, tracer dose, body size and cerebellar gray matter uptake. Preliminary results show that these models generalize well to a small test dataset. This may allow for quantitative analysis with no blood sampling. Presented herein is an approach for predicting this anchor using brain imaging and electronic health record (EHR) data.

EHR and PET brain imaging data were gathered for 95 subjects that previously underwent [11C]-DASB scans. EHR included demographics (i.e., weight, gender, etc.), and blood workup (i.e., chemistry, hematology). PET data included 23 regional time activity curves and injected dose (ID). Heart rate (HR) and blood pressure measurements were taken on the PET scan day. Derived variables included estimated total plasma volume (eTPV-Nadler formula and hematocrit), and sum 50-90 min gray matter cerebellum activity (CERsum). Scatterplots and $R^2$ values were calculated for each variable vs. the SIME blood-based anchor. Variables with $R^2 > 0.1$ (ID/TPV, CERsum, HR) were used to develop a linear model for predicting the anchor. Data were randomly partitioned into 2/3 training and 1/3 testing subsets. The MATLAB "lasso" function was applied to the training data with 10-fold cross validation to select the optimal tuning parameter (lambda) and the resulting estimated model applied to the test set.

Figure 73:
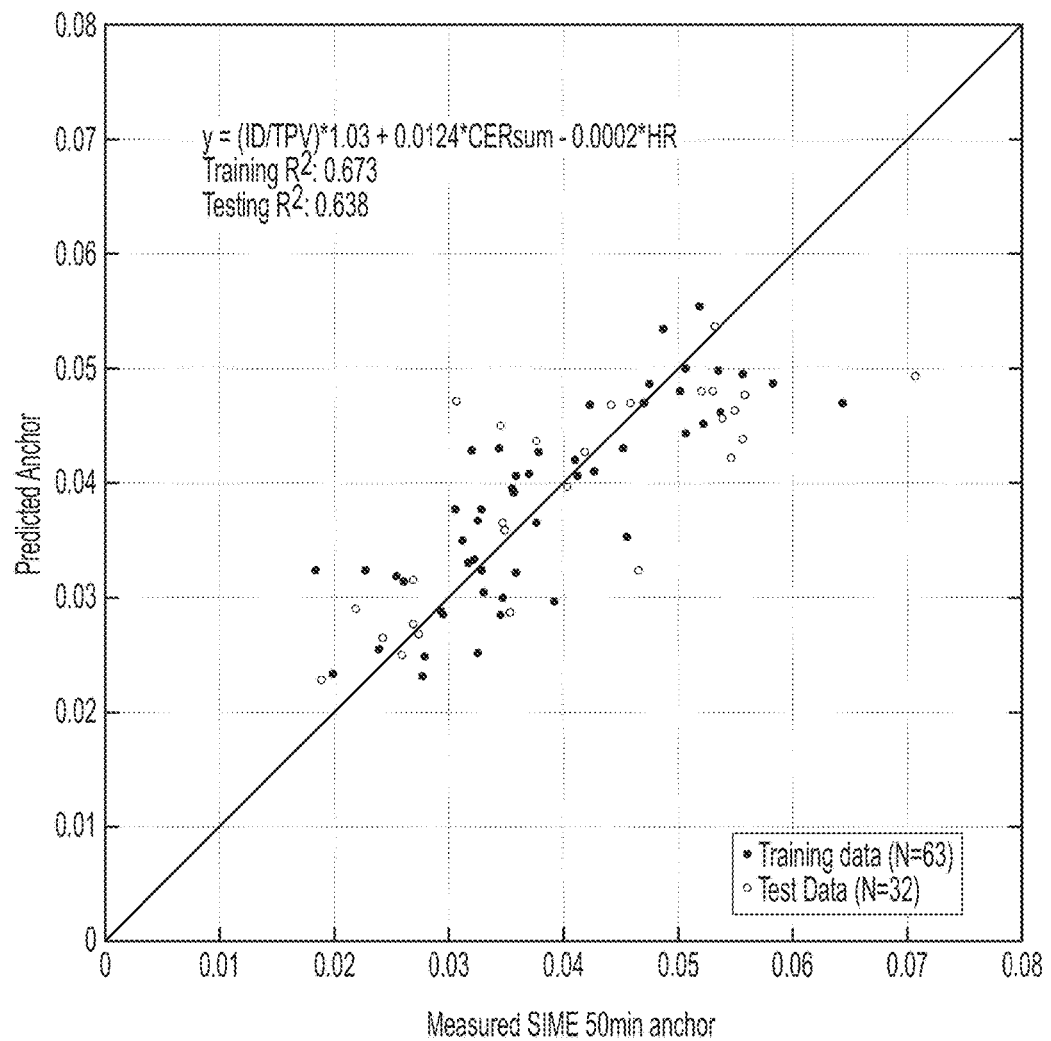
FIG. 73 shows predicted versus measured SIME 50 minute anchor.

The model with minimum cross validation MSE was: anchor=(ID/TPV)*1.03+0.0124*CERsum−0.0002*HR. Achieving an $R^2$ of 0.672 and 0.638 for training and test data, respectively. Results are shown in FIG. 73.

A model for predicting the SIME individual anchor for [11C]-DASB was developed. Results indicate that over 60% of the variance in [11C]-DASB metabolism can be explained by variability in HR, eTPV and cerebellar gray matter uptake. Machine learning approaches can further improve anchor prediction, and the effect of prediction errors on distribution volume estimates can be assessed.

Example 7: Combining Brain Imaging Data with Electronic Health Records to Non-Invasively Quantify [11C]-DASB Binding Positron emission tomography (PET) is used for quantifying the distribution of receptors and proteins in the brain and the body. Quantitative analysis of PET data requires both the metabolite-corrected arterial input function (AIF) and the tissue time activity curves (TACs) derived from the image data for estimation of distribution volume and related outcome measures (Innis et al., Journal of Cerebral Blood Flow & Metabolism, vol. 27, no. 9, pp. 1533-1539, 2007). The AIF is measured in order to account for inter- and intra-individual variance in tracer availability due to metabolism and clearance. Blood samples are collected from the radial artery during the PET scan to calculate the AIF. This procedure adds risk, cost and patient discomfort to the demands of PET studies.

Significant progress has been made over the years towards less invasive PET analysis. Reference tissue methods have been developed but require the existence of a reference region devoid of specific binding, which for [11C]-DASB does not exist (Parsey et al., Biological Psychiatry, vol. 59, no. 9, pp. 821-828, May 2006). Image-derived input function (IDIF) approaches recover the AIF by extracting signal from the carotid artery or cranial blood pools. IDIF methods are prone to partial volume effects and still require blood samples to scale the signal (Zanotti-Fregonara et al., Journal of Cerebral Blood Flow & Metabolism, vol. 29, no. 11, pp. 18251835, 2009). Minimally invasive AIF estimation is possible with simultaneous estimation (SIME) (Ogden et al., Journal of Cerebral Blood Flow & Metabolism, vol. 30, no. 4, pp. 816-826, December 2009), but at least one blood sample still needed as an individual anchor value for identifiability.

For [11C]-DASB, this sample is optimally taken 50 minutes after injection (Ogden et al., Journal of Cerebral Blood Flow & Metabolism, vol. 30, no. 4, pp. 816-826, December 2009). This single blood sample adds risk and discomfort to the study and leaves the PET analysis reliant on the accuracy of a single data point. Population pharmacokinetics and pharmacodynamics (PPKD) is a field centered around predicting metabolite corrected blood levels of pharmaceutical compounds at various time points after injection/ingestion. This is done by aggregating blood data from multiple studies and searching for covariates (e.g. age, lab tests, etc.) that explain the variability in drug blood concentration (Hoeben et al., Clinical Pharmacokinetics, vol. 52, no. 11, pp. 1005-1015, June 2013). As a PET tracer is also a pharmaceutical compound, similar covariate screening approaches may be effective for [11C]-DASB. PET imaging data may add additional information on tracer blood concentrations.

Previous work suggests that combining supplementary information (e.g. weight, dose, etc.) with signal from cranial blood vessel improve prediction of the AIF (O'Sullivan et al., IEEE Transactions on Medical Imaging, vol. 29, no. 3, pp. 610-624, March 2010). However, this technique was developed with the [18F]-FDG tracer, for which the AIF does not require metabolite correction, and thus the imaging data is highly correlated with the AIF. It is not clear if such an approach could translate to [11C]-DASB where the AIF profile is highly dependent on the rate of tracer metabolism and clearance.

As described herein, [11C]-DASB brain imaging and electronic health record (EHR) data are combined to develop a model for predicting the [11C]-DASB SIME anchor.

Data Collection

In this retrospective IRB approved study, EHR and PET brain imaging data were gathered for 228 subjects who had undergone [11C]-DASB scans at The Kreitchman PET Center at Columbia University Medical Center from 2004 to 2012. EHR data collected prior to the PET scan date and included demographics (e.g., weight, gender, etc.), blood workup (e.g., chemistry, hematology, thyroid panel) and urinalysis (e.g., pH). PET data included sum 50-90 minute gray matter cerebellar activity (CER), injected dose (ID), injected mass, tracer specific activity, and the metabolite-corrected AIF. Heart rate (HR) and blood pressure (BP) were obtained within hours before and after the PET scan. Only subjects that had weight, height and AIF data available were included in the study. The final data set consisted of 95 subjects and 92 initial variables. Descriptive statistics for the subjects are shown in FIG. 93.

Heart Rate and Blood Pressure

HR was measured manually via radial pulse rate before (HRpre) and after (HRpost) the PET scan. Systolic (SBP) and diastolic (DBP) BP measurements were obtained with a sphygmomanometer before (SBPpre, DBPpre) and after (SBPpost, DBPpost) the scan. HR and BP were manually transcribed from handwritten notes left on the PET protocol form by clinical technicians. Missing or illegible measurements were marked as NaN. Vital signs were not assessed at consistent times, ranging between 9 and 1 hours for prescan and between 2 and 8 hours for post-scan measurements. Therefore, variables that represent the closest and average vitals were calculated: HRclosest, SBPclosest, DBPclosest, HRavg, SBPavg, DBPavg. The following derived variables were also calculated based on HR and BP: mean arterial pressure (MAP), estimated cardiac output (CO) and pulse pressure (PP), using Eq. 1-3.

$$MAP = BP_{diastole} + \frac{1}{3}(BP_{systole} - BP_{diastole}) \quad (1)$$

$$PP = BPSys - BPDias \quad (2)$$

$$COest = HR \times PP \quad (3)$$

Summary statistics for vitals are shown in FIG. 94.

Derived Variables

Body mass index (BMI), body surface area (BSA), estimated total blood volume (eTBV), estimated total plasma volume (eTPV), and estimated resting metabolic rate (eRMR) were derived from the weight (W), height (H), and hematocrit (Hct):

$$BMI = 703 * W / H \quad (4)$$

$$BSA = \sqrt{(W * H)/3131} \quad (5)$$

$$eTBV = \begin{cases} 0.006012H^3 + 14.6W + 604, & \text{male} \\ 0.005835H^3 + 15.0W + 183, & \text{female} \end{cases} \quad (6)$$

$$eTPV = eTBV \times (1 - Hct) \quad (7)$$

$$eGFR = \begin{cases} 175Crt^{-1.184}Age^{-0.203}, & \text{male} \\ 129.85Crt^{-1.154}Age^{-0.203}, & \text{female} \end{cases} \quad (8)$$

$$eGFR_{BSA} = eGFR * BSA \quad (9)$$

The estimated glomerular filtration rate (eGFR) was calculated from the blood creatine level (Crt) as $$eRMR = \begin{cases} 4.5W + 15.9H - 5Age + 5, & \text{male} \\ 4.5W + 15.9H - 5Age - 161, & \text{female} \end{cases} \quad (10)$$

Other calculated variables include osmolarity gap, albumin corrected calcium, blood viscosity, anion gap, BUN Creatine ratio, and plasma osmolarity using standard clinical formulas. Two additional variants of Eq. (9) were calculated using BUN and Albumin (GFR5, GFR5$_{BSA}$).

Variable Selection

The combination of EHR, PET, demographics, vitals and derived variables amounted to 92 initial predictors, as shown in FIG. 95.

Note that Total Plasma (TP) is the total radioactivity count in each blood sample taken at time t, where the AIF(t) =ParentFraction(t)×TP(t). For [11C]-DASB, the response variable is the SIME 50 minute anchor (SA50), or SA50=AIF(t=50 min). A multi-stage approach was used to screen variables that may be useful in predicting SA50. First, correlation with SA50 was examined, and variables retained if $R^2 > 0:1$. Second, new variables were created by normalizing each variable to the ID, as is done when calculating standardized uptake values. If the correlation of the ID/variable ratio and SA50 met the following criteria, $R^2 > R^2_{ID} = 0:18$, then this new variable was retained for further analysis. Finally, a search for two variable interaction terms was conducted. A total of 4186 (92 choose 2) multivariate regression models were evaluated, each consisting of two predictors with (mdl*) and without (mdl) an interaction term (*). If, $R^2_{mdl*} > R^2_{mdl}$ AND $R^2_{mdl*} > 0:1$ AND $p^* < 0:05$, the interaction term was retained as a prospective predictor.

Statistical Analysis

The final feature set consisted of 56 features (10 individual, 31 ID/variable ratios, and 15 interaction terms) that made it through one of the three feature screening stages. Predictors used for model development are shown in FIG. 96.

The data was partitioned into 10% testing (n=9) and 90% training (n=86) subsets. A total of 27,720 (56 choose 3) three variable, 367,290 (56 choose 4) four variable, 3,819,816 (56 choose 5) five variable, and 32,468,436 (56 choose 6) six variable linear multivariate models were considered. Bootstrapped average $R^2$ was calculated from training each model 10 times using randomly drawn samples with replacement from the training data and evaluating on the entire training data. Models with the highest average $R^2$ in each category were applied to the training and test data.

Results

Results for top models in terms of average $R^2$ with and without TP are shown in FIG. 97.

All the models yielded $R^2>0:7$. Increasing the number of variables from three to six yielded an $R^2$ gain of 0.105 and 0.111 with and without TP, respectively. With TP, variables in common were: CER and HR. Other variables present were: BP, eosin, ID, BSA, SpecificActivity and pH. For models without TP, variables in common were: CER, BP, HR, ID, eosin. Other variables present included: Weight, eTBV, and eRMR. It appears that to increase $R^2$ by 0.1 information about ID and body size is useful. Including TP in model improved $R^2$ by only 0.015 and 0.009 for the three and six variable model, respectively.

Figure 74A:
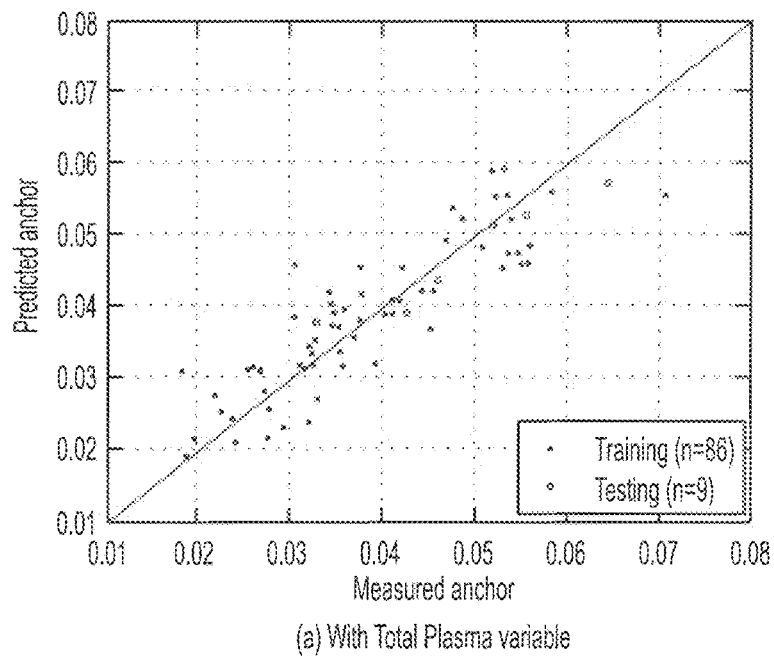
FIGS. 74A-74B show SIME anchor prediction with (FIG. 74A) and (FIG. 74B) without total plasma.
Figure 74B:
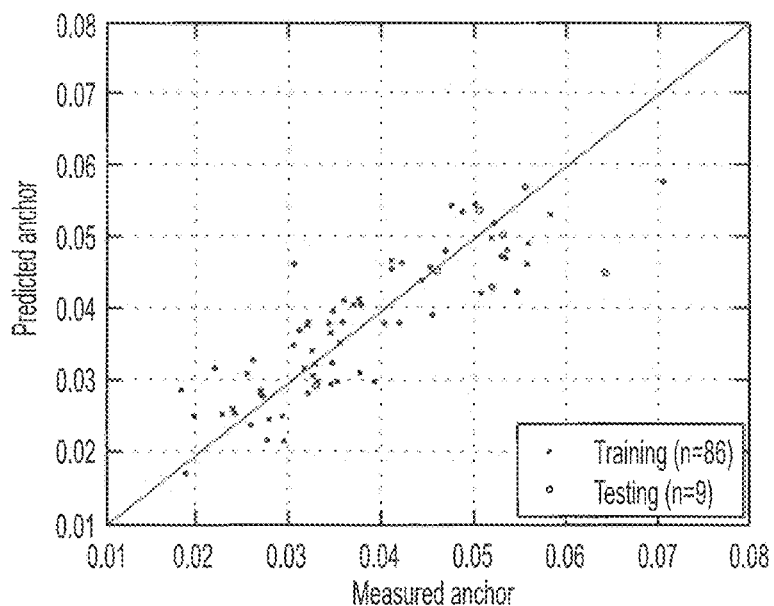
Figure 75:
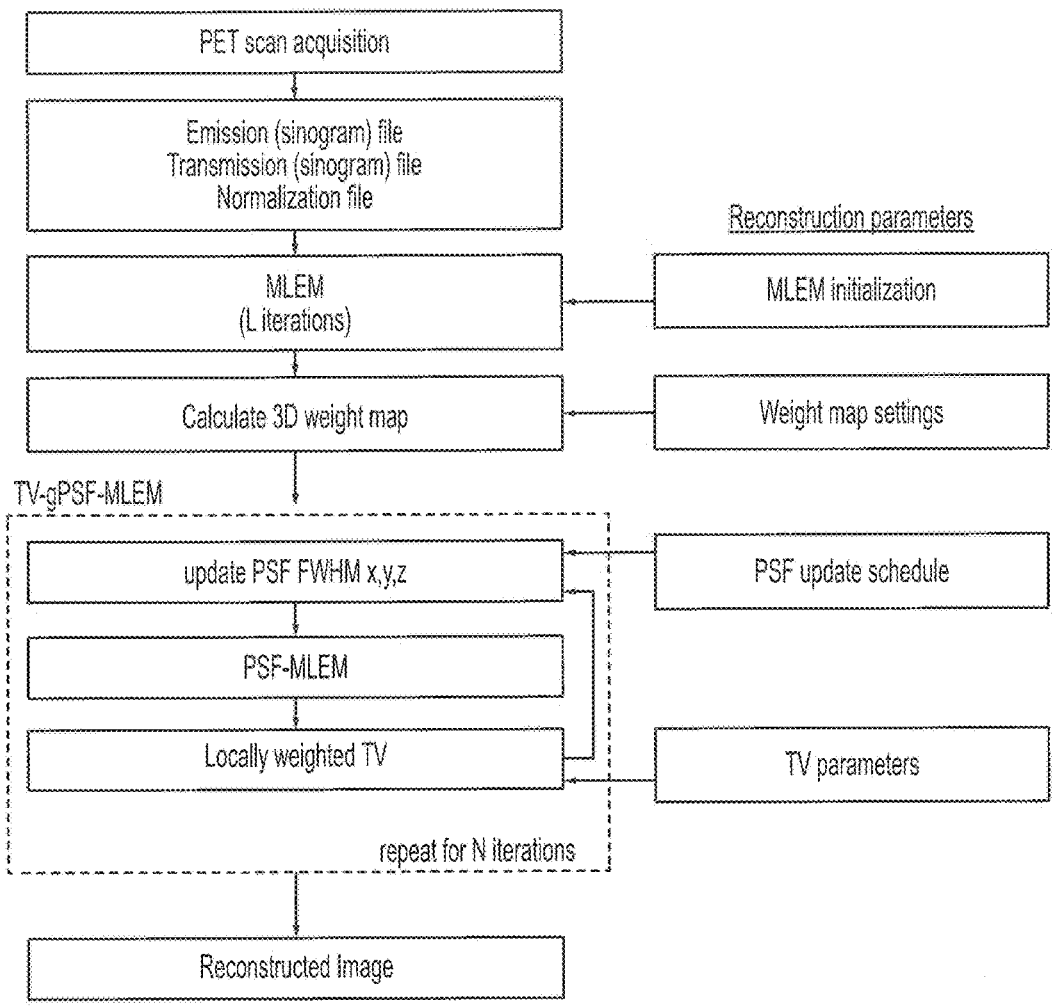
FIG. 75 shows a flowchart for one embodiment of the methods described herein.

The top six-variable models with and without TP were applied to training and test data. Plots of predicted vs. measured anchor points are show in FIG. 74. Including TP appears to result in a more uniform scattering of points around the identity line, also better predictions for the test data. One test point appears to be an outlier when TP is not included. This could be due to the fact that TP is very accurately measured via blood sampling on the same day of the PET scan, while all other variables were measured hours, days or weeks prior to the scan time.

Conclusions

Models for predicting the SIME individual anchor for [11C]-DASB were developed using machine learning techniques. Results indicates that >80% of the variance in [11C]-DASB metabolism may be explained by variability in HR, BP, ID, body size, and cerebellar gray matter uptake. This is encouraging because this was a retrospective study using data acquired sometimes anywhere from hours (i.e. HR, BP) to weeks (i.e. eosin, pH) from the PET scan date. Furthermore, HR, which appears as an important variable in all the models, was measured via manual radial pulse rate. Weight, a measure on which many other important predictors were based (i.e. eTBV, eRMR, CO) was measured up-to months before the scan. Finally, an extensive evaluation of outliers was not done. Despite these drawbacks, the performance of the models was encouraging and indicates that better predictions of the [11C]-DASB anchor may be achieved with careful data collection in a prospective study. It is important to recognize the models presented here are the top models in each category in terms of $R^2$. Many other models with comparable $R^2$ are not shown due to space constraints. Evaluation of TP variable, more advanced machine-learning techniques, and outlier removal can be performed.

Example 8: Non-Invasive Quantification of Brain Radioligand Binding by Combining Electronic Health Records and Dynamic PET Imaging Data Quantitative analysis of positron emission tomography (PET) brain imaging data requires a metabolite-corrected arterial input function (AIF) for estimation of distribution volume and related outcome measures. Collecting arterial blood samples adds risk, cost, measurement error, and patient discomfort to PET studies. Minimally invasive AIF estimation is possible with simultaneous estimation (SIME), but at least one arterial blood sample is necessary. In this study, we describe a non-invasive SIME (nSIME) approach that utilizes a pharmacokinetic input function model and constraints derived from machine learning applied to electronic health record (EHR) data. We evaluated the performance of nSIME on an EHR database of 95 subjects who had [11C]-DASB PET scans recording along with measured arterial input functions. Comparing SIME and nSIME PET outcome measures, the results indicate that nSIME is a promising alternative to invasive AIF measurement. The general framework presented here may be expanded to other metabolized radioligands, potentially enabling quantitative analysis of PET studies without blood sampling.

Positron emission tomography (PET) uses radioactively tagged probes (radioligands) for the in vivo quantification of blood flow, metabolism, protein distribution, gene expression and drug target occupancy in the brain. Fully quantitative analysis of PET data requires both the arterial input function (AIF) that describes the amount of radioligand available for diffusion into the brain, and the tissue time-activity curves (TACs) derived from dynamic PET images. Kinetic modeling is then performed to estimate important outcome measures of radioligand distribution and binding [1]. To measure the AIF, typically a catheter is inserted into the radial artery at a subject's wrist to sample blood for the duration of the PET scan. After centrifugation, the total radioactivity concentration of radioligand (TP) and its metabolites in the plasma in each blood sample is measured. If the body metabolizes the radioligand, the parent fraction (PF) of unmetabolized compound is assayed in a subset of the blood samples. After fitting PF using a metabolite model the input function is calculated as, which reflects the concentration y of radioligand in plasma that is available to enter the target tissue.

Utilizing the AIF and the TACs, PET imaging can be used to estimate outcome measures related to the 'binding potential' of a radioligand to its target. In particular, one estimate of binding potential BPF is defined as: $BPF=Bavail/KD=(VT-VND)/fP$, where Bavail is the concentration of available receptors, 1/KD is the radioligand affinity to the target, VT is the radioligand "volume of distribution" or volume of radioligand in tissue relative to plasma, VND is the radioligand 'volume of distribution' in a tissue devoid of the target (i.e. fraction of binding not specific to the target of interest), and fP is the free fraction of the radioligand in plasma. VT and VND are estimated from kinetic modeling of the region TACs and the AIF, while fP can be assayed in additional blood samples collected prior to radioligand injection. When fP is not available, or cannot be measured reliably, two other variants binding potential can be calculated: $BPP=fP \, BPF=(VT-VND)$ and $BPND=f_{ND}BPF=(VT-VND)/VND$, where fND is the free fraction of the radioligand in a tissue devoid of target.

Thus, quantification of PET data requires arterial blood sampling to estimate the AIF and to calculate the outcome measures related to the "binding potential" of the radioligand to its target (i.e. BPP or BPND). While arterial sampling is routinely done in research studies, it is invasive, necessitates specific technical expertise, involves laboratory analysis costs, involves significant measurement error, and is a potentially somewhat painful procedure that discourages subject participation in PET studies. If the patient refuses an arterial line, or if arterial cannulation or blood assay fails, the entire study may be dropped from data analysis leaving expensive PET images that cannot be interpreted or analyzed. Even when these challenges are anticipated and addressed by the study design, it may not always be possible to perform arterial blood sampling, such as with vulnerable populations (e.g. elderly, cancer patients), those with movement disorders (e.g people affected by Parkinson's disease) or in a combined Magnetic Resonance Imaging (MRI) and PET scanner due to magnetic interference. Even when blood samples can be obtained, fitting of TP and PF can be challenging due to inherent noise present in the blood measurements, and complex radioligand kinetics such as 'lung trapping' that require adapting and validating a metabolite model [2]. Finally, and most commonly, arterial sampling is impractical in a clinical setting, hindering adoption of quantitative PET outcome measures for clinical use.

The last decade has brought a considerable effort to develop non-invasive AIF estimation techniques [3, 4] that can be broadly categorized as non-invasive (i.e. without blood samples), such as 'reference tissue' and population-based approaches, and minimally invasive (i.e. with few blood samples), such as image derived input functions (IDIF).

Reference tissue methods use only imaging data to estimate kinetic parameters of tissue TACs, based on the specification that a valid reference region devoid of the target (e.g. receptor or protein of interest) exists and can be identified [5]. This approach allows estimation of BPND only. For many radioligands currently employed in brain studies, a reference region truly devoid of the target cannot be identified or the region commonly used as a reference actually has measurable specific binding. Even when a reference region is identifiable, there may be high bias and variance in BPND values calculated with the reference tissue methods when compared to using the AIF, as is the case with [11C]-(R)-PK11195 (targeting microglia) [6], and [11C]-ABP (targeting the metabotropic glutamate receptor subtype 5) [7]. Population-based approaches define a template AIF, typically generated from AIF values derived from blood samples collected across several studies with the same radioligand. The template AIF is applied to new subjects after adjusting by a scaling factor based on their injected dose and body mass [8], or based on cerebellar activity [9]. Even when the scaling factor is derived invasively from arterial blood samples the shape of the AIF can vary greatly between subjects. To date, population approaches have only been used successfully with selected radioligands (e.g. [18F]-FDG [9], [11C]-PIB [10]).

With these limitations in mind, most efforts have focused on developing minimally invasive IDIF methods that can yield individualized estimates of the AIF. These approaches are based on estimating the AIF from dynamic PET imaging data. A common IDIF approach involves averaging the signal from a region of interest (ROI) placed over the carotid artery identified directly on PET images manually [11], by automated segmentation techniques [12], or with the help of a co-registered MRI image [13]. Alternatively, clustering [14, 15] or independent component analysis [16] can be used to extract the blood signal from blood vessels in the brain. The drawback of all these approaches is that they require at least one blood sample for scaling of the estimated AIF, and at least three or more samples for metabolite correction [3]. Another class of IDIF approaches is based on simultaneous estimation (SIME) of multiple TACs, with the underlying assumption that the AIF is the same for all ROIs. SIME exploits a parametric model for the unknown AIF and seeks to estimate model parameters simultaneously with the kinetic parameters related to the binding, while fitting several ROIs at the same time. Recent work has shown that SIME can recover the AIF using only a single arterial blood sample as an anchor (or constraint) that ensures model identifiability [17]. A third alterative for a 'less' invasive IDIF is to measure TP and PF from venous blood sampling [3]. Drawing venous blood does not require arterial catheterization by trained personnel, making it more practical in research and clinical settings. For some radioligands, this substitution is nearly equivalent as with [18F]-FDG [11, 18] and [11C]-WAY [19]. The equivalence between arterial and venous blood must be determined separately for each radioligand and often does not hold. This procedure still requires considerable effort with regards to blood draws and the metabolite correction assay.

A totally non-invasive AIF estimation approach is needed to overcome the above challenges and drawbacks with existing IDIF techniques. Our proposed solution taps into the field of population pharmacokinetics and pharmacodynamics (PPKD) that focuses on predicting metabolite corrected blood levels of pharmaceutical compounds at various time points after injection. This is done by aggregating blood data from many subjects to determine what measures (e.g. age, body mass index, glomerular filtration rate, etc.) explain the variance in drug blood concentration [20]. Previous work suggests that combining supplementary information (e.g. weight, height, injected dose) with signal from cranial blood vessels improves IDIF-based AIF estimation [21]. However, this technique was developed for the radioligand [18F]-FDG for which metabolites are not present in the blood (i.e. PF=1). It is not clear whether such an approach could translate to radioligands that undergo significant metabolism.

In this study, we bridge PPKD and PET brain imaging by merging SIME with predicted constraints on the parameters of the AIF model derived from machine learning applied to electronic health record (EHR) data. We previously demonstrated the feasibility of using EHR data to predict the metabolite corrected radioligand blood concentration of a single blood sample [22]. Here we develop an algorithm for non-invasively estimating the full AIF curve and validate it on brain PET data acquired with the radioligand [11C]-DASB that binds the serotonin transporter.

Subjects and Data

In a study approved by the Institute Review Board, PET and EHR data were obtained from 228 subjects who had undergone [11C]-DASB scans at The Kreitchman PET Center at Columbia University Medical Center from 2004 to 2012. Health records consisted of data collected prior to the PET scan date and included demographics (e.g., age, gender, etc.), clinical details (height, weight, heart rate and blood pressure), clinical laboratory test results (e.g., blood chemistry, clinical blood counts, lipid profile, protein levels, thyroid panel) and urinalysis (e.g., pH). Heart rate (HR) and blood pressure (BP) were obtained within a few hours before and/or after the PET scan. PET data included regional brain TACs, injected dose (ID), injected mass, radioligand specific activity and measured AIF based on full arterial blood sampling. Only 95 subjects that had weight, height and useable AIF data were included in the analysis presented here. Descriptive statistics for these subjects are shown in FIG. 98.

Vitals and Hemodynamic Related Variables

HR was measured manually via radial pulse rate before (HR_pre) and after (HR_post) the PET scan. Systolic (BPs) and diastolic (BPd) BP measurements were obtained with a sphygmomanometer before (BPs_pre, BPd_pre) and after (BPs_post, BPd_post) the PET scan. HR and BP were manually transcribed from handwritten notes made on a PET protocol form by clinical technicians. Missing or illegible measurements were marked as "Not a Number" and discarded. Vital signs were not assessed at consistent times;

they ranged from 9 to 1 hours for pre-scan and from 2 to 8 hours for post-scan measurements. Therefore, variables that represent the "closest" and "average" vitals were also calculated: HR_closest, BPs_closest, BPd_closest, HR_avg, BPs_avg, BPd_avg. Summary statistics for vitals are shown in FIG. 98.

The following hemodynamics related variables were also derived from HR and BP measures: mean arterial pressure (MAP), pulse pressure (PP) and a very simplified estimated cardiac output (eCO), using the assumption that PP is proportional to stroke volume (SV) [23].

Additional Derived Variables

The following variables were also derived from the age (A), weight (W), height (H), and hematocrit (Hct) of each subject: body mass index (BMI), body surface area (BSA) using Mosteller's equation [24], estimated total blood volume (eTBV) using Nadler's equation [25], estimated total plasma volume (eTPV), defined as eTPV=eTBV·(1−Hct), and estimated resting metabolic (eRMR) rate using Mifflin's equation [26]. The glomerular filtration rate (GFR) was estimated using two Modification of Diet and Renal Disease (MDRD) formulae [27]: the simplified version that uses blood creatinine level (eGFR) and a more complex version that incorporates blood urea nitrogen and albumin (eGFR5). Since the MDRD formulae are implicitly adjusted for BSA and reported as ml/min/1.73 m², two additional variants, eGFRBSA and eGFR5BSA, were calculated adjusting the MDRD to each individual's BSA and dividing by 1.73 so that units are in ml/min corresponding to physiological units of GFR [28]. Other calculated variables included osmolality gap, albumin corrected calcium, blood viscosity, anion gap, BUN:Crt ratio, and plasma osmolality using standard clinical formulae.

PET Image Acquisition and Processing

Brain PET acquisition and processing, as well as arterial blood analysis, were previously described in detail [2, 29]. Briefly, PET imaging was performed with the ECAT HR+ (Siemens/CTI, Knoxville, Tenn.). After a 10-minute the transmission scan, between 5 and 20 millicuries of [11C]-DASB was administered intravenously as short infusion over 30 sec. Emission data were collected for 100 min over 19 frames of increasing duration: 3×20 sec, 3×1 min, 3×2 min, 2×5 min, and 8×10 min. Images were reconstructed to a 128×128 matrix (pixel size of 2.5 mm×2.5 mm). PET images were motion corrected and co-registered to an accompanying 1.5T or a 3T MRI image. The TACs were obtained from 7 manually traced ROIs on the MRI that were transferred to the co-registered PET scan. These ROIs were previously used for SIME with [11C]-DASB [17] and include: gray matter cerebellum, midbrain, amygdala, dorsal caudate, hippocampus, temporal lobe, ventral striatum. Thirty-one arterial blood samples were collected during the PET scan. TP was measured from each blood sample using a well counter after centrifugation. PF was calculated after measurement of parent radioligand and metabolites concentrations with a high-pressure liquid chromatography assay from a subset of these blood samples.

Estimation of the AIF

The discrete time course of the AIF can be described as: $y[t_n]=TP[t_n]\times PF[t_n]$. The $TP[t_n]$ are measured from n=1, ..., N blood samples taken at time points to during the PET scan. When metabolite correction is used, $PF[t_n]$ is estimated by interpolating a fitted metabolism function to $PF[t_m]$, calculated after performing a high-performance liquid chromatography assay on m=1, ..., M blood samples, typically M<<N. Indeed, fewer samples are analyzed for metabolites since it is expensive and laborious, and since the radioligand is no longer detectable in later time points if rapidly metabolized. We note that for a small group of radioligands PF(t)=1 (e.g. [18F]-FDG), and metabolite correction is therefore not needed. However, this tends to be an exception and not the rule. The final continuous-time AIF curve y(t) is estimated by fitting an input function model to the measured samples $y[t_m]$.

The continuous PF(t) function was estimated by fitting $PF[t_m]$ with a damped bi-exponential function as:

$$PF(t) = t^{\alpha}(C_1 e^{-\lambda_1 t} + C_2 e^{-\lambda_{cal} t}) \quad (1)$$

where $\lambda_{cal}$ is a calculated time constant equal to $\lambda_{cal}=\lambda_{CER}-\lambda_{TP}$, using the terminal rate of washout of cerebellar activity $\lambda_{CER}$ and the smallest elimination rate c constant of the total plasma $\lambda_{TP}$ [2]. The discrete-time AIF curve $y[t_n]$ was calculated and fitted with the following 8-parameter input function model:

$$C_P(t|\theta^{IF}) = \begin{cases} \alpha t & t < t_p \\ A_1 e^{-\lambda_1 t} + A_2 e^{-\lambda_2 t} + A_3 e^{-\lambda_3 t} & t \geq t_p \end{cases} \quad (2)$$

where $C_p(t|\theta^{IF})$ is the AIF in continuous time, including the some parameters $\theta^{IF}$ related to the input function model including the time of the peak of the input function $t_p$, the slope $\alpha$, and the scale $A_l$ and rate constants $\lambda_l$ of the 3-exponential function (l=1, 2, 3), adjusted during the fit.

Time Activity Curves Modeling

Figure 76:
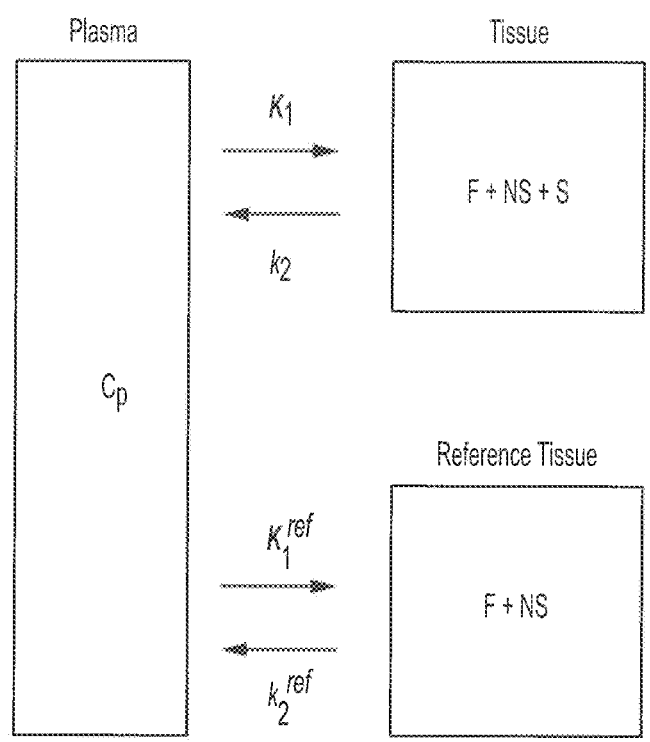
FIG. 76 shows one-tissue compartmental (1TC) model of radioligand transfer from plasma into the target and reference tissues. Cp is the concentration of radioligand in the arterial plasma, K1 is the rate constant for transfer from the arterial plasma to the tissue, where free (F), non-specific (NS) and specific (S) binding are aggregated in the same compartment, k2 is the transfer rate constant from the tissue back to the plasma, and K1ref and k2ref are rate constants for a reference tissue that is devoid of specific binding.

For the [11C]-DASB radioligand, the transfer of radioligand from the vascular compartment into the brain tissues can be represented by a one-tissue compartment (1TC) model [30], as shown in FIG. 76. In this model, $K_1$ is the transfer rate of the radioligand from the arterial plasma to the tissue, where free (F), non-specific (NS) and specific (S) binding are aggregated into a single compartment, $k_2$ is the transfer rate constant from the tissue back to the plasma, and $K_1^{ref}$ and $k_2^{ref}$ are transfer rate constants for a reference tissue devoid of specific binding.

Mathematically, the regional TAC is encoded as a concentration function $f$ of the radioligand in the tissue that can be formulated as a convolution integral between the AIF, modeled with the parametric input function model $C_p$, and the tissue impulse response function $K_1 e^{-k_2 t}$ $$f(t, \theta^{IF}, K_1, k_2) = K_1 e^{-k_2 t} \otimes C_P(t|\theta^{IF}) \quad (3)$$

After collecting blood samples, $\theta^{IF}$ is first estimated by non-linear least squares fitting of a continuous model of (2) to the measured metabolite-corrected arterial data $y[t_n]$. The resulting estimate $\hat{\theta}^{IF}$ is substituted into (3). The rate constants are then estimated using iterative weighted non-linear least squares minimization of the following function:

$$\sum_{j=1}^{J} w_j [Y_j - f(t_j|\theta^{IF}, K_1, k_2)]^2 \quad (4)$$

where $r_j$ is the measured TAC from a brain region at points j=1 ... J specified at time $t_j$, and $w_j$ are weights here set to the frame duration of each time point.

Simultaneous Estimation (SIME)

The SIME approach simultaneously estimates the TAC parameters from multiple regions r, which are fitted at the same time. The parameters describing the IDIF are estimated by minimizing the following combined objective function:

$$\phi(t, \theta^{IF}, \psi_r, \ldots, \psi_R) = \qquad (5)$$

$$\sum_{r=1}^{R} \sum_{j=1}^{J} w_j [Y_{rj} - f(t_j | \theta^{IF}, \psi_r)]^2 + [y[t_{opt}] - C_P(t_{opt} | \theta^{IF})]^2$$

where $y[t_{opt}]$ is the metabolite-corrected radioligand concentration in the plasma measured at the pre-determined optimum sampling time $t_{opt}$, $C_P(t_{opt}|\theta^{IF})$ is the AIF model evaluated using the estimated parameters $\theta^{IF}$ at time $t_{opt}$, $\psi_r$ is the vector of TAC parameters for the region r, $\psi_r = (K_{r1}, k_{r2})$, and $r_{rj}$ is the TAC measured from region r at time $t_j$. Minimization of this cost function is done with simulated annealing, a robust optimization technique for finding the global optimum [31].

Pharmacokinetic (PK) AIF Model

General characteristics of an AIF curve (FIG. 78) include a bolus or short infusion phase followed by a post-infusion phase. During the infusion phase the radioligand concentration increases until it peaks generally when infusion stops. The input function model of (2) has been utilized within SIME and previously applied to several radioligands [17]. This model assumes a linear rise from time zero to the peak at $t=t_p$ during the infusion phase and a decrease modeled by the sum of 3 exponentials during the post-infusion phase. As graphically shown in FIG. 77a, after infusion starts at $t=0$ the radioligand accumulates only in the central compartment for the infusion duration T Then, immediately after infusion ceases, the distribution into other compartments in the body, and elimination phases begin.

Following this model, it is clear that if the infusion rate $k_o$ is constant there will be a linear increase in the radioligand concentration in the central compartment, until infusion stops and the radioligand is distributed and eliminated. If a small volume of drug were injected almost instantaneously (e.g. a vaccine injection) the model in FIG. 77a would be reasonable. In reality however, the radioligand is usually diluted into a volume of several mL of saline or water and then infused manually, or with an infusion pump over a duration of ~10-60 seconds. In this case infusion and elimination phases occur simultaneously and cannot be segregated. The infusion phase is non-linear and typically begins with a delay relative to the PET acquisition due to blood travel time from the brain to the blood measurement site in the arm.

Figures 77A, 77B:
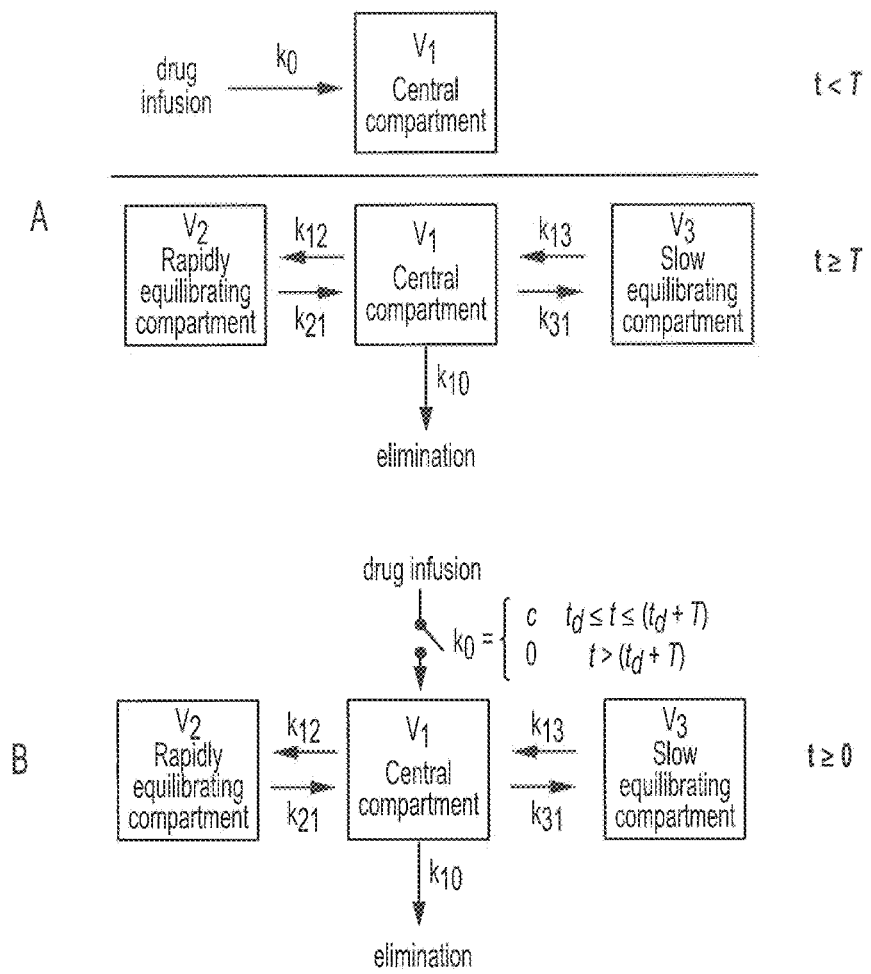
FIGS. 77A-77B show compartmental representation of AIF models from which equations are derived. (a) Simple AIF model of (2) (Eq. 2 of Example 8), where the radioligand is infused into a virtual 'central compartment' for the duration of time T at a rate k0. Once infusion stops, the radioligand diffuses into other compartments and undergoes elimination. The rates of transfer between compartments are given by the k's (rate constants), V1 are volumes of each compartment l=1 . . . 3. (b) Three compartment pharmacokinetic (PK) model of the AIF. The PET scan acquisition starts at t=0, and after a delay $t_d$ the radioligand infusion begins. As infusion is occurring, the radioligand is simultaneously accumulated in the central compartment, distributed to other compartments, and eliminated from the body.

A more realistic representation of this system is described in FIG. 77b, with a compartmental model, a delayed shunt based infusion mechanism, and all compartments and data collection active at $t>0$. After a delay time $t_d$, infusion begins and proceeds at a constant rate c. As the radioligand is infused it simultaneously distributes into other compartments and is eliminated from the body through multiple pathways at a total rate $k_{lo}$. After the infusion duration T, the shunt is closed, the infusion stops, while the distribution and elimination phases continue. This model has been described previously in the pharmacokinetic literature and is known as a three-compartment PK model of the drug plasma concentration [32], for which a combined infusion and post-infusion equation is readily derived using Laplace transforms and given by:

$$C_p^{PK}(t|\theta^{PK}) = \begin{cases} \sum_{l=1}^{3} B_l(e^{-\lambda_l(t-t_d)} - 1), & t < T \\ \sum_{l=1}^{3} B_l(e^{-\lambda_l T} - 1)e^{-\lambda_l(t-t_d)}, & t \geq T \end{cases} \qquad (6)$$

where $C_p^{PK}(t|\theta^{PK})$ is the concentration of parent radioligand in the plasma in continuous time, including some parameters $\theta^{PK}$ related to the PK input function model (e.g. $t_d$, $B_l$, $\lambda_l$, T). $B_l$ and $\lambda_l$ are respectively the scaling and rate constants for the $l^{th}$ compartment of the input function, and $t_d$ and T are respectively the delay and infusion duration.

Figure 78:
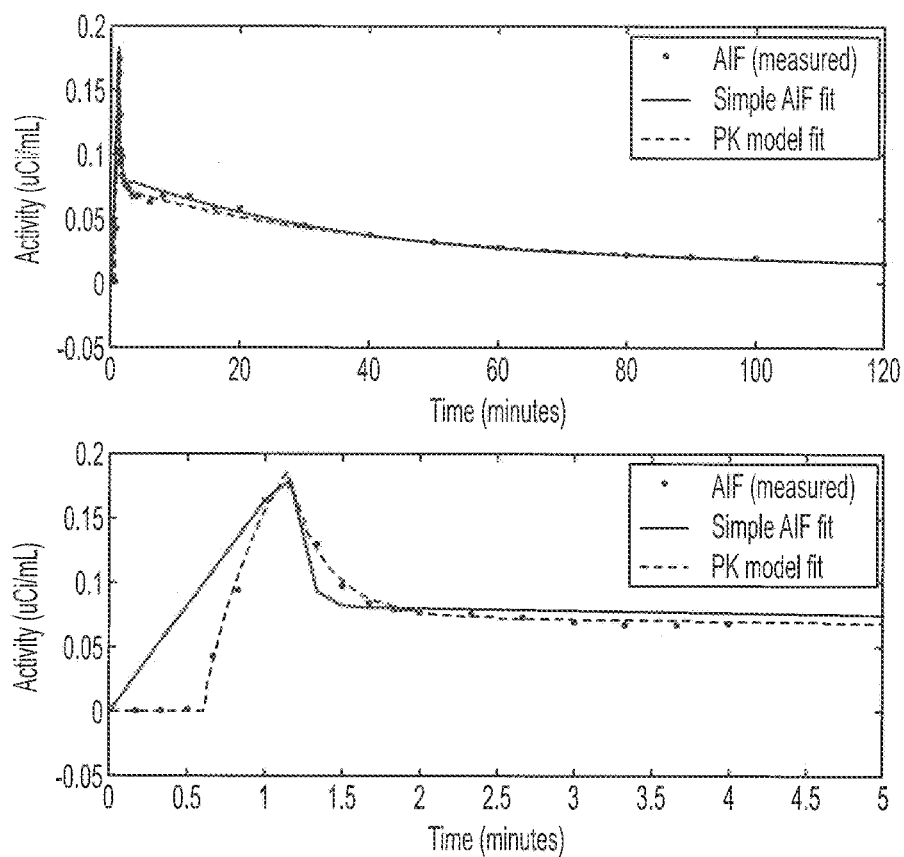
FIG. 78 shows comparison of AIF curves: Measured AIF (black dots), AIF fitted with non-linear least squares using a simple model of (2) (Eq. 2 of Example 8) and currently used by SIME (solid line), and proposed PK AIF model of (6) (Eq. 6 of Example 8) (dashed line).

We note that infusion and post-infusion components share the same parameters, which allows the model to take advantage of data acquired during infusion to describe the data acquired post-infusion. An example of the application of the simple and the PK-based AIF models from (2) and (6) are shown in FIG. 78. A variation of this model has been previously utilized in PET but did not include a delay term, and was only described by a set of ordinary differential equations which were fit to the data using Levenberg-Marquardt optimizer [33]. The explicit parametric formulation of the PK model provided in (6) enables this model to be utilized with the SIME cost function.

In the PK literature the scaling constants, $B_l$, can be directly related to the scaling constants, $A_l$, of the post-infusion portion of the simplified model in (2). These $A_s$ can be used to calculate a number of important PK parameters:

$$A_l = ID \frac{B_l(e^{-\lambda_l T} - 1)\lambda_l T}{(1 - e^{-\lambda_l T})} \qquad (7)$$

$$\cdot AUC = \sum_{l=1}^{3} \frac{A_l}{\lambda_l}, \quad \cdot C_0 = \sum_{l=1}^{3} A_l = \frac{ID}{V_c}, \quad \cdot CL_s = \frac{ID}{AUC} \qquad (8)$$

where ID is the injected dose of radioligand (in mL), AUC is the area under the curve of the input function, $C_o$ is the concentration of the radioligand in the central compartment at $t=0$ (assuming an instantaneous injection), $V_c = V_1$ and is the volume of the central compartment, and $CL_s$ is the clearance rate of the radioligand from the body.

Non-Invasive SIME (nSIME) Objective Function

SIME requires a constraint to ensure identifiability of the model. Currently, this constraint is based on one measured blood sample taken at an empirically determined optimum sampling time. For [11C]-DASB, this sample is taken at $t_{opt} = 50$ minutes after injection. It is used to measure $TP[t_{opt}=50]$ and $PF[t_{opt}=50]$, allowing us to sample the AIF at that optimal time, $y[t_{opt}=50]$, which for clarity we will refer to hereinafter as AIF50.

From population pharmacokinetic studies we know that it is possible to make individualized predictions for $CL_s$, AUC and $C_o$ for many pharmaceutical compounds [20]. Such prediction is typically performed using mixed-effects modeling to identify significant covariates among various indicative variables derived from weight, height, etc. In this work, we propose to investigate the development of a predictive model for AIF50 that uses non-invasive patient information. The predicted blood sample value pAIF50 then replaces AIF50, thus making SIME completely blood-free. To provide additional robustness, we also predict the PK variable AUC, which is more stable measure than AIF50 as it is calculated from multiple time point samples. We then incorporate the predicted value pAUC as an additional constraint within SIME. The combined objective function with predicted constraints becomes:

$$\phi(t, \theta^{PK}, \psi_r^{tac}, \ldots, \psi_R^{tac}) = \sum_{r=1}^{R}\sum_{j=1}^{J} w_j[Y_{rj} - f(t_j \mid \theta^{PK}, \psi_r)]^2 + \qquad (9)$$
$$v[pAIF50 - C_p^{PK}(t_{opt} \mid \theta^{PK})]^2 + z[pAUC - AUC(\theta^{PK})]^2$$

where pAIF50 and pAUC are the predicted AIF50 and AUC constraints, v and z are empirical weights, and the function AUC is given by:

$$AUC(\theta^{PK}) = \int_0^\infty C_p^{PK}(t \mid \theta^{PK}) dt \qquad (10)$$

Figure 79:
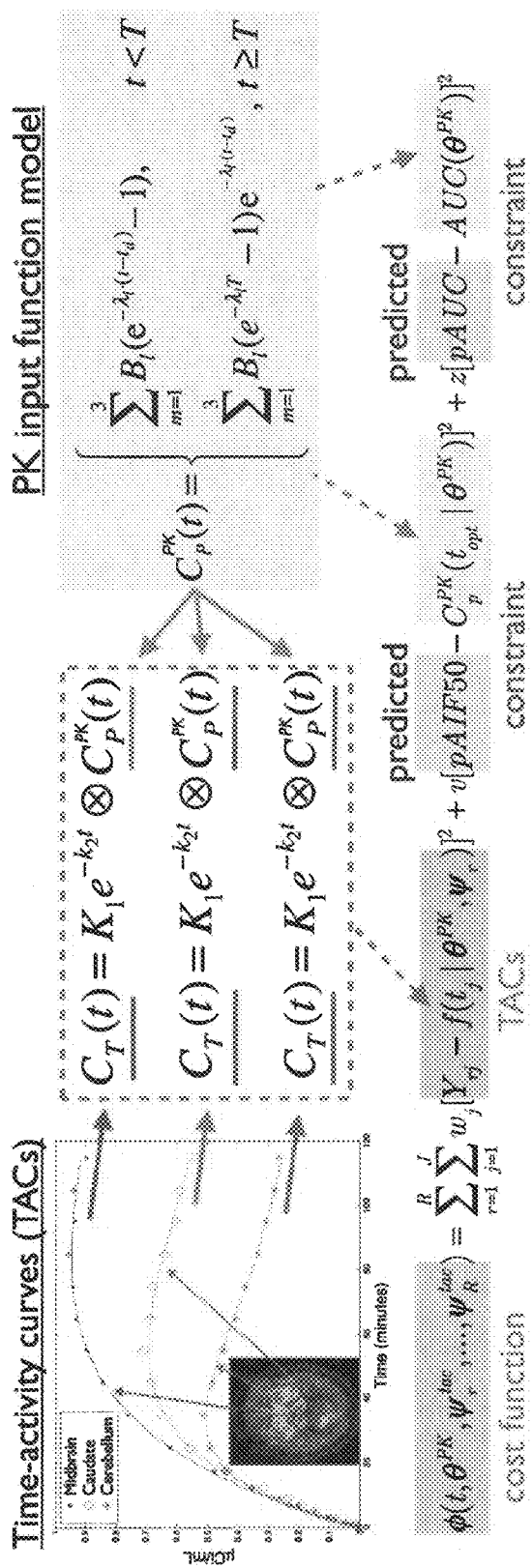
FIG. 79 shows overview of the nSIME approach that shows elements of the cost function being minimized using simulated annealing. Shape and scale of the input function are inferred from simultaneous fitting of TACs constrained by predicted AIF50 (pAIF50) and predicted AUC (pAUC).

Following [17, 34], the empirical weight for the AIF50 constraint was set to v=100 to ensure that the estimated input function passes through pAIF50. The weight for the AUC constraint was empirically set to z=5 such that the two constraint error terms have similar magnitude and contribute equally to the cost function. An overview of the nSIME approach is shown in FIG. 79.

Selection of Non-Invasive Patient Variables

The non-invasive patient information available for the predictive model combines EHR, PET image-derived information, demographics, vitals and derived variables, amounting to a total of 91 potential predictors. We include $TPsum = \int_{50}^{\infty} TP(t)dt$ corresponding to the integration of TP values from 50 minutes after the injection to the end of the scan. We also include $\lambda_{cal}$ from (1) and use it to estimate the portion of ID eliminated from the body after 50 minutes due to first order clearance, defined as $eID50 = IDe^{(-\lambda_{cal}50)}$. Although the above are technically invasive measures, in the future TP and $\lambda_{cal}$ may be replaced with IDIF methods (see Section I), or with a PET wrist scanner [35]. The list of the 94 predictor variables is reported in FIG. 100.

The following multi-stage approach is proposed to screen for variables that may be useful in predicting AIF50 and AUC. First, all variables are screened based on their correlations with the measured AIF50 and retained if $R^2 > 0.1$. Second, we generate a series of normalized ID variables by dividing each predictor variable into ID, since interactions between dose and physiology are expected for some variables. The normalized ID variable is retained for further analysis if the $R^2$ correlating it with AIF50 is greater then the $R^2$ correlating it with ID. Finally, we conducted a search of two-variable interaction terms. A total of 4371 (choose 2 out of 94) multivariate regression models are evaluated, each consisting of two predictors with and without interaction terms. The interaction term is retained if the $R^2$ of the model with the interaction term is both greater than 0.1, and is greater than the $R^2$ of the model without the interaction term, and the p-value of the interaction term is greater than 0.05. The entire screening procedure is repeated for AUC. Predictors that met above criterion for AIF50 and AUC are shown in FIG. 101.

SIME Constraints Prediction

The final task consists of identifying a model that relates selected predictor variables to the response variables AIF50 and AUC. Potential learning approaches include linear regression (LR), gradient boosting and random forests (RF). Linear regression seeks linear combination predictors that minimize the sum of squared error (SSE). It is well known that LR is highly susceptible to outlying observations, especially in large dimensional spaces (i.e. when the number of predictors is large). Various outlier detection metrics have been previously developed (e.g. deviance, studentized residuals, etc.) that may be used to detect unreliable observations, but they are difficult to interpret and performance of LR is limited when the number of predictors P is large. Boosting and RF remain robust to large P thanks to the aggregation of predictions over multiple models, each model having been built with small subsets of randomly selected predictors (i.e. small P). Gradient boosting employs an iterative procedure, where at each iteration a weak learner is selected that best fits the residuals. Weak learners can be for example linear regression models with P=3 randomly selected predictors. The predictive model is then built as a weighted average of predictions of the weak models (typically 100 or more). With RF, the weak learners are built as decision trees, where a split decision at each node of the tree is made to optimize an entropy measure on randomly selected subset of predictor variables. Typically, 100-200 trees need to be trained for a stable classifier and a robust predictive model.

Figure 80:
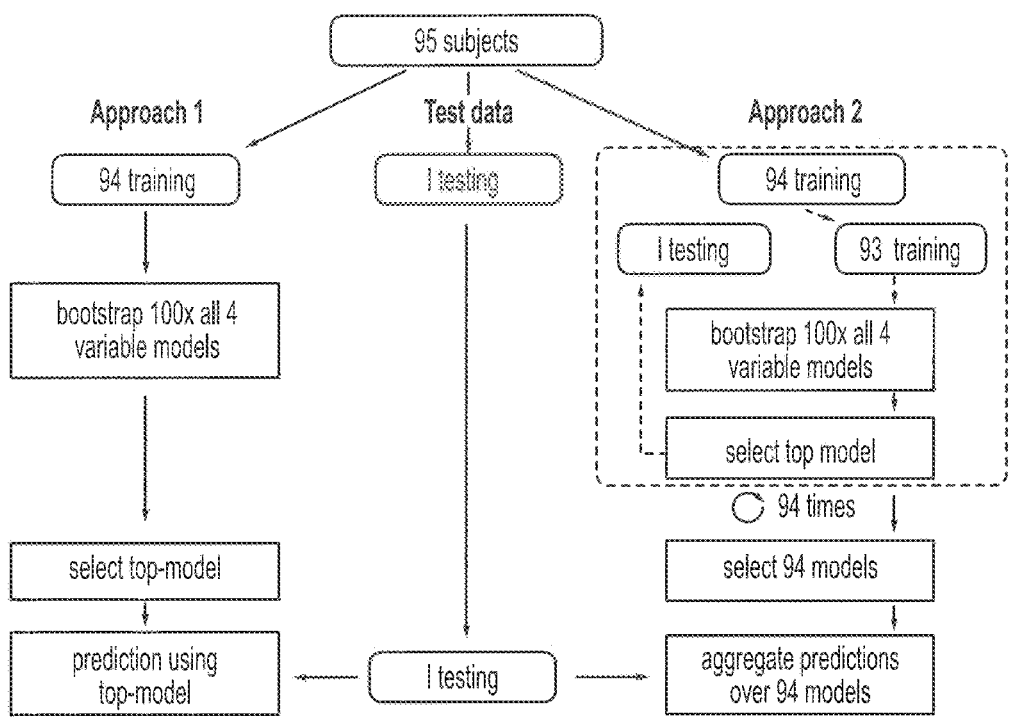
FIG. 80 shows machine learning approaches: Approach 1=Top-model, Approach 2=aggregated model.

While for some applications RF and gradient boosting have been known to yield higher performance over LR, they are also more complex and are difficult to interpret. Instead, we developed two approaches that combine the simplicity and interpretability of LR with robustness to outliers and noise of RF and gradient boosting. The first approach consists of a bootstrapped best-model selection procedure, and the second approach is designed as a new bootstrapped model aggregation method. For clarity, a flow diagram for both approaches is shown in FIG. 80.

Bootstrapped Top-Model Selection:

First, a leave-one-out procedure is employed where one of the subjects is left out for testing and the rest of the subjects (N=94) are used for training. Second, for the training set, all possible four variable LR models are assessed leading to 367,290 (choose 4 out of 56) for AIF50 and 270,725 (choose 4 out of 52) for AUC. Third, bootstrapped average $R^2$ correlations are calculated from training each model 100 times using randomly drawn samples with replacement from the training data. Fourth, the model with the highest $R^2$ is applied to the test data. The procedure is repeated 95 times, once for each observation.

Bootstrapped Aggregate Model Selection:

This procedure utilizes two nested leave-one-out loops to find a set of models that are aggregated and whose predictions are averaged. First, data set of 95 observations is split into test-level1 and training-level1 (N=94). Second, the training set training-level1 is split again into test-level2 and training-level2 (N=93). Third, for the training set training-level2, all possible four variable (P=4) LR models are assessed: 367,290 (choose 4 out of 56) for AIF50 and 270,725 (choose 4 out of 52) for AUC. Fourth, bootstrapped average $R^2$ correlations are calculated from training each model 100 times using randomly drawn samples with replacement from the training data. Fifth, the model with the "best" (minimal error) prediction for the test set test-level2 is selected. Repeating this procedure for all 94 training-level1 observations, we generate 94 optimal LR predictive models. Finally, these 94 models are aggregated (averaged) to predict the test-level1 observation.

The advantage of this approach is threefold: (1) all possible 4-variable LR models are tested; (2) each training data point contributes only with a weight of 1/94 to the overall prediction, thereby reducing impact of outlying observations without removing points from the training data; (3) since training points span a large range of values, selecting the LR predictive model with the 'minimal error' for each point yields a set of models optimal for narrow ranges of values, improving the chances that at least some of the models will provide reasonable predictions for any test point.

Performance Evaluation

Predicted pAIF50 and pAUC values obtained using the two proposed approaches are incorporated as constraints into the nSIME objective function of (9). Either the measured or nSIME derived input function can be substituted into (4) to estimate kinetic rate constants and to derive the following outcome measures of interest ($V_T$, $BP_P$ and $BP_{ND}$), as described in Section I. For each region and subject, the above measures were estimated using kinetic modeling with the measured AIF (from full arterial sampling) and nSIME. Agreement between the two approaches was assessed via correlation and regression analysis on the estimates, using the nSIME derived AIF as a dependent variable and the measured AIF as the independent variable.

Results

Prediction of AIF50 and AUC

Figures 81A, 81B, 81C, 81D:
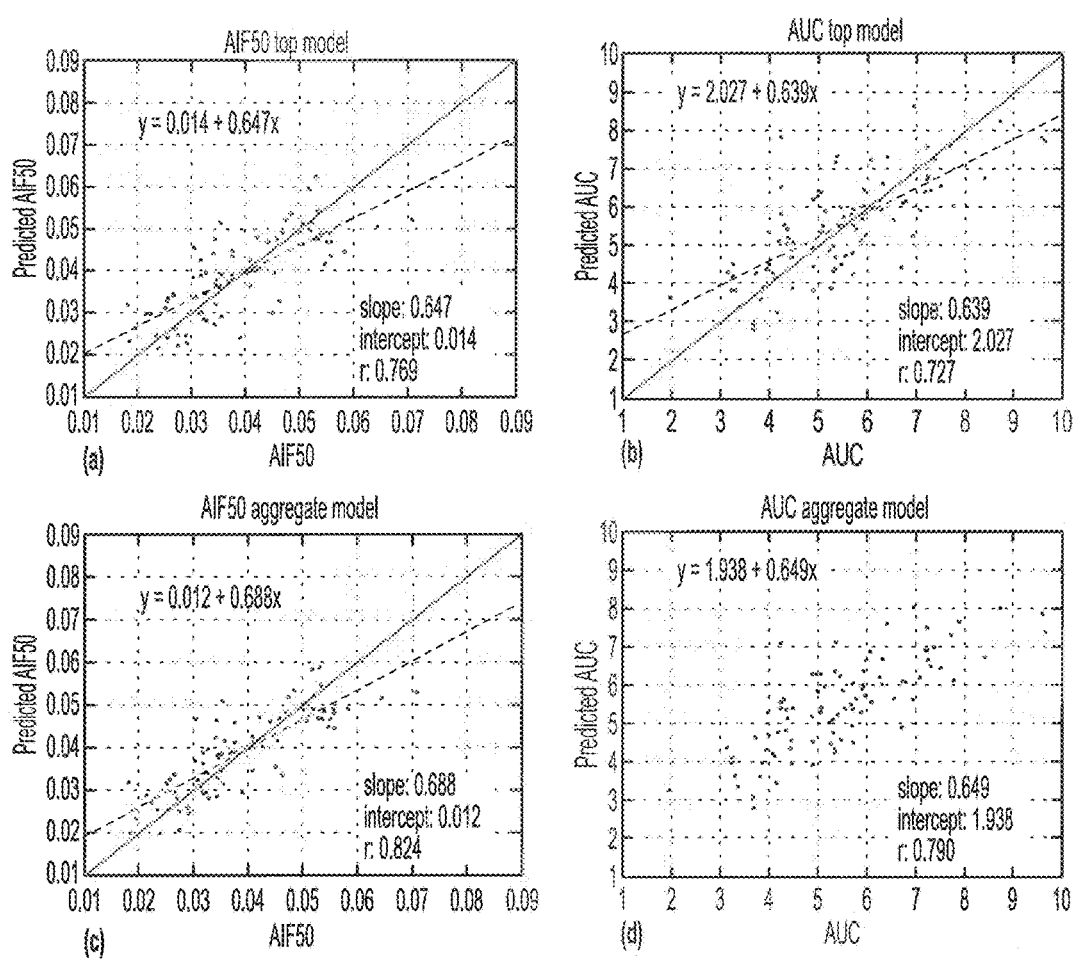
FIGS. 81A-81D show scatter plots comparing out-of-sample predicted constraints (pAIF50, pAUC) to measured values (AIF50, AUC). Results from the two proposed predictive models are plotted: bootstrapped top-model (top-row), bootstrapped aggregated model (bottom row). The identity (solid line) and the fitted linear regression line (dotted), the egression line equation, and slope and intercept are included for reference. Correlations (r) between predicted and measured constraints are shown in the bottom right corner of each plot.
Figure 82:
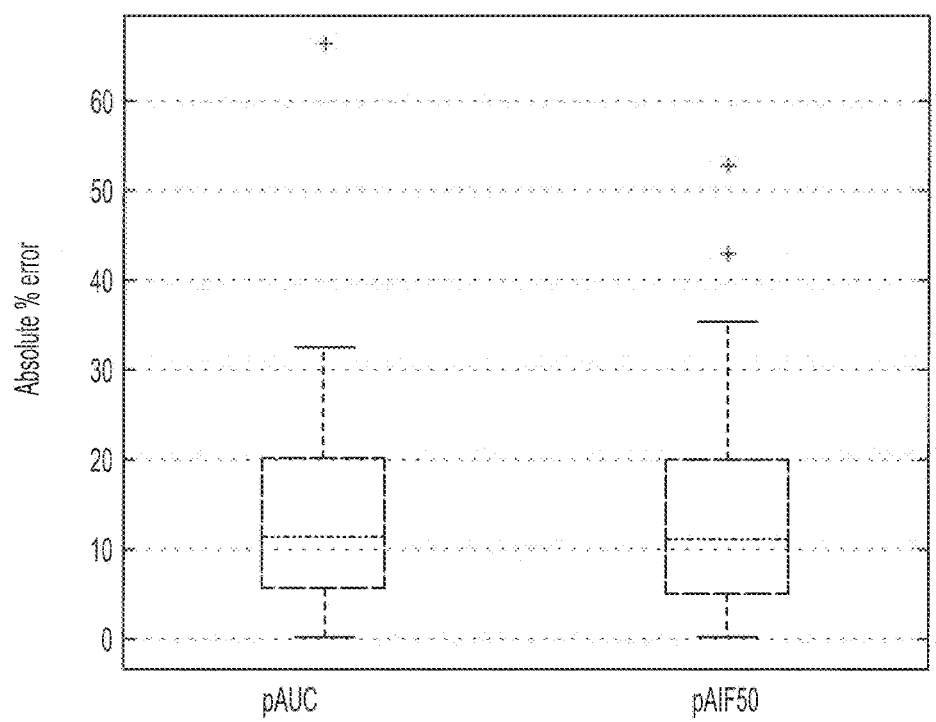
FIG. 82 shows absolute percent error for the predicted variables pAUC and pAIF50. Boxplots show the 1st and 3rd quartile as bottom and top box boundaries, and median value as the red line. Whiskers indicate 1.5 times lower and upper inter-quartile range (IQR) with red (+) indicates outliers.

Predictions from the two machine learning approaches are shown as scatter plots in FIG. 81 for AIF50 and AUC variables. The top-model approach used the top bootstrapped model (with respect to R) while the aggregated model is the average of 94 models with the least error in predicting the 94 training points. The top-model and aggregate model predictions yielded respectively an average bootstrapped correlation between predicted and measured values (r) of 0.769 (FIG. 81a) and 0.824 (FIG. 81c) for AIF50 and 0.727 (FIG. 81b) and 0.790 (FIG. 81d) for AUC. Therefore both prediction models returned high correlation values (above 0.72) for the two predicted values and the aggregated model yielded higher correlations for both variables. Prediction errors are plotted as boxplots in FIG. 82. Absolute percent error for pAUC and pAIF50, for most subjects, were within the 1st-3rd quartile intervals: [5.5%-20.2%] and [4.8%-19.9%], respectively. One subject had a pAIF50 error>60% and two subjects had pAUC errors>40%.

To assess the relative importance of predictors for AIF50 and AUC values, we calculated the frequency at which each predictor variable was selected by the top-model. In our case, with 4 variables per bootstrapped model and 95 predictors, a particular predictor present in N top-models has a relative frequency of 100×N/(4×95)=10.5%. Frequencies of a subset of the predictor variables are reported in FIG. 102 for pAIF50 and pAUC. For pAIF50, the top three most frequent predictor variables were CERsum (34.7%), TPsum (22.9%) and the interaction term HRpost:TPsum (13.9%). For pAUC the top three most frequent predictor variables were TPsum (26.8%), CERsum (24.7%) and the interaction term BSA:PPpost (18.4%).

Overall, for pAIF50, 35.5% and 17.0% of all selected predictor variables contained respectively a heart rate- or blood pressure-based term. In contrast, for AUC, 0.3% and 33.1% of all selected predictor variables contained respectively a heart rate- and blood pressure-based term.

AIF Estimations

Figures 83A, 83B, 83C, 83D:
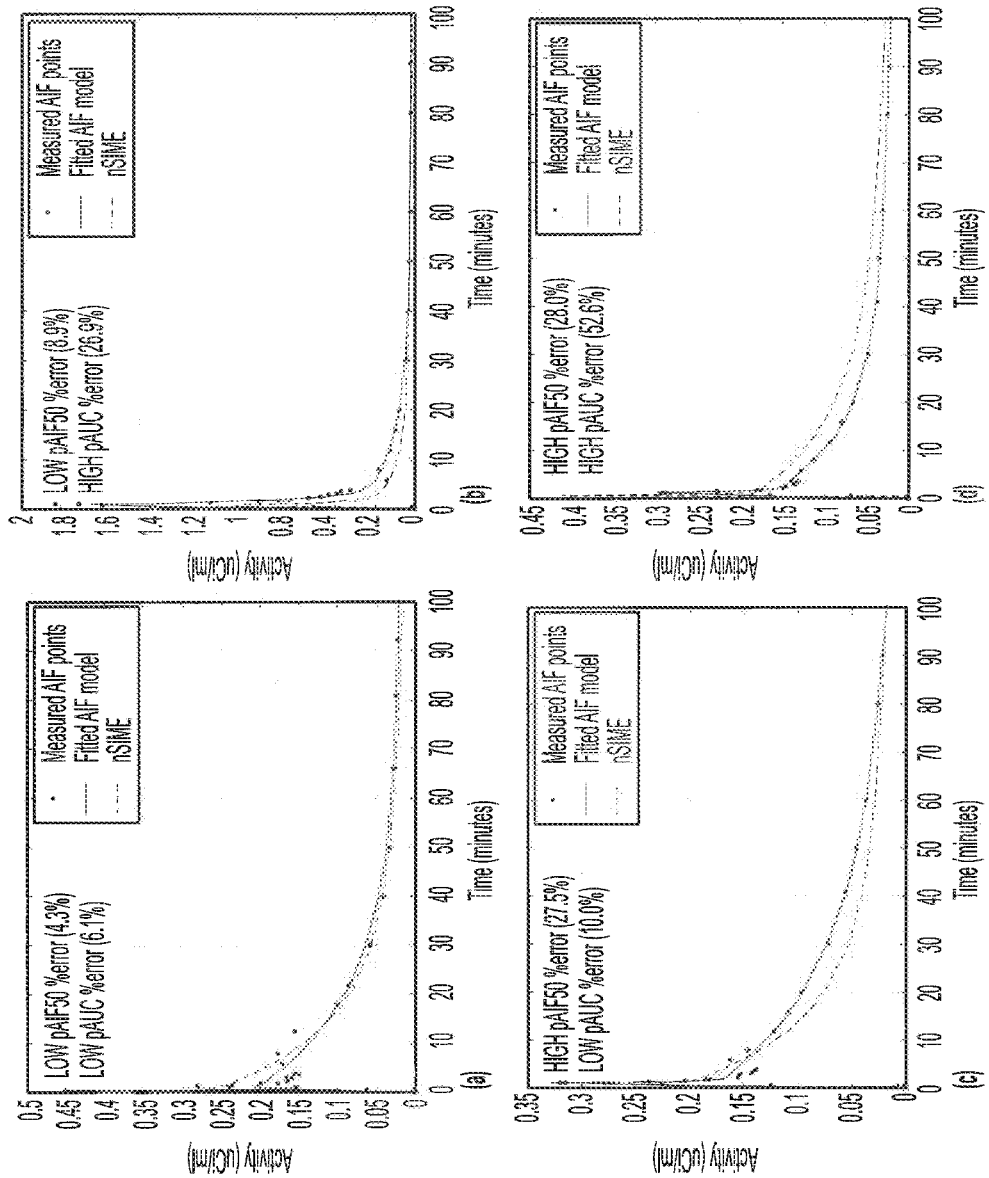
FIGS. 83A-83D show comparison of AIF curves derived from blood measures (black dots) and fitted with the model (Equation 2 of Example 8) (solid line) and nSIME with aggregate model predicted constraints (dashed line). Four representative cases are illustrated, with low/high pAIF50 (a, c) or low/high pAUC (b,d) percent errors.

Measured and nSIME-derived input functions are shown for representative cases in FIG. 83. To illustrate the separate effects that errors in pAUC and pAIF50 impart on the input function estimation, subjects were selected with two different error levels for (pAIF50/pAUC): (FIG. 83a) low/low; (FIG. 83b) low/high; (FIG. 83c) high/low and (FIG. 83d) high/high. A 'low' is below the 1st quartile and a 'high' error above the 3rd quartile reported in FIG. 82. It appears that AIF50 primarily impacts the height and shape of the tail portion of the curve (beyond 40+ minutes), while AUC controls the offset of the entire curve.

Figures 84A, 84B:
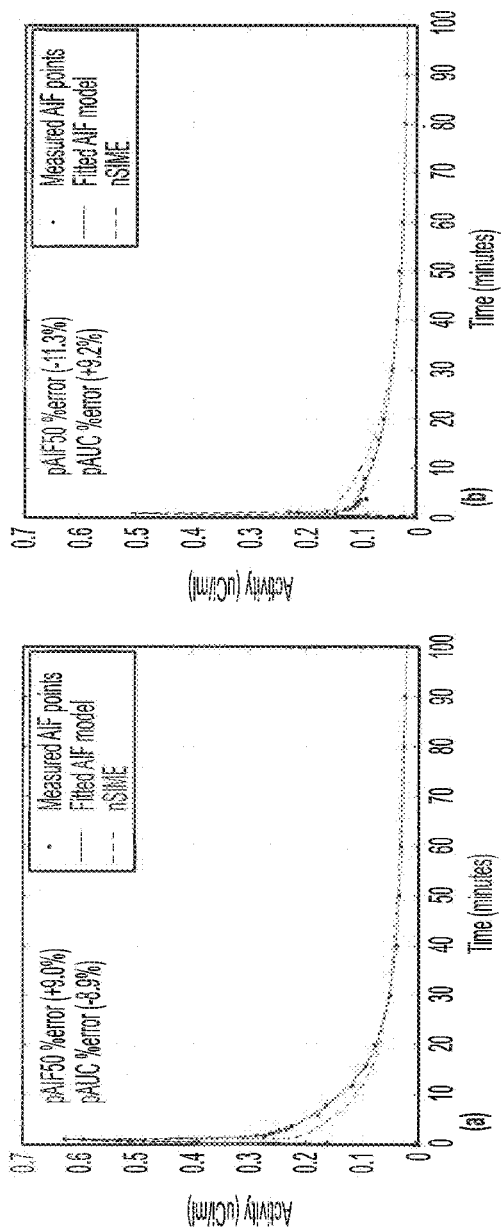
FIGS. 84A-84B shows behavior of nSIME derived AIF input functions when errors of pAIF50 and pAUC are of opposite signs. In (a), pAUC error is negative and pAIF50 error is positive while in (b), pAUC error is positive and pAIF50 error is negative. In both cases, the recovered curve matches well the AIF tail portion beyond the 30 minutes time point

We see that the tail part of the curve is best recovered when pAIF50 error is low while the initial part of the curve is heavily influenced by pAUC. When pAUC error is high, the initial part is over- or under-estimated, driven by the sign and magnitude of the pAUC error. In general, it is difficult to disentangle the influence of pAUC and pAIF50 since the constraints are working together and in conjunction with the dynamic PET imaging data to recover the shape of the AIF curve. So it is not clear which measure is driving the objective function for a given subject. We illustrate on FIG. 84 two cases where pAUC and pAIF50 errors are large and have opposite signs, and therefore the two constraints compensate for one another. In FIG. 84a, pAUC error is −8.9% and pAIF50 error is +9.0%, while in FIG. 84b pAIF50 error is +9.2% while pAIF50 error is −11.3%. In both cases nSIME was able to recover the input function quite well, especially the tail part, beyond 30+ minutes. This suggests that the constraints are counteracting one another and ultimately reduce the impact of their individual errors. For such cases having multiple constraints appears to yield benefits for AIF recovery.

Outcome Measures

Figure 85:
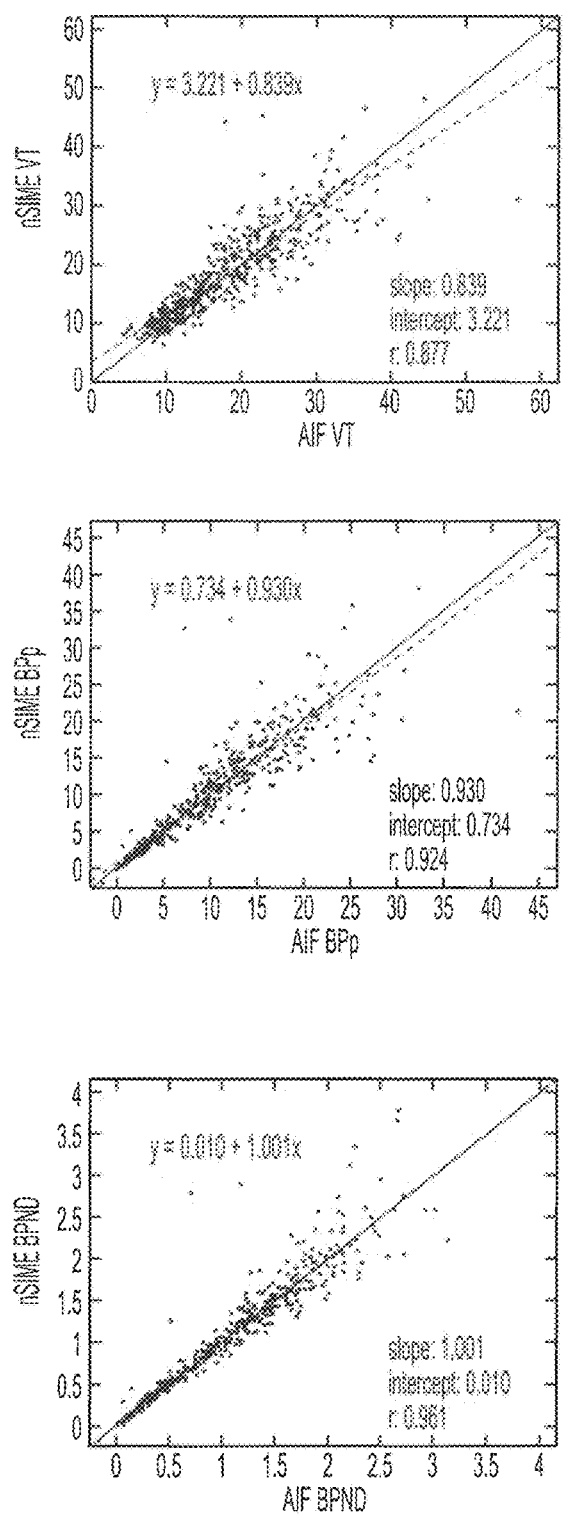
FIG. 85 shows scatterplots of estimated outcome variables $V_T$, $BP_P$, and $BP_{ND}$ from nSIME-derived versus measured AIF. Identity (solid black) and regression line (dashed black) are included for reference. The slope and intercept of the regression line, and the Pearson's correlation coefficient are reported in each plot.

Kinetic modeling outcome measures were computed using blood and nSIME-derived AIF. Scatterplots for $V_T$, $BP_{ND}$ and $BP_P$ are shown in FIG. 85. All nSIME estimations returned a high correlation value, lowest being for $V_T$ with r=0.877. Binding potential measures showed high correlations with r=0.924 for $BP_P$ and r=0.961 for $BP_{ND}$. A few outlying points are observed in the upper-left quadrant for all measures, corresponding to large pAIF50 or pAUC errors for two brain regions in one particular subject.

Discussion

We have introduced the concept of nSIME, as a new simultaneous estimation framework to enable full non-invasive quantitative PET imaging. This framework replaces blood-based radioligand measures by a robust PK input function model and multiple non-invasive constraints based on machine learning on EHR data. Our results on a large database of [11C]-DASB brain PET images showed that nSIME predictions of volume of distribution and binding potentials were highly correlated with estimates based on full arterial blood sampling.

In this evaluation, we also discovered specific covariates that appear to be related to [11C]-DASB metabolism and clearance from the body, which may be useful for understanding and interpreting the radioligand kinetics. CERsum was frequently included in the predictive models, which is interesting because the cerebellum is commonly used as a reference region for [11C]-DASB [30].

Another interesting result is that HR and BP appear more important for AIF50 prediction, while body size related terms (e.g. BSA, eGFR, eTBV) appear more frequently selected for AUC predictive models. There are two plausible explanations for the association of HR and BP with [11C]-DASB metabolism. The first is that from a hemodynamic point of view, the higher HR and BP, the greater the cardiac output and thus blood flow. Indeed, it has been shown that radioligand uptake is altered during anesthesia because of reduced HR, BP, and thus blood flow [36]. Secondly, [11C]-DASB binds the serotonin transporter which regulates levels of serotonin. Associations between cardiac repolarization intervals [37] and heart rate variability [38] have been linked to serotonin transporter function. The relationship between body size terms and AUC is possibly more straightforward and can be inferred from FIG. 77b. Body size impacts the volume of the compartments and as in (8) plasma concentration of radioligand decreases when radioligand is diluted into a larger plasma volume.

These results are particularly encouraging since EHR data are heterogeneous and some measures are quite crude. For example, the EHR data was gathered from retrospective studies and included measures acquired anywhere from hours (vitals—HR, BP) to weeks (e.g. hematocrit, creatinine) from the PET scan time. Weight was measured up to months before the scan and HR was measured via manual radial pulse rate.

Two predictive models were proposed for AIF50 and AUC, and confirmed the possibility to recovery the AIF of the [11C]-DASB radioligand without blood samples. Some outliers remain and might very well be due to erroneous EHR measures and/or errors in measured blood samples, to be confirmed with a carefully designed and quality-controlled prospective study.

Measurement of TP, which appeared frequently in our predictive models for AIF50 and AUC, can be supplemented with IDIF approaches. Previous works have demonstrated that a PET signal from carotid arteries can be obtained and scaled using the maximum value for [18F]-FDG [39] or the average of four hottest pixels for [11C]-flumazenil [40]. Both approaches require PET images to be reconstructed using an iterative expectation maximization (EM) reconstruction algorithm, and use a model of the scanner point spread function to correct for partial volume effects. EM routines are implemented on most modern PET scanner consoles and are readily available for post-hoc use with open source packages such as STIR [41], which has built-in support for many PET cameras. Our retrospective PET images were reconstructed with filtered back projection and therefore are not compatible with such IDIF approaches. Replication of the presented study using non-invasive TP measures from EM-reconstructed PET images is the subject of future work.

One important factor affecting nSIME prediction accuracy is the availability of a large training set of data consisting of PET images, EHR data and blood-based arterial input functions, from which to build a predictive model for the constraints. The number of subjects needed for 'training' still needs to be investigated and likely varies from radioligand to radioligand. It is also plausible that the subject population may influence results. In this study, we included patients with multiple disorders, ranging in age from 19 to 64 years old for which data were acquired between 2004 and 2012.

As an alternative to our approach, it is possible to estimate [11C]-DASB $BP_{ND}$ using a reference tissue approach. A previous study evaluated several such approaches with 209 [11C]-DASB subjects using the cerebellum as a reference region. Comparable performance was reached with the simplified reference tissue method, (r=0.933, slope=0.972) or a multilinear reference tissue model (MRTM), (r=0.973, slope=0.947). With nSIME, albeit with fewer subjects, our results for $BP_{ND}$ yielded a slope that is closer to identity and correlation values that were between the two. This previous study noted poor performance with [11C]-DASB on the voxel analysis when comparing MRTM reference tissue method to LEGA using full arterial blood sampling (r=0.508) [42]. Possibly, nSIME could perform better because the estimated input function could be used with LEGA. In general, we emphasize that reference tissue approaches are limited to estimating $BP_{ND}$ only while our approach is not.

Finally, [11C]-DASB is one of the more challenging radioligands to analyze because it has metabolite kinetics affected by lung trapping [2] and undergoes significant metabolism [30]. Our approach does not require any assumptions with respect to these issues. Since we estimate the AIF directly, metabolite modeling is not needed and any level of metabolism can be handled implicitly. Thus, nSIME approach may be applied to any radioligand once a model for predicting constraints has been developed.

REFERENCES

[1] R. B. Innis, V. J. Cunningham, J. Delforge, M. Fujita, A. Gjedde, R. N. Gunn, et al., "Consensus nomenclature for in vivo imaging of reversibly binding radioligands," J Cereb Blood Flow Metab, vol. 27, pp. 1533-9, September 2007.

[2] R. V. Parsey, A. Ojha, R. T. Ogden, K. Erlandsson, D. Kumar, M. Landgrebe, et al., "Metabolite considerations in the in vivo quantification of serotonin transporters using 11C-DASB and PET in humans," J Nucl Med, vol. 47, pp. 1796-802, November 2006.

[3] P. Zanotti-Fregonara, K. Chen, J. S. Liow, M. Fujita, and R. B. Innis, "Image-derived input function for brain PET studies: many challenges and few opportunities," J Cereb Blood Flow Metab, vol. 31, pp. 1986-98, October 2011.

[4] P. Zanotti-Fregonara, M. Fadaili el, R. Maroy, C. Comtat, A. Souloumiac, S. Jan, et al., "Comparison of eight methods for the estimation of the image-derived input function in dynamic [(18)F]-FDG PET human brain studies," J Cereb Blood Flow Metab, vol. 29, pp. 1825-35, November 2009.

[5] R. N. Gunn, S. R. Gunn, and V. J. Cunningham, "Positron emission tomography compartmental models," J Cereb Blood Flow Metab, vol. 21, pp. 635-52, June 2001.

[6] M. A. Kropholler, R. Boellaard, A. Schuitemaker, H. Folkersma, B. N. van Berckel, and A. A. Lammertsma, "Evaluation of reference tissue models for the analysis of [11C](R)-PK11195 studies," J Cereb Blood Flow Metab, vol. 26, pp. 1431-41, November 2006.

[7] S. M. Ametamey, V. Treyer, J. Streffer, M. T. Wyss, M. Schmidt, M. Blagoev, et al., "Human PET studies of metabotropic glutamate receptor subtype 5 with 11C-ABP688," J Nucl Med, vol. 48, pp. 247-52, February 2007.

[8] T. Tsuchida, N. Sadato, Y. Yonekura, S. Nakamura, N. Takahashi, K. Sugimoto, et al., "Noninvasive measurement of cerebral metabolic rate of glucose using standardized input function," J Nucl Med, vol. 40, pp. 1441-5, September 1999.

[9] M. Bentourkia, "Kinetic modeling of PET-FDG in the brain without blood sampling," Comput Med Imaging Graph, vol. 30, pp. 447-51, December 2006.

[10] B. J. Lopresti, W. E. Klunk, C. A. Mathis, J. A. Hoge, S. K. Ziolko, X. Lu, et al., "Simplified quantification of Pittsburgh Compound B amyloid imaging PET studies: a comparative analysis," J Nucl Med, vol. 46, pp. 1959-72, December 2005.

[11] K. Chen, D. Bandy, E. Reiman, S.-C. Huang, M. Lawson, D. Feng, et al., "Noninvasive Quantification of the Cerebral Metabolic Rate for Glucose Using Positron Emission Tomography, 18F-Fluoro-2-Deoxyglucose, the Patlak Method, and an Image-Derived Input Function," J Cereb Blood Flow Metab, vol. 18, pp. 716-723, 1998.

[12] M. Schain, S. Benjaminsson, K. Varnas, A. Forsberg, C. Halldin, A. Lansner, et al., "Arterial input function derived from pairwise correlations between PET-image voxels," J Cereb Blood Flow Metab, vol. 33, pp. 1058-65, July 2013.

[13] E. K. Fung, B. Planeta-Wilson, T. Mulnix, and R. E. Carson, "A Multimodal Approach to Image-Derived Input Functions for Brain PET," IEEE Nucl Sci Symp Conf Rec (1997), vol. 2009, pp. 2710-2714, Oct. 24, 2009.

[14] P. Zanotti-Fregonara, R. Maroy, C. Comtat, S. Jan, V. Gaura, A. Bar-Hen, et al., "Comparison of 3 Methods of Automated Internal Carotid Segmentation in Human Brain PET Studies: Application to the Estimation of Arterial Input Function," J Nucl Med, vol. 50, pp. 461-467, Mar. 1, 2009 2009.

[15] M. Liptrot, K. H. Adams, L. Martiny, L. H. Pinborg, M. N. Lonsdale, N. V. Olsen, et al., "Cluster analysis in kinetic modelling of the brain: a noninvasive alternative to arterial sampling," Neuroimage, vol. 21, pp. 483-93, February 2004.

[16] M. Naganawa, Y. Kimura, K. Ishii, K. Oda, K. Ishiwata, and A. Matani, "Extraction of a plasma time-activity curve from dynamic brain PET images based on independent component analysis," IEEE Trans Biomed Eng, vol. 52, pp. 201-10, February 2005.

[17] R. T. Ogden, F. Zanderigo, S. Choy, J. J. Mann, and R. V. Parsey, "Simultaneous estimation of input functions: an empirical study," Journal of cerebral blood flow and metabolism: official journal of the International Society of Cerebral Blood Flow and Metabolism, vol. 30, pp. 816-26, April 2010.

[18] K. Chen, X. Chen, R. Renaut, G. E. Alexander, D. Bandy, H. Guo, et al., "Characterization of the image-derived carotid artery input function using independent component analysis for the quantitation of [18F] fluorodeoxyglucose positron emission tomography images," Phys Med Biol, vol. 52, pp. 7055-71, Dec. 7, 2007.

[19] A. Hahn, L. Nics, P. Baldinger, W. Wadsak, M. Savli, C. Kraus, et al., "Application of image-derived and venous input functions in major depression using [carbonyl-(11)C]WAY-100635," Nucl Med Biol, vol. 40, pp. 371-7, April 2013.

[20] P. L. Bonate. (2011). Pharmacokinetic-pharmacodynamic modeling and simulation (2nd ed.).

[21] F. O'Sullivan, J. Kirrane, M. Muzi, J. N. O'Sullivan, A. M. Spence, D. A. Mankoff, et al., "Kinetic quantitation of cerebral PET-FDG studies without concurrent blood sampling: statistical recovery of the arterial input function," IEEE Trans Med Imaging, vol. 29, pp. 610-24, March 2010.

[22] A. Mikhno, F. Zanderigo, R. T. Ogden, M. Mikhno, H. Nagendra, J. J. Mann, et al., "Combining brain imaging data with electronic health records to non-invasively quantify [11C] DASB binding," 2014, pp. 732-735.

[23] I. Starr, T. G. Schnabel, Jr., S. I. Askovitz, and A. Schild, "Studies made by simulating systole at necropsy. IV. On the relation between pulse pressure and cardiac stroke volume, leading to a clinical method of estimating cardiac output from blood pressure and age," Circulation, vol. 9, pp. 648-63, May 1954.

[24] R. D. Mosteller, "Simplified calculation of body-surface area," N Engl J Med, vol. 317, p. 1098, Oct. 22, 1987.

[25] S. B. Nadler, J. H. Hidalgo, and T. Bloch, "Prediction of blood volume in normal human adults," Surgery, vol. 51, pp. 224-32, February 1962.

[26] M. D. Mifflin, S. T. St Jeor, L. A. Hill, B. J. Scott, S. A. Daugherty, and Y. O. Koh, "A new predictive equation for resting energy expenditure in healthy individuals," Am J Clin Nutr, vol. 51, pp. 241-7, February 1990.

[27] A. S. Levey, J. P. Bosch, J. B. Lewis, T. Greene, N. Rogers, and D. Roth, "A more accurate method to estimate glomerular filtration rate from serum creatinine: a new prediction equation. Modification of Diet in Renal Disease Study Group," Ann Intern Med, vol. 130, pp. 461-70, Mar. 16, 1999.

[28] L. A. Stevens, T. D. Nolin, M. M. Richardson, H. I. Feldman, J. B. Lewis, R. Rodby, et al., "Comparison of drug dosing recommendations based on measured GFR and kidney function estimating equations," Am J Kidney Dis, vol. 54, pp. 33-42, July 2009.

[29] R. V. Parsey, J. M. Kent, M. A. Oquendo, M. C. Richards, M. Pratap, T. B. Cooper, et al., "Acute occupancy of brain serotonin transporter by sertraline as measured by [11C]DASB and positron emission tomography," Biol Psychiatry, vol. 59, pp. 821-8, May 1, 2006.

[30] R. T. Ogden, A. Ojha, K. Erlandsson, M. A. Oquendo, J. J. Mann, and R. V. Parsey, "In vivo quantification of serotonin transporters using [(11)C]DASB and positron emission tomography in humans: modeling considerations," J Cereb Blood Flow Metab, vol. 27, pp. 205-17, January 2007.

[31] S. Kirkpatrick, C. D. Gelatt, Jr., and M. P. Vecchi, "Optimization by simulated annealing," Science, vol. 220, pp. 671-80, May 13, 1983.

[32] M. Gibaldi and D. Perrier, "Pharmacokinetics Second Edition Revised and Expanded," ed: Marcel Dekker, New York, 1982.

[33] M. M. Graham, "Physiologic smoothing of blood time-activity curves for PET data analysis," J Nucl Med, vol. 38, pp. 1161-8, July 1997.

[34] K.-P. Wong, S. R. Meikle, D. Feng, and M. J. Fulham, "Estimation of input function and kinetic parameters using simulated annealing: application in a flow model," IEEE Transactions on Nuclear Science, vol. 49, pp. 707-713, 2002.

[35] A. Kriplani, D. J. Schlyer, P. Vaska, S. Southekal, S. J. Park, C. L. Woody, et al., "Feasibility studies for extracting an Input Function for Quantitative Positron Emission Tomography using a Wrist Scanner," in Bioengineering Conference, 2007. NEBC '07. IEEE 33rd Annual Northeast, 2007, pp. 51-53.

[36] A. K. Alstrup, A. M. Landau, J. E. Holden, S. Jakobsen, A. C. Schacht, H. Audrain, et al., "Effects of anesthesia and species on the uptake or binding of radioligands in vivo in the Gottingen minipig," Biomed Res Int, vol. 2013, p. 808713, 2013.

[37] E. Kauppila, E. Vanninen, S. Kaurijoki, L. Karhunen, K. H. Pietilainen, A. Rissanen, et al., "Influence of serotonin transporter gene polymorphism (5-HTTLPR polymorphism) on the relation between brain 5-HT transporter binding and heart rate corrected cardiac repolarization interval," PLoS One, vol. 8, p. e50303, 2013.

[38] E. H. Kang, I. S. Lee, J. E. Park, K. J. Kim, and B. H. Yu, "Platelet serotonin transporter function and heart rate variability in patients with panic disorder," J Korean Med Sci, vol. 25, pp. 613-8, April 2010.

[39] B. J. Parker and F. Dagan, "Graph-based Mumford-Shah segmentation of dynamic PET with application to input function estimation," Nuclear Science, IEEE Transactions on, vol. 52, pp. 79-89, 2005.

[40] J. E. Mourik, M. Lubberink, U. M. Klumpers, E. F. Comans, A. A. Lammertsma, and R. Boellaard, "Partial volume corrected image derived input functions for dynamic PET brain studies: methodology and validation for [11C]flumazenil," Neuroimage, vol. 39, pp. 1041-50, Feb. 1, 2008.

[41] K. Thielemans, S. Mustafovic, and C. Tsoumpas, "STIR: software for tomographic image reconstruction release 2," in IEEE Nucl Sci Symp Conf Rec, 2006, pp. 2174-2176.

[42] F. Zanderigo, R. T. Ogden, and R. V. Parsey, "Reference region approaches in PET: a comparative study on multiple radioligands," J Cereb Blood Flow Metab, vol. 33, pp. 888-97, June 2013.

Example 9: Enhancement of the Raphe Nuclei in PET Data with gPSF-MLEM

Figure 86:
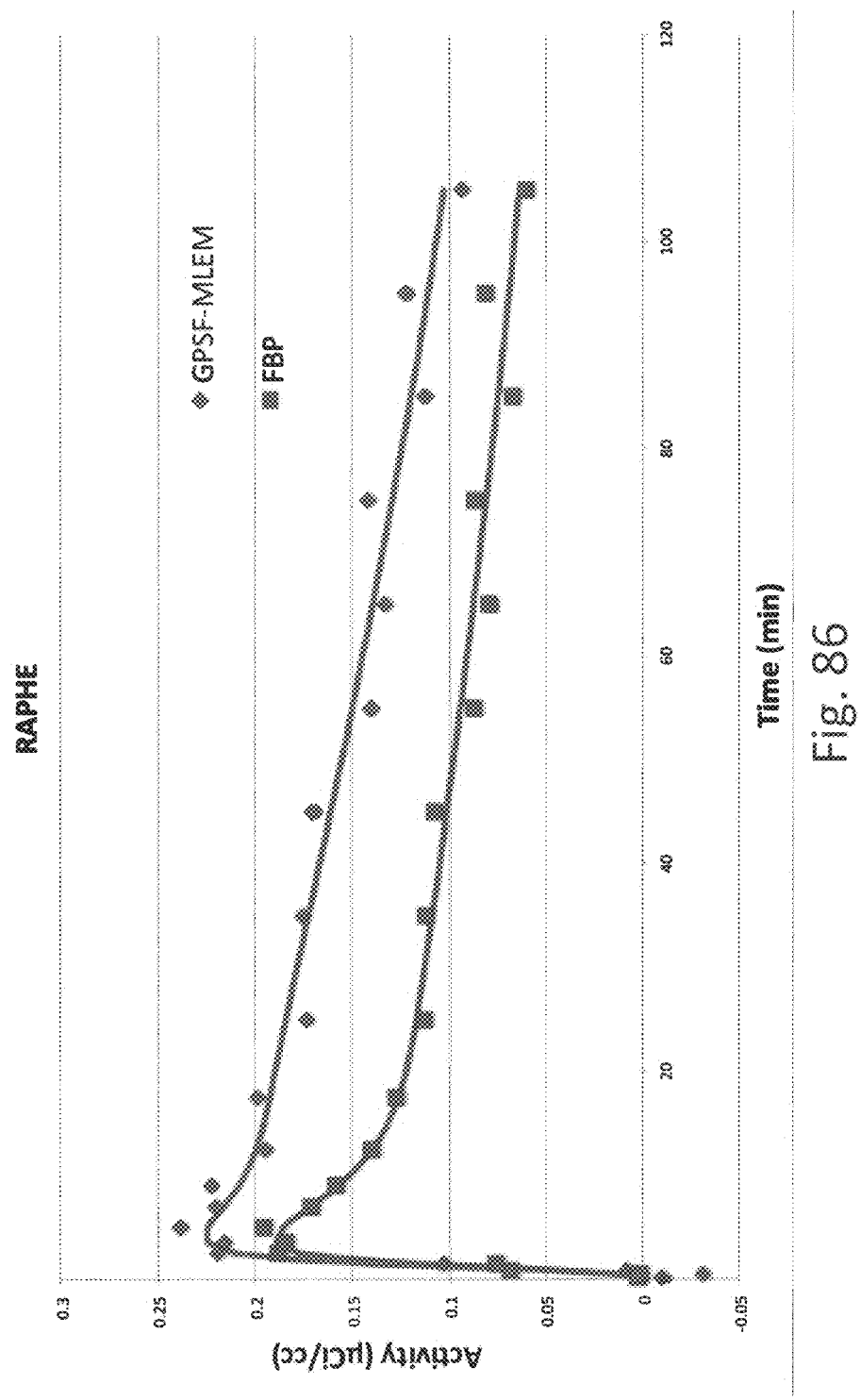
FIG. 86 shows a time-activity curve for gPSF-MLEM (diamonds) and FBP (squares) reconstructed data.
Figure 88A:
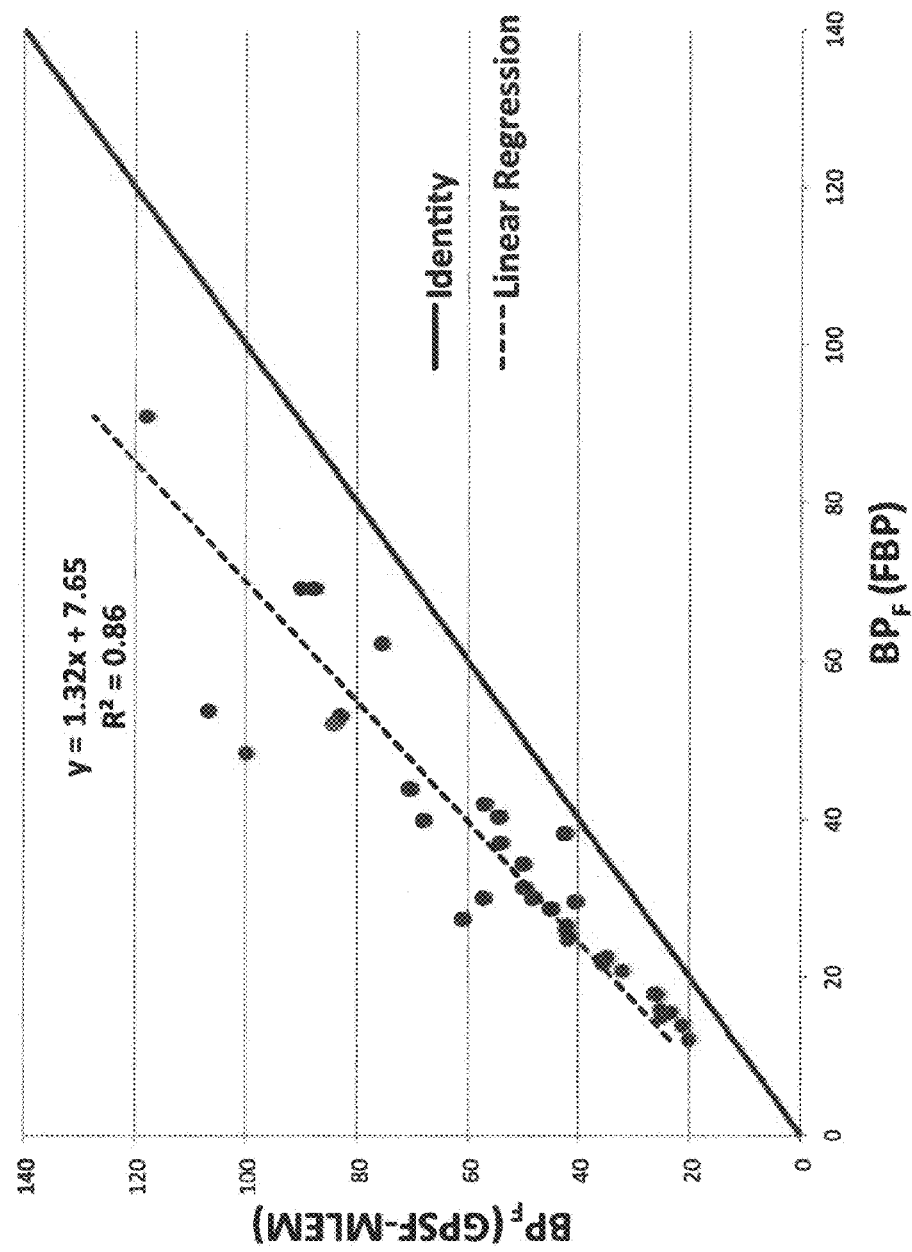
FIGS. 88A-88B show a scatter plot of gPSF-MLEM versus FBP binding potential (BPF) values that were calculated from kinetic modeling of the time-activity curves of the raphe (FIG. 88A) and dorsal prefrontal cortex (DPFC) (FIG. 88B).
Figure 88B:
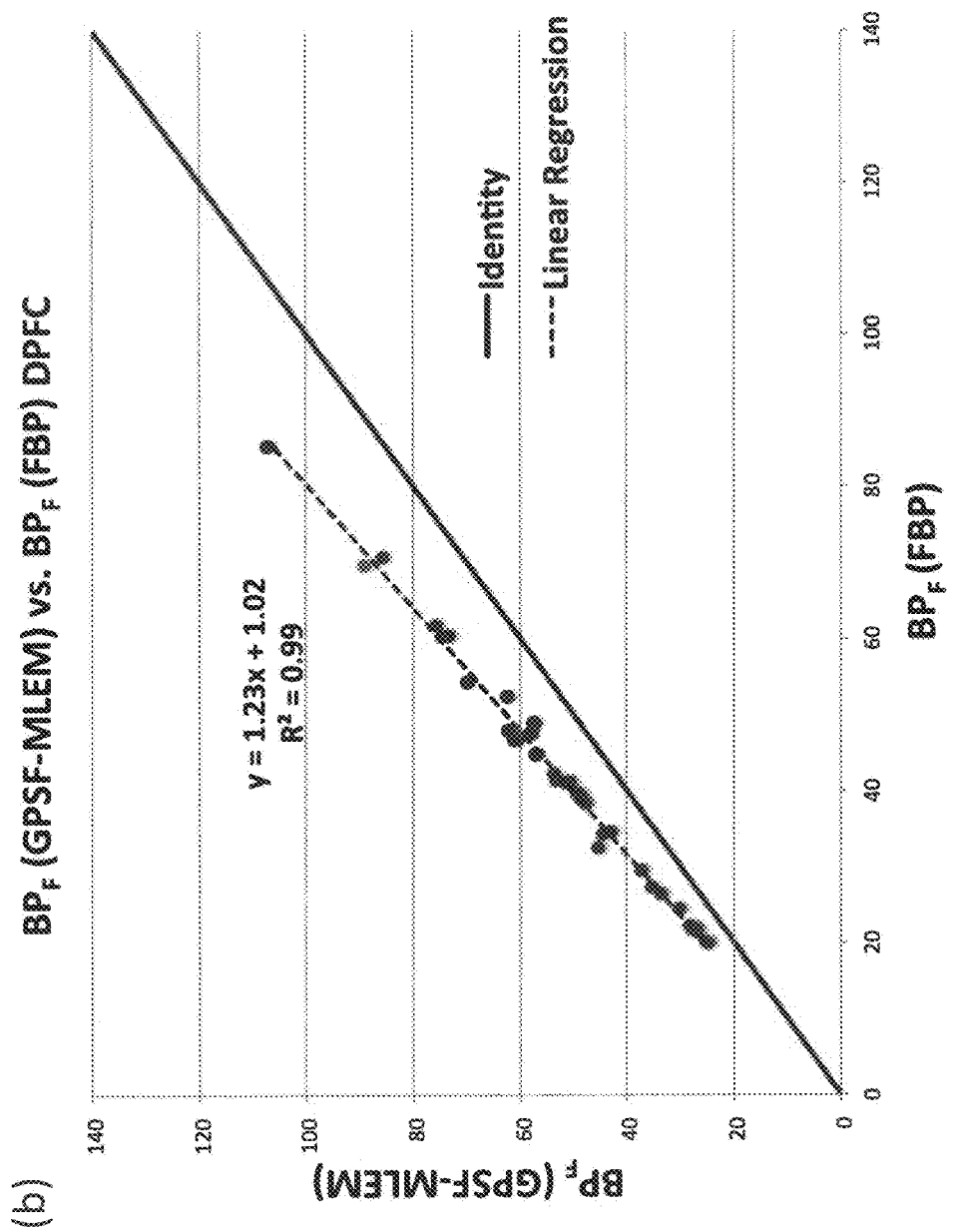
Figure 89A:
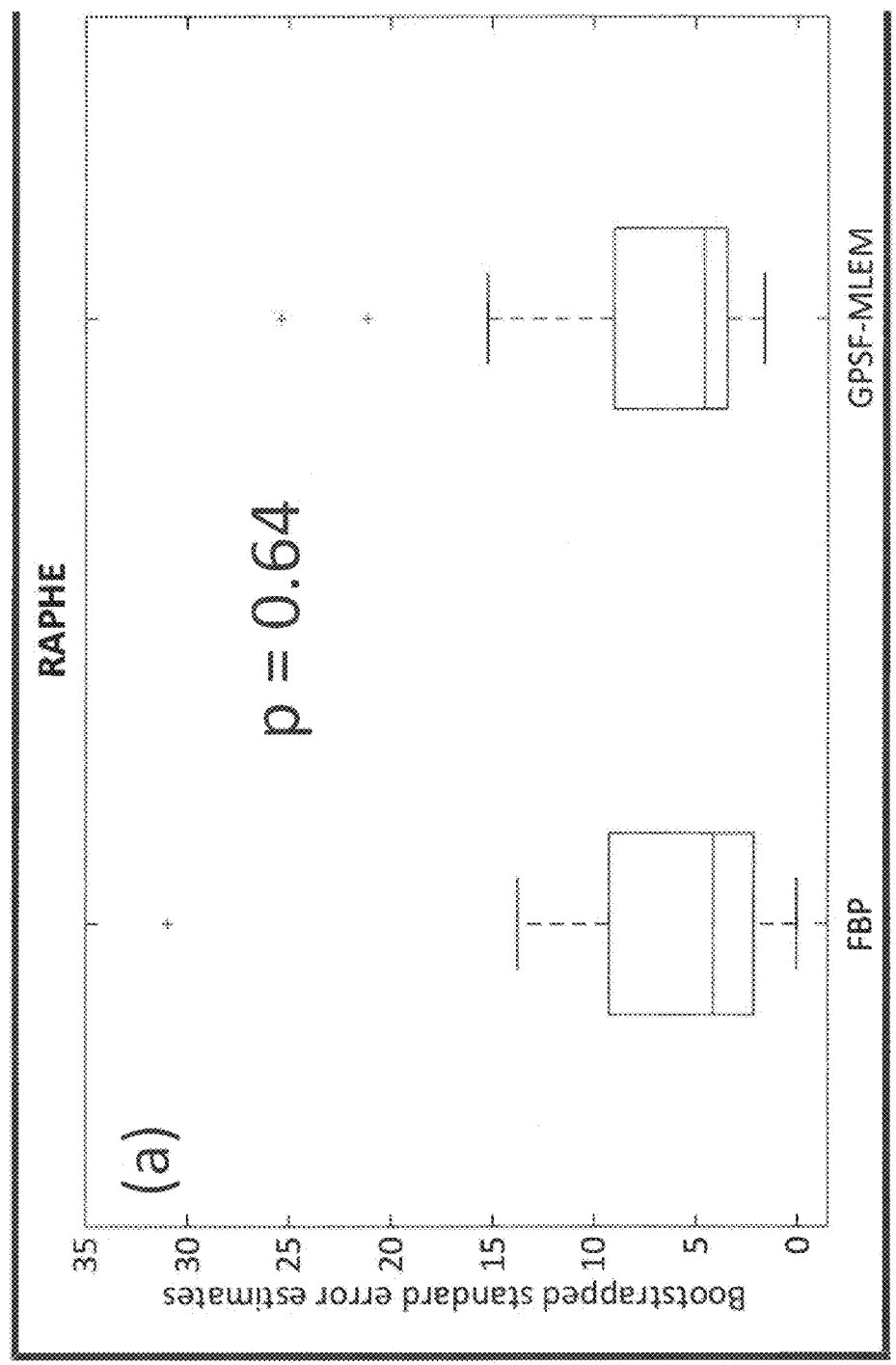
FIGS. 89A-B show the bootstrapped errors of the BPF estimates for the raphe (FIG. 89A) and DPFC (FIG. 89B).
Figure 89B:
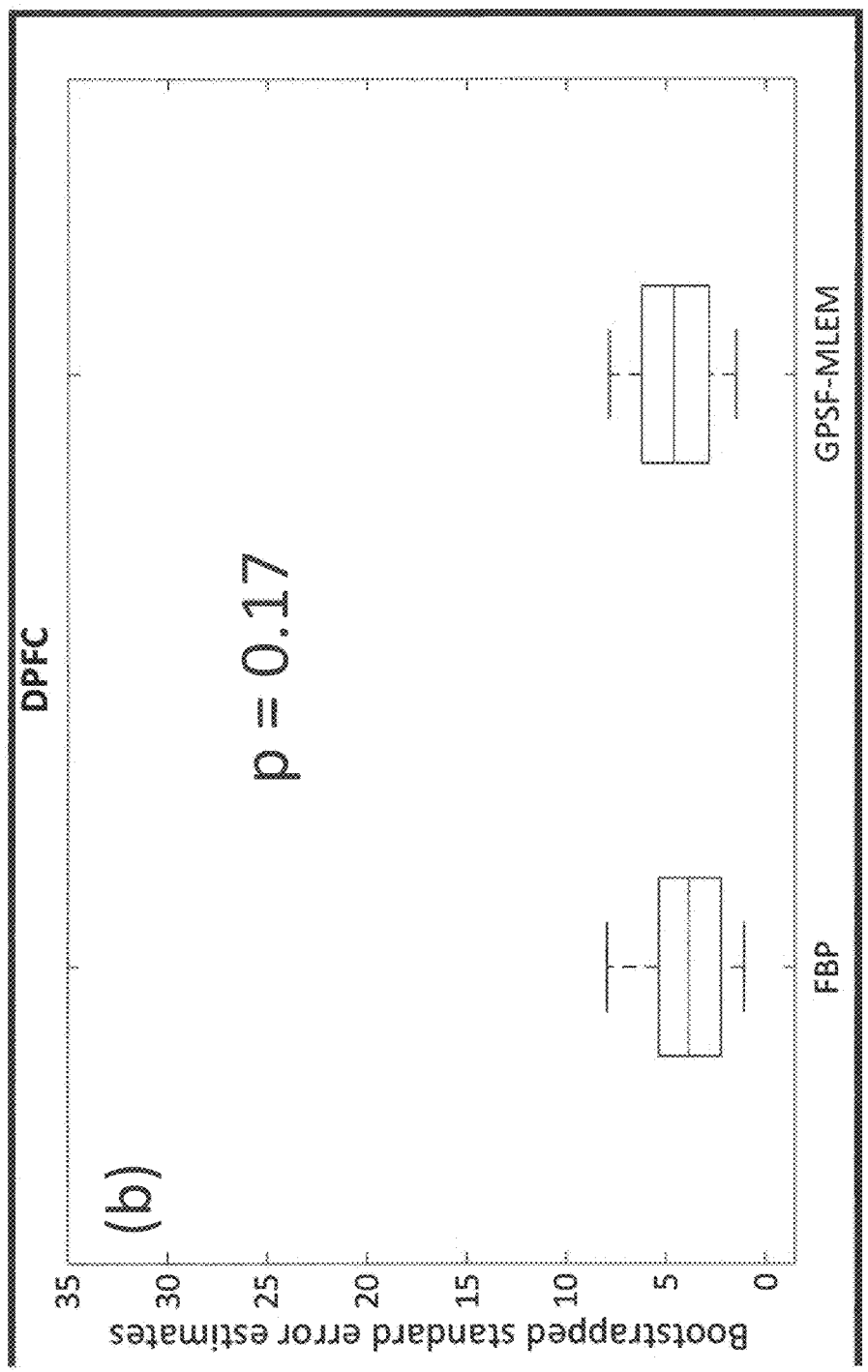

FIGS. 86-89 show the results of applying the gPSF-MLEM method to dynamic radioligand [11C]-WAY scans acquired in a clinical population of 35 subjects. FIG. 86 shows that gPSF-MLEM can be used to reconstruct each time point (or frame) of the PET scan. The time-activity curves of gPSF-MLEM are stable over time and increased as compared to FBP reconstructed data. FIG. 87 shows the FBP and gPSF-MLEM reconstructed images of a short 5-minute PET acquisition, where gPSF-MLEM demonstrates enhanced signal and contrast of the raphe nuclei. FIG. 88 shows a scatter plot of gPSF-MLEM versus FBP binding potential (BPF) values that were calculated from kinetic modeling of the time-activity curves of the raphe and dorsal prefrontal cortex (DPFC). The lower gPSF-MLEM versus FBP BPF correlation in the raphe, as compared to the larger DPFC region, suggest a region size dependent signal recovery pattern with gPSF-MLEM that is consistent with partial volume correction. FIG. 89 shows that bootstrapped errors of the BPF estimates for the raphe and DPFC were not statistically different. gPSF-MLEM can provide benefits for quantification of raphe and other regions by improving signal recovery, kinetic modeling and identification of smaller structures in existing PET images.

Figure 91:
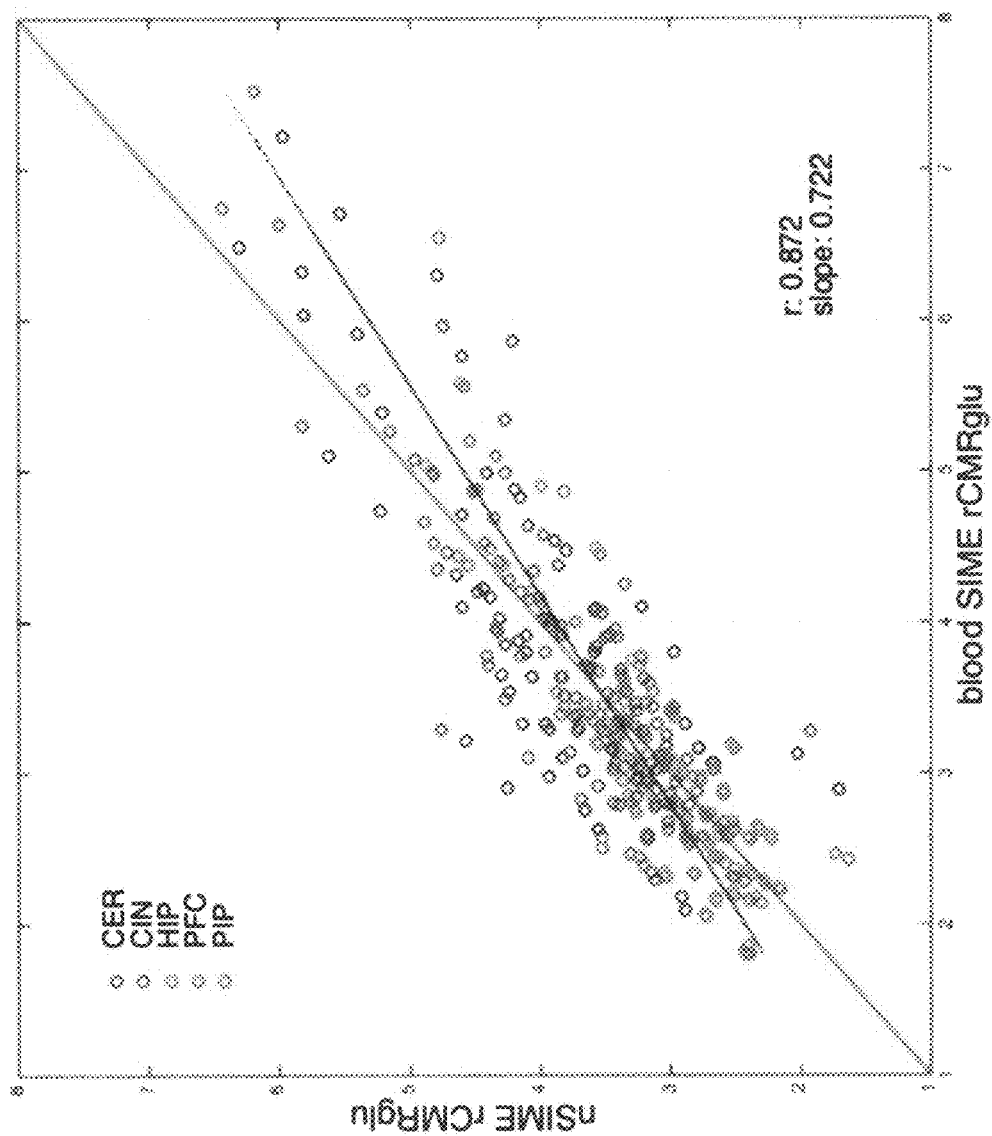
FIG. 91 shows a scatter plot of the nSIME derived rCMRglu versus rCMRglu derived with blood samples and standard (invasive) SIME.
Figures 99A, 99B:
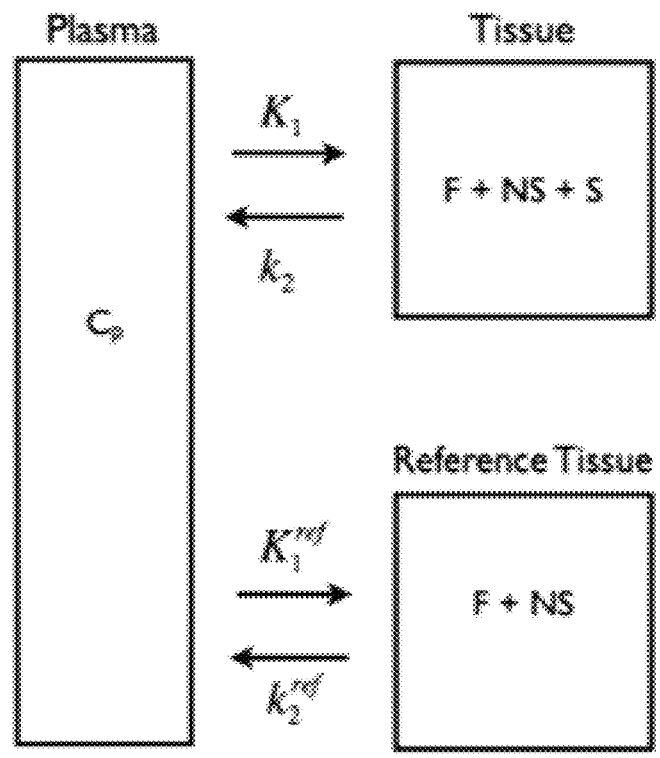
FIGS. 99A-B.

Example 10: Non-Invasive Quantification of [18F]-FDG Radioligand Uptake by Combining Medical Health Records and Dynamic PET Imaging Data FIGS. 90-91 show the results of applying the non-invasive SIME (nSIME) to 71 clinical scans with the [18F]-FDG radioligand. FIG. 90 shows the medical health record best combination of variables most frequently selected to predict the area under the curve (AUC) and 40-minute plasma value (AIF40) for FDG. The "*" represents is an interaction between the two predictors (multiplication of values). FIG. 91 shows a scatter plot of the nSIME-derived rCMRglu versus rCMRglu derived with blood samples and standard (invasive) SIME. There was a high correlation overall (r=0.87) and for each ROI separately: 0.84, 0.83, 0.86, 0.83, 0.85 in cerebellum, cingulate, hippocampus, prefrontal cortex, and parahippocampal gyms, respectively. The high correlations of non-invasive versus invasive rCMRglu (regional cerebral metabolic rate of glucose) outcome measure demonstrates that the nSIME method may be used instead of invasive blood sampling.

What is claimed is:

1. A computer implemented method for reconstructing positron emission tomography (PET) or single-photon emission computed tomography (SPECT) image data, the method comprising:
   (a) generating a PET or a SPECT scan acquisition comprising a plurality of voxels corresponding to an anatomical structure of a subject administered with a radioligand, wherein the scan acquisition comprises:
      (i) a transmission sinogram comprising the plurality of voxels corresponding to the anatomical structure of the subject;
      (ii) an emission sinogram comprising detected coincidence events emitted from the anatomical structure of the subject; and
      (iii) a normalization scan;
   (b) calculating a weight for each voxel of the scan acquisition using iterative reconstruction to generate a 3D weight map; and
   (c) performing at least one of a Total Variation-Point Spread Function-Maximum Likelihood Expectation Maximization (TV-PSF-MLEM) reconstruction, or a Total Variation-gradual Point Spread Function-Maximum Likelihood Expectation Maximization (TV-gPSF-MLEM) reconstruction with the 3D weight map to generate a reconstructed image.

2. The method of claim 1, wherein the iterative reconstruction is a Maximum Likelihood Expectation Maximization (MLEM), Ordered Subsets Expectation Maximization (OSEM), or a maximum a posteriori estimate (MAP).

3. The method of claim 1, further comprising determining the weight for each voxel based on the voxel convergence rate.

4. The method of claim 1, further comprising calculating the weight for each voxel at a window in the neighborhood around each voxel.

5. The method of claim 4, wherein the window in the neighborhood around each voxel is a 3×3×3 window.

6. The method of claim 1, wherein the iterative reconstruction is performed until a first convergence threshold is reached.

7. The method of claim 6, wherein the at least one of the TV-PSF-MLEM reconstruction, or the TV-gPSF-MLEM reconstruction is performed until a second convergence threshold is reached.

8. The method of claim 1, wherein iterative reconstruction is performed for at least a threshold number of iterations.

9. The method of claim 1, 6, or 8, wherein the at least one of the TV-PSF-MLEM reconstruction, or the TV-gPSF-MLEM reconstruction is performed for at least a threshold number of iterations.

10. The method of claim 1, wherein the scan acquisition comprises at least one of emission data, random data, and transmission data.

11. The method of claim 1, wherein the transmission sinogram comprises an attenuation coefficient map.

12. The method of claim 1, wherein the radioligand is a [11C]-WAY radioligand.

13. The method of claim 1, wherein the anatomical structure is a brain structure.

14. The method of claim 1, wherein the subject is a human.

15. The method of claim 1, wherein the radioligand is selected from the group consisting of [11C]-WAY, [11C]-DASB, [11C]-DTBZ, [11C]-FE-CIT, [18F]-dopa, [11C]-dopa, [11C]-, [18F]-CFT, [11C]-RTI-32, [18F]-FP-CIT, [11C]-methylphenidate, [123I]-β-CIT, [123I]-FP-CIT, [123I]-altropane, [99mTc]-TRODAT-1, [11C]-dihydrotetrabenazine, [99mTc]-MHMPAO, [99mTc]-ethylcysteine dimer, [99mTc]-DTPA, [99mTc]-glucoheptonate, [99mTc]-sestamibi, [99mTc]-tetrofosmin, [99mTc]-labelled sulphur colloid, H215O, [18F]-fluorodeoxyglucose, [13N]-ammonium, [15O]-butanol, 113Xe, 15O2, [11C]-CFT, [123I]-IPT, [11C]-SCH23390, [11C]-raclopride, [11C]-FLB456, [11C]-methylspiperone, [18F]-spiperone, [18F]-fluroethylspiperone, [76Br]-bromospiperone, [123I]-eppidepride, [123I]-iodobenzamide, [11C]-BATA, [18F]-2-fluorothoxydazoxan, [11C]-methyltryptophan, [11C]-MDL100907, [18F]-altanserin, [18F]-serpeptone, [11C]-MP4A, [11C]-physostigmine, [18F]-fluoroethozybenzoessamicol, [11C]-vesamicol, [123I]-benzovesamicol, [11C]-tropanylbenylate, [11C]-NMPB, [18F]-FP-TZTP, [123I]-QNB, [11C]-MPA, [11C]-A-85380, [18F]-A-85380, [123I]-A-85380, [11C]-dothiepin, [11C]-carfentenil, [18F]-cyclofoxy, [11C]-diprenorphine, [11C]-flumazenil, [11C]-RO15-4513, [11C]-PK11195, [18F]-PK11195, [123I]-PK11195, [18F]-SPARQ, [11C]-GR205171, [11C]-SCH 442416, [11C]-CNS 5161, [18F]-FDDNP, [11C]-SB13, [123I]-IMPY, and [11C]-carfentenil.

16. A computer implemented method for reconstructing positron emission tomography (PET) or single photon emission computed tomography (SPECT) image data, the method comprising:
  (a) generating a PET or a SPECT scan acquisition comprising a plurality of voxels corresponding to an anatomical structure of a subject administered with a radioligand, wherein the scan acquisition comprises:
    i) a transmission sinogram comprising the plurality of voxels corresponding to the anatomical structure of the subject;
    (ii) an emission sinogram comprising detected coincidence events emitted from the anatomical structure of the subject; and
    (iii) a normalization scan; and
  (b) performing gradual Point Spread Function-Maximum Likelihood Expectation Maximization (gPSF-MLEM) reconstruction with the scan acquisition to generate a reconstructed image.

17. The method of claim 16, wherein the gPSF-MLEM reconstruction is performed until a convergence threshold is reached.

18. The method of claim 16, wherein the gPSF-MLEM reconstruction is performed for at least a threshold number of iterations.

* * * * *